(12) United States Patent
Kerrigan et al.

(10) Patent No.: US 10,654,828 B2
(45) Date of Patent: May 19, 2020

(54) INDOLE DERIVATIVES AND USES THEREOF

(71) Applicant: NOVARTIS AG, Basel (CH)

(72) Inventors: John Ryan Kerrigan, Wakefield, MA (US); Natalie Dales, Arlington, MA (US); George Scott Tria, Arlington, MA (US); Daniel Palacios, Cambridge, MA (US); Paul Gormisky, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/045,993

(22) Filed: Jul. 26, 2018

(65) Prior Publication Data
US 2019/0055219 A1 Feb. 21, 2019

Related U.S. Application Data

(60) Provisional application No. 62/538,428, filed on Jul. 28, 2017.

(51) Int. Cl.
| | |
|---|---|
| *C07D 401/14* | (2006.01) |
| *C07D 405/14* | (2006.01) |
| *C07D 403/14* | (2006.01) |
| *C07D 471/04* | (2006.01) |
| *C07D 487/04* | (2006.01) |
| *C07D 403/04* | (2006.01) |
| *A61P 25/28* | (2006.01) |
| *C07D 471/08* | (2006.01) |
| *C07D 491/04* | (2006.01) |
| *A61P 21/00* | (2006.01) |
| *A61P 27/16* | (2006.01) |
| *C07D 403/12* | (2006.01) |
| *C07D 498/04* | (2006.01) |

(52) U.S. Cl.
CPC ............ *C07D 401/14* (2013.01); *A61P 21/00* (2018.01); *A61P 25/28* (2018.01); *A61P 27/16* (2018.01); *C07D 403/04* (2013.01); *C07D 403/12* (2013.01); *C07D 403/14* (2013.01); *C07D 405/14* (2013.01); *C07D 471/04* (2013.01); *C07D 471/08* (2013.01); *C07D 487/04* (2013.01); *C07D 491/04* (2013.01); *C07D 498/04* (2013.01)

(58) Field of Classification Search
CPC .................................................. C07D 401/14
See application file for complete search history.

(56) References Cited

U.S. PATENT DOCUMENTS

| | | | |
|---|---|---|---|
| 9,050,301 B2 | 6/2015 | Kim et al. | |
| 2007/0191371 A1 | 8/2007 | Bennett et al. | |

FOREIGN PATENT DOCUMENTS

| | | | |
|---|---|---|---|
| WO | WO 2001/037852 A2 | 5/2001 | |
| WO | WO-2004080481 A1 * | 9/2004 | ........... A61K 9/0019 |
| WO | WO 2004/092140 A1 | 10/2004 | |
| WO | WO 2007/090913 A1 | 8/2007 | |
| WO | WO 2013/159094 A2 | 10/2013 | |
| WO | WO 2014/023367 A1 | 2/2014 | |
| WO | WO 2015/056180 A1 | 4/2015 | |
| WO | WO 2017/075715 A1 | 5/2017 | |

OTHER PUBLICATIONS

Vanhaesebroeck "PI3K signalling: the path to discovery and understanding" Nature Reviews | Molecular Cell Biology vol. 13 | Mar. 2012 | 195.*
Vadlakonda "The paradox of Akt-mTOR interactions" Frontiers in Oncology Jun. 2013 | vol. 3 | Article 165.*
Moreira "A small molecule activator of AKT does not reduce ischemic injury of the rat heart" Journal of Translational Medicine (2015) 13:76, 1-10.*
International Search Report and Written Opinion of the International Searching Authority for PCT/IB2018/000959, dated Nov. 16, 2018 (14 pages).
Cristiane H. Squarize et al, "Accelerated Wound Healing by mTOR Activation in Genetically Defined Mouse Models", PLoS ONE, vol. 5, No. 5, (May 1, 2010), pp. 1-10.

(Continued)

*Primary Examiner* — David K O'Dell
(74) *Attorney, Agent, or Firm* — Asimina T. Georges Evangelinos

(57) ABSTRACT

The present disclosure provides a compound of formula (I):

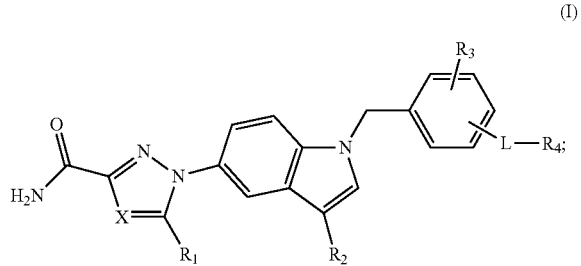

or a pharmaceutically acceptable salt thereof, and its therapeutic uses for activating a growth factor pathway, promoting wound healing, promoting tissue repair, and treating hearing loss, skeletal muscle loss, organ degeneration, tissue damage, neurodegeneration, and muscular atrophy. The disclosure further provides pharmaceutical compositions and combinations. The present disclosure also relates to the use of such compounds for research or other non-therapeutic purposes.

17 Claims, No Drawings

(56) References Cited

OTHER PUBLICATIONS

Wang, Yizhong et al., "Synthesis and Evaluation of Photoreactive Tetrazole Amino Acids" Organic Letters, (Jun. 10, 2009) vol. 11. No. 16. pp. 3570-3573.
El Khadem, Hassan, et al. "Mass Spectra of 5-Styryl and 5-Acylpyrazoles", (Aug. 1974) Journal of Heterocyclic Chemistry, vol. 11 (4), pp. 575-585.

\* cited by examiner

INDOLE DERIVATIVES AND USES THEREOF

CROSS-REFERENCE TO RELATED APPLICATIONS

This application claims the benefit of U.S. Provisional Application No. 62/538,428, filed Jul. 28, 2017, which is incorporated by reference in its entirety.

FIELD

The disclosure provides indole compounds and the use thereof as growth factor pathway activators.

BACKGROUND

Growth factors are signaling molecules which bind their cognate cell surface receptors initiating signaling cascades that stimulate a variety of cellular processes including growth, metabolism, survival, migration and differentiation. One of the key growth factor signaling pathways is the PI3K (Phosphoinositide 3 Kinase)/Akt/mTOR (Mechanistic Target of Rapamycin) pathway. Akt (also called Protein Kinase B, PKB) is a serine/threonine kinase that mediates growth factor signaling by phosphorylating multiple cellular targets. (Manning B D, Cantley L C. AKT/PKB signaling: navigating downstream. Cell. 2007 Jun. 29; 129(7):1261-74.)

Impaired growth factor signaling can lead to various disease conditions including skeletal muscle loss, hearing loss, degeneration of a number of organ systems and delayed wound healing. (Rüegg M A, Glass D J. Molecular mechanisms and treatment options for muscle wasting diseases. Annu Rev Pharmacol Toxicol. 2011; 51:373-95; Yamamoto N, Nakagawa T, Ito J. Application of insulin-like growth factor-1 in the treatment of inner ear disorders. Front Pharmacol. 2014 Sep. 10; 5:208; Böhm F, Köhler U A, Speicher T, Werner S. Regulation of liver regeneration by growth factors and cytokines. EMBO Mol Med. 2010 August; 2(8):294-305; Sadaba M C, Martín-Estal I, Puche J E, Castilla-Cortázar I. Insulin-like growth factor 1 (IGF-1) therapy: Mitochondrial dysfunction and diseases. Biochim Biophys Acta. 2016 July; 1862(7):1267-78; Bach L A, Hale L J. Insulin-like growth factors and kidney disease. Am J Kidney Dis. 2015 February; 65(2):327-36; Mitchell A C, Briquez P S, Hubbell J A, Cochran J R. Engineering growth factors for regenerative medicine applications. Acta Biomater. 2016 January; 30:1-12.) With the dramatic rise in the prevalence of diabetes, age and diabetes-associated non-healing chronic wounds are a critical health problem in the world today. (Demidova-Rice T N, Hamblin M R, Herman I M. Acute and impaired wound healing: pathophysiology and current methods for drug delivery, part 1: normal and chronic wounds: biology, causes, and approaches to care. Adv Skin Wound Care. 2012 July; 25(7):304-14.) Injury typically induces expression of growth factor receptors, and growth factors are involved in all stages of the wound healing process: coagulation, inflammation, formation of granulation tissue and remodeling or scar formation. (Demidova-Rice T N, Hamblin M R, Herman I M. Acute and impaired wound healing: pathophysiology and current methods for drug delivery, part 2: role of growth factors in normal and pathological wound healing: therapeutic potential and methods of delivery. Adv Skin Wound Care. 2012 August; 25(8):349-70; Goldman R. Growth factors and chronic wound healing: past, present, and future. Adv Skin Wound Care. 2004 January-February; 17(1):24-35.) Chronic wounds (vascular ulcers, diabetic ulcers and pressure ulcers) are characterized by decreased density of growth factor receptors and reduced mitogenic response to growth factors. (Demidova-Rice T N et al., supra, Adv Skin Wound Care. 2012 August; 25(8):349-70; Goldman R., supra, Adv Skin Wound Care. 2004 January-February; 17(1):24-35.)

The current paradigm for treating chronic wounds involves debridement (surgical or with debridement agents), control of infection and inflammation (with antibiotics and anti-inflammatory agents), correction of moisture imbalance (with wound dressings) and promotion of re-epithelialization/granulation tissue formation (with growth factors). (Demidova-Rice T N et al., supra, Adv Skin Wound Care. 2012 July; 25(7):304-14.) IGF-1/Insulin are well validated in wound healing both in preclinical and clinical settings, and mouse models of activated PI3K/Akt/mTOR signaling axis show accelerated wound closure. (Mori R, Tanaka K, de Kerckhove M, Okamoto M, Kashiyama K, Tanaka K, Kim S, Kawata T, Komatsu T, Park S, Ikematsu K, Hirano A, Martin P, Shimokawa I. Reduced FOXO1 expression accelerates skin wound healing and attenuates scarring. Am J Pathol. 2014 September; 184(9):2465-79; Lima M H, Caricilli A M, de Abreu L L, Araújo E P, Pelegrinelli F F, Thirone A C, Tsukumo D M, Pessoa A F, dos Santos M F, de Moraes M A, Carvalheira J B, Velloso L A, Saad M J. Topical insulin accelerates wound healing in diabetes by enhancing the AKT and ERK pathways: a double-blind placebo-controlled clinical trial. PLoS One. 2012; 7(5):e3697; Harding K, Aldons P, Edwards H, Stacey M, Finlayson K, Gibb M, Jenkins L, Shooter G, Lonkhuyzen D V, Lynam E, Heinrichs E L, Upton Z. Effectiveness of an acellular synthetic matrix in the treatment of hard-to-heal leg ulcers. Int Wound J. 2014 April; 11(2):129-37; Balaji S, LeSaint M, Bhattacharya S S, Moles C, Dhamija Y, Kidd M, Le L D, King A, Shaaban A, Crombleholme T M, Bollyky P, Keswani S G. Adenoviral-mediated gene transfer of insulin-like growth factor 1 enhances wound healing and induces angiogenesis. J Surg Res. 2014 July; 190(1):367-77; Squarize C H, Castilho R M, Bugge T H, Gutkind J S. Accelerated wound healing by mTOR activation in genetically defined mouse models. PLoS One. 2010 May 13; 5(5):e10643.)

The only FDA approved treatment for chronic wounds is Becaplermin (Regranex) which contains recombinant PDGF and has had limited efficacy. (Eaglstein W H, Kirsner R S, Robson M C. Food and Drug Administration (FDA) drug approval end points for chronic cutaneous ulcer studies. Wound Repair Regen. 2012 November-December; 20(6): 793-6.) Recombinant PDGF has several drawbacks as a treatment for chronic wounds, including its short half-life in the protease-rich hostile wound microenvironment and insufficient delivery mechanisms. A need remains for growth factor pathway activators that bypass growth factor receptors (which are downregulated in chronic wounds), have increased stability, and pose no risk for immunogenicity.

SUMMARY

The disclosure provides compounds, pharmaceutically acceptable salts thereof, pharmaceutical compositions thereof and combinations thereof. The compounds can or may activate growth factor pathways, including the PI3K/Akt/mTOR pathway.

In one aspect, the disclosure provides a compound of formula (I):

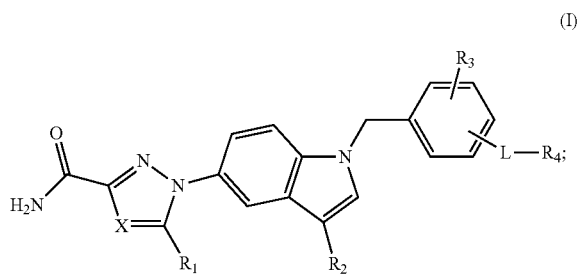

(I)

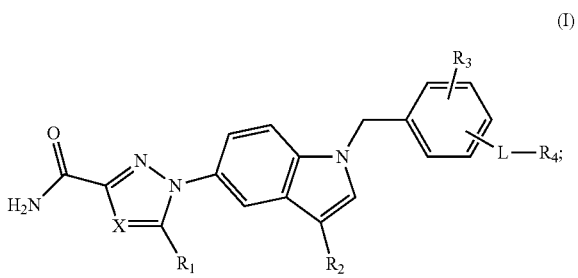

(I)

or a pharmaceutically acceptable salt thereof.

In another aspect, the disclosure provides a pharmaceutical composition comprising a compound of formula (I), or a pharmaceutically acceptable salt thereof, e.g., in a therapeutically effective amount, and one or more pharmaceutically acceptable carriers.

In another aspect, the disclosure provides a pharmaceutical combination comprising a compound of formula (I) or a pharmaceutically acceptable salt thereof, e.g., in a therapeutically effective amount, and one or more other therapeutic agents.

In another aspect, the disclosure provides a method of activating a growth factor pathway in a subject in need thereof, comprising administering to the subject a therapeutically effective amount of a compound of formula (I) or a pharmaceutically acceptable salt thereof, or a pharmaceutical composition of the compound or a pharmaceutically acceptable salt thereof.

In another aspect, the disclosure provides a method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound of formula (I) or a pharmaceutically acceptable salt thereof, or a pharmaceutical composition of the compound or a pharmaceutically acceptable salt thereof.

Further, the compounds or methods described herein may be used for research (e.g., studying growth factor signaling pathways) and other non-therapeutic purposes.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference for all purposes. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of compounds, compositions and methods disclosed herein will be apparent from the following detailed description and claims.

DETAILED DESCRIPTION

In one aspect, the disclosure provides a compound of formula (I) or a pharmaceutically acceptable salt thereof:

wherein:

L is absent, —$C_{1-4}$alkyl-, NH, O, S, NHCO or CONH;

X is CH or N;

$R_1$ is H, $C_{1-4}$alkyl, $C_{1-4}$haloalkyl, or 3-6 membered cycloalkyl;

$R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$ hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH_2)_n$-(5-10 membered heteroaryl optionally substituted with 1-3 $C_{1-4}$alkyl groups);

$R_3$ is H, halo, —OH, $C_{1-4}$alkyl, $C_{1-4}$alkoxy, $C_{1-4}$haloalkyl or $C_{1-4}$ haloalkoxy;

$R_4$ is a substituted $C_{2-4}$alkynyl, a substituted or unsubstituted 4-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (═O), —CN, nitro, $C_{1-4}$alkyl, —$C_{1-4}$alkyl-(3-6 membered cycloalkyl), $C_{1-4}$ alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl;

$R_5$ and $R_6$ are each, independently, selected from H, $C_{1-4}$alkyl, $C_{1-4}$hydroxyalkyl, —CO—$C_{1-4}$ alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl or $C_{1-4}$hydroxyalkyl groups; and n is 0 or 1.

In an embodiment, the disclosure provides a compound of formula (I) or a pharmaceutically acceptable salt thereof:

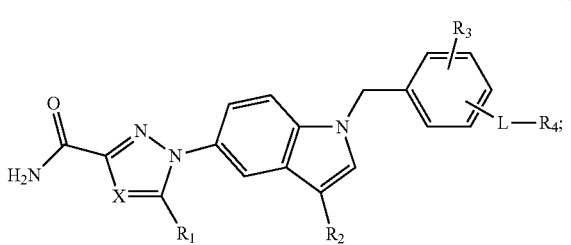

(I)

wherein:

L is absent, O, S, NHCO or CONH;

X is CH or N;

$R_1$ is H, $C_{1-4}$alkyl, $C_{1-4}$haloalkyl, or 3-6 membered cycloalkyl;

$R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH_2)_n$-(5-10 membered heteroaryl optionally substituted with 1-3 $C_{1-4}$alkyl groups);

$R_3$ is H, halo, —OH, $C_{1-4}$alkyl, $C_{1-4}$alkoxy, $C_{1-4}$haloalkyl or $C_{1-4}$ haloalkoxy;

$R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (=O), —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$ alkyl-$NR_5R_6$, —$NR_5R_6$, —$C_{1-4}$ alkyl-$NR_5R_6$ and —CO—$C_{1-4}$alkyl;

$R_5$ and $R_6$ are each, independently, selected from H, $C_{1-4}$alkyl, $C_{1-4}$hydroxyalkyl, —CO—$C_{1-4}$ alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl groups; and n is 0 or 1.

In the formulas, a line traversing a ring and bonded to a substituent group (e.g., an R group) means that the substituent may be bound in place of hydrogen to any ring atom where the valency of the atom allows. For example, the $R_3$ group in formula (I) may be bound to any carbon atom of the phenyl ring traversed by the line, except for the carbon atom bound to the rest of the molecule through the methylene group. Where the line traverses one ring of a fused bicyclic ring system, it will be understood that the substituent may be bound in place of hydrogen to any ring atom in either ring where the valency of the atom allows.

As used herein, the term "compound(s) disclosed herein" refers to compound(s) of formula (I), and subformulae thereof. The terms "compound" and "pharmaceutically acceptable salt" include the specified compounds and pharmaceutically acceptable salts in any form, including any solid form thereof (including any polymorphic form thereof), any solvate or hydrate form thereof, and any solution thereof.

As used herein, the term "$C_{1-4}$alkyl" refers to a straight or branched hydrocarbon chain radical group consisting solely of carbon and hydrogen atoms, containing no unsaturation, having from one to four carbon atoms, and which is attached to the rest of the molecule by a single bond. Examples of $C_{1-4}$alkyl groups include, but are not limited to, methyl, ethyl, n-propyl, n-butyl, 1-methylethyl (iso-propyl), 1-methylpropyl (sec-butyl), 2-methylpropyl (iso-butyl), 1,1-dimethylethyl (t-butyl), and the like. Analogous terms referring to alkyl groups having different numbers of carbon atoms (e.g., "$C_{1-6}$alkyl") refer to analogous alkyl groups having the specified numbers of carbon atoms.

As used herein, the term "—$C_{1-4}$alkyl-" refers to a straight or branched divalent hydrocarbon chain consisting solely of carbon and hydrogen atoms, containing no unsaturation, having from one to four carbon atoms, and which is attached to the rest of the molecule by single bonds. Examples of —$C_{1-4}$alkyl-groups include, but are not limited to, methylene, ethylene, n-propylene, n-butylene, 1-methylethylene, and the like. Analogous terms referring to groups having different numbers of carbon atoms (e.g., "—$C_{1-6}$alkyl-") refer to analogous groups having the specified numbers of carbon atoms.

As used herein, the term "$C_{1-4}$haloalkyl" refers to a $C_{1-4}$alkyl group, wherein one or more of the hydrogen atoms of the $C_{1-4}$alkyl group is replaced by a halo group. Examples of $C_{1-4}$haloalkyl include, but are not limited to, trifluoromethyl, 2,2,2-trifluoroethyl, 1,1-difluoroethyl, and the like. Analogous terms referring to haloalkyl groups having different numbers of carbon atoms (e.g., "$C_{1-6}$haloalkyl") refer to analogous haloalkyl groups having the specified numbers of carbon atoms.

As used herein, the term "—$C_{1-4}$alkyl-$NR_5R_6$" refers to a $C_{1-4}$alkyl group, wherein one or more of the hydrogen atoms (e.g., one hydrogen atom) of the $C_{1-4}$alkyl group is replaced by an $NR_5R_6$ group. Analogous terms referring to alkyl-$NR_5R_6$ groups having different numbers of carbon atoms (e.g., "—$C_{1-6}$alkyl-$NR_5R_6$") refer to analogous alkyl-$NR_5R_6$ groups having the specified numbers of carbon atoms.

As used herein, the term "halo" refers to bromo, chloro, fluoro or iodo.

As used herein, the term "$C_{1-4}$alkoxy" refers to a radical of the formula —$OR_a$ where $R_a$ is a $C_{1-4}$alkyl group. Examples of $C_{1-4}$alkoxy include, but are not limited to, methoxy, ethoxy, propoxy, isopropoxy, butoxy, isobutoxy, and the like. Analogous terms referring to alkoxy groups having different numbers of carbon atoms (e.g., "$C_{1-6}$alkoxy") refer to analogous alkoxy groups having the specified numbers of carbon atoms.

As used herein, the term "$C_{1-4}$alkoxy-$C_{1-4}$alkyl" refers to a $C_{1-4}$alkyl group, wherein one or more of the hydrogen atoms (e.g., one hydrogen atom) of the $C_{1-4}$alkyl group are each independently replaced by a $C_{1-4}$alkoxy group. Analogous terms referring to alkoxy-alkyl groups having different numbers of carbon atoms (e.g., "$C_{1-6}$alkoxy-$C_{1-6}$alkyl") refer to analogous alkoxy-alkyl groups having the specified numbers of carbon atoms.

As used herein, the term "$C_{1-4}$haloalkoxy" refers to a $C_{1-4}$alkoxy group, wherein one or more of the hydrogen atoms of the $C_{1-4}$alkyl group are each independently replaced by a halo group. Examples of $C_{1-4}$haloalkoxy include, but are not limited to, trifluoromethoxy, 2,2,2-trifluoroethoxy, 1,1-difluoroethoxy, and the like. Analogous terms referring to haloalkoxy groups having different numbers of carbon atoms (e.g., "$C_{1-6}$haloalkoxy") refer to analogous haloalkoxy groups having the specified numbers of carbon atoms.

As used herein, the term "$C_{1-4}$hydroxyalkyl" refers to a $C_{1-4}$alkyl group, wherein one or more of the hydrogen atoms (e.g., one hydrogen atom) of the $C_{1-4}$alkyl group are each replaced by OH. Examples of $C_{1-4}$hydroxyalkyl include, but are not limited to, hydroxy-methyl, 2-hydroxy-ethyl, 2-hydroxy-propyl, 3-hydroxy-propyl, and the like. Analogous terms referring to hydroxyalkyl groups having different numbers of carbon atoms (e.g., "$C_{1-6}$hydroxyalkyl") refer to analogous hydroxyalkyl groups having the specified numbers of carbon atoms.

As used herein, the term "$C_{2-4}$alkynyl" refers to a straight or branched hydrocarbon chain radical group consisting solely of carbon and hydrogen atoms, containing at least one triple bond, having from two to four carbon atoms, and which is attached to the rest of the molecule by a single bond. Examples of $C_{2-4}$alkynyl include, but are not limited to, ethynyl, prop-1-ynyl, but-1-ynyl, 1-methylprop-2-ynyl, and the like. Analogous terms referring to alkynyl groups having different numbers of carbon atoms (e.g., "$C_{2-6}$alkynyl") refer to analogous alkynyl groups having the specified numbers of carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. Examples of cycloalkyl groups include, but are not limited to, cyclopropyl, cyclobutyl, cyclopentyl, cyclohexyl, and the like.

As used herein, the term "—$C_{1-4}$alkyl-(3-6 membered cycloalkyl)" refers to a $C_{1-4}$alkyl group, wherein one or more of the hydrogen atoms (e.g., one hydrogen atom) of the $C_{1-4}$alkyl group are each independently replaced by a 3-6 membered cycloalkyl group. Analogous terms referring to alkyl-cycloalkyl groups having different numbers of carbon atoms (e.g., "—$C_{1-6}$alkyl-(3-8 membered cycloalkyl") refer to analogous alkyl-cycloalkyl groups having the specified number of carbon atoms.

As used herein, the term "heterocyclyl" refers to a stable, saturated or unsaturated, non-aromatic, mono- or bicyclic (fused, bridged, or spiro) ring radical having the specified number of ring atoms and comprising one or more heteroatoms individually selected from nitrogen, oxygen and sulfur. The heterocyclyl radical may be bonded via a carbon atom or heteroatom. Examples of heterocyclyl groups include, but are not limited to, azetidinyl, oxetanyl, pyrrolinyl, pyrrolidinyl, tetrahydrofuryl, tetrahydrothienyl, piperidyl, piperazinyl, tetrahydropyranyl, morpholinyl, perhydroazepinyl, and the like.

As used herein, the term "-(4-10 membered heterocyclyl)-$C_{1-4}$alkyl" refers to a 4-10 membered heterocyclyl group, wherein one or more of the hydrogen atoms (e.g., one hydrogen atom) bound to one of the ring atoms are each independently replaced by a $C_{1-4}$alkyl group. Analogous terms referring to heterocyclyl-alkyl groups having different numbers of ring or alkyl group carbon atoms (e.g., "-(4-8 membered heterocyclyl)-$C_{1-6}$alkyl") refer to analogous heterocyclyl-alkyl groups having the specified number of atoms.

As used herein, the term "aryl" refers to a stable, aromatic, mono- or bicyclic ring radical having the specified number of ring atoms. Examples of aryl groups include, but are not limited to, phenyl, 1-naphthyl, 2-naphthyl, and the like.

As used herein, the term "heteroaryl" refers to a stable, aromatic, mono- or bicyclic ring radical having the specified number of ring atoms and comprising one or more heteroatoms individually selected from nitrogen, oxygen and sulfur. The heteroaryl radical may be bonded via a carbon atom or heteroatom. Examples of heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl, pyridyl, quinolinyl, isoquinolinyl, indolyl, and the like.

As used herein, the term "fused heterocyclyl-aryl" refers to a stable bicyclic ring radical having the specified number of ring atoms and comprising a heterocyclyl ring (as defined above) fused to an aryl ring (as defined above). The radical may be bonded via a carbon atom or heteroatom on either the heterocyclyl ring or the aryl ring. Examples of fused heterocyclyl-aryl groups include, but are not limited to, the following:

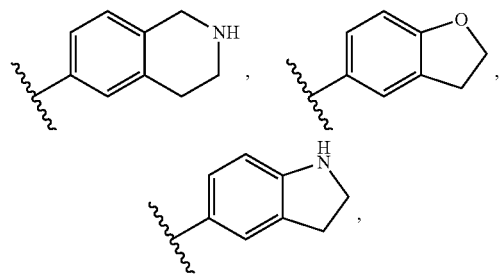

and the like.

As used herein, the term "fused heterocyclyl-heteroaryl" refers to a stable bicyclic ring radical having the specified number of ring atoms and comprising a heterocyclyl ring (as defined above) fused to a heteroaryl ring (as defined above). The radical may be bonded via a carbon atom or heteroatom on either the heterocyclyl ring or the heteroaryl ring. Examples of fused heterocyclyl-heteroaryl groups include, but are not limited to, the following:

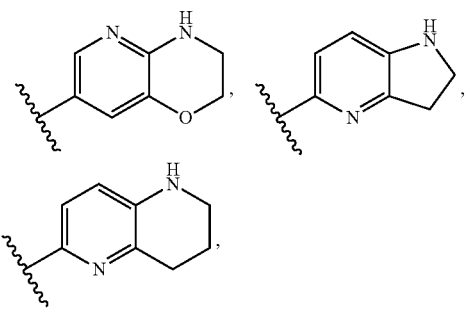

and the like.

As used herein, the term "optionally substituted" means that the group in question may be substituted, for example, with the specified number of identified groups, but that such substitution is not required. For example, a group that is "optionally substituted with 1-3 $C_{1-4}$alkyl groups" may be unsubstituted or may be substituted with 1, 2, or 3 $C_{1-4}$ alkyl groups.

Various embodiments of the disclosure are described herein. It will be recognized that features specified in each embodiment may be combined with other specified features, including as indicated in the enumerated embodiments below, to provide further embodiments of the present disclosure.

It is understood that in the following embodiments, combinations of substituents and/or variables of the depicted formulae are permissible only if such contributions result in stable compounds.

Embodiment 1

A compound of formula (I) or a pharmaceutically acceptable salt thereof:

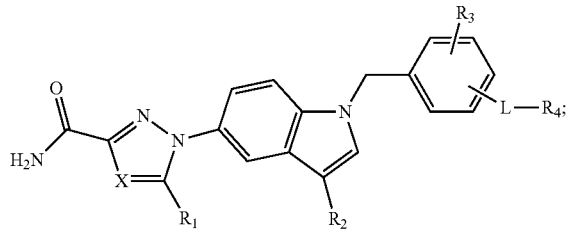

(I)

wherein:

L is absent, —$C_{1-4}$alkyl-, NH, O, S, NHCO or CONH;

X is CH or N;

$R_1$ is H, $C_{1-4}$alkyl, $C_{1-4}$haloalkyl, or 3-6 membered cycloalkyl;

$R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$ hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH_2)_n$-(5-10 membered heteroaryl optionally substituted with 1-3 $C_{1-4}$alkyl groups);

$R_3$ is H, halo, —OH, $C_{1-4}$alkyl, $C_{1-4}$alkoxy, $C_{1-4}$haloalkyl or $C_{1-4}$ haloalkoxy;

$R_4$ is a substituted $C_{2-4}$alkynyl, a substituted or unsubstituted 4-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (=O), —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl;

$R_5$ and $R_6$ are each, independently, selected from H, $C_{1-4}$alkyl, $C_{1-4}$hydroxyalkyl, —CO—$C_{1-4}$ alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl or $C_{1-4}$hydroxyalkyl groups; and n is 0 or 1.

Embodiment 2

A compound according to embodiment 1 or a pharmaceutically acceptable salt thereof, wherein L is absent, O, S, NHCO or CONH;

$R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (=O), —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$ alkyl-$NR_5R_6$, —$NR_5R_6$, —$C_{1-4}$ alkyl-$NR_5R_6$ and —CO—$C_{1-4}$alkyl;

$R_5$ and $R_6$ are each, independently, selected from H, $C_{1-4}$alkyl, $C_{1-4}$hydroxyalkyl, —CO—$C_{1-4}$ alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl groups.

Embodiment 3

A compound according to embodiment 1 or 2, wherein the compound is of formula (I-A):

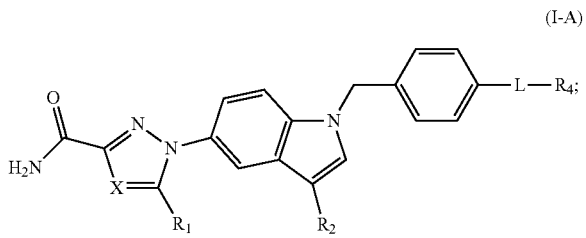

(I-A)

or a pharmaceutically acceptable salt thereof.

Embodiment 4

A compound according to embodiment 1 or 2, wherein the compound is of formula (I-B):

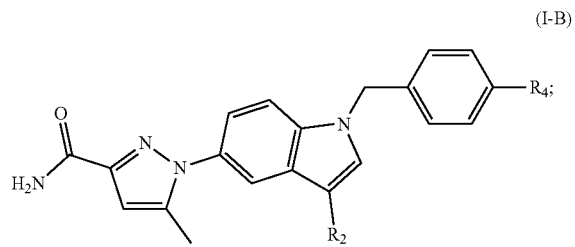

(I-B)

or a pharmaceutically acceptable salt thereof.

Embodiment 5

A compound according to embodiment 1 or 3 or a pharmaceutically acceptable salt thereof, wherein L is —$C_{1-4}$alkyl-, NH, O, S, NHCO or CONH.

Embodiment 6

A compound according to any one of embodiments 1-3 or a pharmaceutically acceptable salt thereof, wherein L is O, S, NHCO or CONH.

Embodiment 7

A compound according to any one of embodiments 1-3 or a pharmaceutically acceptable salt thereof, wherein L is absent.

Embodiment 8

A compound according to any one of embodiments 1-3 or a pharmaceutically acceptable salt thereof, wherein L is $CH_2$.

Embodiment 9

A compound according to any one of embodiments 1-3 or a pharmaceutically acceptable salt thereof, wherein L is NH.

Embodiment 10

A compound according to any one of embodiments 1-3 and 5-9 or a pharmaceutically acceptable salt thereof, wherein X is CH.

Embodiment 11

A compound according to any one of embodiments 1-3 and 5-9 or a pharmaceutically acceptable salt thereof, wherein X is N.

Embodiment 12

A compound according to any one of embodiments 1-3 and 5-11 or a pharmaceutically acceptable salt thereof, wherein $R_1$ is H or $C_{1-4}$alkyl.

Embodiment 13

A compound according to embodiment 12 or a pharmaceutically acceptable salt thereof, wherein $R_1$ is H.

Embodiment 14

A compound according to embodiment 12 or a pharmaceutically acceptable salt thereof, wherein $R_1$ is $C_{1-4}$alkyl (e.g., $CH_3$).

Embodiment 15

A compound according to embodiment 14 or a pharmaceutically acceptable salt thereof, wherein $R_1$ is 3-6 membered cycloalkyl (e.g., cyclopropyl).

Embodiment 16

A compound according to any one of embodiments 1-15 or a pharmaceutically acceptable salt thereof, wherein $R_2$ is —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 17

A compound according to any one of embodiments 1-15 or a pharmaceutically acceptable salt thereof, wherein $R_2$ is H, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 18

A compound according to any one of embodiments 1-15 or a pharmaceutically acceptable salt thereof, wherein $R_2$ is H, —OH, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 19

A compound according to any one of embodiments 1-15 or a pharmaceutically acceptable salt thereof, wherein $R_2$ is H, —OH, halo, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$ alkyl groups).

Embodiment 20

A compound according to any one of embodiments 1-15 or a pharmaceutically acceptable salt thereof, wherein $R_2$ is H, —OH, halo, —CN, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 21

A compound according to any one of embodiments 1-15 or a pharmaceutically acceptable salt thereof, wherein $R_2$ is H, —OH, halo, —CN, nitro, $C_{1-4}$alkyl, $C_{1-4}$ alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 22

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 23

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH_2)_n$-(5-10 membered heteroaryl optionally substituted with 1-3 $C_{1-4}$alkyl groups)

Embodiment 24

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$hydroxyalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 25

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, a 5-10 membered heterocyclyl optionally substituted with 1-3 $C_{1-4}$alkyl groups, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 26

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, —$(CH_2)_n$-(6 or 10 membered aryl optionally substituted with 1-3 $C_{1-4}$alkyl groups), or —$(CH)_n$-(5-10 membered heteroaryl optionally substituted with 1-3 $C_{1-4}$alkyl groups).

Embodiment 27

A compound according to any one of embodiments 1-15 or a pharmaceutically acceptable salt thereof, wherein $R_2$ is H, —OH, halo, —CN, nitro, $C_{1-4}$alkoxy, $C_{1-4}$ alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, or —$(CH)_n$-(5-10 membered heteroaryl optionally substituted with 1-3 $C_{1-4}$alkyl groups).

Embodiment 28

A compound according to any one of embodiments 1-15 or a pharmaceutically acceptable salt thereof, wherein $R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, or —$(CH_2)_n$-(6 or 10 membered aryl optionally substituted with 1-3 $C_{1-4}$alkyl groups).

Embodiment 29

A compound according to any one of embodiments 1-28 or a pharmaceutically acceptable salt thereof, wherein n is 0.

Embodiment 30

A compound according to any one of embodiments 1-28 or a pharmaceutically acceptable salt thereof, wherein n is 1.

Embodiment 31

A compound according to any one of embodiments 1-15 or a pharmaceutically acceptable salt thereof, wherein $R_2$ is H, $C_{1-4}$alkyl, $C_{1-4}$alkoxy-$C_{1-4}$alkyl, $C_{1-4}$hydroxyalkyl, or a 5-10 membered heterocyclyl optionally substituted with 1-3 $C_{1-4}$alkyl groups.

Embodiment 32

A compound according to embodiment 31 or a pharmaceutically acceptable salt thereof, wherein $R_2$ is selected from a group consisting of: H, $CH_3$,

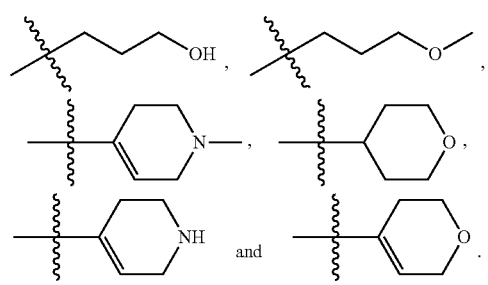

Embodiment 33

A compound according to embodiment 31 or a pharmaceutically acceptable salt thereof, wherein $R_2$ is selected from a group consisting of: H,

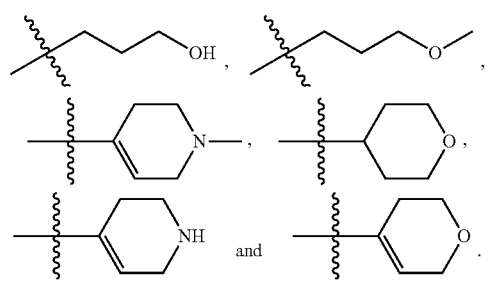

Embodiment 34

A compound according to embodiment 31 or a pharmaceutically acceptable salt thereof, wherein $R_2$ is $C_{1-4}$alkyl.

Embodiment 35

A compound according to embodiment 31 or a pharmaceutically acceptable salt thereof, wherein $R_2$ is H.

Embodiment 36

A compound according to any one of embodiments 1-2 and 5-35 or a pharmaceutically acceptable salt thereof, wherein $R_3$ is H, halo, —OH, or $C_{1-4}$alkyl.

Embodiment 37

A compound according to embodiment 36 or a pharmaceutically acceptable salt thereof, wherein $R_3$ is H.

Embodiment 38

A compound according to embodiment 36 or a pharmaceutically acceptable salt thereof, wherein $R_3$ is $C_{1-4}$alkyl.

Embodiment 39

A compound according to any one of embodiments 1 and 3-38 or a pharmaceutically acceptable salt thereof, wherein $R_4$ is a substituted or unsubstituted 4-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 40

A compound according to any one of embodiments 1 and 3-38 or a pharmaceutically acceptable salt thereof, wherein $R_4$ is a substituted $C_{2-4}$alkynyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 41

A compound according to any one of embodiments 1 and 3-38 or a pharmaceutically acceptable salt thereof, wherein $R_4$ is a substituted $C_{2-4}$alkynyl, a substituted or unsubstituted 4-10 membered heterocyclyl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 42

A compound according to any one of embodiments 1 and 3-38 or a pharmaceutically acceptable salt thereof, wherein $R_4$ is a substituted $C_{2-4}$alkynyl, a substituted or unsubstituted 4-10 membered heterocyclyl, a substituted or unsubstituted 5-10 membered heteroaryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 43

A compound according to any one of embodiments 1 and 3-38 or a pharmaceutically acceptable salt thereof, wherein $R_4$ is a substituted $C_{2-4}$alkynyl, a substituted or unsubstituted 4-10 membered heterocyclyl, a substituted or unsubstituted 5-10 membered heteroaryl, a substituted or unsubstituted 5-10 membered fused heterocyclyl-aryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_5$ and —CO—$C_{1-4}$alkyl.

Embodiment 44

A compound according to any one of embodiments 1 and 3-38 or a pharmaceutically acceptable salt thereof, wherein $R_4$ is a substituted $C_{2-4}$alkynyl, a substituted or unsubstituted 4-10 membered heterocyclyl, a substituted or unsubstituted 5-10 membered heteroaryl, a substituted or unsubstituted 5-10 membered fused heterocyclyl-aryl, or a substituted or unsubstituted 5-10 membered fused heterocyclyl-heteroaryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 45

A compound according to any one of embodiments 1-38 or a pharmaceutically acceptable salt thereof, wherein $R_4$ is a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$ alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 46

A compound according to any one of embodiments 1-38 or a pharmaceutically acceptable salt thereof, wherein $R_4$ is a substituted $C_{2-4}$alkynyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$ hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 47

A compound according to any one of embodiments 1-38 or a pharmaceutically acceptable salt thereof, wherein $R_4$ is a substituted $C_{2-4}$alkynyl, a substituted or unsubstituted 5-10 membered heterocyclyl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$ hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 48

A compound according to any one of embodiments 1-38 or a pharmaceutically acceptable salt thereof, wherein $R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 49

A compound according to any one of embodiments 1-38 or a pharmaceutically acceptable salt thereof, wherein $R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$ alkyl.

Embodiment 50

A compound according to any one of embodiments 1-38 or a pharmaceutically acceptable salt thereof, wherein $R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, or a substituted or unsubstituted 5-10 membered fused heterocyclyl-heteroaryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 51

A compound according to any one of embodiments 1 and 3-38 or a pharmaceutically acceptable salt thereof, wherein $R_4$ is a substituted or unsubstituted 4-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 52

A compound according to any one of embodiments 1 and 3-38 or a pharmaceutically acceptable salt thereof, wherein $R_4$ is a substituted or unsubstituted 4-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, $C_{1-4}$alkyl, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, —$SO_2NR_5R_6$, —$CONR_5R_6$, —CO—NH—$C_{1-4}$alkyl-$NR_5R_6$, —$NR_5R_6$, and —$C_{1-4}$alkyl-$NR_5R_6$.

Embodiment 53

A compound according to any one of embodiments 1 and 3-38 or a pharmaceutically acceptable salt thereof, wherein $R_4$ is a substituted or unsubstituted 4-10 membered heterocyclyl, wherein when $R_4$ is substituted, $R_4$ is substituted with 1-3 substituents independently selected from halo, —OH, $C_{1-4}$alkyl, —$SO_2$—$C_{1-4}$alkyl, —$C_{1-4}$alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, —$SO_2NR_5R_6$, —$CONR_5R_6$, —CO—NH—$C_{1-4}$ alkyl-$NR_5R_6$, —$NR_5R_6$, and —$C_{1-4}$alkyl-$NR_5R_6$.

Embodiment 54

A compound according to any one of embodiments 1-38 or a pharmaceutically acceptable salt thereof, wherein $R_4$ is a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$ alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl.

Embodiment 55

A compound according to any one of embodiments 1-38 or a pharmaceutically acceptable salt thereof, wherein $R_4$ is a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo, $C_{1-4}$alkyl, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, —$SO_2NR_5R_6$, —$CONR_5R_6$, —CO—NH—$C_{1-4}$alkyl-$NR_5R_6$, —$NR_5R_6$, and —$C_{1-4}$alkyl-$NR_5R_6$.

Embodiment 56

A compound according to any one of embodiments 1-38 or a pharmaceutically acceptable salt thereof, wherein $R_4$ is a substituted or unsubstituted 5-10 membered heterocyclyl, wherein when $R_4$ is substituted, $R_4$ is substituted with 1-3 substituents independently selected from halo, —OH, $C_{1-4}$alkyl, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, —$SO_2NR_5R_6$, —$CONR_5R_6$, —CO—NH—$C_{1-4}$alkyl-$NR_5R_6$, —$NR_5R_6$, and —$C_{1-4}$alkyl-$NR_5R_6$.

Embodiment 57

A compound according to any one of embodiments 1-38 or a pharmaceutically acceptable salt thereof, wherein $R_4$ is a substituted or unsubstituted 5-10 membered heterocyclyl, wherein when $R_4$ is substituted, $R_4$ is substituted with 1-3 substituents independently selected from halo, —OH, and $C_{1-4}$alkyl.

Embodiment 58

A compound according to any one of embodiments 1-38 or a pharmaceutically acceptable salt thereof, wherein $R_4$ is a substituted or unsubstituted 5-10 membered heterocyclyl, wherein when $R_4$ is substituted, $R_4$ is substituted with 1-3 $C_{1-4}$alkyl substituents.

Embodiment 59

A compound according to any one of embodiments 1-38 or a pharmaceutically acceptable salt thereof, wherein $R_4$ is a substituted or unsubstituted 6 or 10 membered aryl, wherein when $R_4$ is substituted, $R_4$ is substituted with 1-3 substituents independently selected from halo, —OH, $C_{1-4}$alkyl, —$NR_5R_6$, and —$C_{1-4}$alkyl-$NR_5R_6$.

Embodiment 60

A compound according to any one of embodiments 1-38 or a pharmaceutically acceptable salt thereof, wherein $R_4$ is selected from a group consisting of:

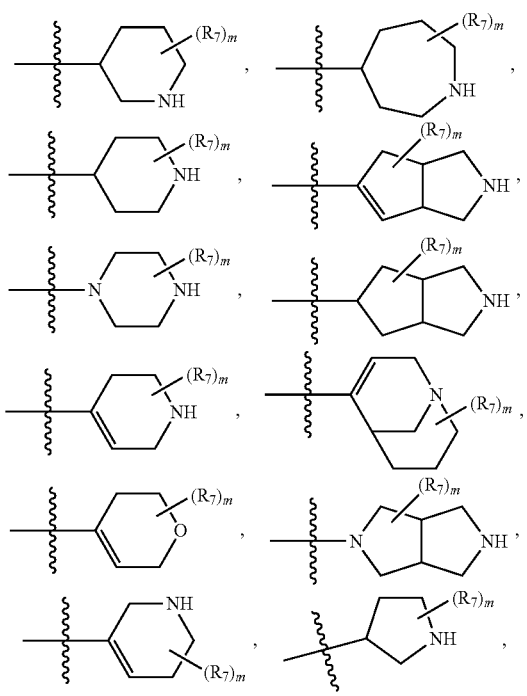

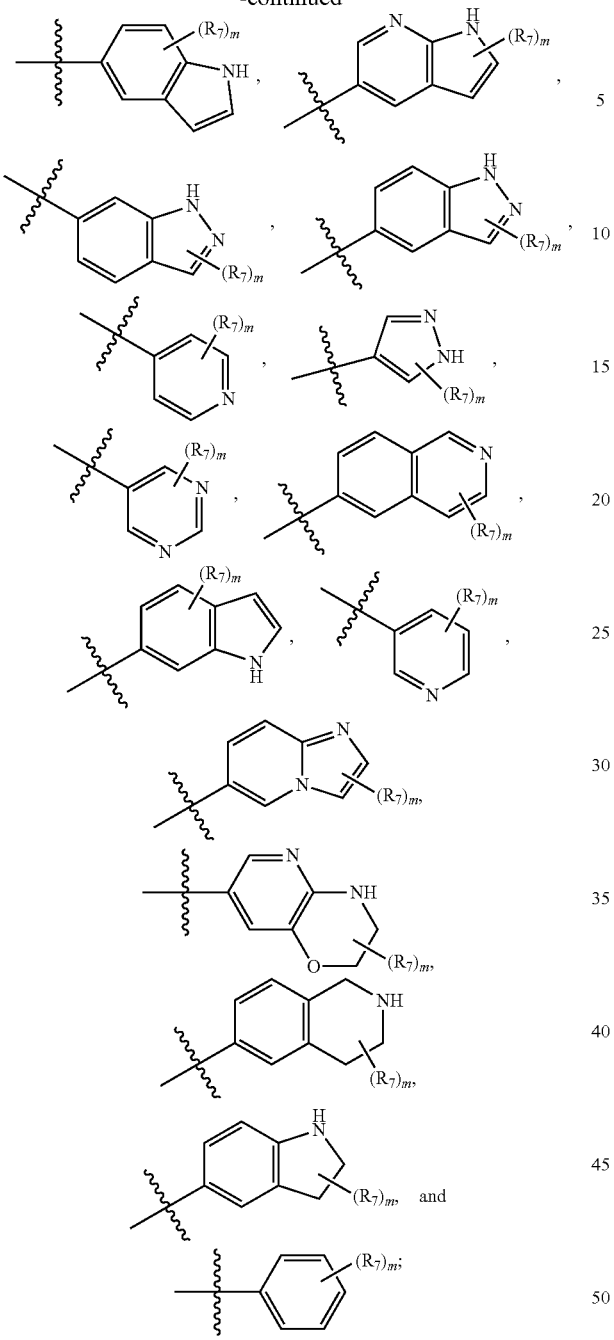

each occurrence of $R_7$ is independently selected from halo, —OH, oxo, —CN, nitro, $C_{1-4}$alkyl, —$C_{1-4}$alkyl-(3-6 membered cycloalkyl), $C_{1-4}$alkoxy, —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, —$NR_5R_6$, —$C_{1-4}$alkyl-$NR_5R_6$ and —CO—$C_{1-4}$alkyl; and m is 0, 1, 2, or 3.

Embodiment 61

A compound according to embodiment 60 or a pharmaceutically acceptable salt thereof, wherein $R_4$ is selected from a group consisting of:

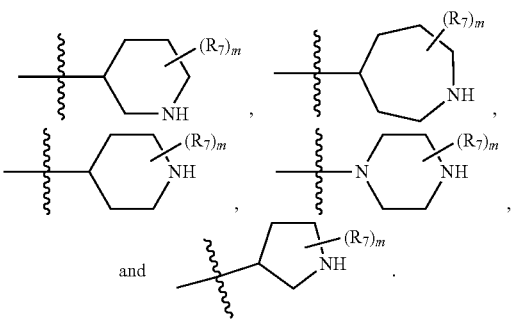

Embodiment 62

A compound according to embodiment 60 or a pharmaceutically acceptable salt thereof, wherein $R_4$ is selected from a group consisting of:

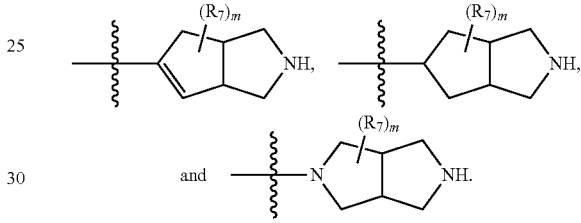

Embodiment 63

A compound according to embodiment 60 or a pharmaceutically acceptable salt thereof, wherein $R_4$ is selected from a group consisting of:

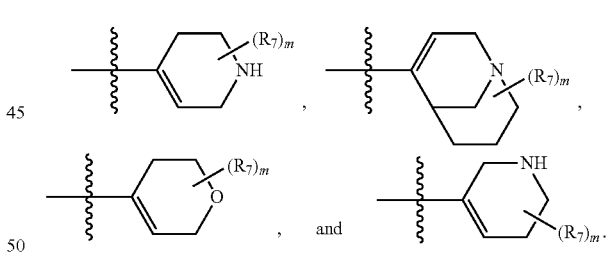

Embodiment 64

A compound according to embodiment 60 or a pharmaceutically acceptable salt thereof, wherein $R_4$ is selected from a group consisting of:

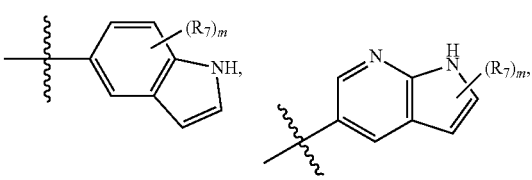

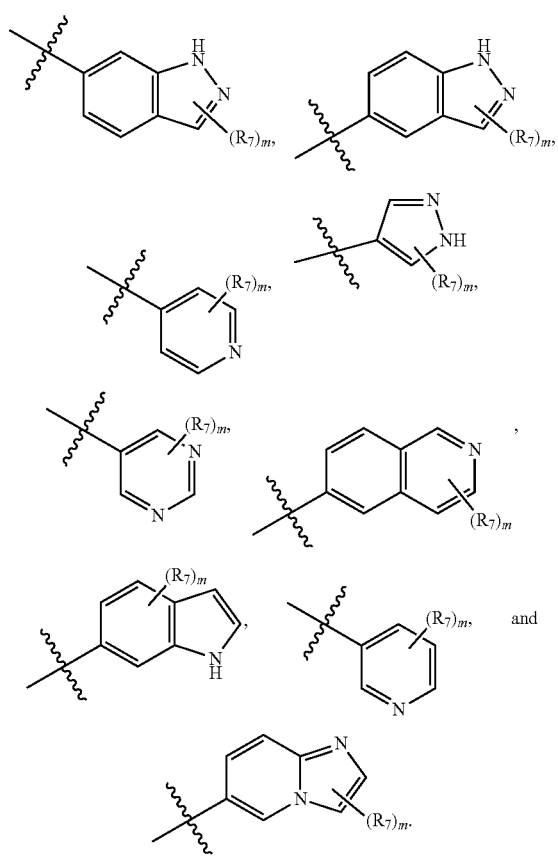

Embodiment 65

A compound according to embodiment 60 or a pharmaceutically acceptable salt thereof, wherein $R_4$ is selected from a group consisting of:

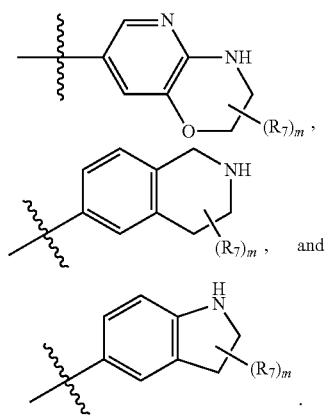

Embodiment 66

A compound according to embodiment 60 or a pharmaceutically acceptable salt thereof, wherein $R_4$ is

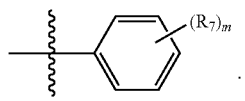

Embodiment 67

A compound according to embodiment 60 or a pharmaceutically acceptable salt thereof, wherein $R_4$ is

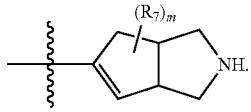

Embodiment 68

A compound according to embodiment 60 or a pharmaceutically acceptable salt thereof, wherein $R_4$ is

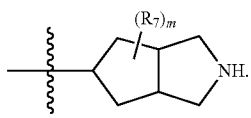

Embodiment 69

A compound according to embodiment 60 or a pharmaceutically acceptable salt thereof, wherein $R_4$ is

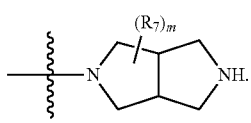

Embodiment 70

A compound according to embodiment 60 or a pharmaceutically acceptable salt thereof, wherein $R_4$ is

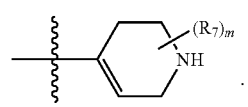

Embodiment 71

A compound according to embodiment 60 or a pharmaceutically acceptable salt thereof, wherein $R_4$ is

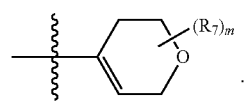

Embodiment 72

A compound according to any one of embodiments 60-71 or a pharmaceutically acceptable salt thereof, wherein each occurrence of $R_7$ is independently selected from halo, —OH, oxo, —CN, nitro, $C_{1-4}$alkyl, —$C_{1-4}$alkyl-(3-6 membered cycloalkyl), $C_{1-4}$alkoxy, $C_{1-4}$hydroxyalkyl, —$NR_5R_6$, and —$C_{1-4}$alkyl-$NR_5R_6$.

Embodiment 73

A compound according to any one of embodiments 60-71 or a pharmaceutically acceptable salt thereof, wherein each occurrence of $R_7$ is independently selected from —$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, and —$SO_2NR_5R_6$.

Embodiment 74

A compound according to any one of embodiments 60-71 or a pharmaceutically acceptable salt thereof, wherein each occurrence of $R_7$ is independently selected from —CO—$C_{1-4}$hydroxyalkyl, —$CONR_5R_6$, —CO—$C_{1-4}$alkyl-$NR_5R_6$, —CO—NH—$C_{1-4}$alkyl-$NR_5R_6$, and —CO—$C_{1-4}$alkyl.

Embodiment 75

A compound according to any one of embodiments 60-71 or a pharmaceutically acceptable salt thereof, wherein each occurrence of $R_7$ is independently selected from $C_{1-4}$alkyl and $C_{1-4}$alkoxy.

Embodiment 76

A compound according to any one of embodiments 60-71 or a pharmaceutically acceptable salt thereof, wherein each occurrence of $R_7$ is $C_{1-4}$alkyl.

Embodiment 77

A compound according to any one of embodiments 60-76 or a pharmaceutically acceptable salt thereof, wherein m is 0.

Embodiment 78

A compound according to any one of embodiments 60-76 or a pharmaceutically acceptable salt thereof, wherein m is 0 or 1.

Embodiment 79

A compound according to any one of embodiments 60-76 or a pharmaceutically acceptable salt thereof, wherein m is 1.

Embodiment 80

A compound according to any one of embodiments 60-76 or a pharmaceutically acceptable salt thereof, wherein m is 1 or 2.

Embodiment 81

A compound according to any one of embodiments 60-76 or a pharmaceutically acceptable salt thereof, wherein m is 2.

Embodiment 82

A compound according to any one of embodiments 60-76 or a pharmaceutically acceptable salt thereof, wherein m is 1, 2, or 3.

Embodiment 83

A compound according to any one of embodiments 1-38 or a pharmaceutically acceptable salt thereof, wherein $R_4$ is selected from a group consisting of:

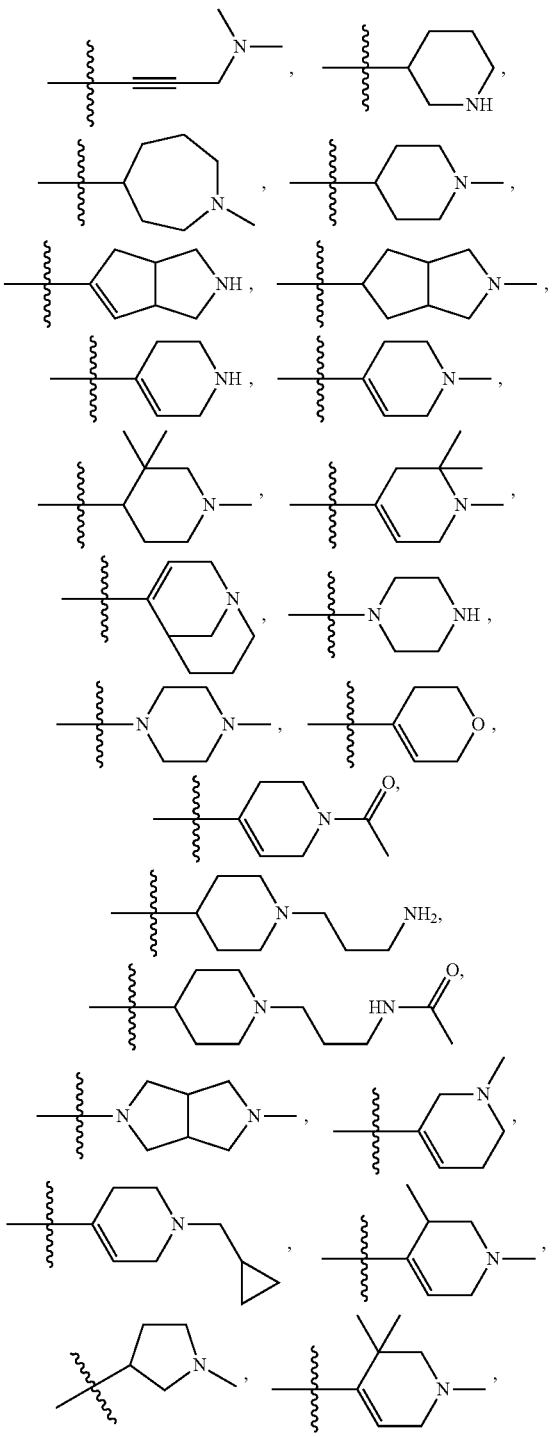

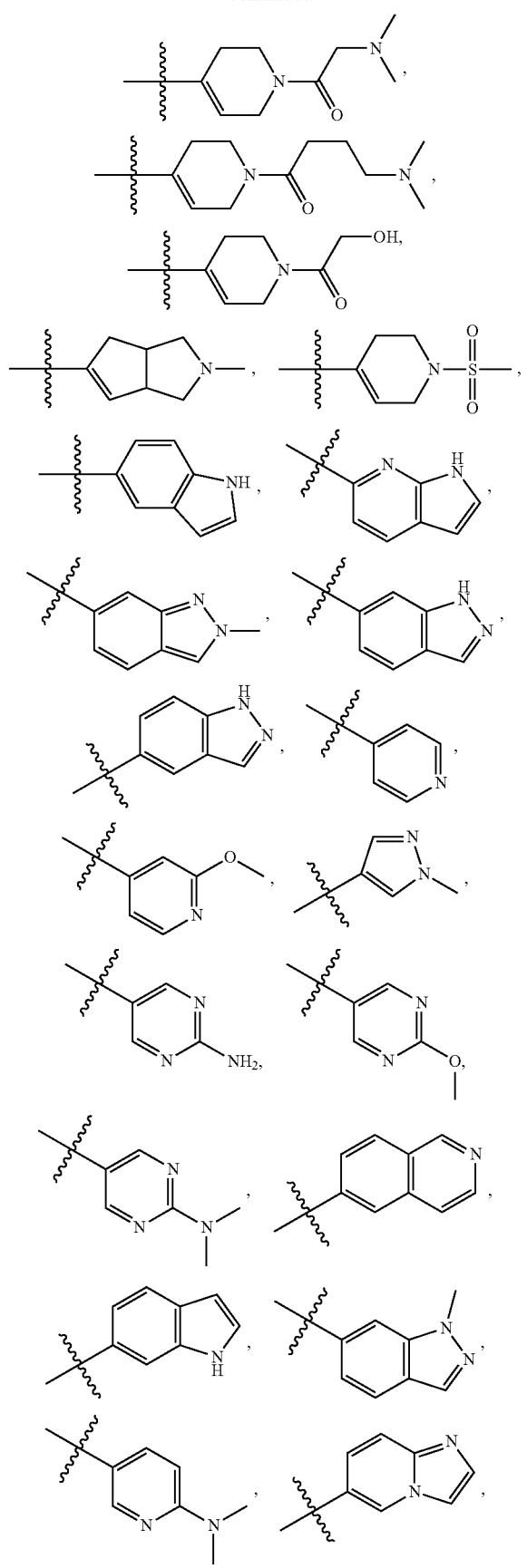
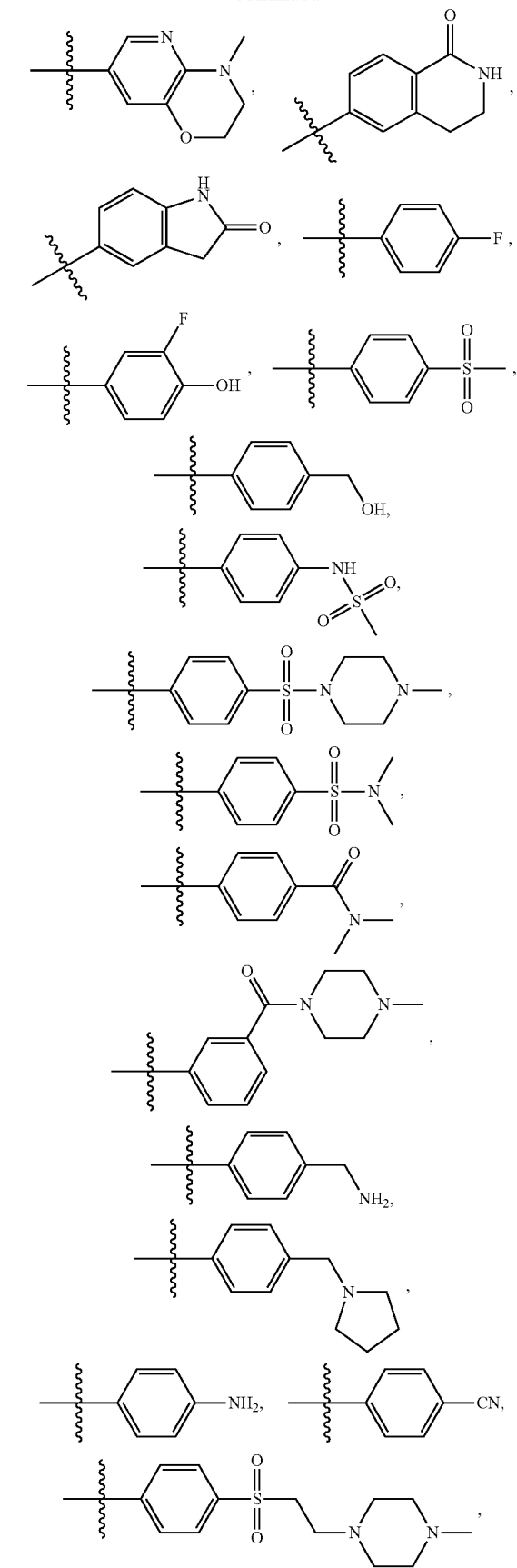

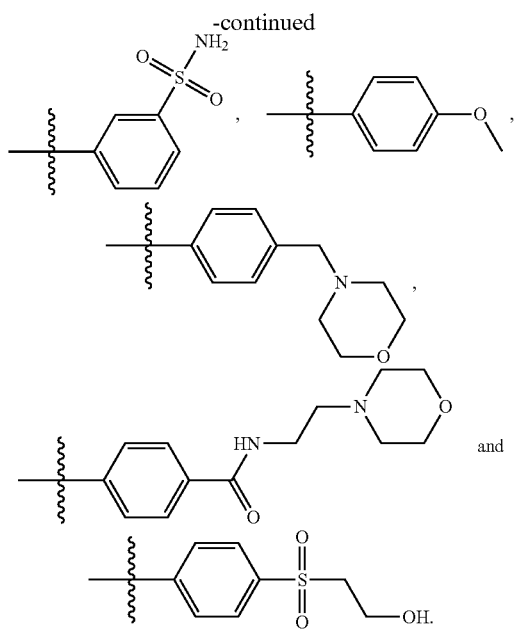

Embodiment 84

A compound according to any one of embodiments 1-38 or a pharmaceutically acceptable salt thereof, wherein $R_4$ is selected from a group consisting of:

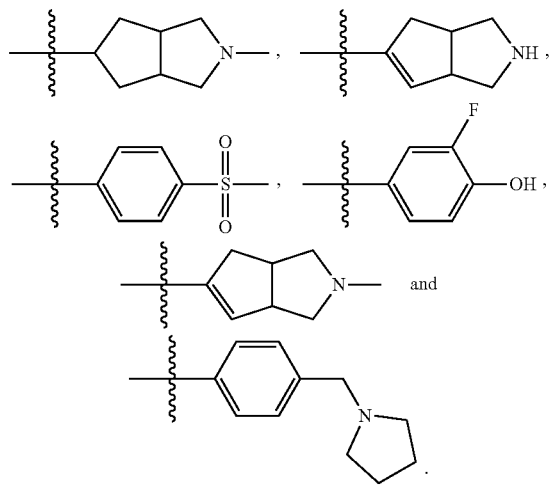

Embodiment 85

A compound according to any one of embodiments 1-38 or a pharmaceutically acceptable salt thereof, wherein $R_4$ is or

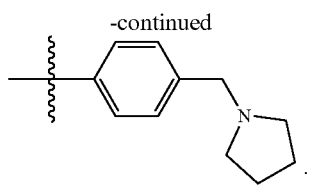

Embodiment 86

A compound according to any one of embodiments 1 and 3-38 or a pharmaceutically acceptable salt thereof, wherein $R_4$ is selected from a group consisting of:

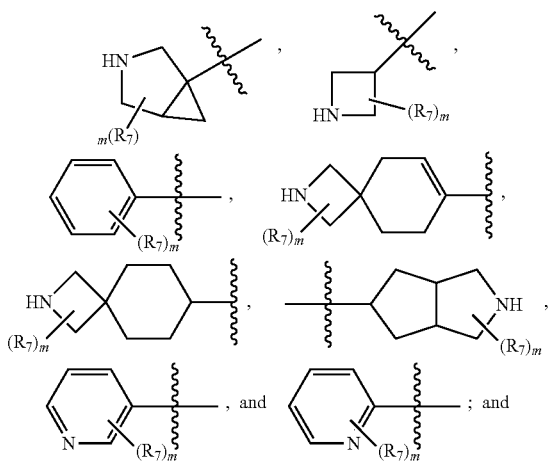

each occurrence of $R_7$ is independently selected from halo, —OH, oxo, —CN, nitro, $C_{1-4}$alkyl, —$C_{1-4}$ alkyl-(3-6 membered cycloalkyl), $C_{1-4}$alkoxy, —$SO_2$—$C_{1-4}$alkyl, —$C_{1-4}$ alkyl-$SO_2$—$C_{1-4}$alkyl, —$SO_2$—$C_{1-4}$hydroxyalkyl, —$SO_2$—$C_{1-4}$alkyl-$NR_5R_6$, —$NHSO_2$—$C_{1-4}$alkyl, $C_{1-4}$hydroxyalkyl, —$SO_2NR_5R_6$, —CO—$C_{1-4}$ hydroxyalkyl, —$CONR_5R_6$, —CO—$C_{1-4}$alkyl-$NR_5R_6$, —CO—NH—$C_{1-4}$ alkyl-$NR_5R_6$, —$NR_5R_6$, —$C_{1-4}$alkyl-$NR_5R_6$ and —CO—$C_{1-4}$alkyl; and m is 0, 1, 2, or 3.

Embodiment 87

A compound according to embodiment 80 or a pharmaceutically acceptable salt thereof, wherein $R_4$ is selected from a group consisting of:

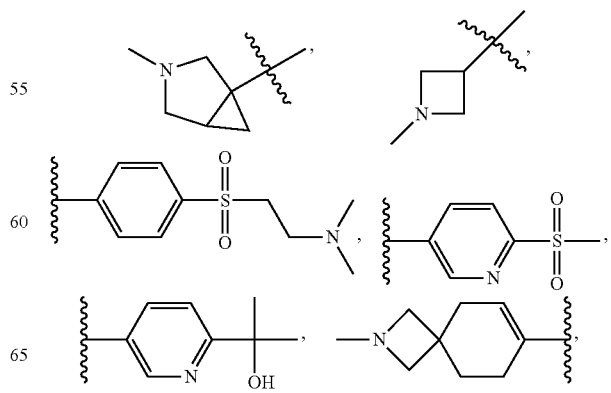

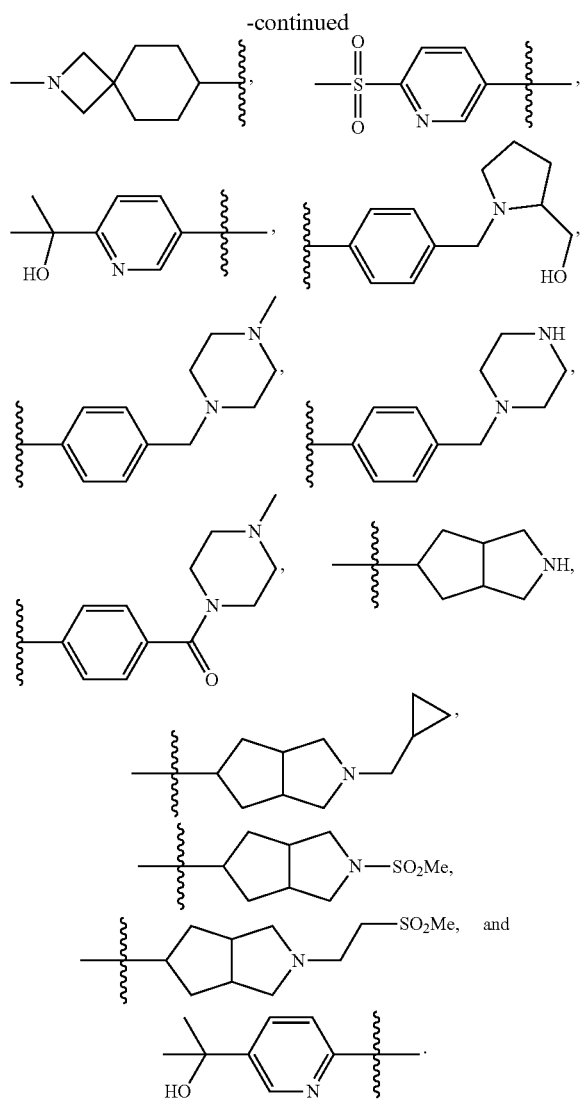

Embodiment 88

A compound according to any one of embodiments 1, 3-56, 59-74, 77-82, and 86 or a pharmaceutically acceptable salt thereof, wherein $R_5$ and $R_6$ are each, independently, selected from H and $C_{1-4}$alkyl; or $R_5$ and $R_6$, together with the nitrogen atom to which they are attached, form a 5-7 membered heterocyclyl optionally substituted with 1-3 $C_{1-4}$alkyl or $C_{1-4}$hydroxyalkyl groups.

Embodiment 89

A compound according to any one of embodiments 1-56, 59-74, 77-82, and 86 or a pharmaceutically acceptable salt thereof, wherein $R_5$ and $R_6$ are each independently selected from H and $C_{1-4}$alkyl; or $R_5$ and $R_6$, together with the nitrogen atom to which they are attached, form a 5-7 membered heterocyclyl optionally substituted with 1-3 $C_{1-4}$alkyl groups.

Embodiment 90

A compound according to any one of embodiments 1-56, 59-74, 77-82, and 86 or a pharmaceutically acceptable salt thereof, wherein $R_5$ and $R_6$ are each $C_{1-4}$alkyl; or $R_5$ and $R_6$, together with the nitrogen atom to which they are attached, form a 5-7 membered heterocyclyl optionally substituted with 1-3 $C_{1-4}$alkyl groups.

Embodiment 91

A compound according to any one of embodiments 1-56, 59-74, 77-82, and 86 or a pharmaceutically acceptable salt thereof, wherein $R_5$ and $R_6$ are each H.

Embodiment 92

A compound according to any one of embodiments 1-56, 59-74, 77-82, and 86 or a pharmaceutically acceptable salt thereof, wherein $R_5$ and $R_6$ are each $C_{1-4}$ alkyl.

Embodiment 93

A compound according to any one of embodiments 1-56, 59-74, 77-82, and 86 or a pharmaceutically acceptable salt thereof, wherein $R_5$ and $R_6$ are each $CH_3$.

Embodiment 94

A compound according to any one of embodiments 1, 3-56, 59-74, 77-82, and 86 or a pharmaceutically acceptable salt thereof, wherein $R_5$ and $R_6$, together with the nitrogen atom to which they are attached, form a 5-7 membered heterocyclyl optionally substituted with 1-3 $C_{1-4}$alkyl or $C_{1-4}$hydroxyalkyl groups.

Embodiment 95

A compound according to any one of embodiments 1-56, 59-74, 77-82, and 86 or a pharmaceutically acceptable salt thereof, wherein $R_5$ and $R_6$, together with the nitrogen atom to which they are attached, form a 5-7 membered heterocyclyl optionally substituted with 1-3 $C_{1-4}$alkyl groups.

Embodiment 96

A compound according to any one of embodiments 1, 3-56, 59-74, 77-82, and 86 or a pharmaceutically acceptable salt thereof, wherein $R_5$ and $R_6$, together with the nitrogen atom to which they are attached, form a pyrrolidine, morpholine, piperazine, or piperidine ring optionally substituted with 1-3 $C_{1-4}$alkyl or $C_{1-4}$hydroxyalkyl groups.

Embodiment 97

A compound according to any one of embodiments 1-56, 59-74, 77-82, and 86 or a pharmaceutically acceptable salt thereof, wherein $R_5$ and $R_6$, together with the nitrogen atom to which they are attached, form a pyrrolidine, morpholine, piperazine, or piperidine ring optionally substituted with 1-3 $C_{1-4}$alkyl.

Embodiment 98

A compound according to embodiment 1 or 2 or a pharmaceutically acceptable salt thereof, wherein the compound is selected from a group consisting of:
5-methyl-1-(1-(4-(1-methyl-1,2,3,6-tetrahydropyridin-4-yl)benzyl)-1H-indol-5-yl)-1H-pyrazole-3-carboxamide;
5-methyl-1-(1-(4-(pyridin-4-yl)benzyl)-1H-indol-5-yl)-1H-pyrazole-3-carboxamide;

1-(1-(4-(3,6-dihydro-2H-pyran-4-yl)benzyl)-1H-indol-5-yl)-5-methyl-1H-pyrazole-3-carboxamide;

1-(1-(4-(1-acetyl-1,2,3,6-tetrahydropyridin-4-yl)benzyl)-1H-indol-5-yl)-5-methyl-1H-pyrazole-3-carboxamide;

1-(1-((4'-cyano-[1,1'-biphenyl]-4-yl)methyl)-1H-indol-5-yl)-5-methyl-1H-pyrazole-3-carboxamide;

5-methyl-1-(1-((4'-(methylsulfonyl)-[1,1'-biphenyl]-4-yl)methyl)-1H-indol-5-yl)-1H-pyrazole-3-carboxamide;

1-(1-(4-(imidazo[1,2-a]pyridin-6-yl)benzyl)-1H-indol-5-yl)-5-methyl-1H-pyrazole-3-carboxamide;

5-methyl-1-(1-(4-(1-methyl-1,2,5,6-tetrahydropyridin-3-yl)benzyl)-1H-indol-5-yl)-1H-pyrazole-3-carboxamide;

5-methyl-1-(1-(4-(4-methyl-3,4-dihydro-2H-pyrido[3,2-b][1,4]oxazin-7-yl)benzyl)-1H-indol-5-yl)-1H-pyrazole-3-carboxamide;

5-methyl-1-(1-(4-(2-methyl-2H-indazol-6-yl)benzyl)-1H-indol-5-yl)-1H-pyrazole-3-carboxamide;

5-methyl-1-(1-((4'-((4-methylpiperazin-1-yl)sulfonyl)-[1,1'-biphenyl]-4-yl)methyl)-1H-indol-5-yl)-1H-pyrazole-3-carboxamide;

5-methyl-1-(1-((3'-(4-methylpiperazine-1-carbonyl)-[1,1'-biphenyl]-4-yl)methyl)-1H-indol-5-yl)-1H-pyrazole-3-carboxamide;

1-(1-((4'-(N,N-dimethylsulfamoyl)-[1,1'-biphenyl]-4-yl)methyl)-1H-indol-5-yl)-5-methyl-1H-pyrazole-3-carboxamide;

1-(1-(4-(1H-indazol-6-yl)benzyl)-1H-indol-5-yl)-5-methyl-1H-pyrazole-3-carboxamide;

1-(1-((3'-fluoro-4'-hydroxy-[1,1'-biphenyl]-4-yl)methyl)-1H-indol-5-yl)-5-methyl-1H-pyrazole-3-carboxamide;

1-(1-(4-(1H-pyrrolo[2,3-b]pyridin-5-yl)benzyl)-1H-indol-5-yl)-5-methyl-1H-pyrazole-3-carboxamide;

1-(1-(4-(1H-indazol-5-yl)benzyl)-1H-indol-5-yl)-5-methyl-1H-pyrazole-3-carboxamide;

1-(1-(4-(isoquinolin-6-yl)benzyl)-1H-indol-5-yl)-5-methyl-1H-pyrazole-3-carboxamide;

5-methyl-1-(1-(4-(1-methyl-1H-pyrazol-4-yl)benzyl)-1H-indol-5-yl)-1H-pyrazole-3-carboxamide;

5-methyl-1-(1-((3'-sulfamoyl-[1,1'-biphenyl]-4-yl)methyl)-1H-indol-5-yl)-1H-pyrazole-3-carboxamide;

1-(1-(4-(1H-indol-6-yl)benzyl)-1H-indol-5-yl)-5-methyl-1H-pyrazole-3-carboxamide;

5-methyl-1-(1-(4-(1-methyl-1H-indazol-6-yl)benzyl)-1H-indol-5-yl)-1H-pyrazole-3-carboxamide;

1-(1-(4-(6-(dimethylamino)pyridin-3-yl)benzyl)-1H-indol-5-yl)-5-methyl-1H-pyrazole-3-carboxamide;

1-(1-(4-(2-methoxypyridin-4-yl)benzyl)-1H-indol-5-yl)-5-methyl-1H-pyrazole-3-carboxamide;

5-methyl-1-(1-(4-(1-oxo-1,2,3,4-tetrahydroisoquinolin-6-yl)benzyl)-1H-indol-5-yl)-1H-pyrazole-3-carboxamide;

1-(1-((4'-amino-[1,1'-biphenyl]-4-yl)methyl)-1H-indol-5-yl)-5-methyl-1H-pyrazole-3-carboxamide;

1-(1-((4'-fluoro-[1,1'-biphenyl]-4-yl)methyl)-1H-indol-5-yl)-5-methyl-1H-pyrazole-3-carboxamide;

1-(1-(4-(2-methoxypyrimidin-5-yl)benzyl)-1H-indol-5-yl)-5-methyl-1H-pyrazole-3-carboxamide;

1-(1-(4-(2-aminopyrimidin-5-yl)benzyl)-1H-indol-5-yl)-5-methyl-1H-pyrazole-3-carboxamide;

1-(1-((4'-methoxy-[1,1'-biphenyl]-4-yl)methyl)-1H-indol-5-yl)-5-methyl-1H-pyrazole-3-carboxamide;

5-methyl-1-(1-(4-(2-oxoindolin-5-yl)benzyl)-1H-indol-5-yl)-1H-pyrazole-3-carboxamide;

1-(1-((4'-(hydroxymethyl)-[1,1'-biphenyl]-4-yl)methyl)-1H-indol-5-yl)-5-methyl-1H-pyrazole-3-carboxamide;

5-methyl-1-(1-((4'-(methylsulfonamido)-[1,1'-biphenyl]-4-yl)methyl)-1H-indol-5-yl)-1H-pyrazole-3-carboxamide;

1-(1-((4'-(aminomethyl)-[1,1'-biphenyl]-4-yl)methyl)-1H-indol-5-yl)-5-methyl-1H-pyrazole-3-carboxamide;

1-(1-((4'-(dimethylcarbamoyl)-[1,1'-biphenyl]-4-yl)methyl)-1H-indol-5-yl)-5-methyl-1H-pyrazole-3-carboxamide;

1-(1-(4-(2-(dimethylamino)pyrimidin-5-yl)benzyl)-1H-indol-5-yl)-5-methyl-1H-pyrazole-3-carboxamide;

5-methyl-1-(1-((4'-(morpholinomethyl)-[1,1'-biphenyl]-4-yl)methyl)-1H-indol-5-yl)-1H-pyrazole-3-carboxamide;

5-methyl-1-(1-((4'-((2-morpholinoethyl)carbamoyl)-[1,1'-biphenyl]-4-yl)methyl)-1H-indol-5-yl)-1H-pyrazole-3-carboxamide;

5-methyl-1-(1-(4-(1-methylpyrrolidin-3-yl)benzyl)-1H-indol-5-yl)-1H-pyrazole-3-carboxamide;

(S)-5-methyl-1-(1-(4-(1-methylpyrrolidin-3-yl)benzyl)-1H-indol-5-yl)-1H-pyrazole-3-carboxamide;

(R)-5-methyl-1-(1-(4-(1-methylpyrrolidin-3-yl)benzyl)-1H-indol-5-yl)-1H-pyrazole-3-carboxamide;

5-methyl-1-(1-(4-(piperidin-3-yl)benzyl)-1H-indol-5-yl)-1H-pyrazole-3-carboxamide;

5-methyl-1-(1-(4-(1-methylpiperidin-4-yl)benzyl)-1H-indol-5-yl)-1H-pyrazole-3-carboxamide;

5-methyl-1-(1-(4-(1,2,3,6-tetrahydropyridin-4-yl)benzyl)-1H-indol-5-yl)-1H-pyrazole-3-carboxamide;

5-methyl-1-(1-(4-(1-(methylsulfonyl)-1,2,3,6-tetrahydropyridin-4-yl)benzyl)-1H-indol-5-yl)-1H-pyrazole-3-carboxamide;

1-(1-(4-(1-(2-hydroxyacetyl)-1,2,3,6-tetrahydropyridin-4-yl)benzyl)-1H-indol-5-yl)-5-methyl-1H-pyrazole-3-carboxamide;

1-(1-(4-(1-(cyclopropylmethyl)-1,2,3,6-tetrahydropyridin-4-yl)benzyl)-1H-indol-5-yl)-5-methyl-1H-pyrazole-3-carboxamide;

1-(1-(4-(1-(dimethylglycyl)-1,2,3,6-tetrahydropyridin-4-yl)benzyl)-1H-indol-5-yl)-5-methyl-1H-pyrazole-3-carboxamide;

1-(1-(4-(1-(3-aminopropyl)piperidin-4-yl)benzyl)-1H-indol-5-yl)-5-methyl-1H-pyrazole-3-carboxamide;

1-(1-(4-(1-(3-acetamidopropyl)piperidin-4-yl)benzyl)-1H-indol-5-yl)-5-methyl-1H-pyrazole-3-carboxamide;

1-(1-(4-(1-(dimethylglycyl)-1,2,3,6-tetrahydropyridin-4-yl)benzyl)-1H-indol-5-yl)-5-methyl-1H-pyrazole-3-carboxamide;

5-methyl-1-(1-(4-(piperazin-1-yl)benzyl)-1H-indol-5-yl)-1H-pyrazole-3-carboxamide;

5-methyl-1-(1-(4-(4-methylpiperazin-1-yl)benzyl)-1H-indol-5-yl)-1H-pyrazole-3-carboxamide;

5-methyl-1-(1-(4-(5-methylhexahydropyrrolo[3,4-c]pyrrol-2(1H)-yl)benzyl)-1H-indol-5-yl)-1H-pyrazole-3-carboxamide;

1-(1-(4-(3-(dimethylamino)prop-1-yn-1-yl)benzyl)-1H-indol-5-yl)-5-methyl-1H-pyrazole-3-carboxamide;

1-(1-(4-(1-azabicyclo[3.3.1]non-3-en-4-yl)benzyl)-1H-indol-5-yl)-5-methyl-1H-pyrazole-3-carboxamide;

1-(1-(4-((5S)-1-azabicyclo[3.3.1]non-3-en-4-yl)benzyl)-1H-indol-5-yl)-5-methyl-1H-pyrazole-3-carboxamide;

1-(1-(4-((5R)-1-azabicyclo[3.3.1]non-3-en-4-yl)benzyl)-1H-indol-5-yl)-5-methyl-1H-pyrazole-3-carboxamide;

5-methyl-1-(1-(4-(1,2,2-trimethyl-1,2,3,6-tetrahydropyridin-4-yl)benzyl)-1H-indol-5-yl)-1H-pyrazole-3-carboxamide;

5-methyl-1-(1-(4-(1,3,3-trimethyl-1,2,3,6-tetrahydropyridin-4-yl)benzyl)-1H-indol-5-yl)-1H-pyrazole-3-carboxamide;

5-methyl-1-(1-(4-(1,3,3-trimethylpiperidin-4-yl)benzyl)-1H-indol-5-yl)-1H-pyrazole-3-carboxamide;

(S)-5-methyl-1-(1-(4-(1,3,3-trimethylpiperidin-4-yl)benzyl)-1H-indol-5-yl)-1H-pyrazole-3-carboxamide;
(R)-5-methyl-1-(1-(4-(1,3,3-trimethylpiperidin-4-yl)benzyl)-1H-indol-5-yl)-1H-pyrazole-3-carboxamide;
1-(1-(4-(1,3-dimethyl-1,2,3,6-tetrahydropyridin-4-yl)benzyl)-1H-indol-5-yl)-5-methyl-1H-pyrazole-3-carboxamide;
(S)-1-(1-(4-(1,3-dimethyl-1,2,3,6-tetrahydropyridin-4-yl)benzyl)-1H-indol-5-yl)-5-methyl-1H-pyrazole-3-carboxamide;
(R)-1-(1-(4-(1,3-dimethyl-1,2,3,6-tetrahydropyridin-4-yl)benzyl)-1H-indol-5-yl)-5-methyl-1H-pyrazole-3-carboxamide;
1-(1-((4'-((2-hydroxyethyl)sulfonyl)-[1,1'-biphenyl]-4-yl)methyl)-1H-indol-5-yl)-5-methyl-1H-pyrazole-3-carboxamide;
5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide;
1-(3-(3,6-dihydro-2H-pyran-4-yl)-1-((4'-(methylsulfonyl)-[1,1'-biphenyl]-4-yl)methyl)-1H-indol-5-yl)-5-methyl-1H-pyrazole-3-carboxamide;
5-methyl-1-(3-(1-methyl-1,2,3,6-tetrahydropyridin-4-yl)-1-((4'-(methylsulfonyl)-[1,1'-biphenyl]-4-yl)methyl)-1H-indol-5-yl)-1H-pyrazole-3-carboxamide;
5-methyl-1-(1-((4'-(methylsulfonyl)-[1,1'-biphenyl]-4-yl)methyl)-3-(tetrahydro-2H-pyran-4-yl)-1H-indol-5-yl)-1H-pyrazole-3-carboxamide;
5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide;
1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide;
1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide;
(cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide;
(cis)-5-methyl-1-(1-(4-((2-methyl-1,2,3,3a,4,6a-hexahydrocyclopenta[c]pyrrol-5-yl)benzyl)-1H-indol-5-yl)-1H-pyrazole-3-carboxamide;
5-methyl-1-(1-(4-((3aR,6aS)-2-methyloctahydrocyclopenta[c]pyrrol-5-yl)benzyl)-1H-indol-5-yl)-1H-pyrazole-3-carboxamide;
5-methyl-1-(1-(4-((3aR,5r,6aS)-2-methyloctahydrocyclopenta[c]pyrrol-5-yl))benzyl)-1H-indol-5-yl)-1H-pyrazole-3-carboxamide;
5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide;
5-methyl-1-(1-(4-((3aR,6aS)-2-methyloctahydrocyclopenta[c]pyrrol-5-yl)benzyl)-1H-indol-5-yl)-1H-1,2,4-triazole-3-carboxamide;
5-methyl-1-(1-(4-((3aR,5r,6aS)-2-methyloctahydrocyclopenta[c]pyrrol-5-yl))benzyl)-1H-indol-5-yl)-1H-1,2,4-triazole-3-carboxamide;
5-methyl-1-(1-((4'-(pyrrolidin-1-ylmethyl)-[1,1'-biphenyl]-4-yl)methyl)-1H-indol-5-yl)-1H-1,2,4-triazole-3-carboxamide;
5-methyl-1-(1-(4-(1-methylazepan-4-yl)benzyl)-1H-indol-5-yl)-1H-pyrazole-3-carboxamide;
(S)-5-methyl-1-(1-(4-(1-methylazepan-4-yl)benzyl)-1H-indol-5-yl)-1H-pyrazole-3-carboxamide; and
(R)-5-methyl-1-(1-(4-(1-methylazepan-4-yl)benzyl)-1H-indol-5-yl)-1H-pyrazole-3-carboxamide.

Embodiment 99

A compound according to embodiment 1 or a pharmaceutically acceptable salt thereof, wherein the compound is selected from a group consisting of:
5-methyl-1-(1-(4-(2-methyl-2-azaspiro[3.5]non-6-en-7-yl)benzyl)-1H-indol-5-yl)-1H-pyrazole-3-carboxamide;
5-methyl-1-(1-(4-(2-methyl-2-azaspiro[3.5]nonan-7-yl)benzyl)-1H-indol-5-yl)-1H-pyrazole-3-carboxamide;
1-(1-((4'-((2-(dimethylamino)ethyl)sulfonyl)-[1,1'-biphenyl]-4-yl)methyl)-1H-indol-5-yl)-5-methyl-1H-pyrazole-3-carboxamide;
5-methyl-1-(1-(4-(6-(methylsulfonyl)pyridin-3-yl)benzyl)-1H-indol-5-yl)-1H-pyrazole-3-carboxamide;
1-(1-(4-(5-(2-hydroxypropan-2-yl)pyridin-2-yl)benzyl)-1H-indol-5-yl)-5-methyl-1H-pyrazole-3-carboxamide;
1-(1-(4-(6-(2-hydroxypropan-2-yl)pyridin-3-yl)benzyl)-1H-indol-5-yl)-5-methyl-1H-pyrazole-3-carboxamide;
5-methyl-1-(1-(4-((1-methylpyrrolidin-3-yl)methyl)benzyl)-1H-indol-5-yl)-1H-pyrazole-3-carboxamide;
5-methyl-1-(1-(4-((1-methylazetidin-3-yl)methyl)benzyl)-1H-indol-5-yl)-1H-pyrazole-3-carboxamide;
5-methyl-1-(1-(4-((1R,5S)-3-methyl-3-azabicyclo[3.1.0]hexan-1-yl)benzyl)-1H-indol-5-yl)-1H-pyrazole-3-carboxamide;
1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;
(S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;
(R)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;
5-methyl-1-(1-((4'-((4-methylpiperazin-1-yl)methyl)-[1,1'-biphenyl]-4-yl)methyl)-1H-indol-5-yl)-1H-pyrazole-3-carboxamide;
5-methyl-1-(1-((4'-(piperazin-1-ylmethyl)-[1,1'-biphenyl]-4-yl)methyl)-1H-indol-5-yl)-1H-pyrazole-3-carboxamide;
5-methyl-1-(1-((4'-(4-methylpiperazine-1-carbonyl)-[1,1'-biphenyl]-4-yl)methyl)-1H-indol-5-yl)-1H-pyrazole-3-carboxamide;
5-methyl-1-(1-(4-((1-methylpyrrolidin-3-yl)amino)benzyl)-1H-indol-5-yl)-1H-pyrazole-3-carboxamide;
(S)-5-methyl-1-(1-(4-((1-methylpyrrolidin-3-yl)amino)benzyl)-1H-indol-5-yl)-1H-pyrazole-3-carboxamide;
(R)-5-methyl-1-(1-(4-((1-methylpyrrolidin-3-yl)amino)benzyl)-1H-indol-5-yl)-1H-pyrazole-3-carboxamide;
1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide;
5-methyl-1-(1-(4-((3aR,5r,6aS)-octahydrocyclopenta[c]pyrrol-5-yl)benzyl)-1H-indol-5-yl)-1H-pyrazole-3-carboxamide;
1-(1-(4-((3aR,5r,6aS)-2-(cyclopropylmethyl)octahydrocyclopenta[c]pyrrol-5-yl)benzyl)-1H-indol-5-yl)-5-methyl-1H-pyrazole-3-carboxamide;
5-methyl-1-(1-(4-((3aR,5r,6aS)-2-(methylsulfonyl)octahydrocyclopenta[c]pyrrol-5-yl)benzyl)-1H-indol-5-yl)-1H-pyrazole-3-carboxamide;
5-methyl-1-(1-(4-((3aR,5r,6aS)-2-(2-(methylsulfonyl)ethyl)octahydrocyclopenta[c]pyrrol-5-yl)benzyl)-1H-indol-5-yl)-1H-pyrazole-3-carboxamide; and
5-methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide.

Embodiment 100

A compound according to embodiment 1 or 2 or a pharmaceutically acceptable salt thereof, wherein the compound is 5-methyl-1-(1-(4-(1-methyl-1,2,3,6-tetrahydropyridin-4-yl)benzyl)-1H-indol-5-yl)-1H-pyrazole-3-carboxamide.

Embodiment 101

A compound according to embodiment 1 or 2 or a pharmaceutically acceptable salt thereof, wherein the compound is 5-methyl-1-(1-(4-(pyridin-4-yl)benzyl)-1H-indol-5-yl)-1H-pyrazole-3-carboxamide.

Embodiment 102

A compound according to embodiment 1 or 2 or a pharmaceutically acceptable salt thereof, wherein the compound is 1-(1-(4-(3,6-dihydro-2H-pyran-4-yl)benzyl)-1H-indol-5-yl)-5-methyl-1H-pyrazole-3-carboxamide.

Embodiment 103

A compound according to embodiment 1 or 2 or a pharmaceutically acceptable salt thereof, wherein the compound is 1-(1-(4-(1-acetyl-1,2,3,6-tetrahydropyridin-4-yl)benzyl)-1H-indol-5-yl)-5-methyl-1H-pyrazole-3-carboxamide.

Embodiment 104

A compound according to embodiment 1 or 2 or a pharmaceutically acceptable salt thereof, wherein the compound is 1-(1-((4'-cyano-[1,1'-biphenyl]-4-yl)methyl)-1H-indol-5-yl)-5-methyl-1H-pyrazole-3-carboxamide.

Embodiment 105

A compound according to embodiment 1 or 2 or a pharmaceutically acceptable salt thereof, wherein the compound is 5-methyl-1-(1-((4'-(methylsulfonyl)-[1,1'-biphenyl]-4-yl)methyl)-1H-indol-5-yl)-1H-pyrazole-3-carboxamide.

Embodiment 106

A compound according to embodiment 1 or 2 or a pharmaceutically acceptable salt thereof, wherein the compound is 1-(1-(4-(imidazo[1,2-a]pyridin-6-yl)benzyl)-1H-indol-5-yl)-5-methyl-1H-pyrazole-3-carboxamide.

Embodiment 107

A compound according to embodiment 1 or 2 or a pharmaceutically acceptable salt thereof, wherein the compound is 5-methyl-1-(1-(4-(1-methyl-1,2,5,6-tetrahydropyridin-3-yl)benzyl)-1H-indol-5-yl)-1H-pyrazole-3-carboxamide.

Embodiment 108

A compound according to embodiment 1 or 2 or a pharmaceutically acceptable salt thereof, wherein the compound is 5-methyl-1-(1-(4-(4-methyl-3,4-dihydro-2H-pyrido[3,2-b][1,4]oxazin-7-yl)benzyl)-1H-indol-5-yl)-1H-pyrazole-3-carboxamide.

Embodiment 109

A compound according to embodiment 1 or 2 or a pharmaceutically acceptable salt thereof, wherein the compound is 5-methyl-1-(1-(4-(2-methyl-2H-indazol-6-yl)benzyl)-1H-indol-5-yl)-1H-pyrazole-3-carboxamide.

Embodiment 110

A compound according to embodiment 1 or 2 or a pharmaceutically acceptable salt thereof, wherein the compound is 5-methyl-1-(1-((4'-((4-methylpiperazin-1-yl)sulfonyl)-[1,1'-biphenyl]-4-yl)methyl)-1H-indol-5-yl)-1H-pyrazole-3-carboxamide.

Embodiment 111

A compound according to embodiment 1 or 2 or a pharmaceutically acceptable salt thereof, wherein the compound is 5-methyl-1-(1-((3'-(4-methylpiperazine-1-carbonyl)-[1,1'-biphenyl]-4-yl)methyl)-1H-indol-5-yl)-1H-pyrazole-3-carboxamide.

Embodiment 112

A compound according to embodiment 1 or 2 or a pharmaceutically acceptable salt thereof, wherein the compound is 1-(1-((4'-(N,N-dimethylsulfamoyl)-[1,1'-biphenyl]-4-yl)methyl)-1H-indol-5-yl)-5-methyl-1H-pyrazole-3-carboxamide.

Embodiment 113

A compound according to embodiment 1 or 2 or a pharmaceutically acceptable salt thereof, wherein the compound is 1-(1-(4-(1H-indazol-6-yl)benzyl)-1H-indol-5-yl)-5-methyl-1H-pyrazole-3-carboxamide.

Embodiment 114

A compound according to embodiment 1 or 2 or a pharmaceutically acceptable salt thereof, wherein the compound is 1-(1-((3'-fluoro-4'-hydroxy-[1,1'-biphenyl]-4-yl)methyl)-1H-indol-5-yl)-5-methyl-1H-pyrazole-3-carboxamide.

Embodiment 115

A compound according to embodiment 1 or 2 or a pharmaceutically acceptable salt thereof, wherein the compound is 1-(1-(4-(1H-pyrrolo[2,3-b]pyridin-5-yl)benzyl)-1H-indol-5-yl)-5-methyl-1H-pyrazole-3-carboxamide.

Embodiment 116

A compound according to embodiment 1 or 2 or a pharmaceutically acceptable salt thereof, wherein the compound is 1-(1-(4-(1H-indazol-5-yl)benzyl)-1H-indol-5-yl)-5-methyl-1H-pyrazole-3-carboxamide.

Embodiment 117

A compound according to embodiment 1 or 2 or a pharmaceutically acceptable salt thereof, wherein the compound is 1-(1-(4-(isoquinolin-6-yl)benzyl)-1H-indol-5-yl)-5-methyl-1H-pyrazole-3-carboxamide.

Embodiment 118

A compound according to embodiment 1 or 2 or a pharmaceutically acceptable salt thereof, wherein the compound is 5-methyl-1-(1-(4-(1-methyl-1H-pyrazol-4-yl)benzyl)-1H-indol-5-yl)-1H-pyrazole-3-carboxamide.

Embodiment 119

A compound according to embodiment 1 or 2 or a pharmaceutically acceptable salt thereof, wherein the compound is 5-methyl-1-(1-((3'-sulfamoyl-[1,1'-biphenyl]-4-yl)methyl)-1H-indol-5-yl)-1H-pyrazole-3-carboxamide.

Embodiment 120

A compound according to embodiment 1 or 2 or a pharmaceutically acceptable salt thereof, wherein the compound is 1-(1-(4-(1H-indol-6-yl)benzyl)-1H-indol-5-yl)-5-methyl-1H-pyrazole-3-carboxamide.

Embodiment 121

A compound according to embodiment 1 or 2 or a pharmaceutically acceptable salt thereof, wherein the compound is 5-methyl-1-(1-(4-(1-methyl-1H-indazol-6-yl)benzyl)-1H-indol-5-yl)-1H-pyrazole-3-carboxamide.

Embodiment 122

A compound according to embodiment 1 or 2 or a pharmaceutically acceptable salt thereof, wherein the compound is 1-(1-(4-(6-(dimethylamino)pyridin-3-yl)benzyl)-1H-indol-5-yl)-5-methyl-1H-pyrazole-3-carboxamide.

Embodiment 123

A compound according to embodiment 1 or 2 or a pharmaceutically acceptable salt thereof, wherein the compound is 1-(1-(4-(2-methoxypyridin-4-yl)benzyl)-1H-indol-5-yl)-5-methyl-1H-pyrazole-3-carboxamide.

Embodiment 124

A compound according to embodiment 1 or 2 or a pharmaceutically acceptable salt thereof, wherein the compound is 5-methyl-1-(1-(4-(1-oxo-1,2,3,4-tetrahydroisoquinolin-6-yl)benzyl)-1H-indol-5-yl)-1H-pyrazole-3-carboxamide.

Embodiment 125

A compound according to embodiment 1 or 2 or a pharmaceutically acceptable salt thereof, wherein the compound is 1-(1-((4'-amino-[1,1'-biphenyl]-4-yl)methyl)-1H-indol-5-yl)-5-methyl-1H-pyrazole-3-carboxamide.

Embodiment 126

A compound according to embodiment 1 or 2 or a pharmaceutically acceptable salt thereof, wherein the compound is 1-(1-((4'-fluoro-[1,1'-biphenyl]-4-yl)methyl)-1H-indol-5-yl)-5-methyl-1H-pyrazole-3-carboxamide.

Embodiment 127

A compound according to embodiment 1 or 2 or a pharmaceutically acceptable salt thereof, wherein the compound is 1-(1-(4-(2-methoxypyrimidin-5-yl)benzyl)-1H-indol-5-yl)-5-methyl-1H-pyrazole-3-carboxamide.

Embodiment 128

A compound according to embodiment 1 or 2 or a pharmaceutically acceptable salt thereof, wherein the compound is 1-(1-(4-(2-aminopyrimidin-5-yl)benzyl)-1H-indol-5-yl)-5-methyl-1H-pyrazole-3-carboxamide.

Embodiment 129

A compound according to embodiment 1 or 2 or a pharmaceutically acceptable salt thereof, wherein the compound is 1-(1-((4'-methoxy-[1,1'-biphenyl]-4-yl)methyl)-1H-indol-5-yl)-5-methyl-1H-pyrazole-3-carboxamide.

Embodiment 130

A compound according to embodiment 1 or 2 or a pharmaceutically acceptable salt thereof, wherein the compound is 5-methyl-1-(1-(4-(2-oxoindolin-5-yl)benzyl)-1H-indol-5-yl)-1H-pyrazole-3-carboxamide.

Embodiment 131

A compound according to embodiment 1 or 2 or a pharmaceutically acceptable salt thereof, wherein the compound is 1-(1-((4'-(hydroxymethyl)-[1,1'-biphenyl]-4-yl)methyl)-1H-indol-5-yl)-5-methyl-1H-pyrazole-3-carboxamide.

Embodiment 132

A compound according to embodiment 1 or 2 or a pharmaceutically acceptable salt thereof, wherein the compound is 5-methyl-1-(1-((4'-(methylsulfonamido)-[1,1'-biphenyl]-4-yl)methyl)-1H-indol-5-yl)-1H-pyrazole-3-carboxamide.

Embodiment 133

A compound according to embodiment 1 or 2 or a pharmaceutically acceptable salt thereof, wherein the compound is 1-(1-((4'-(aminomethyl)-[1,1'-biphenyl]-4-yl)methyl)-1H-indol-5-yl)-5-methyl-1H-pyrazole-3-carboxamide.

Embodiment 134

A compound according to embodiment 1 or 2 or a pharmaceutically acceptable salt thereof, wherein the compound is 1-(1-((4'-(dimethylcarbamoyl)-[1,1'-biphenyl]-4-yl)methyl)-1H-indol-5-yl)-5-methyl-1H-pyrazole-3-carboxamide.

Embodiment 135

A compound according to embodiment 1 or 2 or a pharmaceutically acceptable salt thereof, wherein the compound is 1-(1-(4-(2-(dimethylamino)pyrimidin-5-yl)benzyl)-1H-indol-5-yl)-5-methyl-1H-pyrazole-3-carboxamide.

Embodiment 136

A compound according to embodiment 1 or 2 or a pharmaceutically acceptable salt thereof, wherein the compound is 5-methyl-1-(1-((4'-(morpholinomethyl)-[1,1'-biphenyl]-4-yl)methyl)-1H-indol-5-yl)-1H-pyrazole-3-carboxamide.

Embodiment 137

A compound according to embodiment 1 or 2 or a pharmaceutically acceptable salt thereof, wherein the compound is 5-methyl-1-(1-((4'-((2-morpholinoethyl)carbamoyl)-[1,1'-biphenyl]-4-yl)methyl)-1H-indol-5-yl)-1H-pyrazole-3-carboxamide.

Embodiment 138

A compound according to embodiment 1 or 2 or a pharmaceutically acceptable salt thereof, wherein the compound is 5-methyl-1-(1-(4-(1-methylpyrrolidin-3-yl)benzyl)-1H-indol-5-yl)-1H-pyrazole-3-carboxamide.

Embodiment 139

A compound according to embodiment 1 or 2 or a pharmaceutically acceptable salt thereof, wherein the compound is (S)-5-methyl-1-(1-(4-(1-methylpyrrolidin-3-yl)benzyl)-1H-indol-5-yl)-1H-pyrazole-3-carboxamide.

Embodiment 140

A compound according to embodiment 1 or 2 or a pharmaceutically acceptable salt thereof, wherein the compound is (R)-5-methyl-1-(1-(4-(1-methylpyrrolidin-3-yl)benzyl)-1H-indol-5-yl)-1H-pyrazole-3-carboxamide.

Embodiment 141

A compound according to embodiment 1 or 2 or a pharmaceutically acceptable salt thereof, wherein the compound is 5-methyl-1-(1-(4-(piperidin-3-yl)benzyl)-1H-indol-5-yl)-1H-pyrazole-3-carboxamide.

Embodiment 142

A compound according to embodiment 1 or 2 or a pharmaceutically acceptable salt thereof, wherein the compound is (S)-5-methyl-1-(1-(4-(piperidin-3-yl)benzyl)-1H-indol-5-yl)-1H-pyrazole-3-carboxamide.

Embodiment 143

A compound according to embodiment 1 or 2 or a pharmaceutically acceptable salt thereof, wherein the compound is (R)-5-methyl-1-(1-(4-(piperidin-3-yl)benzyl)-1H-indol-5-yl)-1H-pyrazole-3-carboxamide.

Embodiment 144

A compound according to embodiment 1 or 2 or a pharmaceutically acceptable salt thereof, wherein the compound is 5-methyl-1-(1-(4-(1-methylpiperidin-4-yl)benzyl)-1H-indol-5-yl)-1H-pyrazole-3-carboxamide.

Embodiment 145

A compound according to embodiment 1 or 2 or a pharmaceutically acceptable salt thereof, wherein the compound is 5-methyl-1-(1-(4-(1,2,3,6-tetrahydropyridin-4-yl)benzyl)-1H-indol-5-yl)-1H-pyrazole-3-carboxamide.

Embodiment 146

A compound according to embodiment 1 or 2 or a pharmaceutically acceptable salt thereof, wherein the compound is 5-methyl-1-(1-(4-(1-(methylsulfonyl)-1,2,3,6-tetrahydropyridin-4-yl)benzyl)-1H-indol-5-yl)-1H-pyrazole-3-carboxamide.

Embodiment 147

A compound according to embodiment 1 or 2 or a pharmaceutically acceptable salt thereof, wherein the compound is 1-(1-(4-(1-(2-hydroxyacetyl)-1,2,3,6-tetrahydropyridin-4-yl)benzyl)-1H-indol-5-yl)-5-methyl-1H-pyrazole-3-carboxamide.

Embodiment 148

A compound according to embodiment 1 or 2 or a pharmaceutically acceptable salt thereof, wherein the compound is 1-(1-(4-(1-(cyclopropylmethyl)-1,2,3,6-tetrahydropyridin-4-yl)benzyl)-1H-indol-5-yl)-5-methyl-1H-pyrazole-3-carboxamide.

Embodiment 149

A compound according to embodiment 1 or 2 or a pharmaceutically acceptable salt thereof, wherein the compound is 1-(1-(4-(1-(dimethylglycyl)-1,2,3,6-tetrahydropyridin-4-yl)benzyl)-1H-indol-5-yl)-5-methyl-1H-pyrazole-3-carboxamide.

Embodiment 150

A compound according to embodiment 1 or 2 or a pharmaceutically acceptable salt thereof, wherein the compound is 1-(1-(4-(1-(3-aminopropyl)piperidin-4-yl)benzyl)-1H-indol-5-yl)-5-methyl-1H-pyrazole-3-carboxamide.

Embodiment 151

A compound according to embodiment 1 or 2 or a pharmaceutically acceptable salt thereof, wherein the compound is 1-(1-(4-(1-(3-acetamidopropyl)piperidin-4-yl)benzyl)-1H-indol-5-yl)-5-methyl-1H-pyrazole-3-carboxamide.

Embodiment 152

A compound according to embodiment 1 or 2 or a pharmaceutically acceptable salt thereof, wherein the compound is 1-(1-(4-(1-(dimethylglycyl)-1,2,3,6-tetrahydropyridin-4-yl)benzyl)-1H-indol-5-yl)-5-methyl-1H-pyrazole-3-carboxamide.

Embodiment 153

A compound according to embodiment 1 or 2 or a pharmaceutically acceptable salt thereof, wherein the compound is 5-methyl-1-(1-(4-(piperazin-1-yl)benzyl)-1H-indol-5-yl)-1H-pyrazole-3-carboxamide.

Embodiment 154

A compound according to embodiment 1 or 2 or a pharmaceutically acceptable salt thereof, wherein the compound is 5-methyl-1-(1-(4-(4-methylpiperazin-1-yl)benzyl)-1H-indol-5-yl)-1H-pyrazole-3-carboxamide.

Embodiment 155

A compound according to embodiment 1 or 2 or a pharmaceutically acceptable salt thereof, wherein the compound is 5-methyl-1-(1-(4-(5-methylhexahydropyrrolo[3,4-c]pyrrol-2(1H)-yl)benzyl)-1H-indol-5-yl)-1H-pyrazole-3-carboxamide.

Embodiment 156

A compound according to embodiment 1 or 2 or a pharmaceutically acceptable salt thereof, wherein the compound is 1-(1-(4-(3-(dimethylamino)prop-1-yn-1-yl)benzyl)-1H-indol-5-yl)-5-methyl-1H-pyrazole-3-carboxamide.

Embodiment 157

A compound according to embodiment 1 or 2 or a pharmaceutically acceptable salt thereof, wherein the compound is 1-(1-(4-(1-azabicyclo[3.3.1]non-3-en-4-yl)benzyl)-1H-indol-5-yl)-5-methyl-1H-pyrazole-3-carboxamide.

Embodiment 158

A compound according to embodiment 1 or 2 or a pharmaceutically acceptable salt thereof, wherein the compound is 1-(1-(4-((5S)-1-azabicyclo[3.3.1]non-3-en-4-yl)benzyl)-1H-indol-5-yl)-5-methyl-1H-pyrazole-3-carboxamide.

Embodiment 159

A compound according to embodiment 1 or 2 or a pharmaceutically acceptable salt thereof, wherein the compound is 1-(1-(4-((5R)-1-azabicyclo[3.3.1]non-3-en-4-yl)benzyl)-1H-indol-5-yl)-5-methyl-1H-pyrazole-3-carboxamide.

Embodiment 160

A compound according to embodiment 1 or 2 or a pharmaceutically acceptable salt thereof, wherein the compound is 5-methyl-1-(1-(4-(1,2,2-trimethyl-1,2,3,6-tetrahydropyridin-4-yl)benzyl)-1H-indol-5-yl)-1H-pyrazole-3-carboxamide.

Embodiment 161

A compound according to embodiment 1 or 2 or a pharmaceutically acceptable salt thereof, wherein the compound is 5-methyl-1-(1-(4-(1,3,3-trimethyl-1,2,3,6-tetrahydropyridin-4-yl)benzyl)-1H-indol-5-yl)-1H-pyrazole-3-carboxamide.

Embodiment 162

A compound according to embodiment 1 or 2 or a pharmaceutically acceptable salt thereof, wherein the compound is 5-methyl-1-(1-(4-(1,3,3-trimethylpiperidin-4-yl)benzyl)-1H-indol-5-yl)-1H-pyrazole-3-carboxamide.

Embodiment 163

A compound according to embodiment 1 or 2 or a pharmaceutically acceptable salt thereof, wherein the compound is (S)-5-methyl-1-(1-(4-(1,3,3-trimethylpiperidin-4-yl)benzyl)-1H-indol-5-yl)-1H-pyrazole-3-carboxamide.

Embodiment 164

A compound according to embodiment 1 or 2 or a pharmaceutically acceptable salt thereof, wherein the compound is (R)-5-methyl-1-(1-(4-(1,3,3-trimethylpiperidin-4-yl)benzyl)-1H-indol-5-yl)-1H-pyrazole-3-carboxamide.

Embodiment 165

A compound according to embodiment 1 or 2 or a pharmaceutically acceptable salt thereof, wherein the compound is 1-(1-(4-(1,3-dimethyl-1,2,3,6-tetrahydropyridin-4-yl)benzyl)-1H-indol-5-yl)-5-methyl-1H-pyrazole-3-carboxamide.

Embodiment 166

A compound according to embodiment 1 or 2 or a pharmaceutically acceptable salt thereof, wherein the compound is (S)-1-(1-(4-(1,3-dimethyl-1,2,3,6-tetrahydropyridin-4-yl)benzyl)-1H-indol-5-yl)-5-methyl-1H-pyrazole-3-carboxamide.

Embodiment 167

A compound according to embodiment 1 or 2 or a pharmaceutically acceptable salt thereof, wherein the compound is (R)-1-(1-(4-(1,3-dimethyl-1,2,3,6-tetrahydropyridin-4-yl)benzyl)-1H-indol-5-yl)-5-methyl-1H-pyrazole-3-carboxamide.

Embodiment 168

A compound according to embodiment 1 or 2 or a pharmaceutically acceptable salt thereof, wherein the compound is 1-(1-((4'-((2-hydroxyethyl)sulfonyl)-[1,1'-biphenyl]-4-yl)methyl)-1H-indol-5-yl)-5-methyl-1H-pyrazole-3-carboxamide.

Embodiment 169

A compound according to embodiment 1 or 2 or a pharmaceutically acceptable salt thereof, wherein the compound is 5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide.

Embodiment 170

A compound according to embodiment 1 or 2 or a pharmaceutically acceptable salt thereof, wherein the compound is 1-(3-(3,6-dihydro-2H-pyran-4-yl)-1-((4'-(methylsulfonyl)-[1,1'-biphenyl]-4-yl)methyl)-1H-indol-5-yl)-5-methyl-1H-pyrazole-3-carboxamide.

Embodiment 171

A compound according to embodiment 1 or 2 or a pharmaceutically acceptable salt thereof, wherein the compound is 5-methyl-1-(3-(1-methyl-1,2,3,6-tetrahydropyridin-4-yl)-1-((4'-(methylsulfonyl)-[1,1'-biphenyl]-4-yl)methyl)-1H-indol-5-yl)-1H-pyrazole-3-carboxamide.

Embodiment 172

A compound according to embodiment 1 or 2 or a pharmaceutically acceptable salt thereof, wherein the compound is 5-methyl-1-(1-((4'-(methylsulfonyl)-[1,1'-biphenyl]-4-yl)methyl)-3-(tetrahydro-2H-pyran-4-yl)-1H-indol-5-yl)-1H-pyrazole-3-carboxamide.

Embodiment 173

A compound according to embodiment 1 or 2 or a pharmaceutically acceptable salt thereof, wherein the compound is 5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide.

Embodiment 174

A compound according to embodiment 1 or 2 or a pharmaceutically acceptable salt thereof, wherein the compound is 1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide.

Embodiment 175

A compound according to embodiment 1 or 2 or a pharmaceutically acceptable salt thereof, wherein the compound is 1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide.

Embodiment 176

A compound according to embodiment 1 or 2 or a pharmaceutically acceptable salt thereof, wherein the compound is (cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide.

Embodiment 177

A compound according to embodiment 1 or 2 or a pharmaceutically acceptable salt thereof, wherein the compound is 1-(1-(4-((3aS,6aR)-1,2,3,3a,4,6a-hexahydrocyclopenta[c]pyrrol-5-yl)benzyl)-1H-indol-5-yl)-5-methyl-1H-pyrazole-3-carboxamide.

Embodiment 178

A compound according to embodiment 1 or 2 or a pharmaceutically acceptable salt thereof, wherein the compound is 1-(1-(4-((3aR,6aS)-1,2,3,3a,4,6a-hexahydrocyclopenta[c]pyrrol-5-yl)benzyl)-1H-indol-5-yl)-5-methyl-1H-pyrazole-3-carboxamide.

Embodiment 179

A compound according to embodiment 1 or 2 or a pharmaceutically acceptable salt thereof, wherein the compound is (cis)-5-methyl-1-(1-(4-((2-methyl-1,2,3,3a,4,6a-hexahydrocyclopenta[c]pyrrol-5-yl)benzyl)-1H-indol-5-yl)-1H-pyrazole-3-carboxamide.

Embodiment 180

A compound according to embodiment 1 or 2 or a pharmaceutically acceptable salt thereof, wherein the compound is 5-methyl-1-(1-(4-((3aS,6aR)-2-methyl-1,2,3,3a,4,6a-hexahydrocyclopenta[c]pyrrol-5-yl)benzyl)-1H-indol-5-yl)-1H-pyrazole-3-carboxamide.

Embodiment 181

A compound according to embodiment 1 or 2 or a pharmaceutically acceptable salt thereof, wherein the compound is 5-methyl-1-(1-(4-((3aR,6aS)-2-methyl-1,2,3,3a,4,6a-hexahydrocyclopenta[c]pyrrol-5-yl)benzyl)-1H-indol-5-yl)-1H-pyrazole-3-carboxamide.

Embodiment 182

A compound according to embodiment 1 or 2 or a pharmaceutically acceptable salt thereof, wherein the compound is 5-methyl-1-(1-(4-((3aR,6aS)-2-methyloctahydrocyclopenta[c]pyrrol-5-yl)benzyl)-1H-indol-5-yl)-1H-pyrazole-3-carboxamide.

Embodiment 183

A compound according to embodiment 1 or 2 or a pharmaceutically acceptable salt thereof, wherein the compound is 5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide.

Embodiment 184

A compound according to embodiment 1 or 2 or a pharmaceutically acceptable salt thereof, wherein the compound is 5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide.

Embodiment 185

A compound according to embodiment 1 or 2 or a pharmaceutically acceptable salt thereof, wherein the compound is 5-methyl-1-(1-(4-((3aR,6aS)-2-methyloctahydrocyclopenta[c]pyrrol-5-yl)benzyl)-1H-indol-5-yl)-1H-1,2,4-triazole-3-carboxamide.

Embodiment 186

A compound according to embodiment 1 or 2 or a pharmaceutically acceptable salt thereof, wherein the compound is 5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide.

Embodiment 187

A compound according to embodiment 1 or 2 or a pharmaceutically acceptable salt thereof, wherein the compound is 5-methyl-1-(1-(4-((3aR,5s,6aS)-2-methyloctahydrocyclopenta[c]pyrrol-5-yl)benzyl)-1H-indol-5-yl)-1H-1,2,4-triazole-3-carboxamide.

Embodiment 188

A compound according to embodiment 1 or 2 or a pharmaceutically acceptable salt thereof, wherein the compound is 5-methyl-1-(1-((4'-(pyrrolidin-1-ylmethyl)-[1,1'-biphenyl]-4-yl)methyl)-1H-indol-5-yl)-1H-1,2,4-triazole-3-carboxamide.

Embodiment 189

A compound according to embodiment 1 or 2 or a pharmaceutically acceptable salt thereof, wherein the compound is 5-methyl-1-(1-(4-(1-methylazepan-4-yl)benzyl)-1H-indol-5-yl)-1H-pyrazole-3-carboxamide.

Embodiment 190

A compound according to embodiment 1 or 2 or a pharmaceutically acceptable salt thereof, wherein the compound is (S)-5-methyl-1-(1-(4-(1-methylazepan-4-yl)benzyl)-1H-indol-5-yl)-1H-pyrazole-3-carboxamide.

Embodiment 191

A compound according to embodiment 1 or 2 or a pharmaceutically acceptable salt thereof, wherein the compound is (R)-5-methyl-1-(1-(4-(1-methylazepan-4-yl)benzyl)-1H-indol-5-yl)-1H-pyrazole-3-carboxamide.

Embodiment 192

A compound according to embodiment 1 or a pharmaceutically acceptable salt thereof, wherein the compound is 5-methyl-1-(1-(4-(2-methyl-2-azaspiro[3.5]non-6-en-7-yl)benzyl)-1H-indol-5-yl)-1H-pyrazole-3-carboxamide.

Embodiment 193

A compound according to embodiment 1 or a pharmaceutically acceptable salt thereof, wherein the compound is 5-methyl-1-(1-(4-(2-methyl-2-azaspiro[3.5]nonan-7-yl)benzyl)-1H-indol-5-yl)-1H-pyrazole-3-carboxamide.

Embodiment 194

A compound according to embodiment 1 or a pharmaceutically acceptable salt thereof, wherein the compound is 1-(1-((4'-((2-(dimethylamino)ethyl)sulfonyl)-[1,1'-biphenyl]-4-yl)methyl)-1H-indol-5-yl)-5-methyl-1H-pyrazole-3-carboxamide.

Embodiment 195

A compound according to embodiment 1 or a pharmaceutically acceptable salt thereof, wherein the compound is 5-methyl-1-(1-(4-(6-(methylsulfonyl)pyridin-3-yl)benzyl)-1H-indol-5-yl)-1H-pyrazole-3-carboxamide.

Embodiment 196

A compound according to embodiment 1 or a pharmaceutically acceptable salt thereof, wherein the compound is 1-(1-(4-(5-(2-hydroxypropan-2-yl)pyridin-2-yl)benzyl)-1H-indol-5-yl)-5-methyl-1H-pyrazole-3-carboxamide.

Embodiment 197

A compound according to embodiment 1 or a pharmaceutically acceptable salt thereof, wherein the compound is 1-(1-(4-(6-(2-hydroxypropan-2-yl)pyridin-3-yl)benzyl)-1H-indol-5-yl)-5-methyl-1H-pyrazole-3-carboxamide.

Embodiment 198

A compound according to embodiment 1 or a pharmaceutically acceptable salt thereof, wherein the compound is 5-methyl-1-(1-(4-((1-methylpyrrolidin-3-yl)methyl)benzyl)-1H-indol-5-yl)-1H-pyrazole-3-carboxamide.

Embodiment 199

A compound according to embodiment 1 or a pharmaceutically acceptable salt thereof, wherein the compound is (S)-5-methyl-1-(1-(4-((1-methylpyrrolidin-3-yl)methyl)benzyl)-1H-indol-5-yl)-1H-pyrazole-3-carboxamide.

Embodiment 200

A compound according to embodiment 1 or a pharmaceutically acceptable salt thereof, wherein the compound is (R)-5-methyl-1-(1-(4-((1-methylpyrrolidin-3-yl)methyl)benzyl)-1H-indol-5-yl)-1H-pyrazole-3-carboxamide.

Embodiment 201

A compound according to embodiment 1 or a pharmaceutically acceptable salt thereof, wherein the compound is 5-methyl-1-(1-(4-((1-methylazetidin-3-yl)methyl)benzyl)-1H-indol-5-yl)-1H-pyrazole-3-carboxamide.

Embodiment 202

A compound according to embodiment 1 or a pharmaceutically acceptable salt thereof, wherein the compound is 5-methyl-1-(1-(4-((1R,5S)-3-methyl-3-azabicyclo[3.1.0]hexan-1-yl)benzyl)-1H-indol-5-yl)-1H-pyrazole-3-carboxamide.

Embodiment 203

A compound according to embodiment 1 or a pharmaceutically acceptable salt thereof, wherein the compound is 1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide.

Embodiment 204

A compound according to embodiment 1 or a pharmaceutically acceptable salt thereof, wherein the compound is (S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide.

Embodiment 205

A compound according to embodiment 1 or a pharmaceutically acceptable salt thereof, wherein the compound is (R)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide.

Embodiment 206

A compound according to embodiment 1 or a pharmaceutically acceptable salt thereof, wherein the compound is 5-methyl-1-(1-((4'-((4-methylpiperazin-1-yl)methyl)-[1,1'-biphenyl]-4-yl)methyl)-1H-indol-5-yl)-1H-pyrazole-3-carboxamide.

Embodiment 207

A compound according to embodiment 1 or a pharmaceutically acceptable salt thereof, wherein is

49

5-methyl-1-(1-((4'-(piperazin-1-ylmethyl)-[1,1'-biphenyl]-4-yl)methyl)-1H-indol-5-yl)-1H-pyrazole-3-carboxamide.

Embodiment 208

A compound according to embodiment 1 or a pharmaceutically acceptable salt thereof, wherein the compound is 5-methyl-1-(1-((4'-(4-methylpiperazine-1-carbonyl)-[1,1'-biphenyl]-4-yl)methyl)-1H-indol-5-yl)-1H-pyrazole-3-carboxamide.

Embodiment 209

A compound according to embodiment 1 or a pharmaceutically acceptable salt thereof, wherein the compound is an enantiomer of 5-methyl-1-(1-(4-((1-methylpyrrolidin-3-yl)amino)benzyl)-1H-indol-5-yl)-1H-pyrazole-3-carboxamide.

Embodiment 210

A compound according to embodiment 1 or a pharmaceutically acceptable salt thereof, wherein the compound is another enantiomer of 5-methyl-1-(1-(4-((1-methylpyrrolidin-3-yl)amino)benzyl)-1H-indol-5-yl)-1H-pyrazole-3-carboxamide.

Embodiment 211

A compound according to embodiment 1 or a pharmaceutically acceptable salt thereof, wherein the compound is another enantiomer of (S)-5-methyl-1-(1-(4-((1-methylpyrrolidin-3-yl)amino)benzyl)-1H-indol-5-yl)-1H-pyrazole-3-carboxamide.

Embodiment 212

A compound according to embodiment 1 or a pharmaceutically acceptable salt thereof, wherein the compound is another enantiomer of (R)-5-methyl-1-(1-(4-((1-methylpyrrolidin-3-yl)amino)benzyl)-1H-indol-5-yl)-1H-pyrazole-3-carboxamide.

Embodiment 213

A compound according to embodiment 1 or a pharmaceutically acceptable salt thereof, wherein the compound is 1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide.

Embodiment 214

A compound according to embodiment 1 or a pharmaceutically acceptable salt thereof, wherein the compound is 5-methyl-1-(1-(4-((3aR,5r,6aS)-octahydrocyclopenta[c]pyrrol-5-yl)benzyl)-1H-indol-5-yl)-1H-pyrazole-3-carboxamide.

Embodiment 215

A compound according to embodiment 1 or a pharmaceutically acceptable salt thereof, wherein the compound is 1-(1-(4-((3aR,5r,6aS)-2-(cyclopropylmethyl)octahydrocyclopenta[c]pyrrol-5-yl)benzyl)-1H-indol-5-yl)-5-methyl-1H-pyrazole-3-carboxamide.

50

Embodiment 216

A compound according to embodiment 1 or a pharmaceutically acceptable salt thereof, wherein the compound is 5-methyl-1-(1-(4-((3aR,5r,6aS)-2-(methylsulfonyl)octahydrocyclopenta[c]pyrrol-5-yl)benzyl)-1H-indol-5-yl)-1H-pyrazole-3-carboxamide.

Embodiment 217

A compound according to embodiment 1 or a pharmaceutically acceptable salt thereof, wherein the compound is 5-methyl-1-(1-(4-((3aR,5r,6aS)-2-(2-(methylsulfonyl)ethyl)octahydrocyclopenta[c]pyrrol-5-yl)benzyl)-1H-indol-5-yl)-1H-pyrazole-3-carboxamide.

Embodiment 218

A compound according to embodiment 1 or a pharmaceutically acceptable salt thereof, wherein the compound is 5-methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide.

Embodiment 219

A compound according to any one of embodiments 1-218. In this embodiment, the compound is present in its non-salt form.

Embodiment 220

A pharmaceutical composition comprising a therapeutically effective amount of a compound according to any one of embodiments 1-219 or a pharmaceutically acceptable salt thereof, and one or more pharmaceutically acceptable carriers.

Embodiment 221

A pharmaceutical composition comprising a compound according to any one of embodiments 1-219 or a pharmaceutically acceptable salt thereof, and one or more pharmaceutically acceptable carriers.

Embodiment 222

A method of activating a growth factor pathway in a subject in need thereof, the method comprising administering to the subject a therapeutically effective amount of a compound of any one of embodiments 1-219 or a pharmaceutically acceptable salt thereof, or a pharmaceutical composition of embodiment 220 or 221.

Embodiment 223

A method of embodiment 222, wherein the growth factor pathway comprises the PI3K/Akt/mTOR pathway.

Embodiment 224

A method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound of any one of embodiments 1-219 or a pharmaceutically acceptable salt thereof, or a pharmaceutical composition of embodiment 220 or 221.

Embodiment 225

A method of embodiment 224, wherein the method comprises promoting wound healing.

Embodiment 226

A method of embodiment 225, wherein the method comprises promoting healing of a chronic wound.

Embodiment 227

A method of embodiment 226, wherein the chronic wound is a vascular ulcer.

Embodiment 228

A method of embodiment 226, wherein the chronic wound is a diabetic ulcer.

Embodiment 229

A method of embodiment 226, wherein the chronic wound is a pressure ulcer.

Embodiment 230

A method of embodiment 224, wherein the method comprises promoting tissue repair.

Embodiment 231

A method of embodiment 224, wherein the method comprises treating hearing loss.

Embodiment 232

A method of embodiment 224, wherein the method comprises treating skeletal muscle loss.

Embodiment 233

A method of embodiment 224, wherein the method comprises treating organ degeneration.

Embodiment 234

A method of embodiment 224, wherein the method comprises treating tissue damage.

Embodiment 235

A method of embodiment 224, wherein the method comprises treating neurodegeneration.

Embodiment 236

A method of embodiment 224, wherein the method comprises treating muscular atrophy.

Embodiment 237

A compound of any one of embodiments 1-219 or a pharmaceutically acceptable salt thereof, or a pharmaceutical composition of embodiment 220 or 221, for use in activating a growth factor pathway in a subject in need thereof.

Embodiment 238

A compound, pharmaceutically acceptable salt thereof, or pharmaceutical composition of embodiment 237, wherein the growth factor pathway comprises the PI3K/Akt/mTOR pathway.

Embodiment 239

A compound of any one of embodiments 1-219 or a pharmaceutically acceptable salt thereof, or a pharmaceutical composition of embodiment 220 or 221, for use in promoting wound healing, promoting tissue repair, or treating hearing loss, skeletal muscle loss, organ degeneration, tissue damage, neurodegeneration, or muscular atrophy in a subject in need thereof.

Embodiment 240

A compound, pharmaceutically acceptable salt thereof, or pharmaceutical composition of embodiment 239, for use in promoting wound healing.

Embodiment 241

A compound, pharmaceutically acceptable salt thereof, or pharmaceutical composition of embodiment 240, wherein promoting wound healing comprises promoting healing of a chronic wound.

Embodiment 242

A compound, pharmaceutically acceptable salt thereof, or pharmaceutical composition of embodiment 241, wherein the chronic wound is a vascular ulcer.

Embodiment 243

A compound, pharmaceutically acceptable salt thereof, or pharmaceutical composition of embodiment 241, wherein the chronic wound is a diabetic ulcer.

Embodiment 244

A compound, pharmaceutically acceptable salt thereof, or pharmaceutical composition of embodiment 241, wherein the chronic wound is a pressure ulcer.

Embodiment 245

A compound, pharmaceutically acceptable salt thereof, or pharmaceutical composition of embodiment 239, for use in promoting tissue repair.

Embodiment 246

A compound, pharmaceutically acceptable salt thereof, or pharmaceutical composition of embodiment 239, for use in treating hearing loss.

Embodiment 247

A compound, pharmaceutically acceptable salt thereof, or pharmaceutical composition of embodiment 239, for use in treating skeletal muscle loss.

Embodiment 248

A compound, pharmaceutically acceptable salt thereof, or pharmaceutical composition of embodiment 239, for use in treating organ degeneration.

Embodiment 249

A compound, pharmaceutically acceptable salt thereof, or pharmaceutical composition of embodiment 239, for use in treating tissue damage.

Embodiment 250

A compound, pharmaceutically acceptable salt thereof, or pharmaceutical composition of embodiment 239, for use in treating neurodegeneration.

Embodiment 251

A compound, pharmaceutically acceptable salt thereof, or pharmaceutical composition of embodiment 239, for use in treating muscular atrophy.

Embodiment 252

Use of a compound of any one of embodiments 1-219 or a pharmaceutically acceptable salt thereof, or a pharmaceutical composition of embodiment 220 or 221, for the manufacture of a medicament for activating a growth factor pathway in a subject in need thereof.

Embodiment 253

Use of embodiment 252, wherein the growth factor pathway comprises the PI3K/Akt/mTOR pathway.

Embodiment 254

Use of a compound of any one of embodiments 1-219 or a pharmaceutically acceptable salt thereof, or a pharmaceutical composition of embodiment 220 or 221, for the manufacture of a medicament for promoting wound healing, promoting tissue repair, or treating hearing loss, skeletal muscle loss, organ degeneration, tissue damage, neurodegeneration, or muscular atrophy in a subject in need thereof.

Embodiment 255

Use of embodiment 254, wherein the medicament is for promoting wound healing.

Embodiment 256

Use of embodiment 255, wherein promoting wound healing comprises promoting healing of a chronic wound.

Embodiment 257

Use of embodiment 256, wherein the chronic wound is a vascular ulcer.

Embodiment 258

Use of embodiment 256, wherein the chronic wound is a diabetic ulcer.

Embodiment 259

Use of embodiment 256, wherein the chronic wound is a pressure ulcer.

Embodiment 260

Use of embodiment 254, wherein the medicament is for promoting tissue repair.

Embodiment 261

Use of embodiment 254, wherein the medicament is for treating hearing loss.

Embodiment 262

Use of embodiment 254, wherein the medicament is for treating skeletal muscle loss.

Embodiment 263

Use of embodiment 254, wherein the medicament is for treating organ degeneration, tissue damage, neurodegeneration, or muscular atrophy.

Embodiment 264

Use of embodiment 254, wherein the medicament is for treating tissue damage.

Embodiment 265

Use of embodiment 254, wherein the medicament is for treating neurodegeneration.

Embodiment 266

Use of embodiment 254, wherein the medicament is for treating muscular atrophy.

Embodiment 267

A pharmaceutical combination comprising a therapeutically effective amount of a compound according to any one of embodiments 1-219 or a pharmaceutically acceptable salt thereof, and at least one other therapeutic agent.

Embodiment 268

A pharmaceutical combination comprising a compound according to any one of embodiments 1-219 or a pharmaceutically acceptable salt thereof, and at least one other therapeutic agent.

Embodiment 269

A pharmaceutical combination according to embodiment 267 or 268, wherein the at least one other therapeutic agent comprises becaplermin (Regranex®).

Embodiment 270

A pharmaceutical composition according to embodiment 220 or 221, further comprising at least one other therapeutic agent.

Embodiment 271

A pharmaceutical composition according to embodiment 270, where the at least one other therapeutic agent comprises becaplermin (Regranex®).

Embodiment 272

A kit comprising a first pharmaceutical composition according to embodiment 220 or 221 and a second pharmaceutical composition comprising at least one other therapeutic agent.

Embodiment 273

A kit according to embodiment 272, wherein the at least one other therapeutic agent comprises becaplermin (Regranex®).

Embodiment 274

A method according to any one of embodiments 222-236, wherein the compound, pharmaceutically acceptable salt, or pharmaceutical composition is administered simultaneously with, or before or after, one or more other therapeutic agents.

Embodiment 275

A method according embodiment 274, wherein the one or more other therapeutic agents comprise becaplermin (Regranex®).

Embodiment 276

A compound, pharmaceutically acceptable salt thereof, or pharmaceutical composition of any one of embodiments 237-251, wherein the compound, pharmaceutically acceptable salt, or pharmaceutical composition is prepared for administration with at least one other therapeutic agent.

Embodiment 277

A compound, pharmaceutically acceptable salt thereof, or pharmaceutical composition of any one of embodiments 237-251, wherein the compound, pharmaceutically acceptable salt, or pharmaceutical composition is administered with at least one other therapeutic agent.

Embodiment 278

A compound, pharmaceutically acceptable salt thereof, or pharmaceutical composition of embodiment 276 or 277, wherein the at least one other therapeutic agent comprises becaplermin (Regranex®).

Embodiment 279

Use according to any one of embodiments 252-266, wherein the medicament is prepared for administration with at least one other therapeutic agent.

Embodiment 280

Use according to embodiment 279, wherein the at least one other therapeutic agent comprises becaplermin (Regranex®).

Isomeric Variants

Except where otherwise specified, the compounds disclosed herein include all stereoisomers (including diastereoisomers, enantiomers, and mixtures thereof), double-bond isomers, atropisomers, rotamers, tautomers, and isotopic variants of the specified compounds. The compounds can be present as a single stereoisomer (or double-bond isomer) or as a mixture thereof, for example as pure optical isomers, or as stereoisomer mixtures, such as racemates and diastereoisomer mixtures, depending on the number of stereocenters. Optically active (R)- and (S)-stereoisomers may be prepared using chiral synthons or chiral reagents, or resolved using conventional techniques.

Except where otherwise specified, each stereocenter (e.g., stereogenic carbon atom) of any compound disclosed herein may be present in a single configuration (e.g., (R)- or (S)-) or in a mixture of configurations ((R,S)—). Except where otherwise specified, each double bond of any compound disclosed herein may, if possible, be present in a single configuration (cis-(Z)- or trans-(E)-), or in a mixture of configurations.

Where a particular enantiomer is specified, a compound disclosed herein shall be understood to have at least 50% enantiomeric excess. In certain embodiments, a compound disclosed herein has at least 60% enantiomeric excess, at least 70% enantiomeric excess, at least 80% enantiomeric excess, at least 90% enantiomeric excess, at least 95% enantiomeric excess, or at least 99% enantiomeric excess.

Where a particular diastereomer is specified, a compound disclosed herein shall be understood to have at least 50% diastereomeric excess. In certain embodiments, a compound disclosed herein has at least 60% diastereomeric excess, at least 70% diastereomeric excess, at least 80% diastereomeric excess, at least 90% diastereomeric excess, at least 95% diastereomeric excess, or at least 99% diastereomeric excess.

Any mixtures of stereoisomers or double-bond isomers can be separated on the basis of the physicochemical differences of the constituents, into the pure or substantially pure isomers, for example, by chromatography and/or fractional crystallization. For example, mixtures of enantiomers can be resolved into their optical antipodes by known methods, e.g., by separation of the diastereomeric salts thereof, obtained with an optically active acid or base, and liberating the optically active acidic or basic compound. Suitable optically active acids include tartaric acid, dibenzoyl tartaric acid, diacetyl tartaric acid, di-O,O'-p-toluoyl tartaric acid, mandelic acid, malic acid and camphor-10-sulfonic acid. Racemic products can also be resolved by chiral chromatography, e.g., high pressure liquid chromatography (HPLC) using a chiral adsorbent.

Isotopic Variants

In the compounds disclosed herein, any atom not specifically designated as a particular isotope is meant to represent any isotope of that atom. Thus, unless otherwise specified, each compound disclosed herein includes both unlabeled forms as well as isotopically enriched forms of the compound.

Isotopes that can be incorporated into the compounds disclosed herein include, for example, isotopes of hydrogen, such as deuterium (D or $^2$H) and tritium ($^3$H). Other examples of isotopes that can be incorporated into compounds disclosed herein include isotopes of carbon, nitrogen, oxygen, fluorine, and chlorine, such as $^{11}$C, $^{13}$C, $^{14}$C $^{15}$N, $^{18}$F, and $^{36}$Cl, respectively. Accordingly it should be understood that the disclosure includes compounds that incorporate one or more of any of the aforementioned isotopes, including for example, radioactive isotopes, such as $^{3}$H and $^{14}$C, or those into which non-radioactive isotopes, such as $^{2}$H and $^{13}$C are present.

Isotopically-labeled compounds can generally be prepared by conventional techniques known to those skilled in the art or by processes analogous to those described in the accompanying Examples and Preparations using appropriate isotopically-labeled reagents.

Pharmaceutically Acceptable Salts

As used herein, the terms "salt" or "salts" refers to an acid addition or base addition salt of a compound disclosed herein. "Salts" include in particular "pharmaceutically acceptable salts". The term "pharmaceutically acceptable salts" refers to salts that retain the biological effectiveness and properties of the compounds disclosed herein and which typically are not biologically or otherwise undesirable. Many of the compounds disclosed herein are capable of forming acid addition salts by virtue of the presence of amino groups and other similar groups.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

For example, pharmaceutically acceptable acid addition salts of the compounds disclosed herein include acetate, ascorbate, adipate, aspartate, benzoate, besylate, bromide/hydrobromide, bicarbonate/carbonate, bisulfate/sulfate, camphorsulfonate, caprate, chloride/hydrochloride, chlorotheophyllonate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate and xinafoate salts.

Pharmaceutical Compositions

In another aspect, the present disclosure provides a pharmaceutical composition comprising a compound disclosed herein, or a pharmaceutically acceptable salt thereof, and one or more pharmaceutically acceptable carriers. In further embodiments, the pharmaceutical composition comprises at least two pharmaceutically acceptable carriers, such as those described herein.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

The pharmaceutical composition may contain a compound disclosed herein, or a pharmaceutically acceptable salt thereof in a therapeutically effective amount. As used herein, the term "therapeutically effective amount," when referring to a compound disclosed herein, or a pharmaceutically acceptable salt thereof, refers to an amount of the compound or salt that will elicit a biological or medical response in a subject, such as reduce or inhibit an enzyme or a protein activity, ameliorate certain symptoms, alleviate conditions, slow or delay disease progression, or prevent a disease. In one non-limiting embodiment, the term "therapeutically effective amount" refers to the amount of a compound disclosed herein, or a pharmaceutically acceptable salt thereof, that, when administered to a subject, is effective to activate a growth factor pathway, such as the PI3K/Akt/mTOR pathway.

The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions can be made up in a solid form (including, without limitation, capsules, tablets, pills, granules, powders or suppositories), or in a liquid form (including, without limitation, solutions, gels, suspensions or emulsions). Tablets may be either film coated or enteric coated according to methods known in the art.

Where the pharmaceutical compositions are tablets or gelatin capsules, the tablets or capsules comprise a compound disclosed herein, or a pharmaceutically acceptable salt thereof, and one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

The pharmaceutical composition can be in unit dosage containing about 1-1000 mg, or about 1-500 mg or about 1-250 mg or about 1-150 mg or about 0.5-100 mg, or about 1-50 mg of the compound disclosed herein, or an equivalent amount on a molar basis of a pharmaceutically acceptable salt thereof, for a subject of about 50-70 kg.

The therapeutically effective dosage of the compounds disclosed herein is dependent on a variety of factors, including the species, body weight, age and individual condition of the subject, the particular compound being administered, the route of administration, and the disorder or disease being treated. A physician, clinician or veterinarian of ordinary skill can readily determine the effective amount of the compounds disclosed herein.

Uses of Compounds Disclosed Herein

The compounds disclosed herein, and pharmaceutically acceptable salts thereof, exhibit valuable pharmacological properties, including as growth factor pathway activators. As indicated in the assays described in the Examples, the compounds disclosed herein activate the PI3K/Akt/mTOR pathway downstream of growth factor signaling. Accordingly, the compounds disclosed herein may be used for promoting wound healing (including the healing of chronic wounds, such as vascular ulcers, diabetic ulcers and pressure ulcers), promoting tissue repair, and treating hearing loss, skeletal muscle loss, organ degeneration, tissue damage, neurodegeneration, and muscular atrophy.

Thus, in a further aspect, the disclosure provides a method of activating a growth factor pathway in a subject in need thereof, comprising administering to the subject a therapeutically effective amount of a compound disclosed herein, or a pharmaceutically acceptable salt or pharmaceutical composition thereof. In certain embodiments, the growth factor pathway comprises the PI3K/AKT/mTOR pathway.

In a further aspect, the disclosure provides a method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound disclosed herein, or a pharmaceutically acceptable salt or pharmaceutical composition thereof.

In a further aspect, the disclosure provides a compound disclosed herein, or a pharmaceutically acceptable salt or pharmaceutical composition thereof, for use in activating a growth factor pathway in a subject in need thereof. In certain embodiments, the growth factor pathway comprises the PI3K/Akt/mTOR pathway.

In a further aspect, the disclosure provides a compound disclosed herein, or a pharmaceutically acceptable salt or pharmaceutical composition thereof, for use in promoting wound healing, promoting tissue repair, or treating hearing loss, skeletal muscle loss, organ degeneration, tissue damage, neurodegeneration, or muscular atrophy in a subject in need thereof.

In a further aspect, the disclosure provides the use of a compound disclosed herein, or a pharmaceutically acceptable salt or pharmaceutical composition thereof, for the manufacture of a medicament for activating a growth factor pathway in a subject in need thereof. In certain embodiments, the growth factor pathway comprises the PI3K/Akt/mTOR pathway.

In a further aspect, the disclosure provides the use of a compound disclosed herein, or a pharmaceutically acceptable salt or pharmaceutical composition thereof, for the manufacture of a medicament for promoting wound healing, promoting tissue repair, or treating hearing loss, skeletal muscle loss, organ degeneration, tissue damage, neurodegeneration, or muscular atrophy in a subject in need thereof.

As used herein, the term "subject" refers to a mammal, such as a primate (e.g., a human, male or female), dog, rabbit, guinea pig, pig, rat, or mouse, mice. In certain embodiments, the subject is a primate. In yet other embodiments, the subject is a human.

As used herein, the terms "treat", "treating" or "treatment," when referring to any disease or disorder, refer to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

Compounds described herein, once produced, can be characterized using a variety of assays known to those skilled in the art to determine whether the compounds have biological activity. For example, the molecules can be characterized by assays, including but not limited to those assays described below, to determine whether they have a predicted activity, e.g., activation or inhibition activity and/or specificity to a specific protein (e.g., Akt or forkhead box O family (FOXO) 3a (FoxO3a)).

In yet another aspect, the compounds described herein may be used for research (e.g., studying growth factor signaling pathways) and other non-therapeutic purposes.

Combination Therapy

The compounds disclosed herein, and pharmaceutically acceptable salts thereof, may be administered in combination with the standard of care for indications discussed herein. For example, when used for promoting the healing of diabetic ulcers, the compounds, and pharmaceutically acceptable salts thereof, may be administered as an adjunct to the standard of care treatment of diabetic ulcers, including without limitation debridement, infection control (e.g., antimicrobials), pressure relief, and application of an appropriate dressing. See, e.g., I. Kruse et al., *Evaluation and Treatment of Diabetic Foot Ulcers*, 24 Clinical Diabetes 91-93 (2006); Wounds International, *International Best Practice Guidelines: Wound Management in Diabetic Foot Ulcers* (2013) (available at www.woundsinternational.com).

The compounds disclosed herein, and pharmaceutically acceptable salts thereof, may be administered simultaneously with, or before or after, one or more other therapeutic agents. A compound disclosed herein, or a pharmaceutically acceptable salt thereof, may be administered separately, by the same or different route of administration, or together in the same pharmaceutical composition as the other therapeutic agent. The other therapeutic agent may be, for example, a chemical compound, peptide, antibody, antibody fragment or nucleic acid, which is therapeutically active or enhances the therapeutic activity when administered to a patient in combination with a compound disclosed herein, or a pharmaceutically acceptable salt thereof.

Other therapeutic agents useful for administration in combination with the compounds disclosed herein, and pharmaceutically acceptable salts thereof, include without limitation becaplermin (Regranex®).

In one embodiment, the disclosure provides a combination comprising a compound disclosed herein, or a pharmaceutically acceptable salt thereof, and at least one other therapeutic agent as a combined preparation for simultaneous, separate or sequential use in therapy. As used herein, the term "combination" means a fixed combination in one dosage unit form, or a combined administration where a compound disclosed herein and a combination partner may be administered independently at the same time or separately within time intervals that especially allow that the combination partners show a cooperative, e.g. synergistic effect. The single components may be packaged together in a kit or separately. One or both of the components (e.g., powders or liquids) may be reconstituted or diluted to a desired dose prior to administration.

In one embodiment, the disclosure provides a pharmaceutical composition comprising a compound disclosed herein, or a pharmaceutically acceptable salt thereof, and at least one other therapeutic agent. Optionally, the pharmaceutical composition may comprise a pharmaceutically acceptable carrier, as described above.

In one embodiment, the disclosure provides a kit comprising two or more separate pharmaceutical compositions, at least one of which contains a compound disclosed herein, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit may be used for administering different dosage forms, for example, oral and parenteral, for administering the separate compositions at different dosage intervals, or for titrating the separate compositions against one another. To assist compliance, the kit typically comprises directions for administration.

In the combination therapies, the compound disclosed herein and the other therapeutic agent may be manufactured and/or formulated by the same or different manufacturers. Moreover, the compound disclosed herein and the other therapeutic may be brought together into a combination therapy: (i) prior to release of the combination product to physicians (e.g. in the case of a kit comprising the compound disclosed herein and the other therapeutic agent); (ii) by the physician themselves (or under the guidance of the physician) shortly before administration; (iii) in the patient themselves, e.g. during sequential administration of the compound disclosed herein and the other therapeutic agent.

Accordingly, the disclosure provides a method of activating a growth factor pathway, promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound disclosed herein, or a pharmaceutically acceptable salt thereof, wherein the compound disclosed herein, or a pharmaceutically acceptable salt thereof, is administered simultaneously with, or before or after, one or more other therapeutic agents.

The disclosure also provides the use of a compound disclosed herein, or a pharmaceutically acceptable salt thereof, for the manufacture of a medicament for modulating growth factor pathway signaling in a subject in need thereof, wherein the medicament is prepared for administration with another therapeutic agent.

The disclosure also provides a compound disclosed herein, or a pharmaceutically acceptable salt or pharmaceutical composition thereof, for use in activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the compound disclosed herein, or pharmaceutically acceptable salt or pharmaceutical composition thereof, is prepared for administration with at least one other therapeutic agent. The disclosure also provides a compound disclosed herein, or a pharmaceutically acceptable salt or pharmaceutical composition thereof, for use in activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the compound disclosed herein, or pharmaceutically acceptable salt or pharmaceutical composition thereof, is administered with at least one other therapeutic agent.

The disclosure also provides the use of a compound disclosed herein, or a pharmaceutically acceptable salt or pharmaceutical composition thereof, for the manufacture of a medicament for activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the medicament is prepared for administration with at least one other therapeutic agent.

Preparation of Compounds

The following reaction schemes illustrate methods to make compounds disclosed herein. It is understood that one skilled in the art would be able to make these compounds by similar methods or by methods known to one skilled in the art. In general, starting components and reagents may be obtained from commercial vendors such as Sigma Aldrich, Lancaster Synthesis, Inc., Maybridge, Matrix Scientific, TCI, Fluorochem USA, Strem, or other commercial vendors, or may be synthesized according to procedures known to those skilled in the art.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes disclosed herein can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds disclosed herein can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 7th edition, John Wiley & Sons: New York, 2013; Greene, T. W., Wuts, P. G. M., Protective Groups in Organic Synthesis, 3rd edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds disclosed herein.

It will also be appreciated by those skilled in the art that the functional groups of intermediate compounds in the processes described below may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in T. G. M. Wuts et al., *Greene's Protective Groups in Organic Synthesis* (4th ed. 2006). The protecting group may also be a polymer resin, such as a Wang resin or a 2-chlorotrityl-chloride resin.

In general, pyrazole compounds of Formula (I) (X=CH), where $R_2$ is H, can be synthesized by following the general procedure described in General Scheme 1.

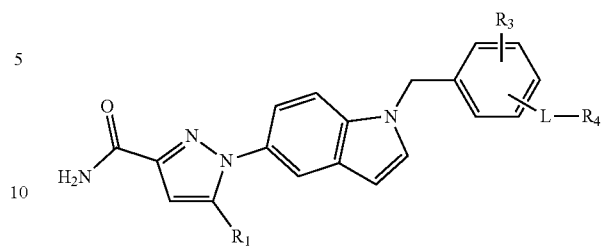

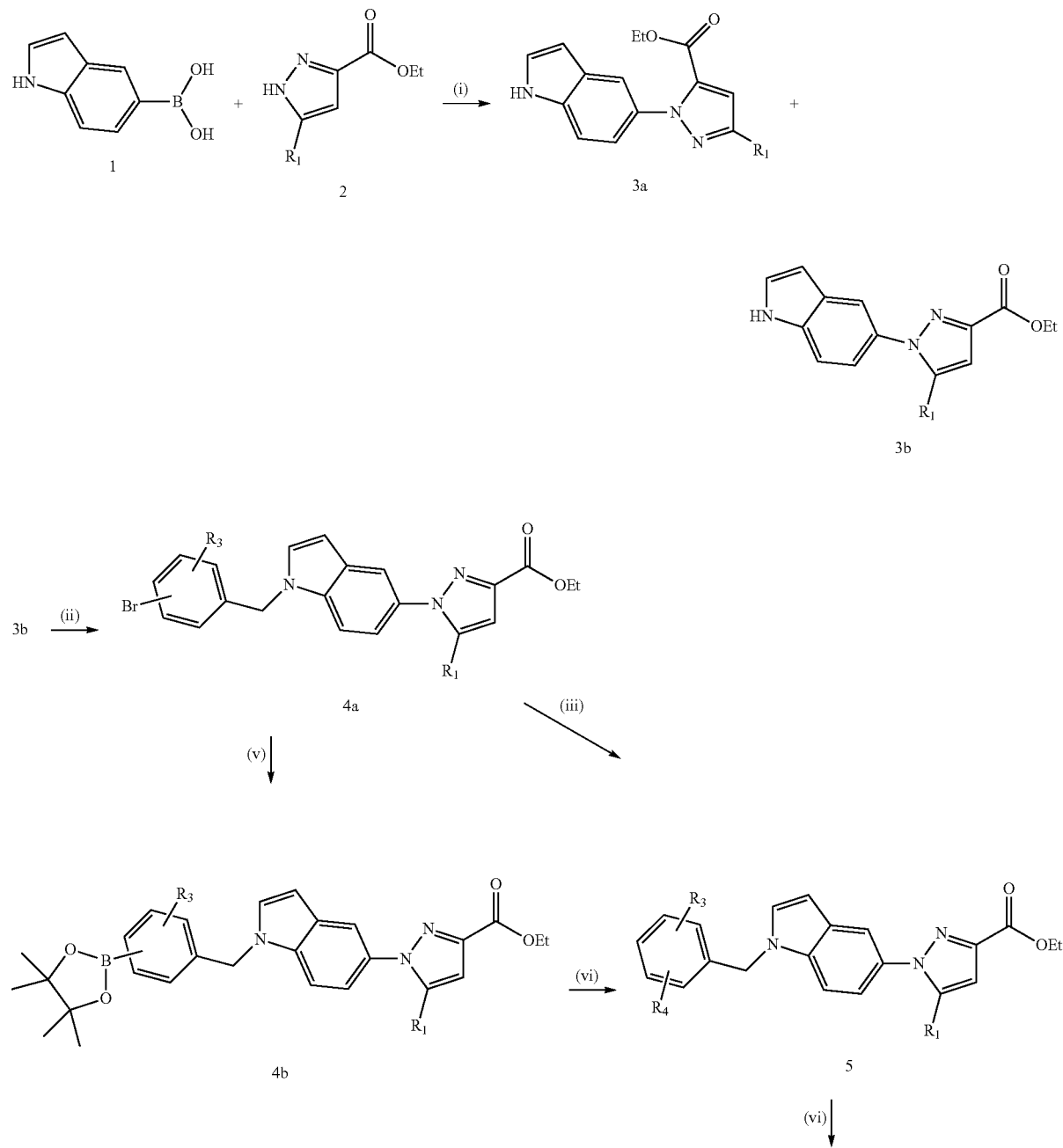

-continued

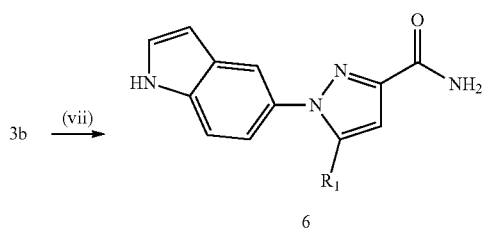

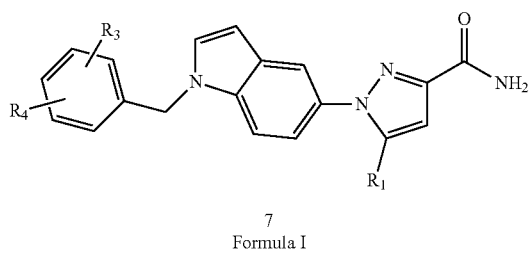

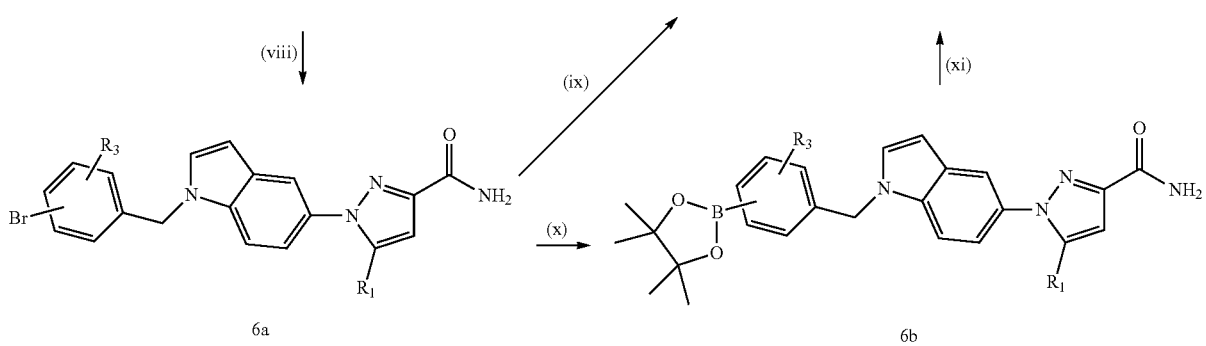

The starting materials for the synthesis described in General Scheme 1 are commercially available or can be prepared according to methods known to one skilled in the art or by methods disclosed herein. In general, the compounds are prepared as described in General Scheme 1 as follows:

In step (i), (1H-indol-5-yl)boronic acid (1) reacts in a Chan-Lam cross-coupling reaction with ethyl 1H-pyrazole-3-carboxylate (2) to provide indole intermediates (3a and 3b) as a mixture of regioisomers which can be separated by recrystallization.

In step (ii), N-alkylation of indole (3b) with a suitable bromomethyl bromobenzene derivative provides aryl bromide intermediate (4a).

In step (iii) a transition metal-mediated cross coupling reaction, such as a Suzuki reaction, between aryl bromide intermediate (4a) and a suitably substituted aryl or heteroaryl boronic acid or boronate ester ($R_4$—$B(OR)_2$), provides ester compound (5).

In step (iv), the ester (5) is then converted to the primary amide via ester hydrolysis followed by amide coupling to provide compound (7), the compound of Formula (I).

Alternatively, in step (v) aryl bromide intermediate (4a) can also be converted to the boronate ester (4b) via Miyaura borylation.

In step (vi), a transition metal-mediated cross coupling reaction, such as a Suzuki reaction, between boronate ester compound (4b) and a suitably substituted aryl or heteroaryl halide or triflate (e.g., $R_4$—Br) provides ester compound (5), which is then converted to compound (7), the compound of Formula (I) as described previously in connection with step (iv).

Alternatively, in step (vii), indole intermediate (3b) can be converted to the primary amide via ester hydrolysis followed by amide coupling to provide indole compound (6).

In step (viii), N-alkylation of indole (6) with a suitable bromomethyl bromobenzene derivative provides aryl bromide intermediate (6a).

In step (ix), a transition metal-mediated cross coupling reaction, such as a Suzuki reaction, between aryl bromide intermediate (6a) and a suitably substituted aryl or heteroaryl boronic acid or boronate ester ($R_4$—$B(OR)_2$), provides compound (7), the compound of Formula (I). Alternatively, a transition metal-mediated cross coupling reaction, such as a Buchwald N-arylation reaction, between halide compound (6a) and a suitable secondary amine compound ($R_4$—H), provides compound (7), the compound of Formula (I).

Alternatively, in step (x), aryl bromide intermediate (6a) can also be converted to the boronate ester (6b) via Miyaura borylation.

In step (xi), a transition metal-mediated cross coupling reaction, such as a Suzuki reaction, between boronate ester compound (6b) and a suitably substituted aryl or heteroaryl halide or triflate (e.g., $R_4$—Br) provides compound (7), the compound of Formula (I).

In general, triazole compounds of Formula (I) (X=N), where $R_2$ is H, can be synthesized by following the general procedure described in General Scheme 2.

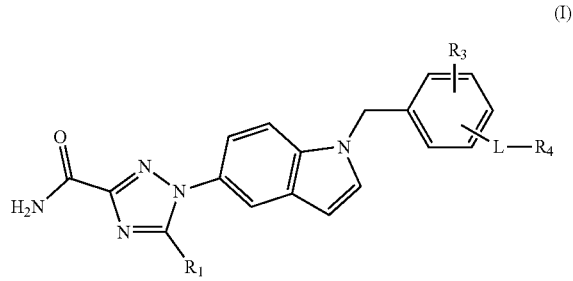

(I)

General Scheme 2. Synthesis of Triazole Compounds Of Formula (I; X = N, R$_2$ = H)

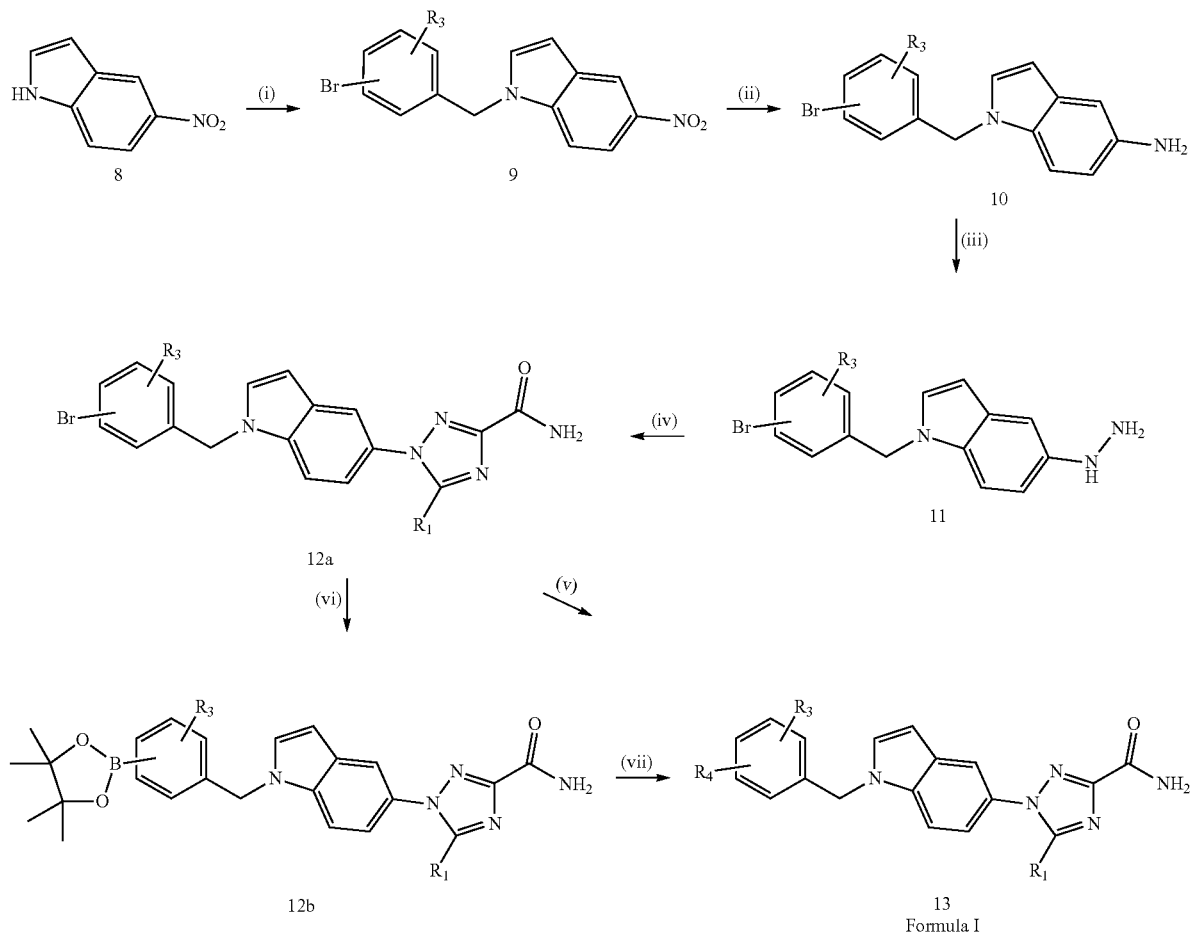

The starting materials for the synthesis described in General Scheme 2 are commercially available or can be prepared according to methods known to one skilled in the art or by methods disclosed herein. In general, the compounds are prepared as described in General Scheme 2 as follows:

In step (i), 5-nitro-1H-indole (8) is alkylated with a suitable bromomethyl bromobenzene derivative to provide aryl bromide intermediate (9).

In step (ii), reduction of the nitro group provides aniline compound (10).

In step (iii), hydrazine formation then provides compound (11).

In step (iv), compound (11) is treated with a suitably substituted diethyl amidomalonate (EtOC(O)CH(NHC(O)R$_1$)C(O)OEt), such as diethyl acetamidomalonate, followed by quenching with aqueous ammonia, to provide triazole (12a).

In step (v), a transition metal-mediated cross coupling reaction, such as a Suzuki reaction, between aryl bromide intermediate (12a) and a suitably substituted aryl or heteroaryl boronic acid or boronate ester (R$_4$—B(OR)$_2$), provides compound (13), the compound of Formula (I).

Alternatively, in step (vi), aryl bromide intermediate (12a) is converted to the boronate ester (12b) via Miyaura borylation.

In step (vii), a transition metal-mediated cross coupling reaction, such as a Suzuki reaction, between boronate ester compound (12b) and a suitably substituted aryl or heteroaryl halide or triflate (e.g., R$_4$—Br) provides compound (13), the compound of Formula (I).

In general, 3-substituted indoles of Formula (I), where R$_2$ is not H, can be synthesized by following the general procedure described in General Scheme 3.

(I)

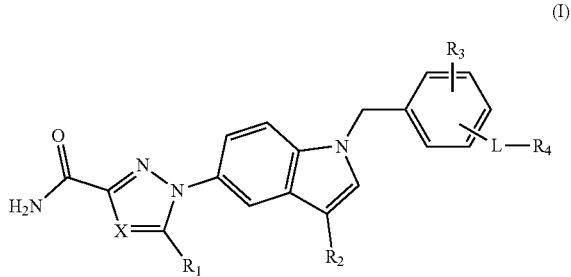

General Scheme 3. Synthesis of Compounds of Formula (I; $R_2 \neq H$)

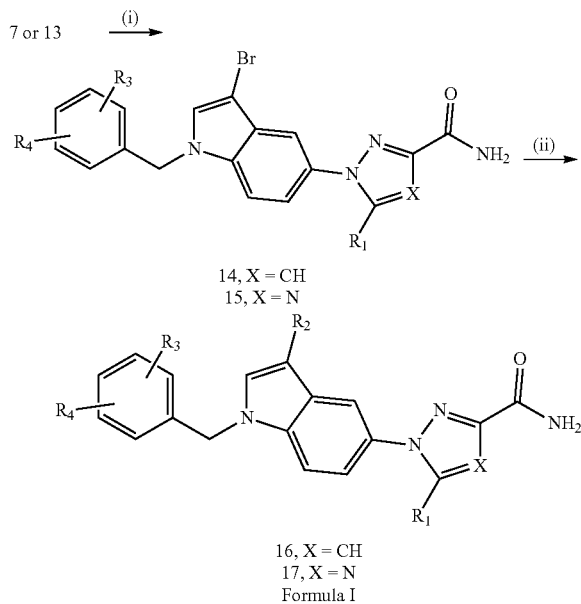

14, X = CH
15, X = N

16, X = CH
17, X = N
Formula I

The starting materials (7) and (13) for the synthesis described in General Scheme 3 are prepared as described in General Schemes 1 and 2, respectively. In general, the compounds are prepared as described in General Scheme 3 as follows:

In step (i) compound (7) or (13) is brominated with n-bromosuccinamide to provide the halide compound (14) or (15).

In step (ii), a transition metal-mediated cross coupling reaction, such as a Suzuki reaction, between halide compound (14) or (15) and a suitably substituted aryl or heteroaryl boronic acid or boronate ester ($R_2$—$B(OR)_2$) provides compound (16) or (17), the compound of Formula (I).

The disclosure further includes any variants of the processes described in General Schemes 1-3 in which an intermediate product obtainable at any stage thereof is used as starting material, and the remaining steps are carried out.

In the synthetic schemes and chemical structures described herein, compounds may be drawn with one particular configuration (e.g., with or without a particular stereoisomer indicated) for simplicity. Such particular configurations or lack thereof are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

EXAMPLES

General Conditions

The following examples are intended to illustrate the disclosure and are not to be construed as being limitations thereon. Temperatures are given in degrees Celsius. If not otherwise specified, all evaporations were performed under reduced pressure, typically between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized in the following examples are commercially available or can be produced by methods known to one of ordinary skill in the art.

Mass spectra were acquired on LC-MS, SFC-MS, or GC-MS systems using electrospray, chemical and electron impact ionization methods.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

Instrumentation

Liquid Chromatography-Mass Spectrometry (LCMS)

The following instrumentation and conditions were used for LCMS analysis:

| | |
|---|---|
| Pump | Waters AcQuity UPLC Binary Solvent Manager |
| Sample Manager | Waters AcQuity UPLC Sample Manager |
| Column Compartment | Waters AcQuity UPLC Column Manager |
| Detector | Waters AcQuity UPLC PDA |
| ELSD | Waters ELSD |
| Mass Spec | Waters SQD |
| Eluent A1 | 0.1% Formic Acid in Water |
| Eluent B1 | 0.1% Formic Acid in Acetonitrile |
| Eluent A2 | 5 mM Ammonium Hydroxide in Water (0.05% TFA instead of Ammonium Hydroxide on CA_SQD) |
| Eluent B2 | 5 mM Ammonium Hydroxide in Acetonitrile (0.05% TFA instead of Ammonium Hydroxide on CA_SQD) |
| Columns | AcQuity UPLC BEH C18 1.7 μm 2.1 × 30 mm |
| | AcQuity UPLC BEH C18 1.7 μm 2.1 × 50 mm |
| | AcQuity UPLC CSH C18 1.7 μm 2.1 × 50 mm |
| Column Temperature | 50° C. |

LCMS Condition A:

| | | | |
|---|---|---|---|
| Flow | | 1.0 mL/min | |
| Stop Time | | 5.20 min | |
| pH | | 2.6 | |
| Gradient | Time | % A (Eluent A1) | % B (Eluent B1) |
| | 0.00 | 98 | 2 |
| | 4.40 | 2 | 98 |

-continued

| | | |
|---|---|---|
| 5.15 | 2 | 98 |
| 5.19 | 98 | 2 |

| | |
|---|---|
| Column | AcQuity UPLC BEH C18 1.7 μm 2.1 × 50 mm |
| Column Temperature | 50° C. |
| UV | 210-400 nm |
| Mass Range | 120-1600 m/z SQD — 120-1250 m/z QDa |
| Scan Time | 0.3 sec |

LCMS Condition B:

| | |
|---|---|
| Flow | 1.0 mL/min |
| Stop Time | 2.00 min |
| pH | 2.6 |

| Gradient | Time | % A (Eluent A1) | % B (Eluent B1) |
|---|---|---|---|
| | 0.00 | 98 | 2 |
| | 0.10 | 98 | 2 |
| | 1.50 | 2 | 98 |
| | 1.80 | 2 | 98 |
| | 1.90 | 98 | 2 |
| | 2.00 | 98 | 2 |

| | |
|---|---|
| Column | AcQuity UPLC BEH C18 1.7 μm 2.1 × 30 mm |
| Column Temperature | 50° C. |
| UV | 210-400 nm |
| Mass Range | 120-1600 m/z SQD — 120-1250 m/z QDa |
| Scan Time | 0.3 sec |

LCMS Condition Q:

Waters Acquity UPLC system
Waters Acquity UPLC BEH C18 1.7 um, 2.1 × 30 mm
(Part# 186002349)
Flow rate: 1 mL/min
Temperature: 55° C. (column temp)
Mobile phase compositions:

0.05% formic acid in water
0.04% formic acid in methanol

| Gradient | Time | % A (Eluent A) | % B (Eluent B) |
|---|---|---|---|
| | 0.00 | 95 | 5 |
| | 0.10 | 95 | 5 |
| | 0.50 | 20 | 80 |
| | 0.60 | 5 | 95 |
| | 0.80 | 5 | 95 |
| | 0.90 | 95 | 5 |
| | 1.15 | 95 | 5 |

Abbreviations

Unless otherwise noted, or where the context dictates otherwise, the following abbreviations shall be understood to have the following meanings:

| Abbreviation | Meaning |
|---|---|
| First generation Xphos Precatalyst | (2-Dicyclohexylphosphino-2',4',6'-triisopropyl-1,1'-biphenyl)[2-(2-aminoethyl)phenyl)]palladium(II) chloride (CAS#1028206-56-5) |
| Second generation Xphos Precatalyst (aka Pd-Xphos G2) | Chloro(2-dicyclohexylphosphino-2',4',6'-triisopropyl-1,1'-biphenyl)[2-(2'-amino-1,1'-biphenyl)]palladium(II) (CAS# 1310584-14-5) |
| BrettPhos Pd $G_3$ | [(2-Di-cyclohexylphosphino-3,6-dimethoxy-2',4',6'-triisopropyl-1,1'-biphenyl)-2-(2-amino-1,1'-biphenyl)]palladium(II) methanesulfonate |
| $PdCl_2$(dppf).DCM (adduct) | CAS# 95464-05-4 |
| 10% Pd/C | Palladium on carbon: 10 wt. % loading (dry basis), matrix activated carbon, wet support, Degussa type E101 NE/W |
| OTf | trifluoromethanesulfonate |
| mm | Millimeters |
| mbar | Millibars |
| MS | Mass spectrometry |
| IR | Infrared (spectroscopy) |
| NMR | Nuclear magnetic resonance (spectroscopy) |
| LC-MS/LCMS | Liquid chromatography-mass spectrometry |
| SFC-MS | Supercritical Fluid Chromatography-mass spectrometry |
| GC-MS | Gas chromatography-mass spectrometry |
| MHz | Megahertz |
| ICON-NMR | Bruker NMR automation software |
| K | Kelvin |
| UPLC | Ultra Performance Liquid Chromatography |
| HPLC | High-performance liquid chromatography |
| PDA | Photodiode Array Detector |
| ELSD | Evaporative light scattering detector |
| SQD | Single Quadrupole Detector |
| mM | Millimolar |
| μM | Micromolar |
| TFA | Trifluoroacetic acid |
| BEH | Waters ® brand Ethylene Bridged Hybrid Silica column technology |
| CSH | Waters ® brand Charged Surface Hybrid Silica column technology |
| mL | Milliliters |
| min | Minute(s) |
| μm | Micrometers |

| Abbreviation | Meaning |
| --- | --- |
| UV | Ultraviolet |
| nm | Nanometers |
| QDa | Waters ® brand Single Quad Detector |
| m/z | Mass-to-charge ratio |
| sec | Seconds |
| THF | Tetrahydrofuran |
| DMSO | Dimethylsulfoxide |
| HPLC | High performance liquid chromatograph |
| ACN/MeCN | Acetonitrile |
| M | Molar |
| EtOAc | Ethyl acetate |
| SCX-BSA | Agilent BondElute SCX-Benzylsulfonic acid cartridge |
| MeOH | Methanol |
| EtOH | Ethanol |
| DCM | Dichloromethane |
| N | Normal (concentration) |
| LiHMDS | Lithium bis(trimethylsilyl)amide |
| Boc | Tert-butoxy carbonyl |
| h | Hours |
| mg | Milligrams |
| mmol | Millimoles |
| eq | Equivalents |
| g | Grams |
| $Et_2O$ | Diethyl ether |
| HATU | 1-[Bis(dimethylamino)methylene]-1H-1,2,3-triazolo[4,5-b]pyridinium 3-oxid hexafluorophosphate |
| DMF | N,N-dimethylformamide |
| PhMe | Toluene |
| DIPEA | Diisopropyl ethyl amine |
| TEA | Triethylamine |
| DEA | Diethylamine |
| SFC | Supercritical Fluid Chromatography |
| HBTU | (2-(1H-benzotriazol-1-yl)-1,1,3,3-tetramethyluronium hexafluorophosphate) |
| PTFE | Polytetrafluoroethylene |
| DMAP | 4-(N,N-dimethylamino)pyridine |
| BINAP | 2,2'-Bis(diphenylphosphino)-1,1'-binaphthyl |
| PhNTf | N-Phenyl-bis(trifluoromethanesulfonimide) |
| FCC | Flash Column Chromatography, normal phase |
| TLC | Thin layer chromatography |
| FBS | Fetal bovine serum |
| GFP | Green Fluorescent Protein |
| AKT | Protein Kinase B |
| $^1$H NMR | Proton nuclear magnetic resonance |
| RT | Room temperature |
| Rt | Retention time |
| psi | Pounds per square inch |
| IPA | Isopropanol |
| 4A | 4 Ångström |
| $AC_{50}$ | Concentration that results in 50% activation or inhibition |
| 9-BBN | 9-Borabicyclo[3.3.1]nonane |

General Methods

General Method I

Representative Procedure for Suzuki Coupling

A microwave vial was charged with aryl halide (1 equivalent), boronic ester (1.5 equivalents), potassium phosphate tribasic (3 equivalents), and 5:1 THF:Water (0.05 M in aryl halide) and the mixture was evacuated and filled with $N_2$ (3×). Then first generation XPhos precatalyst (0.1 equivalents) was added and the mixture was heated in the Biotage® Initiator microwave reactor at 120° C. for 40 min, cooled to ambient temperature, filtered through a 0.45 micron syringe filter and concentrated in vacuo. The crude product was taken up in 90:10 DMSO:Water and purified by preparative HPLC (ACN/Water+0.05% ammonium hydroxide modifier) to provide the desired product.

General Method II

Representative Procedure for Suzuki Coupling

A mixture of a 3-bromoindole intermediate (1 equivalent), boronic acid or ester (1.5-2 equivalents), potassium phosphate tribasic (3 equivalents) and second generation XPhos precatalyst (0.05 equivalents) in 5:1 dioxane/water (0.05 M in aryl halide) in a microwave vial was sealed and degassed via vacuum/nitrogen purge (3×). The microwave vial was then heated in a Biotage® Initiator microwave reactor at 120° C. for 45 min. The mixture was diluted with ethyl acetate and washed with water (3×), and brine (1×). The organic extracts were dried over magnesium sulfate, filtered, and concentrated in vacuo to afford the desired product.

General Method III

Representative Procedure for Suzuki Coupling

To a stirred solution of aryl boronate ester (1 equivalent) in THF:Water (5:1, 0.1M) was added halide or triflate (1.5 equivalents) and sodium carbonate (3 equivalents) and the mixture was evacuated and filled with $N_2$ (3×). Then tetrakis(triphenylphosphine)palladium(0) (0.1 equivalents) was added at ambient temperature. The suspension was again degassed with $N_2$, then sealed and heated at 50° C. for 2 h. The reaction mixture cooled to ambient temperature and diluted with excess EtOAc. The organic layer was washed with water (3×) and brine (3×), dried over anhydrous sodium sulfate and concentrated in vacuo. The crude material was purified by silica gel chromatography in EtOAc:Heptane (0-100%) to provide the desired product.

General Method IV

Representative Procedure for SCX-BSA Cartridge Purification

The crude material was taken up in MeOH and loaded onto the appropriate sized Agilent BondElute SCX-Benzenesulfonic acid cartridge, prewashed with 1:1 MeOH:DCM. The cartridge was then washed with excess 1:1 MeOH:DCM. Then the product was eluted in a 1:1 mixture of DCM:(7N $NH_3$ in MeOH). The basic eluent was concentrated under reduced pressure to afford the desired compound.

General Method V

Representative Procedure for Vinyl Triflate Formation

To ketone (1 equivalent) in THF (0.5 M) at −78° C. was added 1M LiHMDS in THF (1.1 equivalents) dropwise and the resulting solution was allowed to stir for 20 minutes at −78° C. Then 1,1,1-trifluoro-N-phenyl-N-((trifluoromethyl)sulfonyl)methanesulfonamide (1.1 equivalents) in THF (0.5 M) was added and the reaction was allowed to slowly warm to ambient temperature and stir for 18 h. The reaction was then concentrated in vacuo. The crude material was taken up in DCM and washed saturated aqueous ammonium chloride and brine, dried over sodium sulfate and concentrated in vacuo to the desired crude vinyl triflate.

General Method VI

Representative Procedure for N-Methylation

In a pressure vessel, amine (1 equivalent) was dissolved in MeOH (0.05 M), to which was added 37% aqueous formaldehyde (2 equivalents) followed by sodium triacetoxyborohydride (2 equivalents). The reaction mixture was stirred at ambient temperature for 5 min then purified by preparative HPLC to afford the desired N-methylamine.

General Method VII

Representative Procedure for Boc Deprotection with Trifluoroacetic Acid

The Boc protected amine (1 equivalent) was dissolved in DCM (0.2 M). Trifluoroacetic acid (20 equivalents) was added and the resulting mixture was stirred for 1 h at ambient temperature. The mixture was then concentrated and the resulting crude oil was taken up in MeOH and purified by SCX-BSA according to General Method IV to afford the desired amine.

Preparation of Intermediates

Preparation 1

Intermediate I: ethyl 1-(1H-indol-5-yl)-5-methyl-1H-pyrazole-3-carboxylate

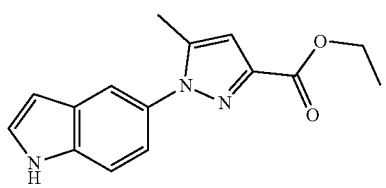 [SMILES: CCOC(=O)c1cc(C)n(-c2ccc3[nH]ccc3c2)n1]

Ethyl 5-methyl-1H-pyrazole-3-carboxylate (500 mg, 3.24 mmol, 1.0 eq), (1H-indol-5-yl)boronic acid (574 mg, 3.57 mmol, 1.1 eq), copper (II) acetate (884 mg, 4.86 mmol, 1.5 eq) and 4 Å molecular sieves were suspended in DCM (16.2 mL) in a vial containing a stir bar. Pyridine (0.525 mL, 5.3 mg, 6.49 mmol, 2.0 eq) was added to the stirring reaction mixture. The reaction was allowed to stir open to air for 42 h. The progress of the reaction was checked by LCMS. Upon completion, the reaction was filtered through celite, washing the filter cake with DCM (40 mL). The filtrate was transferred to a separatory funnel and the organic layer washed with saturated aqueous ammonium chloride (3×30 mL). The organic layer was passed through a phase separator, and excess water was discarded. The organic layer was concentrated under reduced pressure and purified through column chromatography (gradient 5-70% EtOAc in heptane) to afford ethyl 1-(1H-indol-5-yl)-5-methyl-1H-pyrazole-3-carboxylate (Intermediate I) (873 mg, 17%). $^1$H NMR (400 MHz, DMSO-d6) δ 11.40 (s, 1H), 7.67 (d, J=2.0 Hz, 1H), 7.53 (d, J=8.6 Hz, 1H), 7.51-7.48 (m, 1H), 7.18 (dd, J=8.6, 2.1 Hz, 1H), 6.73 (d, J=0.7 Hz, 1H), 6.54 (d, J=2.0 Hz, 1H), 4.28 (q, J=7.1 Hz, 2H), 2.30-2.24 (m, 3H), 1.29 (t, J=7.1 Hz, 3H).

Preparation 2

Intermediate II: Synthesis of 1-(1-(4-bromobenzyl)-1H-indol-5-yl)-5-methyl-1H-pyrazole-3-carboxamide

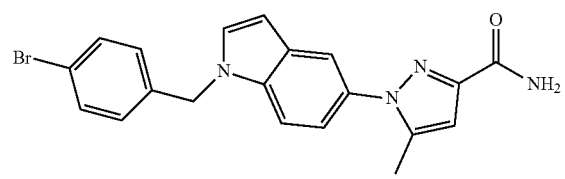 [SMILES: Cc1cc(C(N)=O)nn1-c1ccc2c(ccn2Cc2ccc(Br)cc2)c1]

Step 1: 1-(1H-indol-5-yl)-5-methyl-1H-pyrazole-3-carboxylic acid

Ethyl 1-(1H-indol-5-yl)-5-methyl-1H-pyrazole-3-carboxylate (Intermediate I) (6.8 g, 25.3 mmol, 1.0 eq) was suspended in THF (100 mL) and MeOH (25 mL). A 2M aqueous solution of LiOH (25.3 mL, 50.5 mmol, 2.0 eq) was added and the reaction was heated to 50° C. for 2 h. The reaction was then cooled to room temperature. LCMS analysis indicated that the reaction was not complete. An additional portion of solid LiOH mono-hydrate (5.3 g, 126 mmol, 5.0 eq) was added and the reaction was heated at 50° C. for an additional hour, at which time the reaction was complete by LCMS analysis. The reaction was allowed to cool to room temperature and was concentrated under reduced pressure. The crude reaction mixture was cooled in an ice bath, and 6N HCl was added until the pH of the mixture reached 2, and a thick white precipitate had formed. The precipitate was collected by vacuum filtration and washed with water. The solids were further washed with $Et_2O$ (2×50 mL). The resulting solids were dissolved in warm 3:1 EtOAc:EtOH and concentrated under reduced pressure. The solids were re-concentrated from an additional portion of 3:1 EtOAc:EtOH (100 mL), and the solids dried under hi-vacuum to afford 1-(1H-indol-5-yl)-5-methyl-1H-pyrazole-3-carboxylic acid, which was used in the subsequent step without further purification.

Step 2: 1-(1H-indol-5-yl)-5-methyl-1H-pyrazole-3-carboxamide

To a flask containing 1-(1H-indol-5-yl)-5-methyl-1H-pyrazole-3-carboxylic acid (7 g, 25.2 mmol, 87% pure, 1.0 eq) and a stir bar was added HATU (11.52 g, 30.3 mmol, 1.2 eq), DCM (100 mL) and DMF (20 mL). The suspension was stirred at room temperature, and a 0.5M solution of ammonia in 1,4-dioxane (86 mL, 42.9 mmol, 1.7 eq) was added followed by DIPEA (13.23 mL, 9.79 g, 76 mmol, 3.0 eq). The reaction was stirred at room temperature overnight, and the progress of the reaction was monitored by LCMS. The reaction was quenched with water to dissolve the solids. The reaction mixture was partitioned between a 1M aqueous citric acid solution (100 mL) and EtOAc (200 mL) and transferred to a separatory funnel. The layers were separated and the organic layer washed with a 1:1 mixture of a 1M aqueous citric acid solution and a 20% aqueous NaCl solution. The combined aqueous layers were back extracted with EtOAc (250 mL). The combined organic layers were washed with a 20% aqueous NaCl solution (250 mL), dried over sodium sulfate and filtered. The filtrate was concentrated to a volume of ~200 mL at which point a small amount of solid had precipitated. The mixture was stirred at room temperature overnight at which point additional solids had precipitated. The mixture was cooled in an ice bath, and heptane (100 mL) was added dropwise. The solids were collected by vacuum filtration, washed with heptane and $Et_2O$ and dried under hi-vacuum overnight to afford 1-(1H-indol-5-yl)-5-methyl-1H-pyrazole-3-carboxamide, which was used in the subsequent step without further purification.

Step 3: 1-(1-(4-bromobenzyl)-1H-indol-5-yl)-5-methyl-1H-pyrazole-3-carboxamide 1-(1H-indol-5-yl)-5-methyl-1H-pyrazole-3-carboxamide (3.7 g, 15.2 mmol, 1.0 eq) was dissolved in DMF (51 mL) in a flask containing a stir bar. The solution was cooled in an ice bath, and potassium tert-butoxide (1.9 g, 16.7 mmol, 1.1 eq) was added to the stirring solution portionwise over 5 minutes. The reaction was allowed to warm to room temperature and was stirred at room temperature for 40 minutes. The reaction was cooled in an ice bath and 1-bromo-4-(bromomethyl)benzene (3.8 g, 15.2 mmol, 1.0 eq) was added in one portion. The reaction was allowed to warm to room temperature and was stirred overnight. The reaction was quenched with water (100 mL), diluted with EtOAc (200 mL) and transferred to a separatory funnel. The layers were separated and the aqueous layer extracted with EtOAc (2×100 mL). The combined organic layers were dried over sodium sulfate, filtered and concentrated under reduced pressure at 40° C. to remove DMF. The crude material was dried at 40° C. under hi-vacuum overnight and was then purified through column chromatography (gradient 0-5% MeOH in DCM). Fractions containing the product were concentrated under reduced pressure. The resulting solids were suspended in heptane, sonicated for 10 min. and concentrated under reduced pressure (×3). The resulting solids were dried under hi-vacuum overnight to afford 1-(1-(4-bromobenzyl)-1H-indol-5-yl)-5-methyl-1H-pyrazole-3-carboxamide (Intermediate II) (4.8 g, 73%). $^1$H NMR (400 MHz, DMSO-d6) δ 7.70 (d, J=2.0 Hz, 1H), 7.66 (d, J=3.2 Hz, 1H), 7.57 (d, J=8.8 Hz, 1H), 7.55-7.50 (m, 2H), 7.44 (s, 1H), 7.23 (dd, J=8.7, 2.1 Hz, 1H), 7.20-7.15 (m, 3H), 6.60 (d, J=3.1 Hz, 1H), 6.59 (d, J=0.9 Hz, 1H), 5.48 (s, 2H), 2.26 (s, 3H).

Preparation 3

Intermediate III: 5-methyl-1-(1-(4-(4,4,5,5-tetramethyl-1,3,2-dioxaborolan-2-yl)benzyl)-1H-indol-5-yl)-1H-pyrazole-3-carboxamide

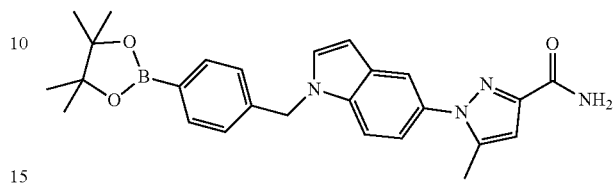

An oven-dried vial containing a stir bar was charged with 1-(1-(4-bromobenzyl)-1H-indol-5-yl)-5-methyl-1H-pyrazole-3-carboxamide (Intermediate II) (1.58 g, 3.9 mmol, 1.0 eq), $PdCl_2$(dppf) (283 mg, 0.39 mmol, 0.1 eq), bis(pinacolato)diboron (2.95 g, 11.6 mmol, 3.0 eq) and potassium acetate (2.28 g, 23.2 mmol, 6.0 eq). The vial was sealed and evacuated under hi-vacuum and backfilled with $N_2$ (×3). Dry, degased 1,4-dioxane (15.5 mL) was added, and the reaction was heated at 100° C. for 1 h. The reaction was allowed the cool to room temperature then filtered through celite. The filter cake was washed with EtOAc and the filtrate was concentrated under reduced pressure. The crude material was adsorbed onto celite and purified by column chromatography (gradient 2-10% MeOH in DCM) to afford 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) (1.6 g, 92%). $^1$H NMR (400 MHz, DMSO-d6) δ 7.70 (d, J=2.1 Hz, 1H), 7.65 (d, J=3.1 Hz, 1H), 7.62 (d, J=8.1 Hz, 2H), 7.52 (d, J=8.7 Hz, 1H), 7.44 (s, 1H), 7.26-7.19 (m, 3H), 7.18 (s, 1H), 6.60 (dd, J=3.2, 0.8 Hz, 1H), 6.58 (d, J=0.9 Hz, 1H), 5.52 (s, 2H), 2.26 (d, J=0.8 Hz, 3H), 1.26 (s, 12H).

Preparation 4

Intermediate IV: 1-(3-bromo-1-((4'-(methylsulfonyl)-[1,1'-biphenyl]-4-yl)methyl)-1H-indol-5-yl)-5-methyl-1H-pyrazole-3-carboxamide

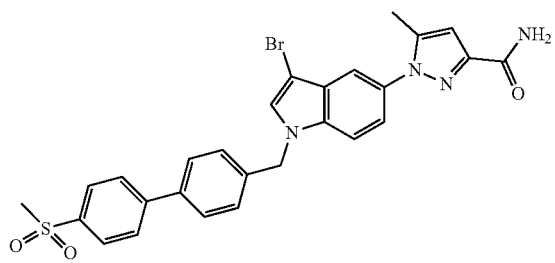 [SMILES: Cc1cc(C(N)=O)nn1-c1ccc2c(c1)c(Br)cn2Cc1ccc(-c2ccc(S(C)(=O)=O)cc2)cc1]

Step 1: 5-methyl-1-(1-((4'-(methylsulfonyl)-[1,1'-biphenyl]-4-yl)methyl)-1H-indol-5-yl)-1H-pyrazole-3-carboxamide A microwave vial containing a stir bar was charged with Pd-Xphos G2 (63.4 mg, 0.09 mmol, 0.1 eq), potassium phosphate tribasic (545 mg, 2.6 mmol, 3.0 eq) and (4-(methylsulfonyl)phenyl)boronic acid (257 mg, 1.3 mmol, 1.5 eq)

and 1-(1-(4-bromobenzyl)-1H-indol-5-yl)-5-methyl-1H-pyrazole-3-carboxamide (Intermediate II) (350 mg, 0.86 mmol, 1.0 eq). The vial was sealed and evacuated under hi-vacuum and then backfilled with N₂. This procedure was repeated 3 times. Degased 1,4-dioxane (14 mL) and degased water (2.9 mL) were added via syringe and the reaction was heated in the microwave at 120° C. for 40 minutes. The reaction was analyzed by LCMS, and there was no starting material apparent. The reaction was transferred to a separatory funnel and diluted with EtOAc (100 mL). The organic phase was washed water (2×10 mL) and brine (1×10 mL), dried over MgSO₄, filtered and concentrated onto celite. Purification by column chromatography (gradient 0-5% MeOH in DCM) afforded 5-methyl-1-(1-((4'-(methylsulfonyl)-[1,1'-biphenyl]-4-yl)methyl)-1H-indol-5-yl)-1H-pyrazole-3-carboxamide (280 mg, Yield 66%). ¹H NMR (400 MHz, Acetone-d6) δ 8.05-7.97 (m, 2H), 7.94-7.88 (m, 2H), 7.74 (dt, J=7.3, 1.8 Hz, 3H), 7.67-7.59 (m, 2H), 7.40 (d, J=8.5 Hz, 2H), 7.27 (dd, J=8.7, 2.0 Hz, 1H), 6.69 (dd, J=3.2, 0.8 Hz, 1H), 6.60 (d, J=0.7 Hz, 1H), 5.65 (s, 2H), 3.15 (s, 3H), 2.32 (d, J=0.7 Hz, 3H).

Step 2: 1-(3-bromo-1-((4'-(methylsulfonyl)-[1,1'-biphenyl]-4-yl)methyl)-1H-indol-5-yl)-5-methyl-1H-pyrazole-3-carboxamide 5-methyl-1-(1-((4'-(methylsulfonyl)-[1,1'-biphenyl]-4-yl)methyl)-1H-indol-5-yl)-1H-pyrazole-3-carboxamide (295 mg, 0.61 mmol, 1.0 eq) was dissolved in anhydrous DMF (3 mL). The solution was cooled in an ice bath and N-bromo-succinimide (114 mg, 0.64 mmol, 1.05 eq) was added in one portion. The reaction was stirred for 1 h. LCMS analysis indicated that there was no starting material present. The reaction was quenched with a saturated aqueous solution of sodium thiosulfate (10 mL) and transferred to a separatory funnel. The solution was diluted with EtOAc (75 mL), the layers were separated, and the organic phase was washed with a saturated aqueous solution of sodium thiosulfate (1×10 mL), water (2×10 mL), a saturated aqueous solution of LiCl (1×10 mL) and brine (1×10 mL), dried over MgSO₄, filtered and concentrated onto celite. Purification by column chromatography (gradient 0-10% MeOH in DCM) afforded 1-(3-bromo-1-((4'-(methylsulfonyl)-[1,1'-biphenyl]-4-yl)methyl)-1H-indol-5-yl)-5-methyl-1H-pyrazole-3-carboxamide (Intermediate IV) (250 mg, 73%). ¹H NMR (400 MHz, DMSO-d6) δ 7.98 (dd, J=6.8, 1.8 Hz, 3H), 7.92-7.88 (m, 2H), 7.75 (dd, J=13.2, 8.6 Hz, 3H), 7.55 (d, J=1.8 Hz, 1H), 7.49 (s, 1H), 7.46-7.35 (m, 3H), 7.20 (s, 1H), 6.62 (d, J=0.7 Hz, 1H), 5.58 (s, 2H), 3.24 (s, 3H), 2.31-2.26 (m, 3H).

Preparation 5

Intermediate V: 1-(1-(4-bromobenzyl)-1H-indol-5-yl)-5-methyl-1H-1,2,4-triazole-3-carboxamide

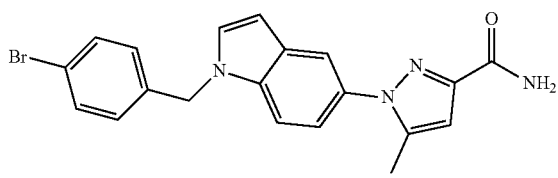 [SMILES: Cc1cc(C(N)=O)nn1-c1ccc2c(ccn2Cc2ccc(Br)cc2)c1]

Step 1: 1-(4-bromobenzyl)-5-nitro-1H-indole

To a stirred solution of 5-nitro-1H indole (50 g, 308 mmol, 1.0 eq) in dry DMF (1500 mL) was added potassium tert-butoxide (40.4 g, 360 mmol, 1.2 eq) followed by 4-bromo-benzyl bromide (82.4 g, 330 mmol, 1.1 eq). The reaction mixture was stirred at room temperature overnight. The progress of the reaction was monitored by TLC and LCMS. Upon completion, the reaction was quenched by addition of cold ammonium chloride solution and diluted with EtOAc (400 mL). The layers were separated and the aqueous layer extracted with EtOAc (2×400 mL). The combined organic layers were washed with ice cold water (3×250 mL), brine (2×150 mL) and a saturated aqueous ammonium chloride solution (2×150 mL). The organic layer was dried over sodium sulfate, filtered and concentrated under reduced pressure. The crude material was purified by column chromatography to afford 1-(4-bromobenzyl)-5-nitro-1H-indole (77 g, 76%). ¹H NMR (400 MHz, DMSO) δ 8.59 (d, J=2.2 Hz, 1H), 8.01 (dd, J=9.1, 2.3 Hz, 1H), 7.78 (d, J=3.2 Hz, 1H), 7.66 (t, J=13.0 Hz, 1H), 7.57-7.47 (m, 2H), 7.18 (d, J=8.5 Hz, 2H), 6.82 (dd, J=3.2, 0.6 Hz, 1H), 5.52 (s, 2H).

Step 2: 1-(4-bromobenzyl)-1H-indol-5-amine

To a stirred solution of 1-(4-bromobenzyl)-5-nitro-1H-indole (77 g, 230 mmol, 1.0 eq) in MeOH (500 mL) and water (500 mL) was added Iron metal (64.2 g, 1.16 mol, 5.0 eq) and solid ammonium chloride (56.35 g, 1.16 mol, 5.0 eq). The reaction mixture was stirred at 60° C. for 2 h. The progress of the reaction was monitored by TLC and LCMS. Upon completion, the reaction mixture was filtered through a pad of celite, and the filter cake was washed with MeOH (500 mL). The filtrate was concentrated under reduced pressure, diluted with ethyl acetate (500 mL), transferred to a separatory funnel and washed with water (2×200 mL) and brine (2×100 mL). The organic layer was dried over sodium sulfate, filtered and concentrated under reduced pressure. The crude material was used in the next step without further purification. 1-(4-bromobenzyl)-1H-indol-5-amine (40 g, 57%)¹H NMR (400 MHz, DMSO-d6) δ 8.59 (d, J=2.2 Hz, 1H), 8.01 (dd, J=9.1, 2.3 Hz, 1H), 7.79 (d, J=3.2 Hz, 1H), 7.68 (d, J=9.1 Hz, 1H), 7.62-7.46 (m, 2H), 7.18 (d, J=8.4 Hz, 2H), 6.85-6.78 (m, 1H), 5.53 (s, 2H).

Step 3: ethyl 1-(1-(4-bromobenzyl)-1H-indol-5-yl)-5-methyl-1H-1,2,4-triazole-3-carboxylate A stirred solution of 1-(4-bromobenzyl)-1H-indol-5-amine (40 g, 130 mmol, 1.0 eq) in MeOH (375 mL) and water (125 mL) was cooled to 0° C. in an ice bath. A 3N solution of HCl in water (303 mL, 910 mmol, 7.0 eq) was added, and after few minutes sodium nitrate (26.9 g, 390 mmol, 3.0 eq) was added portionwise over a period of 30 minutes. The reaction mixture was stirred at that temperature for 1 hour, and then ethyl-2-acetamidomalonate (28 g, 130 mmol, 1.0 eq) and sodium acetate (32 g, 390 mmol, 3.0 eq) were added. The reaction was allowed to warm to room temperature and was stirred at that temperature for 18 h. The reaction mixture was concentrated under reduced pressure, diluted with EtOAc (500 mL) and transferred to a separatory funnel. The organic layer was washed with water (3×200 mL) and brine (2×100 mL), dried over sodium sulfate, filtered and concentrated under reduced pressure. The crude material—ethyl 1-(1-(4-bromobenzyl)-1H-indol-5-yl)-5-methyl-1H-1,2,4-triazole-3-carboxylate (42 g Crude)—was used for the next step without further purification.

Step 4: 1-(1-(4-bromobenzyl)-1H-indol-5-yl)-5-methyl-1H-1,2,4-triazole-3-carboxamide To a stirred solution of ethyl 1-(1-(4-bromobenzyl)-1H-indol-5-yl)-5-methyl-1H-1,2,4-triazole-3-carboxylate (42 g, crude) in MeOH (1000 mL) was added a 7M solution of ammonia in MeOH (500 mL). The reaction was stirred at room temperature overnight. The progress of reaction was monitored by LCMS and TLC. Upon completion, the reaction was concentrated under reduced pressure and diluted with EtOAc (750 mL). The organic layer was washed with water (3×200 mL) and brine (2×50 mL), dried over sodium sulfate, filtered and concentrated under reduced pressure. The crude material was purified by column chromatography to afford 1-(1-(4-bromobenzyl)-1H-indol-5-yl)-5-methyl-1H-1,2,4-triazole-3-carboxamide (15 g, 27.6% over 2 steps). $^1$H NMR (400 MHz, DMSO) δ 7.83-7.80 (m, 2H), 7.79-7.75 (dd, J=22.9, 4.2 Hz, 2H), 7.71-7.63 (dd, J=25.2, 14.9 Hz, 3H), 7.44-7.41 (m, 1H), 7.32 (d, J=8.4 Hz, 2H), 6.64 (d, J=3.0 Hz, 1H), 5.5 (s, 2H), 2.44 (s, 3H).

Preparation of Compounds

Example 1-1: Synthesis of 5-methyl-1-(1-(4-(1-methyl-1,2,3,6-tetrahydropyridin-4-yl)benzyl)-1H-indol-5-yl)-1H-pyrazole-3-carboxamide

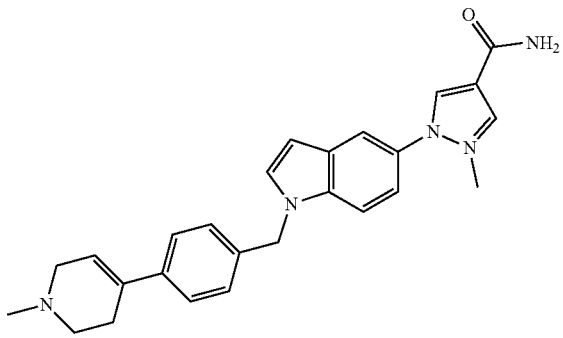

A microwave vial was charged with 1-(1-(4-bromobenzyl)-1H-indol-5-yl)-5-methyl-1H-pyrazole-3-carboxamide (Intermediate II) (500 mg, 1.22 mmol), 1-methyl-4-(4,4,5,5-tetramethyl-1,3,2-dioxaborolan-2-yl)-1,2,3,6-tetrahydropyridine (273 mg, 1.22 mmol), $K_3PO_4$ (778 mg, 3.66 mmol), Water (2.4 mL) and THF (9.8 mL), and the vial was evacuated and filled with $N_2$ (3×). Then first generation Xphos Precatalyst (90.0 mg, 0.122 mmol) was added and the mixture was heated in the microwave at 120° C. for 30 min, cooled to RT, filtered through a 0.45 micron syringe filter and concentrated in vacuo. The crude product was taken up in MeOH and purified by SFC to provide (214 mg, 41%) of 5-methyl-1-(1-(4-(1-methyl-1,2,3,6-tetrahydropyridin-4-yl)benzyl)-1H-indol-5-yl)-1H-pyrazole-3-carboxamide: LCMS Rt=0.50 min (condition Q), MS (M+1)=426.3. $^1$H NMR (400 MHz, DMSO-$d_6$) δ 7.70 (d, J=1.9 Hz, 1H), 7.66 (d, J=3.1 Hz, 1H), 7.58 (d, J=8.7 Hz, 1H), 7.43 (s, 1H), 7.41-7.31 (m, 2H), 7.28-7.12 (m, 4H), 6.65-6.53 (m, 2H), 6.15-6.06 (m, 1H), 5.47 (s, 2H), 3.03-2.94 (m, 2H), 2.54 (t, J=5.6 Hz, 2H), 2.46-2.38 (m, 2H), 2.30-2.21 (m, 6H).

The following compounds were prepared using a similar procedure as in Example 1-1

| Example | Compound | LCMS M + 1, Rt, conditions | 1H NMR, 400 MHz |
|---|---|---|---|
| 1-2 | 5-methyl-1-(1-(4-(pyridin-4-yl)benzyl)-1H-indol-5-yl)-1H-pyrazole-3-carboxamide | 408.2<br>0.53 min<br>Q | N/A |

| Example | Compound | LCMS M + 1, Rt, conditions | 1H NMR, 400 MHz |
|---|---|---|---|
| 1-3 | 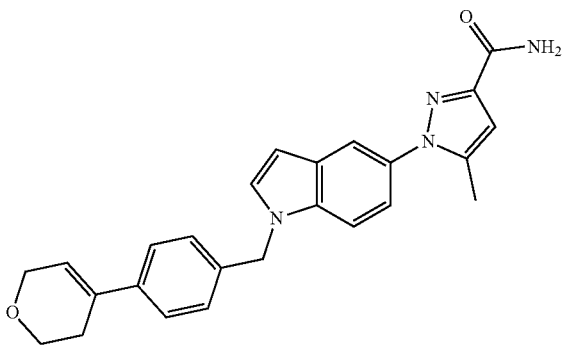<br>1-(1-(4-(3,6-dihydro-2H-pyran-4-yl)benzyl)-1H-indol-5-yl)-5-methyl-1H-pyrazole-3-carboxamide | 413.3<br>2.24 min<br>A | (DMSO-d6) δ 7.70 (d, J = 1.9 Hz, 1H), 7.66 (d, J = 3.1 Hz, 1H), 7.59 (d, J = 8.7 Hz, 1H), 7.46-7.36 (m, 3H), 7.26-7.14 (m, 4H), 6.63-6.54 (m, 2H), 6.26-6.17 (m, 1H), 5.48 (s, 2H), 4.19 (q, J = 2.7 Hz, 2H), 3.79 (t, J = 5.5 Hz, 2H), 2.39 (d, J = 1.7 Hz, 2H), 2.29-2.23 (m, 3H). |
| 1-4 | 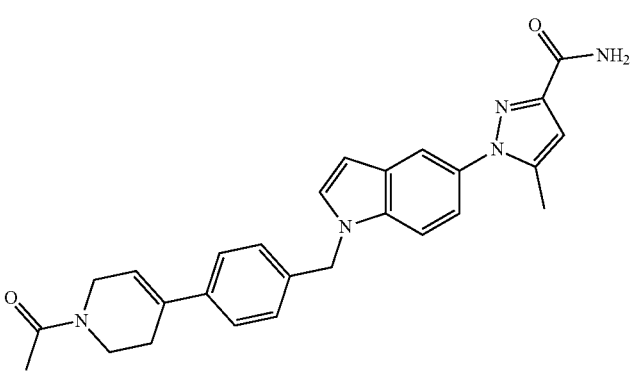<br>1-(1-(4-(1-acetyl-1,2,3,6-tetrahydropyridin-4-yl)benzyl)-1H-indol-5-yl)-5-methyl-1H-pyrazole-3-carboxamide | 454.3<br>1.98 min<br>A | (DMSO-d6) δ 7.70 (d, J = 2.0 Hz, 1H), 7.66 (d, J = 3.1 Hz, 1H), 7.58 (d, J = 8.7 Hz, 1H), 7.47-7.35 (m, 3H), 7.26-7.15 (m, 4H), 6.62-6.56 (m, 2H), 6.17-6.09 (m, 1H), 5.48 (s, 2H), 4.08 (dd, J = 20.7, 2.8 Hz, 2H), 3.60 (dt, J = 11.5, 5.7 Hz, 2H), 2.26 (s, 3H), 2.08-1.99 (m, 3H). |
| 1-5 | 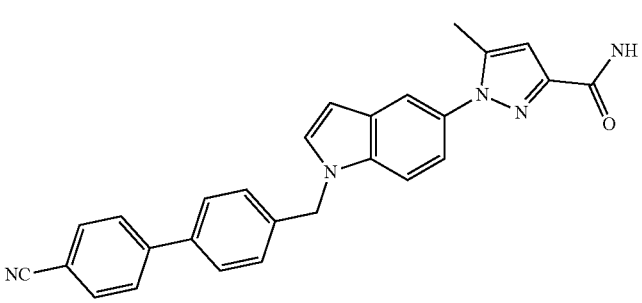<br>1-(1-((4'-cyano-[1,1'-biphenyl]-4-yl)methyl)-1H-indol-5-yl)-5-methyl-1H-pyrazole-3-carboxamide | 432.7<br>2.43 min<br>A | (DMSO-d6) δ 7.93-7.89 (m, 2H), 7.88-7.82 (m, 2H), 7.75-7.69 (m, 4H), 7.63 (d, J = 8.7 Hz, 1H), 7.42 (s, 1H), 7.36 (d, J = 8.4 Hz, 2H), 7.24 (dd, J = 8.7, 2.1 Hz, 1H), 7.17 (s, 1H), 6.64-6.57 (m, 2H), 5.57 (s, 2H), 2.29-2.24 (m, 3H). |

| Example | Compound | LCMS M + 1, Rt, conditions | 1H NMR, 400 MHz |
|---|---|---|---|
| 1-6 | 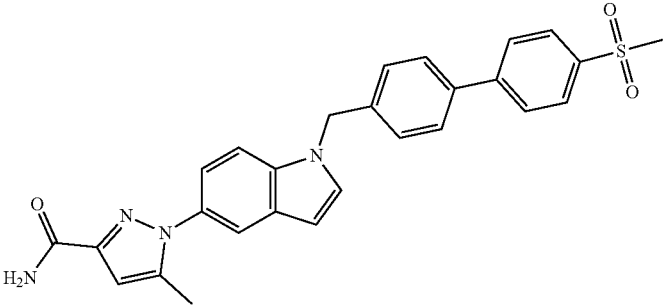 5-methyl-1-(1-((4'-(methylsulfonyl)-[1,1'-biphenyl]-4-yl)methyl)-1H-indol-5-yl)-1H-pyrazole-3-carboxamide | 485.2 2.12 min A | ((Acetone-d6) δ 8.05-7.97 (m, 2H), 7.94-7.88 (m, 2H), 7.74 (dt, J = 7.3, 1.8 Hz, 3H), 7.67-7.59 (m, 2H), 7.40 (d, J = 8.5 Hz, 2H), 7.27 (dd, J = 8.7, 2.0 Hz, 1H), 6.69 (dd, J = 3.2, 0.8 Hz, 1H), 6.60 (d, J = 0.7 Hz, 1H), 5.65 (s, 2H), 3.15 (s, 3H), 2.32 (d, J = 0.7 Hz, 3H). |
| 1-7 | 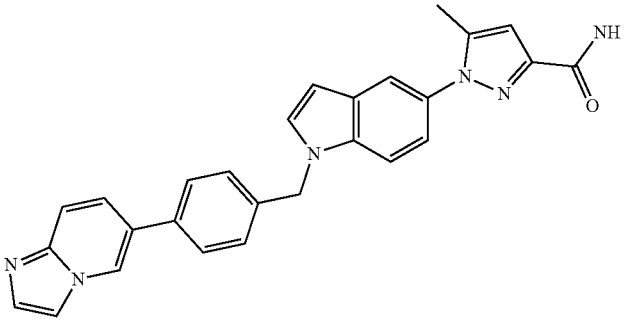 1-(1-(4-(imidazo[1,2-a]pyridin-6-yl)benzyl)-1H-indol-5-yl)-5-methyl-1H-pyrazole-3-carboxamide | 447.3 1.37 min A | (DMSO-d6) δ 8.87 (dd, J = 1.8, 1.0 Hz, 1H), 7.94 (s, 1H), 7.71 (t, J = 2.4 Hz, 2H), 7.69-7.58 (m, 5H), 7.53 (dd, J = 9.4, 1.9 Hz, 1H), 7.42 (s, 1H), 7.36 (d, J = 8.4 Hz, 2H), 7.25 (dd, J = 8.7, 2.1 Hz, 1H), 7.17 (s, 1H), 6.62 (dd, J = 3.1, 0.6 Hz, 1H), 6.59 (d, J = 0.7 Hz, 1H), 5.56 (s, 2H), 2.29-2.25 (m, 3H). |
| 1-8 | 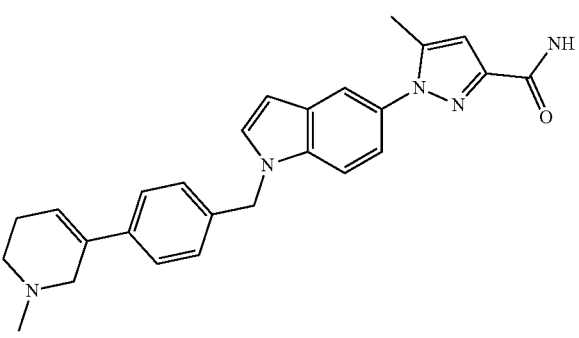 5-methyl-1-(1-(4-(1-methyl-1,2,5,6-tetrahydropyridin-3-yl)benzyl)-1H-indol-5-yl)-1H-pyrazole-3-carboxamide | 426.3 1.30 min A | (Methanol-d4) δ 7.69 (d, J = 1.9 Hz, 1H), 7.54-7.44 (m, 2H), 7.35 (d, J = 8.4 Hz, 2H), 7.26-7.12 (m, 3H), 6.70 (d, J = 0.7 Hz, 1H), 6.69-6.63 (m, 1H), 6.17 (dt, J = 4.0, 2.1 Hz, 1H), 5.47 (s, 2H), 2.65 (t, J = 5.9 Hz, 2H), 2.47 (s, 3H), 2.41 (d, J = 3.7 Hz, 2H), 2.31 (d, J = 0.6 Hz, 3H). |

-continued

| Example | Compound | LCMS M + 1, Rt, conditions | 1H NMR, 400 MHz |
|---|---|---|---|
| 1-9 | 5-methyl-1-(1-(4-(4-methyl-3,4-dihydro-2H-pyrido[3,2-b][1,4]oxazin-7-yl)benzyl)-1H-indol-5-yl)-1H-pyrazole-3-carboxamide | 479.3 0.60 min Q | N/A |
| 1-10 | 5-methyl-1-(1-(4-(2-methyl-2H-indazol-6-yl)benzyl)-1H-indol-5-yl)-1H-pyrazole-3-carboxamide | 461.3 0.63 min Q | (DMSO-d6) δ 8.33 (s, 1H), 7.80-7.62 (m, 7H), 7.45 (s, 1H), 7.35-7.23 (m, 4H), 7.18 (s, 1H), 6.62 (d, J = 2.8 Hz, 1H), 6.59 (s, 1H), 5.55 (s, 2H), 4.17 (s, 3H), 2.27 (s, 3H). |
| 1-11 | 5-methyl-1-(1-((4'-((4-methylpiperazin-1-yl)sulfonyl)-[1,1'-biphenyl]-4-yl)methyl)-1H-indol-5-yl)-1H-pyrazole-3-carboxamide | 569.4 0.53 min Q | (DMSO-d6) δ 7.93-7.86 (m, 2H), 7.81-7.74 (m, 2H), 7.75-7.69 (m, 4H), 7.63 (d, J = 8.7 Hz, 1H), 7.44 (s, 1H), 7.40-7.34 (m, 2H), 7.25 (dd, J = 8.7, 2.0 Hz, 1H), 7.19 (s, 1H), 6.62 (d, J = 3.0 Hz, 1H), 6.59 (s, 1H), 5.58 (s, 2H), 2.99-2.83 (m, 4H), 2.40-2.30 (m, 4H), 2.27 (s, 3H), 2.13 (s, 3H). |
| 1-12 | 5-methyl-1-(1-((3'-(4-methylpiperazine-1-carbonyl)-[1,1'-biphenyl]-4-yl)methyl)-1H-indol-5-yl)-1H-pyrazole-3-carboxamide | 533.4 0.52 min Q | N/A |

| Example | Compound | LCMS M + 1, Rt, conditions | 1H NMR, 400 MHz |
|---|---|---|---|
| 1-13 | 1-(1-((4'-(N,N-dimethylsulfamoyl)-[1,1'-biphenyl]-4-yl)methyl)-1H-indol-5-yl)-5-methyl-1H-pyrazole-3-carboxamide | 514.3 0.63 min Q | (DMSO-d6) δ 7.94-7.85 (m, 2H), 7.83-7.76 (m, 2H), 7.76-7.69 (m, 4H), 7.63 (d, J = 8.8 Hz, 1H), 7.44 (s, 1H), 7.40-7.33 (m, 2H), 7.25 (dd, J = 8.7, 2.0 Hz, 1H), 7.19 (s, 1H), 6.62 (d, J = 3.0 Hz, 1H), 6.59 (s, 1H), 5.58 (s, 2H), 2.63 (s, 6H), 2.27 (s, 3H). |
| 1-14 | 1-(1-(4-(1H-indazol-6-yl)benzyl)-1H-indol-5-yl)-5-methyl-1H-pyrazole-3-carboxamide | 447.2 0.64 min Q | N/A |
| 1-15 | 1-(1-((3'-fluoro-4'-hydroxy-[1,1'-biphenyl]-4-yl)methyl)-1H-indol-5-yl)-5-methyl-1H-pyrazole-3-carboxamide | 441.3 0.63 min Q | N/A |
| 1-16 | 1-(1-(4-(1H-pyrrolo[2,3-b]pyridin-5-yl)benzyl)-1H-indol-5-yl)-5-methyl-1H-pyrazole-3-carboxamide | 447.3 0.63 min Q | (DMSO-d6) δ 11.70 (s, 1H), 8.47 (d, J = 2.1 Hz, 1H), 8.16 (d, J = 1.9 Hz, 1H), 7.76-7.70 (m, 2H), 7.70-7.62 (m, 3H), 7.53-7.47 (m, 1H), 7.45 (s, 1H), 7.38-7.31 (m, 2H), 7.26 (dd, J = 8.7, 2.0 Hz, 1H), 7.18 (s, 1H), 6.62 (d, J = 3.0 Hz, 1H), 6.59 (s, 1H), 6.52-6.44 (m, 1H), 5.55 (s, 2H), 2.27 (s, 3H). |

| Example | Compound | LCMS M + 1, Rt, conditions | 1H NMR, 400 MHz |
|---|---|---|---|
| 1-17 | 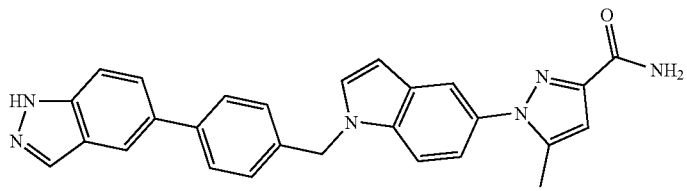<br>1-(1-(4-(1H-indazol-5-yl)benzyl)-1H-indol-5-yl)-5-methyl-1H-pyrazole-3-carboxamide | 447.3 0.63 min Q | (DMSO-d6) δ 13.10 (s, 1H), 8.12-8.08 (m, 1H), 7.98 (s, 1H), 7.73-7.69 (m, 2H), 7.68-7.63 (m, 3H), 7.63-7.57 (m, 2H), 7.44 (s, 1H), 7.36-7.31 (m, 2H), 7.25 (dd, J = 8.7, 2.0 Hz, 1H), 7.21-7.15 (m, 1H), 6.62 (d, J = 2.9 Hz, 1H), 6.59 (s, 1H), 5.54 (s, 2H), 2.27 (s, 3H). |
| 1-18 | 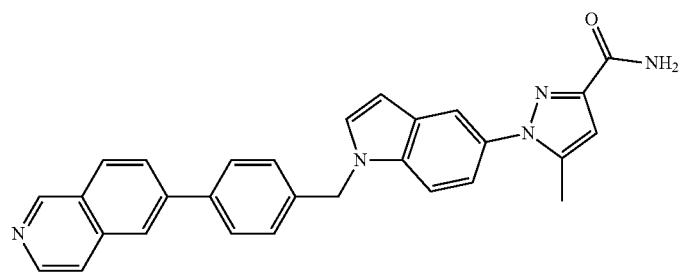<br>1-(1-(4-(isoquinolin-6-yl)benzyl)-1H-indol-5-yl)-5-methyl-1H-pyrazole-3-carboxamide | 458.3 0.60 min Q | (DMSO-d6) δ 9.32 (s, 1H), 8.51 (d, J = 5.7 Hz, 1H), 8.23 (s, 1H), 8.19 (d, J = 8.6 Hz, 1H), 7.98 (dd, J = 8.6, 1.7 Hz, 1H), 7.85 (d, J = 5.9 Hz, 1H), 7.84-7.79 (m, 2H), 7.76-7.70 (m, 2H), 7.65 (d, J = 8.8 Hz, 1H), 7.44 (s, 1H), 7.42-7.36 (m, 2H), 7.26 (dd, J = 8.7, 2.0 Hz, 1H), 7.19 (s, 1H), 6.63 (d, J = 2.7 Hz, 1H), 6.59 (s, 1H), 5.59 (s, 2H), 2.27 (s, 3H). |
| 1-19 | 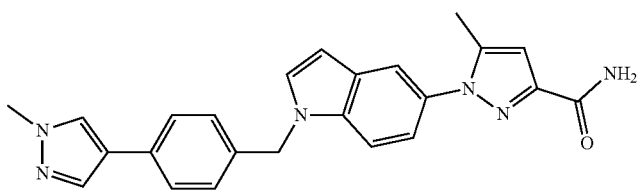<br>5-methyl-1-(1-(4-(1-methyl-1H-pyrazol-4-yl)benzyl)-1H-indol-5-yl)-1H-pyrazole-3-carboxamide | 411.3 0.61 min Q | (DMSO-d6) δ 8.07 (s, 1H), 7.80 (s, 1H), 7.70 (d, J = 2.0 Hz, 1H), 7.67 (d, J = 3.1 Hz, 1H), 7.61 (d, J = 8.8 Hz, 1H), 7.54-7.47 (m, 2H), 7.44 (s, 1H), 7.26-7.20 (m, 3H), 7.18 (s, 1H), 6.63-6.56 (m, 2H), 5.46 (s, 2H), 3.83 (s, 3H), 2.26 (s, 3H). |
| 1-20 | 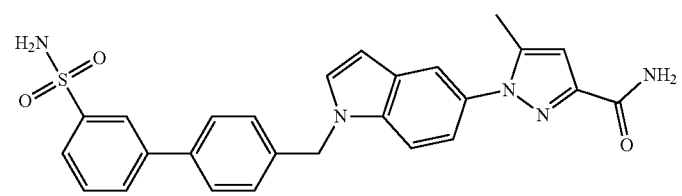<br>5-methyl-1-(1-((3'-sulfamoyl-[1,1'-biphenyl]-4-yl)methyl)-1H-indol-5-yl)-1H-pyrazole-3-carboxamide | 486.2 0.60 min Q | (DMSO-d6) δ 8.08-8.04 (m, 1H), 7.88-7.83 (m, 1H), 7.82-7.77 (m, 1H), 7.74-7.69 (m, 2H), 7.69-7.61 (m, 4H), 7.44 (s, 1H), 7.41-7.33 (m, 4H), 7.25 (dd, J = 8.7, 2.0 Hz, 1H), 7.19 (s, 1H), 6.62 (d, J = 2.9 Hz, 1H), 6.59 (s, 1H), 5.57 (s, 2H), 2.27 (s, 3H). |
| 1-21 | 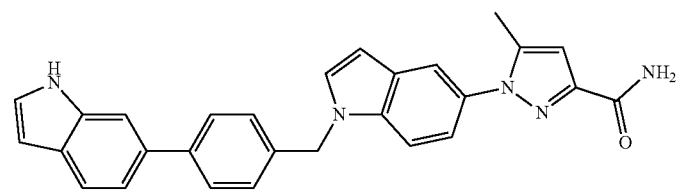<br>1-(1-(4-(1H-indol-6-yl)benzyl)-1H-indol-5-yl)-5-methyl-1H-pyrazole-3-carboxamide | 446.3 0.66 min Q | (DMSO-d6) δ 11.15 (s, 1H), 7.74-7.68 (m, 2H), 7.68-7.60 (m, 3H), 7.60-7.56 (m, 2H), 7.44 (s, 1H), 7.38-7.35 (m, 1H), 7.34-7.30 (m, 2H), 7.28-7.26 (m, 1H), 7.26-7.24 (m, 1H), 7.18 (s, 1H), 6.62 (d, J = 3.1 Hz, 1H), 6.60-6.58 (m, 1H), 6.45-6.41 (m, 1H), 5.54 (s, 2H), 2.27 (s, 3H). |

-continued

| Example | Compound | LCMS M + 1, Rt, conditions | 1H NMR, 400 MHz |
|---|---|---|---|
| 1-22 | 5-methyl-1-(1-(4-(1-methyl-1H-indazol-6-yl)benzyl)-1H-indol-5-yl)-1H-pyrazole-3-carboxamide | 461.2 0.65 min Q | (DMSO-d6) δ 8.04 (s, 1H), 7.87 (s, 1H), 7.79 (d, J = 8.4 Hz, 1H), 7.77-7.69 (m, 4H), 7.65 (d, J = 8.7 Hz, 1H), 7.47-7.33 (m, 4H), 7.25 (dd, J = 8.7, 1.8 Hz, 1H), 7.19 (s, 1H), 6.62 (d, J = 3.0 Hz, 1H), 6.59 (s, 1H), 5.56 (s, 2H), 4.07 (s, 3H), 2.27 (s, 3H). |
| 1-23 | 1-(1-(4-(6-(dimethylamino)pyridin-3-yl)benzyl)-1H-indol-5-yl)-5-methyl-1H-pyrazole-3-carboxamide | 451.3 0.54 min Q | N/A |
| 1-24 | 1-(1-(4-(2-methoxypyridin-4-yl)benzyl)-1H-indol-5-yl)-5-methyl-1H-pyrazole-3-carboxamide | 438.3 0.65 min Q | (DMSO-d6) δ 8.20 (d, J = 5.4 Hz, 1H), 7.77-7.69 (m, 4H), 7.62 (d, J = 8.8 Hz, 1H), 7.44 (s, 1H), 7.38-7.31 (m, 2H), 7.30-7.22 (m, 2H), 7.18 (s, 1H), 7.09-7.04 (m, 1H), 6.62 (d, J = 3.1 Hz, 1H), 6.59 (s, 1H), 5.57 (s, 2H), 3.87 (s, 3H), 2.27 (s, 3H). |
| 1-25 | 5-methyl-1-(1-(4-(1-oxo-1,2,3,4-tetrahydroisoquinolin-6-yl)benzyl)-1H-indol-5-yl)-1H-pyrazole-3-carboxamide | 476.2 0.61 min Q | N/A |
| 1-26 | 1-(1-((4'-amino-[1,1'-biphenyl]-4-yl)methyl)-1H-indol-5-yl)-5-methyl-1H-pyrazole-3-carboxamide | 422.3 0.60 min Q | (DMSO-d6) δ 7.70 (d, J = 2.0 Hz, 1H), 7.68 (d, J = 3.1 Hz, 1H), 7.62 (d, J = 8.7 Hz, 1H), 7.51-7.45 (m, 2H), 7.44 (s, 1H), 7.34-7.28 (m, 2H), 7.28-7.21 (m, 3H), 7.18 (s, 1H), 6.64-6.55 (m, 4H), 5.48 (s, 2H), 5.20 (s, 2H), 2.26 (s, 3H). |

-continued

| Example | Compound | LCMS M + 1, Rt, conditions | 1H NMR, 400 MHz |
|---|---|---|---|
| 1-27 | 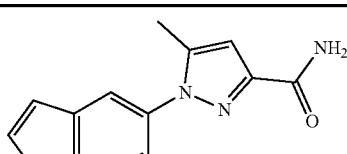<br>1-(1-((4'-amino-[1,1'-biphenyl]-4-yl)methyl)-1H-indol-5-yl)-5-methyl-1H-pyrazole-3-carboxamide | 425.3<br>0.68 min<br>Q | N/A |
| 1-28 | 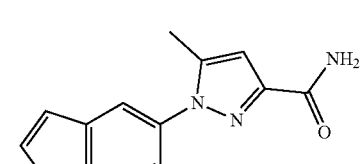<br>1-(1-(4-(2-methoxypyrimidin-5-yl)benzyl)-1H-indol-5-yl)-5-methyl-1H-pyrazole-3-carboxamide | 439.2<br>0.63 min<br>Q | (DMSO-d6) δ 8.89 (s, 2H), 7.73-7.66 (m, 4H), 7.63 (d, J = 8.8 Hz, 1H), 7.44 (s, 1H), 7.38-7.33 (m, 2H), 7.24 (dd, J = 8.7, 2.1 Hz, 1H), 7.18 (s, 1H), 6.61 (d, J = 2.8 Hz, 1H), 6.60-6.58 (m, 1H), 5.55 (s, 2H), 3.95 (s, 3H), 2.27 (s, 3H). |
| 1-29 | 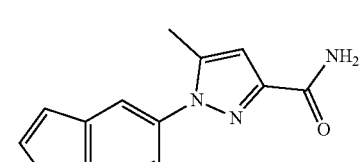<br>1-(1-(4-(2-aminopyrimidin-5-yl)benzyl)-1H-indol-5-yl)-5-methyl-1H-pyrazole-3-carboxamide | 424.2<br>0.58 min<br>Q | N/A |
| 1-30 | 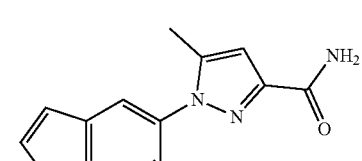<br>1-(1-((4'-methoxy-[1,1'-biphenyl]-4-yl)methyl)-1H-indol-5-yl)-5-methyl-1H-pyrazole-3-carboxamide | 437.3<br>0.68 min<br>Q | N/A |

-continued

| Example | Compound | LCMS M + 1, Rt, conditions | 1H NMR, 400 MHz |
|---|---|---|---|
| 1-31 | 5-methyl-1-(1-(4-(2-oxoindolin-5-yl)benzyl)-1H-indol-5-yl)-1H-pyrazole-3-carboxamide | 462.4 0.62 min Q | (DMS0-d6) δ 10.43 (s, 1H), 7.71 (d, J = 1.9 Hz, 1H), 7.69 (d, J = 3.1 Hz, 1H), 7.63 (d, J = 8.7 Hz, 1H), 7.58-7.52 (m, 2H), 7.50-7.40 (m, 3H), 7.32-7.27 (m, 2H), 7.24 (dd, J = 8.7, 2.0 Hz, 1H), 7.18 (s, 1H), 6.86 (d, J = 8.1 Hz, 1H), 6.61 (d, J = 2.9 Hz, 1H), 6.59 (s, 1H), 5.52 (s, 2H), 3.51 (s, 2H), 2.27 (s, 3H). |
| 1-32 | 1-(1-((4'-(hydroxymethyl)-[1,1'-biphenyl]-4-yl)methyl)-1H-indol-5-yl)-5-methyl-1H-pyrazole-3-carboxamide | 437.4 0.63 min Q | N/A |
| 1-33 | 5-methyl-1-(1-((4'-(methylsulfonamido)-[1,1'-biphenyl]-4-yl)methyl)-1H-indol-5-yl)-1H-pyrazole-3-carboxamide | 500.3 0.62 min Q | (DMSO-d6) δ 9.80 (s, 1H), 7.71 (d, J = 2.0 Hz, 1H), 7.70 (d, J = 3.1 Hz, 1H), 7.65-7.60 (m, 2H), 7.60-7.57 (m, 3H), 7.44 (s, 1H), 7.33-7.29 (m, 2H), 7.28-7.22 (m, 3H), 7.18 (s, 1H), 6.61 (d, J = 2.9 Hz, 1H), 6.59 (s, 1H), 5.53 (s, 2H), 3.00 (s, 3H), 2.27 (s, 3H). |
| 1-34 | 1-(1-((4'-(aminomethyl)-[1,1'-biphenyl]-4-yl)methyl)-1H-indol-5-yl)-5-methyl-1H-pyrazole-3-carboxamide | 436.3 0.52 min Q | (DMSO-d6) δ 7.75-7.67 (m, 2H), 7.67-7.59 (m, 5H), 7.51-7.39 (m, 3H), 7.37-7.30 (m, 2H), 7.25 (dd, J = 8.7, 1.8 Hz, 1H), 7.19 (s, 1H), 6.61 (d, J = 2.9 Hz, 1H), 6.59 (s, 1H), 5.54 (s, 2H), 3.91 (s, 2H), 2.27 (s, 3H). |

| Example | Compound | LCMS M + 1, Rt, conditions | 1H NMR, 400 MHz |
|---|---|---|---|
| 1-35 | 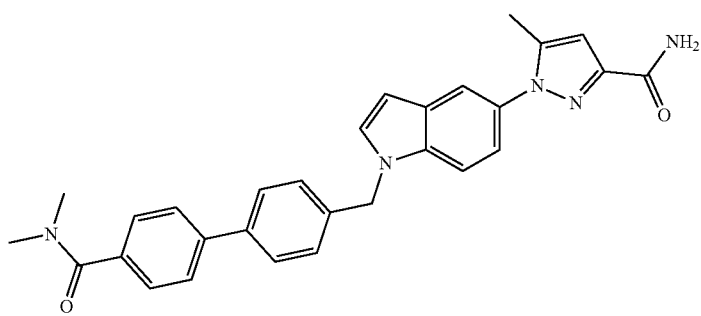<br>1-(1-((4'-(dimethylcarbamoyl)-[1,1'-biphenyl]-4-yl)methyl)-1H-indol-5-yl)-5-methyl-1H-pyrazole-3-carboxamide | 478.4<br>0.62 min<br>Q | N/A |
| 1-36 | 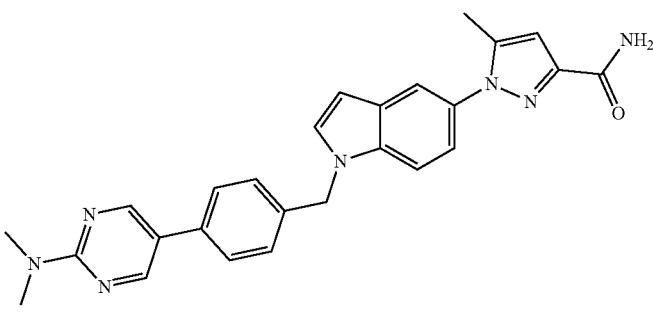<br>1-(1-(4-(2-(dimethylamino)pyrimidin-5-yl)benzyl)-1H-indol-5-yl)-5-methyl-1H-pyrazole-3-carboxamide | 452.3<br>0.65 min<br>Q | N/A |
| 1-37 | 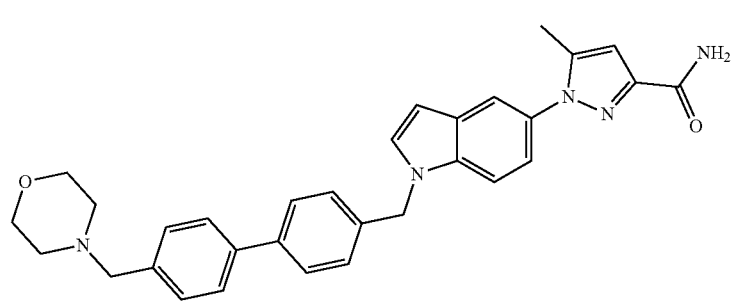<br>5-methyl-1-(1-((4'-(morpholinomethyl)-[1,1'-biphenyl]-4-yl)methyl)-1H-indol-5-yl)-1H-pyrazole-3-carboxamide | 506.4<br>0.53 min<br>Q | N/A |

| Example | Compound | LCMS M + 1, Rt, conditions | 1H NMR, 400 MHz |
|---|---|---|---|
| 1-38 | 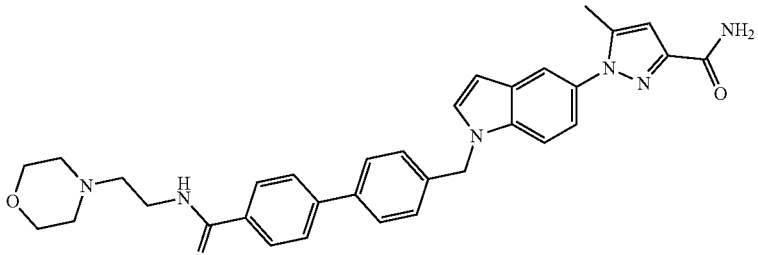<br>5-methyl-1-(1-((4'-((2-morpholinoethyl)carbamoyl)-[1,1'-biphenyl]-4-yl)methyl)-1H-indol-5-yl)-1H-pyrazole-3-carboxamide | 563.5 0.53 min Q | N/A |

Example 2-1: Synthesis of rac-5-methyl-1-(1-(4-(1-methylpyrrolidin-3-yl)benzyl)-1H-indol-5-yl)-1H-pyrazole-3-carboxamide

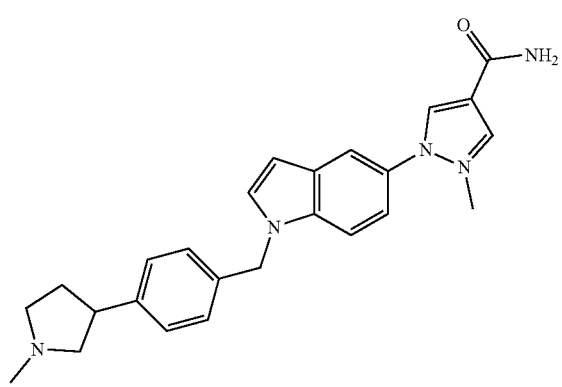

Step 1: tert-butyl 3-(4-((5-(3-carbamoyl-5-methyl-1H-pyrazol-1-yl)-1H-indol-1-yl)methyl)phenyl)-2,5-dihydro-1H-pyrrole-1-carboxylate A reaction vial was charged with 1-(1-(4-bromobenzyl)-1H-indol-5-yl)-5-methyl-1H-pyrazole-3-carboxamide (Intermediate II) (250 mg, 0.611 mmol), tert-butyl 3-(4,4,5,5-tetramethyl-1,3,2-dioxaborolan-2-yl)-2,5-dihydro-1H-pyrrole-1-carboxylate (216 mg, 0.733 mmol), $K_3PO_4$ (389 mg, 1.83 mmol), Water (0.64 mL) and THF (3.2 mL), and the vial was evacuated and filled with $N_2$ (3×). Then $PdCl_2$(dppf).DCM (49.9 mg, 0.061 mmol) was added and the mixture was heated in the microwave at 80° C. for 40 min, cooled to RT, diluted with excess ethyl acetate and filtered through celite. The organic filtrate was concentrated to provide (304 mg) of crude tert-butyl 3-(4-((5-(3-carbamoyl-5-methyl-1H-pyrazol-1-yl)-1H-indol-1-yl)methyl)phenyl)-2,5-dihydro-1H-pyrrole-1-carboxylate: LCMS Rt=1.24 min (condition B), MS (M+1)=498.1.

Step 2: 1-(1-(4-(2,5-dihydro-1H-pyrrol-3-yl)benzyl)-1H-indol-5-yl)-5-methyl-1H-pyrazole-3-carboxamide In a round bottom flask crude tert-butyl 3-(4-((5-(3-carbamoyl-5-methyl-1H-pyrazol-1-yl)-1H-indol-1-yl)methyl)phenyl)-2,5-dihydro-1H-pyrrole-1-carboxylate (304 mg, 0.611 mmol) was dissolved in DCM (1.5 mL). Trifluoroacetic acid (1.2 mL, 15.2 mmol) was added and the resulting mixture was stirred for 1 h at ambient temperature. The mixture was then concentrated and the resulting crude oil was taken up in MeOH and purified by SCX-BSA according to General Method IV to afford (248 mg, 0.611 mmol) of 1-(1-(4-(2,5-dihydro-1H-pyrrol-3-yl)benzyl)-1H-indol-5-yl)-5-methyl-1H-pyrazole-3-carboxamide: LCMS Rt=0.73 min (condition B), MS (M+1)=397.7.

Step 3: 5-methyl-1-(1-(4-(1-methyl-2,5-dihydro-1H-pyrrol-3-yl)benzyl)-1H-indol-5-yl)-1H-pyrazole-3-carboxamide In a pressure vessel, 1-(1-(4-(2,5-dihydro-1H-pyrrol-3-yl)benzyl)-1H-indol-5-yl)-5-methyl-1H-pyrazole-3-carboxamide (50 mg, 0.122 mmol) was dissolved in MeOH (7.6 mL). 37% aqueous formaldehyde (0.056 mL, 0.755 mmol) was added, followed by sodium triacetoxyborohydride (160 mg, 0.755 mmol). The reaction mixture was stirred at ambient temperature for 5 min then purified by preparative HPLC. The purified fractions were dried under lyophilization to afford (155 mg, 0.377 mmol) of 5-methyl-1-(1-(4-(1-methyl-2,5-dihydro-1H-pyrrol-3-yl)benzyl)-1H-indol-5-yl)-1H-pyrazole-3-carboxamide: LCMS Rt=1.31 min (condition A), MS (M+1)=412.2. $^1$H NMR (400 MHz, DMSO-d6) δ 7.70 (d, J=1.9 Hz, 1H), 7.66 (d, J=3.1 Hz, 1H), 7.58 (d, J=8.7 Hz, 1H), 7.44 (s, 1H), 7.35 (d, J=8.2 Hz, 2H), 7.28-7.12 (m, 4H), 6.62-6.56 (m, 2H), 6.28-6.20 (m, 1H), 5.48 (s, 2H), 3.73-3.63 (m, 2H), 3.55-3.48 (m, 2H), 2.41 (s, 3H), 2.26 (s, 3H).

Step 4: 5-methyl-1-(1-(4-(1-methylpyrrolidin-3-yl)benzyl)-1H-indol-5-yl)-1H-pyrazole-3-carboxamide A pressure vessel was charged with 1-(1-(4-(2,5-dihydro-1H-pyrrol-3-yl)benzyl)-1H-indol-5-yl)-5-methyl-1H-pyrazole-3-carboxamide (50 mg, 0.122 mmol), 10% Pd/C (64 mg, 0.061 mmol) and MeOH (2.4 mL). The flask was sealed and charged with hydrogen gas to 50 psi and shaken on a par-shaker for 4 h. The suspension was filtered through celite, and the filtrate was concentrated. The crude material was purified by preparative HPLC and dried under lyophilization to afford 5-methyl-1-(1-(4-(1-methylpyrrolidin-3-yl)benzyl)-1H-indol-5-yl)-1H-pyrazole-3-carboxamide (30.2 mg, 60%): LCMS Rt=1.33 min (condition A), MS (M+1)=414.3. $^1$H NMR (400 MHz, Methanol-d4) δ 7.57 (d, J=1.9 Hz, 1H), 7.40-7.32 (m, 2H), 7.24-7.15 (m, 2H), 7.14-7.05 (m, 3H), 6.58 (d, J=0.7 Hz, 1H), 6.56-6.49 (m, 1H), 5.36 (s, 2H), 3.68-3.47 (m, 2H), 3.48-3.34 (m, 2H), 3.20-3.11 (m, 1H), 2.87 (s, 3H), 2.45-2.33 (m, 1H), 2.18 (s, 3H), 2.13-1.99 (m, 1H).

Examples 2-2 and 2-3: Synthesis of Enantiomers of 5-methyl-1-(1-(4-(1-methylpyrrolidin-3-yl)benzyl)-1H-indol-5-yl)-1H-pyrazole-3-carboxamide

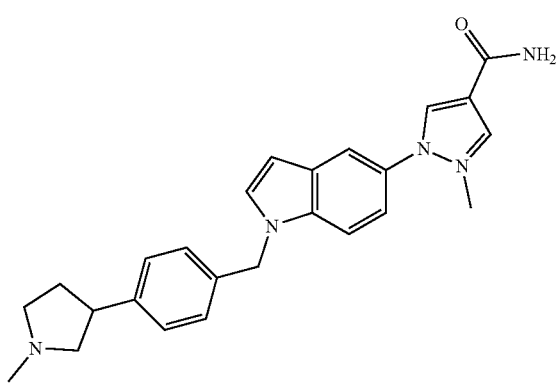

Example 2-1 was purified by Chiral SFC to afford the pure enantiomers. Conditions: The purification of the racemic material was performed using supercritical fluid chromatography on a Thar 80. An isocratic method was developed for the preparative purification utilizing a mobile phase of 40% (1:1) methanol/2-propanol (with 10 mM ammoniated methanol) and 60% carbon dioxide at a flow rate of 80 g/min on the Chiralcel OD-H (21×250 mm, 5 μm). The automated back pressure regulator set point was 100 bar with UV based collection set to observe 240 nm. Two isolates were generated from the purification process.

Example 2-2: Enantiomer 1

5-methyl-1-(1-(4-(1-methylpyrrolidin-3-yl)benzyl)-1H-indol-5-yl)-1H-pyrazole-3-carboxamide (21.8 mg, 11%). SFC Rt=4.9 min. LCMS Rt=1.31 min (condition A), MS (M+1)=414.2. $^1$H NMR (400 MHz, Methanol-d4) δ 7.57 (d, J=1.9 Hz, 1H), 7.40-7.32 (m, 2H), 7.24-7.15 (m, 2H), 7.14-7.05 (m, 3H), 6.58 (d, J=0.7 Hz, 1H), 6.56-6.49 (m, 1H), 5.36 (s, 2H), 3.68-3.47 (m, 2H), 3.48-3.34 (m, 2H), 3.20-3.11 (m, 1H), 2.87 (s, 3H), 2.45-2.33 (m, 1H), 2.18 (s, 3H), 2.13-1.99 (m, 1H).

Example 2-3: Enantiomer 2

5-methyl-1-(1-(4-(1-methylpyrrolidin-3-yl)benzyl)-1H-indol-5-yl)-1H-pyrazole-3-carboxamide (26.0 mg, 13%). SFC Rt=6.3 min. LCMS Rt=1.31 min (condition A), MS (M+1)=414.2. $^1$H NMR (400 MHz, Methanol-d4) δ 7.57 (d, J=1.9 Hz, 1H), 7.40-7.32 (m, 2H), 7.24-7.15 (m, 2H), 7.14-7.05 (m, 3H), 6.58 (d, J=0.7 Hz, 1H), 6.56-6.49 (m, 1H), 5.36 (s, 2H), 3.68-3.47 (m, 2H), 3.48-3.34 (m, 2H), 3.20-3.11 (m, 1H), 2.87 (s, 3H), 2.45-2.33 (m, 1H), 2.18 (s, 3H), 2.13-1.99 (m, 1H).

The following compounds were prepared using a similar procedure as in Example 2-1

| Example | Compound | LCMS M + 1, Rt, conditions | 1H NMR, 400 MHz |
|---|---|---|---|
| 2-4 | 5-methyl-1-(1-(4-(piperidin-3-yl)benzyl)-1H-indol-5-yl)-1H-pyrazole-3-carboxamide | 414.4 1.35 min, A | (Methanol-d4) δ 7.66 (d, J = 1.9 Hz, 1H), 7.50-7.40 (m, 2H), 7.24-7.07 (m, 5H), 6.71-6.65 (m, 1H), 6.61 (d, J = 2.7 Hz, 1H), 5.42 (s, 2H), 3.32 (d, J = 1.7 Hz, 1H), 3.11-3.04 (m, 2H), 2.69-2.59 (m, 2H), 2.34-2.23 (m, 3H), 1.99-1.56 (m, 4H). |

| Example | Compound | LCMS M + 1, Rt, conditions | 1H NMR, 400 MHz |
|---|---|---|---|
| 2-5 | 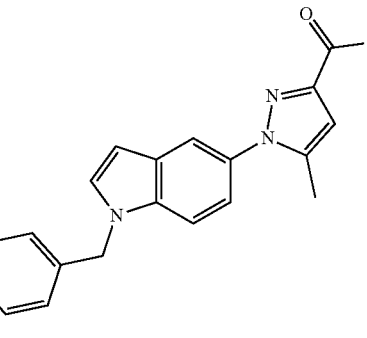<br>5-methyl-1-(1-(4-(1-methylpiperidin-4-yl)benzyl)-1H-indol-5-yl)-1H-pyrazole-3-carboxamide | 428.3<br>1.36 min,<br>A | (DMSO-d6) δ 7.69 (d, J = 1.9 Hz, 1H), 7.64 (d, J = 3.1 Hz, 1H), 7.61 (d, J = 8.8 Hz, 1H), 7.43 (s, 1H), 7.27-7.12 (m, 6H), 6.63-6.54 (m, 2H), 5.44 (s, 2H), 2.87-2.77 (m, 2H), 2.44-2.34 (m, 1H), 2.26 (s, 3H), 2.16 (s, 3H), 1.91 (td, J = 11.4, 2.8 Hz, 2H), 1.77-1.51 (m, 4H). |

Example 3: Synthesis of 5-methyl-1-(1-(4-(1,2,3,6-tetrahydropyridin-4-yl)benzyl)-1H-indol-5-yl)-1H-pyrazole-3-carboxamide

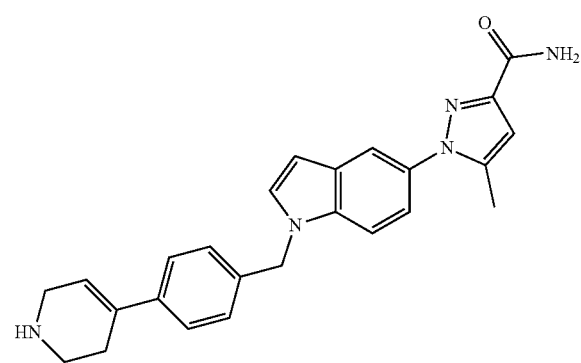 [SMILES: Cc1cc(C(N)=O)nn1-c1ccc2c(ccn2Cc2ccc(C3=CCNCC3)cc2)c1]

Step 1: tert-butyl 4-(4-((5-(3-carbamoyl-5-methyl-1H-pyrazol-1-yl)-1H-indol-1-yl)methyl)phenyl)-5,6-dihydropyridine-1 (2H)-carboxylate (Intermediate II) and tert-butyl 4-(4,4,5,5-tetramethyl-1,3,2-dioxaborolan-2-yl)-5,6-dihydropyridine-1(2H)-carboxylate were reacted according to General Method I for Suzuki coupling to afford tert-butyl 4-(4-((5-(3-carbamoyl-5-methyl-1H-pyrazol-1-yl)-1H-indol-1-yl)methyl)phenyl)-5,6-dihydropyridine-1(2H)-carboxylate: LCMS Rt=1.31 min (condition B), MS (M−55)=456.3.

Step 2: 5-methyl-1-(1-(4-(1,2,3,6-tetrahydropyridin-4-yl)benzyl)-1H-indol-5-yl)-1H-pyrazole-3-carboxamide tert-butyl 4-(4-((5-(3-carbamoyl-5-methyl-1H-pyrazol-1-yl)-1H-indol-1-yl)methyl)phenyl)-5,6-dihydropyridine-1 (2H)-carboxylate (990 mg, 1.94 mmol) was taken up in 4 N Hydrochloric acid in 1,4-dioxane (5 mL). The mixture was stirred for 1 h at ambient temperature then concentrated under reduced pressure. The crude product was taken up in MeOH and purified by SFC to provide (214 mg, 41%) of 5-methyl-1-(1-(4-(1,2,3,6-tetrahydropyridin-4-yl)benzyl)-1H-indol-5-yl)-1H-pyrazole-3-carboxamide: LCMS Rt=1.33 min (condition A), MS (M+1)=412.4. ¹H NMR (400 MHz, DMSO-d6) δ 7.70 (d, J=1.9 Hz, 1H), 7.65 (d, J=3.1 Hz, 1H), 7.59 (d, J=8.7 Hz, 1H), 7.44 (s, 1H), 7.36 (d, J=8.3 Hz, 2H), 7.26-7.13 (m, 4H), 6.63-6.55 (m, 2H), 6.19-6.11 (m, 1H), 5.47 (s, 2H), 3.33 (d, J=2.9 Hz, 2H), 2.88 (t, J=5.6 Hz, 2H), 2.33-2.21 (m, 5H).

Example 4: Synthesis of 5-methyl-1-(1-(4-(1-(methylsulfonyl)-1,2,3,6-tetrahydropyridin-4-yl)benzyl)-1H-indol-5-yl)-1H-pyrazole-3-carboxamide

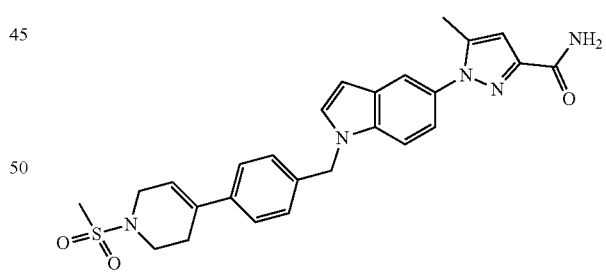

5-methyl-1-(1-(4-(1,2,3,6-tetrahydropyridin-4-yl)benzyl)-1H-indol-5-yl)-1H-pyrazole-3-carboxamide (Example 3) (60 mg, 0.146 mmol) was added to a 7 mL vial and dissolved in THF (1.5 mL) and DMF (0.5 mL). The reaction was cooled to 0° C., DIPEA (0.25 mL, 1.46 mmol) was added, and the reaction mixture was incubated for 10 minutes. Next, methanesulfonyl chloride (0.012 mL, 0.146 mmol) was added, and the reaction was stirred for 1 hour at 0° C. The reaction was then purified by preparative HPLC to afford (16 mg, 21%) of 5-methyl-1-(1-(4-(1-(methylsulfonyl)-1,2,3,6-tetrahydropyridin-4-yl)benzyl)-1H-indol-5-yl)-1H-pyrazole-3-carboxamide: LCMS Rt=2.10 min (condition A), MS (M+1)=490.3. ¹H NMR (400 MHz, Acetone-d6) δ 7.76-7.69 (m, 1H), 7.60-7.54 (m, 2H), 7.48-7.43 (m, 2H), 7.26 (dd, J=8.6, 2.1 Hz, 3H), 7.07 (s, 1H), 6.66 (dd, J=3.2, 0.8 Hz, 1H), 6.62 (d, J=0.8 Hz, 1H), 6.38 (s, 1H), 6.19 (tt, J=3.5, 1.6 Hz, 1H), 5.55 (s, 2H), 3.93 (q, J=2.7 Hz, 2H), 3.48 (t, J=5.7 Hz, 2H), 2.88 (s, 3H), 2.68-2.61 (m, 2H), 2.32 (d, J=0.7 Hz, 3H).

Example 5: Synthesis of 1-(1-(4-(1-(2-hydroxy-acetyl)-1,2,3,6-tetrahydropyridin-4-yl)benzyl)-1H-indol-5-yl)-5-methyl-1H-pyrazole-3-carboxamide

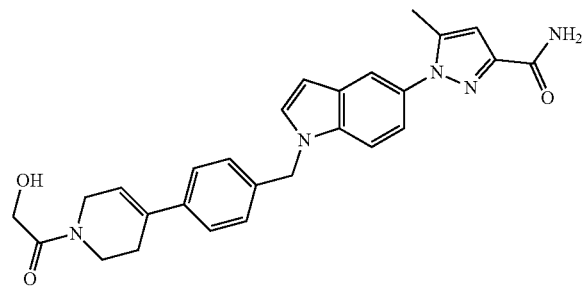 [SMILES: Cc1cc(C(N)=O)nn1-c1ccc2c(ccn2Cc2ccc(C3=CCN(C(=O)CO)CC3)cc2)c1]

5-methyl-1-(1-(4-(1,2,3,6-tetrahydropyridin-4-yl)benzyl)-1H-indol-5-yl)-1H-pyrazole-3-carboxamide (Example 3) (60 mg, 0.146 mmol) was added to a 7 mL vial, followed by 2-hydroxyacetic acid (16 mg, 0.220 mmol) and HBTU (55 mg, 0.146 mmol). The solids were dissolved in DMF (1.5 mL), and DIPEA (0.13 mL, 0.729 mmol) was added. The reaction was stirred for 16 hours and then the solution was passed through a 0.45 uM PTFE membrane and purified by preparative HPLC to afford 1-(1-(4-(1-(2-hydroxy-acetyl)-1,2,3,6-tetrahydropyridin-4-yl)benzyl)-1H-indol-5-yl)-5-methyl-1H-pyrazole-3-carboxamide (23 mg, 33%): LCMS Rt=1.86 min (condition A), MS (M+1)=470.3. ¹H NMR (400 MHz, DMSO-d6) δ 7.70 (d, J=1.9 Hz, 1H), 7.66 (d, J=3.1 Hz, 1H), 7.58 (d, J=8.8 Hz, 1H), 7.46-7.35 (m, 3H), 7.26-7.19 (m, 3H), 7.17 (s, 1H), 6.59 (d, J=2.7 Hz, 2H), 6.13 (d, J=16.9 Hz, 1H), 5.48 (s, 2H), 4.61-4.49 (m, 1H), 4.18-3.99 (m, 4H), 3.67 (s, 1H), 3.52 (t, J=5.5 Hz, 1H), 2.26 (s, 3H).

Example 6: Synthesis of 1-(1-(4-(1-(cyclopropylmethyl)-1,2,3,6-tetrahydropyridin-4-yl)benzyl)-1H-indol-5-yl)-5-methyl-1H-pyrazole-3-carboxamide

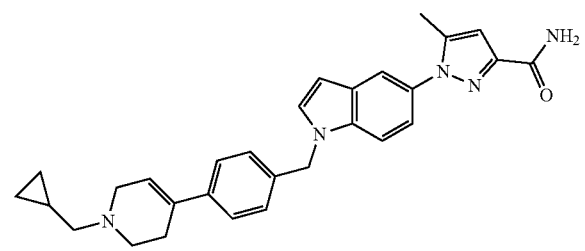 [SMILES: Cc1cc(C(N)=O)nn1-c1ccc2c(ccn2Cc2ccc(C3=CCN(CC4CC4)CC3)cc2)c1]

5-methyl-1-(1-(4-(1,2,3,6-tetrahydropyridin-4-yl)benzyl)-1H-indol-5-yl)-1H-pyrazole-3-carboxamide (Example 3) (40 mg, 0.076 mmol) was added to a 7 mL vial, followed by potassium carbonate (52 mg, 0.38 mmol). The solids were dissolved in DMF, and (bromomethyl)cyclopropane (10 mg, 0.076 mmol) was added. The reaction was stirred for eight hours and was then diluted to 3 mL with DMSO and purified by preparative HPLC to afford 1-(1-(4-(1-(cyclopropylmethyl)-1,2,3,6-tetrahydropyridin-4-yl)benzyl)-1H-indol-5-yl)-5-methyl-1H-pyrazole-3-carboxamide (12 mg, 33%): LCMS Rt=1.44 min (condition A), MS (M+1)=466.5. ¹H NMR (400 MHz, Methanol-d4) δ 8.39 (s, 2H), 7.66 (d, J=1.8 Hz, 1H), 7.49-7.37 (m, 4H), 7.23-7.13 (m, 3H), 6.71-6.66 (m, 1H), 6.63 (dd, J=3.2, 0.6 Hz, 1H), 6.10 (dt, J=3.4, 1.9 Hz, 1H), 5.47 (s, 2H), 3.99-3.85 (m, 2H), 3.52 (t, J=6.0 Hz, 2H), 3.10 (d, J=7.3 Hz, 2H), 2.84 (dt, J=5.9, 3.0 Hz, 2H), 2.32-2.22 (m, 3H), 1.16 (dtd, J=12.2, 7.6, 2.7 Hz, 1H), 0.82-0.72 (m, 2H), 0.51-0.41 (m, 2H).

Example 7: Synthesis of 1-(1-(4-(1-(dimethylglycyl)-1,2,3,6-tetrahydropyridin-4-yl)benzyl)-1H-indol-5-yl)-5-methyl-1H-pyrazole-3-carboxamide

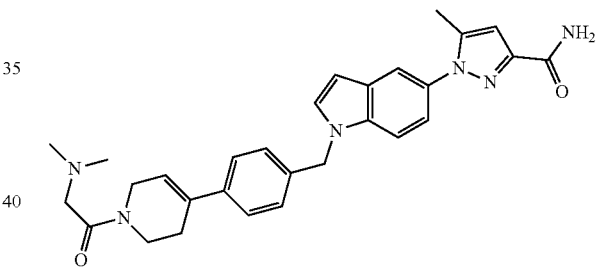

5-methyl-1-(1-(4-(1,2,3,6-tetrahydropyridin-4-yl)benzyl)-1H-indol-5-yl)-1H-pyrazole-3-carboxamide (Example 3) (40 mg, 0.097 mmol) was added to a 7 mL vial, followed by 2-(dimethylamino)acetic acid (15 mg, 0.146 mmol) and HBTU (37 mg, 0.097 mmol). The solids were dissolved in DMF (1 mL), DIPEA (0.1 mL, 0.49 mmol) was added and the reaction was stirred for 16 hours. The reaction was then filtered through 0.45 uM PTFE membrane, diluted to 3 mL with DMSO and purified by preparative HPLC to afford 1-(1-(4-(1-(dimethylglycyl)-1,2,3,6-tetrahydropyridin-4-yl)benzyl)-1H-indol-5-yl)-5-methyl-1H-pyrazole-3-carboxamide (13 mg, 26%): LCMS Rt=1.45 min (condition A), MS (M+1)=497.4. ¹H NMR (400 MHz, Methanol-d4) δ 7.68 (d, J=1.9 Hz, 1H), 7.52-7.43 (m, 2H), 7.38 (d, J=8.3 Hz, 2H), 7.22-7.14 (m, 3H), 6.69 (d, J=0.7 Hz, 1H), 6.64 (dd, J=3.2, 0.7 Hz, 1H), 6.14-6.06 (m, 1H), 5.46 (s, 2H), 4.25 (d, J=2.8 Hz, 1H), 4.17 (d, J=2.8 Hz, 1H), 3.77 (dt, J=7.9, 5.8 Hz, 2H), 3.28 (s, 1H), 3.24 (s, 1H), 2.64-2.54 (m, 1H), 2.54-2.48 (m, 1H), 2.31 (d, J=2.1 Hz, 6H), 2.30-2.28 (m, 3H).

Example 8: Synthesis of 1-(1-(4-(1-(3-aminopropyl)piperidin-4-yl)benzyl)-1H-indol-5-yl)-5-methyl-1H-pyrazole-3-carboxamide

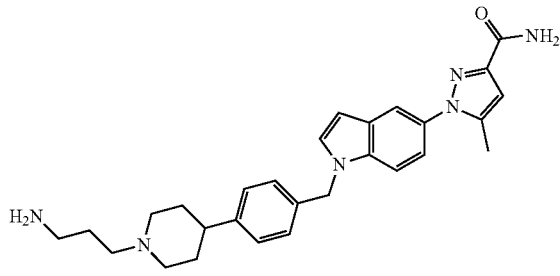 [SMILES: Cc1cc(C(N)=O)nn1-c1ccc2c(ccn2Cc2ccc(C3CCN(CCCN)CC3)cc2)c1]

Step 1: 5-methyl-1-(1-(4-(piperidin-4-yl)benzyl)-1H-indol-5-yl)-1H-pyrazole-3-carboxamide A pressure vessel was charged with 5-methyl-1-(1-(4-(1,2,3,6-tetrahydropyridin-4-yl)benzyl)-1H-indol-5-yl)-1H-pyrazole-3-carboxamide (Example 3) (110 mg, 0.267 mmol), 10% Pd/C (57 mg, 0.053 mmol) and MeOH (2.7 mL). The flask was sealed, charged with hydrogen gas to 50 psi, and shaken on a parr-shaker for 48 h. The suspension was filtered through celite, and the filtrate was concentrated to afford 5-methyl-1-(1-(4-(piperidin-4-yl)benzyl)-1H-indol-5-yl)-1H-pyrazole-3-carboxamide (89.1 mg, 79%): LCMS Rt=1.34 min (condition A), MS (M+1)=414.4. $^1$H NMR (400 MHz, DMSO-d6) δ 7.67 (dd, J=18.5, 2.5 Hz, 2H), 7.61 (d, J=8.7 Hz, 1H), 7.43 (s, 1H), 7.26-7.13 (m, 7H), 6.59 (d, J=3.5 Hz, 2H), 5.50-5.41 (m, 2H), 3.22-3.15 (m, 2H), 2.85-2.73 (m, 2H), 2.67 (td, J=10.3, 8.7, 6.0 Hz, 1H), 2.26 (s, 3H), 1.83-1.56 (m, 4H).

Step 2: tert-butyl (3-(4-(4-((5-(3-carbamoyl-5-methyl-1H-pyrazol-1-yl)-1H-indol-1-yl)methyl)phenyl)piperidin-1-yl)propyl)carbamate 5-methyl-1-(1-(4-(piperidin-4-yl)benzyl)-1H-indol-5-yl)-1H-pyrazole-3-carboxamide (70 mg, 0.169 mmol) was taken up in DMF (1.7 mL). Potassium carbonate (70.2 mg, 0.508 mmol) and tert-butyl (3-bromopropyl)carbamate (43.1 mg, 0.181 mmol) were added, and the resulting suspension was stirred at ambient temperature for 18 h. The reaction was then diluted with EtOAc and washed with water and brine. The organic layer was dried over sodium sulfate and concentrated in vacuo. The crude material was purified by preparative HPLC to afford tert-butyl (3-(4-(4-((5-(3-carbamoyl-5-methyl-1H-pyrazol-1-yl)-1H-indol-1-yl)methyl)phenyl)piperidin-1-yl)propyl)carbamate (8.1 mg, 8%): LCMS Rt=1.64 min (condition A), MS (M+1)=571.4. $^1$H NMR (400 MHz, DMSO-d6) δ 7.69 (d, J=2.0 Hz, 1H), 7.65 (d, J=3.1 Hz, 1H), 7.61 (d, J=8.8 Hz, 1H), 7.43 (s, 1H), 7.27-7.11 (m, 6H), 6.81 (s, 1H), 6.62-6.55 (m, 2H), 5.44 (s, 2H), 2.93 (q, J=6.6 Hz, 4H), 2.42 (s, 1H), 2.29-2.23 (m, 4H), 2.02-1.43 (m, 8H), 1.37 (s, 9H).

Step 3: 1-(1-(4-(1-(3-aminopropyl)piperidin-4-yl)benzyl)-1H-indol-5-yl)-5-methyl-1H-pyrazole-3-carboxamide To a round bottom flask containing tert-butyl (3-(4-(4-((5-(3-carbamoyl-5-methyl-1H-pyrazol-1-yl)-1H-indol-1-yl)methyl)phenyl)piperidin-1-yl)propyl)carbamate (40 mg, 0.070 mmol) was added 4 N HCl in 1,4-dioxane (0.1 mL, 0.421 mmol). The mixture was stirred at ambient temperature for 1.5 h. The mixture was then concentrated, and the resulting crude oil was taken up in MeOH and purified by SCX-BSA according to General Method IV to afford 1-(1-(4-(1-(3-aminopropyl)piperidin-4-yl)benzyl)-1H-indol-5-yl)-5-methyl-1H-pyrazole-3-carboxamide (8.9 mg, 0.019 mmol): LCMS Rt=1.01 min (condition A), MS (M+1)=471.4. $^1$H NMR (400 MHz, DMSO-d6) δ 7.69 (d, J=2.0 Hz, 1H), 7.65 (d, J=3.1 Hz, 1H), 7.61 (d, J=8.7 Hz, 1H), 7.43 (s, 1H), 7.27-7.11 (m, 6H), 6.62-6.56 (m, 2H), 5.44 (s, 2H), 2.92 (d, J=11.3 Hz, 2H), 2.60-2.54 (m, 1H), 2.47-2.37 (m, 2H), 2.35-2.22 (m, 6H), 1.96-1.84 (m, 2H), 1.77-1.44 (m, 7H).

Example 9: Synthesis of 1-(1-(4-(1-(3-acetamidopropyl)piperidin-4-yl)benzyl)-1H-indol-5-yl)-5-methyl-1H-pyrazole-3-carboxamide

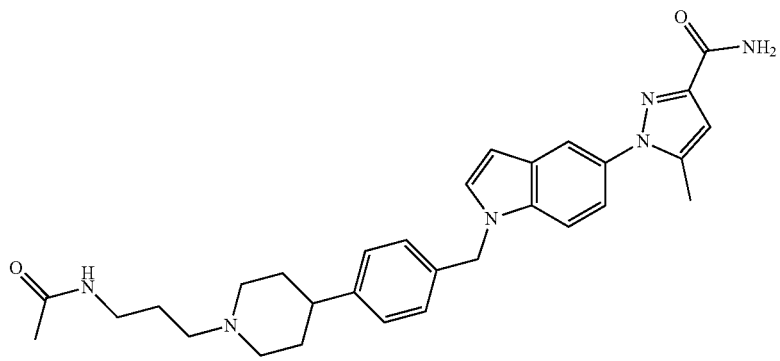 [SMILES: CC(=O)NCCCN1CCC(c2ccc(Cn3ccc4cc(-n5nc(C(N)=O)cc5C)ccc43)cc2)CC1]

A 4 mL reaction vial was charged with 1-(1-(4-(1-(3-aminopropyl)piperidin-4-yl)benzyl)-1H-indol-5-yl)-5-methyl-1H-pyrazole-3-carboxamide (Example 8) (11.3 mg, 0.024 mmol), acetic anhydride (29.4 mg, 0.288 mmol), DMAP (0.15 mg, 0.012 mmol), triethylamine (0.084 mL, 0.600 mmol), and DCM (1.2 mL). The resulting mixture was stirred at ambient temperature for 3 h. The reaction mixture was purified without workup by SCX-BSA according to General Method IV followed by preparative HPLC purification to afford 1-(1-(4-(1-(3-acetamidopropyl)piperidin-4-yl)benzyl)-1H-indol-5-yl)-5-methyl-1H-pyrazole-3-carboxamide (2.8 mg, 22%): LCMS Rt=1.34 min (condition A), MS (M+1)=513.4. $^1$H NMR (400 MHz, DMSO-d6) δ 7.86-7.75 (m, 1H), 7.69 (d, J=1.9 Hz, 1H), 7.65 (d, J=3.1 Hz, 1H), 7.61 (d, J=8.7 Hz, 1H), 7.43 (s, 1H), 7.26-7.11 (m, 6H), 6.58 (d, J=4.0 Hz, 2H), 5.44 (s, 2H), 3.03 (q, J=6.8 Hz, 2H), 2.99-2.86 (m, 2H), 2.46-2.37 (m, 1H), 2.31-2.21 (m, 5H), 2.02-1.83 (m, 2H), 1.77 (s, 3H), 1.74-1.48 (m, 6H).

Example 10: Synthesis of 1-(1-(4-(1-(dimethylglycyl)-1,2,3,6-tetrahydropyridin-4-yl)benzyl)-1H-indol-5-yl)-5-methyl-1H-pyrazole-3-carboxamide

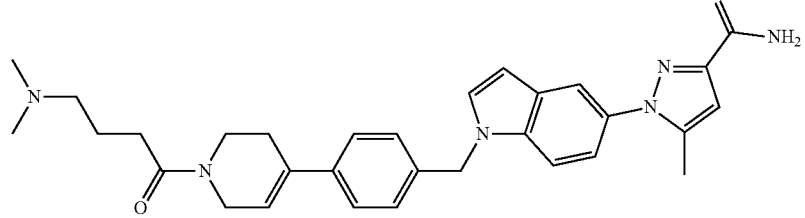

To a stirred solution of 5-methyl-1-(1-(4-(1,2,3,6-tetrahydropyridin-4-yl)benzyl)-1H-indol-5-yl)-1H-pyrazole-3-carboxamide (Example 3) (0.1 g, 0.22 mmol) in dry DMF (2 mL) was added 4-(Dimethylamino)butanoic acid (56 mg, 0.33 mmol), HBTU (84 mg, 0.22 mmol), and DIPEA (145 mg, 1.1 mmol) at ambient temperature. The reaction mixture was allowed to stir for 6 h. The reaction mixture was diluted with EtOAc (50 mL) and washed with water and brine. The organics were separated, dried over anhydrous sodium sulfate and concentrated in vacuo. The crude material was purified by preparative HPLC to afford 1-(1-(4-(1-(dimethylglycyl)-1,2,3,6-tetrahydropyridin-4-yl)benzyl)-1H-indol-5-yl)-5-methyl-1H-pyrazole-3-carboxamide (0.032 g, 29%): LCMS Rt=0.73 min (condition B), MS (M+1)=525.1. $^1$H NMR (400 MHz, Methanol-d4) b 7.69 (d, J=1.8 Hz, 1H), 7.52-7.43 (m, 2H), 7.39 (d, J=8.1 Hz, 2H), 7.27-7.05 (m, 3H), 6.67 (dd, J=19.7, 1.9 Hz, 2H), 6.12 (s, 1H), 5.47 (s, 2H), 4.20 (d, J=5.3 Hz, 2H), 3.77 (dt, J=21.9, 5.7 Hz, 2H), 2.60 (s, 1H), 2.47 (ddd, J=47.7, 27.4, 19.9 Hz, 5H), 2.40-2.19 (m, 9H), 1.84 (dd, J=12.9, 7.5 Hz, 2H).

Example 11-1: Synthesis of 5-methyl-1-(1-(4-(piperazin-1-yl)benzyl)-1H-indol-5-yl)-1H-pyrazole-3-carboxamide

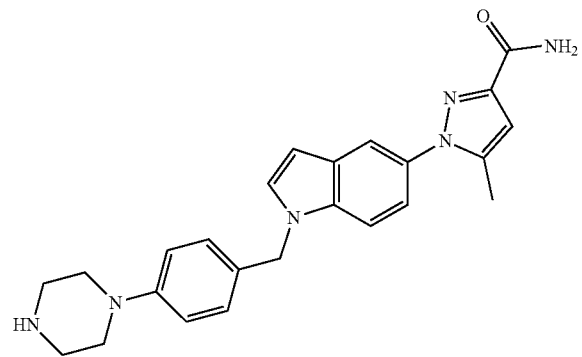 [SMILES: Cc1cc(C(N)=O)nn1-c1ccc2c(ccn2Cc2ccc(N3CCNCC3)cc2)c1]

A solution of 1-(1-(4-bromobenzyl)-1H-indol-5-yl)-5-methyl-1H-pyrazole-3-carboxamide (Intermediate II) (0.1 g, 0.24 mmol), tert-butyl piperazine-1-carboxylate (91 mg, 0.489 mmol), BINAP (15.2 mg, 0.024 mmol), and sodium tert-butoxide (49 mg, 0.513 mmol) in Toluene (Volume: 1222 µl, Ratio: 1.000) was degassed with nitrogen for 5 min. Then tris(dibenzylideneacetone)dipalladium(0) (11.19 mg, 0.012 mmol) was added, and the resulting mixture was heated at 100° C. for 18 h. The reaction was diluted with EtOAc, washed with brine, dried over sodium sulfate and concentrated in vacuo. The crude material was then taken up in Dioxane (1.2 mL) and cooled to 0° C. 4N HCl in 1,4-dioxane (0.31 mL) was added dropwise, and the resulting suspension was stirred at ambient temperature for 45 min. The reaction was then concentrated in vacuo. The crude material was purified by preparative HPLC to afford 5-methyl-1-(1-(4-(piperazin-1-yl)benzyl)-1H-indol-5-yl)-1H-pyrazole-3-carboxamide (10.6 mg, 10.3%): LCMS Rt=1.26 min (condition A), MS (M+1)=415.4. $^1$H NMR (400 MHz, DMSO-d6) δ 7.68 (d, J=2.0 Hz, 1H), 7.65-7.57 (m, 2H), 7.44 (s, 1H), 7.26-7.09 (m, 4H), 6.90-6.82 (m, 2H), 6.62-6.52 (m, 2H), 5.35 (s, 2H), 3.03-2.93 (m, 4H), 2.84-2.74 (m, 4H), 2.26 (s, 3H).

The following compounds were prepared using a similar procedure as in Example 11-1

| Example | Compound | LCMS M + 1, Rt, conditions | 1H NMR, 400 MHz |
|---|---|---|---|
| 11-2 | 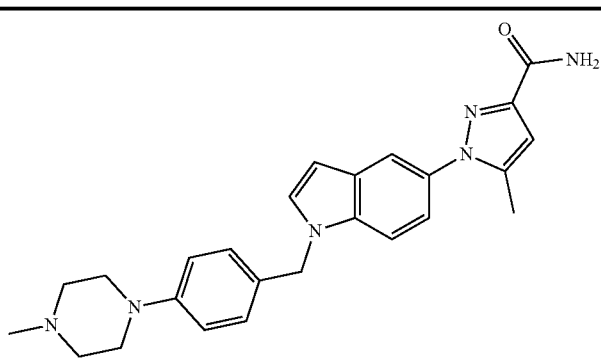<br>5-methyl-1-(1-(4-(4-methylpiperazin-1-yl)benzyl)-1H-indol-5-yl)-1H-pyrazole-3-carboxamide | 429.3<br>1.25 min<br>A | (DMSO-d6) δ 7.68 (d, J = 2.0 Hz, 1H), 7.65-7.57 (m, 2H), 7.44 (s, 1H), 7.28-7.09 (m, 4H), 6.87 (d, J = 8.7 Hz, 2H), 6.65-6.50 (m, 2H), 5.35 (s, 2H), 3.14-3.00 (m, 4H), 2.46-2.34 (m, 4H), 2.26 (s, 3H), 2.19 (s, 3H). |
| 11-3 | 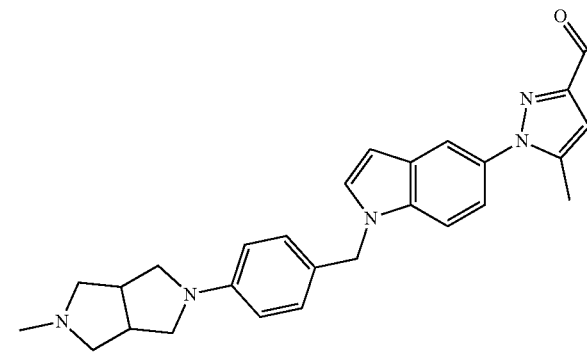<br>5-methyl-1-(1-(4-(5-methylhexahydropyrrolo[3,4-c]pyrrol-2(1H)-yl)benzyl)-1H-indol-5-yl)-1H-pyrazole-3-carboxamide | 455.4<br>1.46 min<br>A | (DMSO-d6) δ 7.67 (d, J = 2.0 Hz, 1H), 7.64-7.57 (m, 2H), 7.44 (s, 1H), 7.25-7.08 (m, 4H), 6.62-6.50 (m, 4H), 5.32 (s, 2H), 3.31-3.25 (m, 2H), 3.01 (dd, J = 9.6, 3.2 Hz, 2H), 2.83 (d, J = 3.2 Hz, 2H), 2.57-2.51 (m, 2H), 2.34 (dd, J = 9.0, 2.9 Hz, 2H), 2.25 (s, 3H), 2.18 (s, 3H). |

Example 12: Synthesis of 1-(1-(4-(3-(dimethylamino)prop-1-yn-1-yl)benzyl)-1H-indol-5-yl)-5-methyl-1H-pyrazole-3-carboxamide

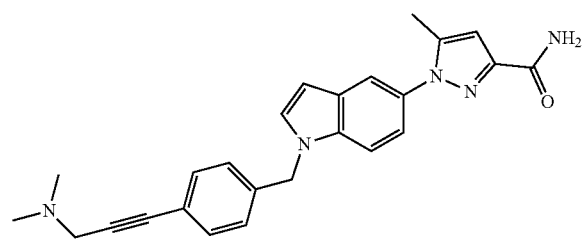 [SMILES: Cc1cc(C(N)=O)nn1-c1ccc2c(ccn2Cc2ccc(C#CCN(C)C)cc2)c1]

1-(1-(4-bromobenzyl)-1H-indol-5-yl)-5-methyl-1H-pyrazole-3-carboxamide (Intermediate II) (75 mg, 0.183 mmol) was added to an oven dried 40 mL vial, followed by N,N-dimethylprop-2-yn-1-amine (23 mg, 0.275 mmol), copper iodide (3.5 mg, 0.018 mmol) and bis(triphenylphosphine)palladium(II) dichloride (13 mg, 0.018 mmol). The solids were dissolved in degassed DMF (2 mL), and degassed triethylamine (0.52 mL, 3.66 mmol) was added. The reaction was stirred at 80° C. for 6 h, and then the reaction mixture was transferred to a 125 mL separatory funnel and diluted with EtOAc (80 mL). The organic phase was washed with water (1×), saturated lithium chloride (3×) and brine (1×), dried over $MgSO_4$ and concentrated onto celite. The crude material was purified by FCC (gradient 0-10% DCM in MeOH, buffered with 3% triethylamine) to afford 1-(1-(4-(3-(dimethylamino)prop-1-yn-1-yl)benzyl)-1H-indol-5-yl)-5-methyl-1H-pyrazole-3-carboxamide (28 mg, 36%): LCMS Rt=1.35 min (condition A), MS (M+1)=412.7. $^1$H NMR (400 MHz, DMSO-d6) δ 7.71 (d, J=2.0 Hz, 1H), 7.66 (d, J=3.1 Hz, 1H), 7.56 (d, J=8.7 Hz, 1H), 7.40 (d, J=8.3 Hz, 3H), 7.26-7.13 (m, 4H), 6.63-6.56 (m, 2H), 5.52 (s, 2H), 2.31-2.25 (m, 8H), 2.20 (s, 2H).

Examples 13 and 14: Synthesis of Enantiomers of 1-(1-(4-(1-azabicyclo[3.3.1]non-3-en-4-yl)benzyl)-1H-indol-5-yl)-5-methyl-1H-pyrazole-3-carboxamide

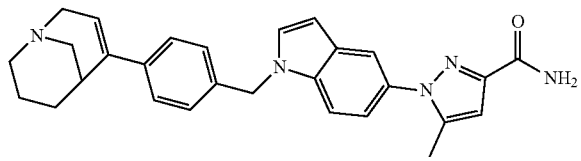 [SMILES: Cc1cc(C(N)=O)nn1-c1ccc2c(ccn2Cc2ccc(C3=CCN4CCCC3C4)cc2)c1]

Step 1: 1-azabicyclo[3.3.1]non-3-en-4-yl trifluoromethanesulfonate

To 1-azabicyclo[3.3.1]nonan-4-one (500 mg, 3.59 mmol) in THF (3.6 mL) cooled to −78° C. was added 1M LiHMDS in THF (4.0 mL, 3.95 mmol) dropwise, and the resulting solution was allowed to stir for 20 minutes at −78° C. Then 1,1,1-trifluoro-N-phenyl-N-(((trifluoromethyl)sulfonyl)methanesulfonamide (1.4 g, 3.95 mmol) in THF (4.0 mL) was added, and the reaction was allowed to slowly warm to room temperature and stir for 18 h. The reaction mixture was then concentrated in vacuo. The crude material was taken up in DCM, washed with saturated aqueous ammonium chloride and brine, dried over sodium sulfate and concentrated in vacuo to afford 974 mg of crude 1-azabicyclo[3.3.1]non-3-en-4-yl trifluoromethanesulfonate.

Step 2: 1-(1-(4-(1-azabicyclo[3.3.1]non-3-en-4-yl)benzyl)-1H-indol-5-yl)-5-methyl-1H-pyrazole-3-carboxamide 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) (200 mg, 0.438 mmol), 1-azabicyclo[3.3.1]non-3-en-4-yl trifluoromethanesulfonate (131 mg, 0.482 mmol), and $Na_2CO_3$ (139 mg, 1.315 mmol) were taken up in THF (3.7 mL) and Water (0.73 mL), and the resulting mixture was degassed with nitrogen for 5 min. Tetrakis(triphenylphosphine)palladium(0) (50.6 mg, 0.044 mmol) was then added, and the resulting mixture was heated at 50° C. for 1 h. The reaction mixture was then diluted with EtOAc, washed with water and brine, dried over sodium sulfate and concentrated in vacuo. The crude material was purified by preparative HPLC to afford a mixture of enantiomers. This mixture was purified by Chiral SFC to afford the pure enantiomers. Conditions: The purification of the racemic material was performed using supercritical fluid chromatography on a Thar 80. An isocratic method was developed for the preparative purification utilizing a mobile phase of 40% (1:1)methanol/2-propanol (with 10 mM ammoniated methanol) and 60% carbon dioxide at a flow rate of 60 g/min on the Chiralpak AD-H (21×250 mm, 5 μm). The automated back pressure regulator set point was 100 bar with UV based collection set to observe 254 nm. Two isolates were generated from the purification process with analysis performed using an isocratic method that was developed utilizing 40% (1:1) methanol/2-propanol (with 10 mM ammonium hydroxide) and 60% carbon dioxide at a flow rate of 5 mL/min on the Chiralpak AD-H (4.6×100 mm, 5 μm). The automated back pressure regulator set point for the analysis was set to 120 bar with both UV and MS analysis performed.

Example 13: Enantiomer 1

1-(1-(4-(1-azabicyclo[3.3.1]non-3-en-4-yl)benzyl)-1H-indol-5-yl)-5-methyl-1H-pyrazole-3-carboxamide (27.5 mg, 13%): SFC Rt=7.9 min. LCMS Rt=1.42 min (condition A), MS (M+1)=452.9. $^1$H NMR (400 MHz, DMSO-d6) δ 7.76-7.53 (m, 3H), 7.53-7.32 (m, 3H), 7.32-7.06 (m, 4H), 6.59 (s, 2H), 6.41 (s, 1H), 5.47 (s, 2H), 3.63 (d, J=18.4 Hz, 1H), 3.23-3.10 (m, 1H), 2.96 (d, J=12.2 Hz, 1H), 2.89-2.71 (m, 3H), 2.26 (s, 3H), 1.78-1.08 (m, 5H).

Example 14: Enantiomer 2

1-(1-(4-(1-azabicyclo[3.3.1]non-3-en-4-yl)benzyl)-1H-indol-5-yl)-5-methyl-1H-pyrazole-3-carboxamide (25.8 mg, 12%): SFC Rt=6.6 min. LCMS Rt=1.42 min (condition A), MS (M+1)=452.9. $^1$H NMR (400 MHz, DMSO-d6) δ 7.76-7.53 (m, 3H), 7.53-7.32 (m, 3H), 7.32-7.06 (m, 4H), 6.59 (s, 2H), 6.41 (s, 1H), 5.47 (s, 2H), 3.63 (d, J=18.4 Hz, 1H), 3.23-3.10 (m, 1H), 2.96 (d, J=12.2 Hz, 1H), 2.89-2.71 (m, 3H), 2.26 (s, 3H), 1.78-1.08 (m, 5H).

Example 15-1: Synthesis of 5-methyl-1-(1-(4-(1,2,2-trimethyl-1,2,3,6-tetrahydropyridin-4-yl)benzyl)-1H-indol-5-yl)-1H-pyrazole-3-carboxamide

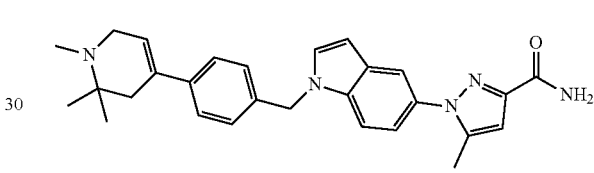

Step 1: tert-butyl 6,6-dimethyl-4-(((trifluoromethyl)sulfonyl)oxy)-5,6-dihydropyridine-1(2H)-carboxylate Tert-butyl 2,2-dimethyl-4-oxopiperidine-1-carboxylate was reacted according to General Method V for vinyl triflate formation to afford tert-butyl 6,6-dimethyl-4-(((trifluoromethyl)sulfonyl)oxy)-5,6-dihydropyridine-1(2H)-carboxylate: $^1$H NMR (400 MHz, Chloroform-d) δ 5.66-5.57 (m, 1H), 3.92 (dt, J=3.6, 2.6 Hz, 2H), 2.23 (dt, J=2.4, 1.2 Hz, 2H), 1.33 (d, J=1.8 Hz, 6H), 1.31 (s, 9H).

Step 2: tert-butyl 4-(4-((5-(3-carbamoyl-5-methyl-1H-pyrazol-1-yl)-1H-indol-1-yl)methyl)phenyl)-6,6-dimethyl-5,6-dihydropyridine-(2H)-carboxylate 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) and tert-butyl 6,6-dimethyl-4-(((trifluoromethyl)sulfonyl)oxy)-5,6-dihydropyridine-1(2H)-carboxylate were reacted according to General Method III for the Suzuki coupling to afford tert-butyl 4-(4-((5-(3-carbamoyl-5-methyl-1H-pyrazol-1-yl)-1H-indol-1-yl)methyl)phenyl)-6,6-dimethyl-5,6-dihydropyridine-1(2H)-carboxylate: LCMS Rt=1.25 min (condition B), MS (M−100)=440.3.

Step 3: 1-(1-(4-(2,2-dimethyl-1,2,3,6-tetrahydropyridin-4-yl)benzyl)-1H-indol-5-yl)-5-methyl-1H-pyrazole-3-carboxamide tert-butyl 4-(4-((5-(3-carbamoyl-5-methyl-1H-pyrazol-1-yl)-1H-indol-1-yl)methyl)phenyl)-6,6-dimethyl-5,6-dihydropyridine-1(2H)-carboxylate was reacted according to General Method VII to afford 1-(1-(4-(2,2-dimethyl-1,2,3,6-tetrahydropyridin-4-yl)benzyl)-1H-indol-5-yl)-5-methyl-1H-pyrazole-3-carboxamide: LCMS Rt=0.98 min (condition B), MS (M+1)=440.3.

Step 4: 5-methyl-1-(1-(4-(1,2,2-trimethyl-1,2,3,6-tetrahydropyridin-4-yl)benzyl)-1H-indol-5-yl)-1H-pyrazole-3-carboxamide 1-(1-(4-(2,2-dimethyl-1,2,3,6-tetrahydropyridin-4-yl)benzyl)-1H-indol-5-yl)-5-methyl-1H-pyrazole-3-carboxamide was reacted according to General Method VI for the N-methylation to afford 5-methyl-1-(1-(4-(1,2,2-trimethyl-1,2,3,6-tetrahydropyridin-4-yl)benzyl)-1H-indol-5-yl)-1H-pyrazole-3-carboxamide: LCMS Rt=1.44 min (condition A), MS (M+1)=454.2. $^1$H NMR (400 MHz, DMSO-d6) δ 7.74-7.63 (m, 2H), 7.58 (d, J=8.8 Hz, 1H), 7.44 (s, 1H), 7.41-7.31 (m, 2H), 7.30-7.10 (m, 4H), 6.64-6.55 (m, 2H), 6.15-5.98 (m, 1H), 5.46 (s, 2H), 3.11-3.04 (m, 2H), 2.29-2.24 (m, 3H), 2.25-2.20 (m, 2H), 2.16 (s, 3H), 0.98 (s, 6H).

The following compounds were prepared using a similar procedure as in Example 15-1

Example 16-1: Synthesis of 5-methyl-1-(1-(4-(1,3,3-trimethylpiperidin-4-yl)benzyl)-1H-indol-5-yl)-1H-pyrazole-3-carboxamide

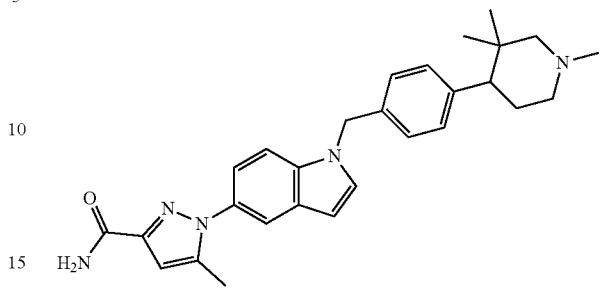

A round bottom flask was charged with 5-methyl-1-(1-(4-(1,3,3-trimethyl-1,2,3,6-tetrahydropyridin-4-yl)benzyl)-1H-indol-5-yl)-1H-pyrazole-3-carboxamide (Example 15-2) (20 mg, 0.044 mmol), 10% Pd/C (23.5 mg, 0.022 mmol) and MeOH (1.8 mL). The flask was sealed and charged with hydrogen gas under atmospheric pressure, and the suspension was stirred at ambient temperature for 18 h. The suspension was filtered through a 0.45 micron syringe filter, and the filtrate was concentrated in vacuo to afford 5-methyl-1-(1-(4-(1,3,3-trimethylpiperidin-4-yl)benzyl)-1H-indol-5-yl)-1H-pyrazole-3-carboxamide (13 mg, 63%): LCMS Rt=1.45 min (condition A), MS (M+1)=456.0. $^1$H NMR

| Example | Compound | LCMS M + 1, Rt, conditions | 1H NMR, 400 MHz |
|---|---|---|---|
| 15-2 | 5-methyl-1-(1-(4-(1,3,3-trimethyl-1,2,3,6-tetrahydropyridin-4-yl)benzyl)-1H-indol-5-yl)-1H-pyrazole-3-carboxamide | 454.1 1.44 min A | (DMSO-d6) δ 7.71 (d, J = 1.9 Hz, 1H), 7.66 (d, J = 3.1 Hz, 1H), 7.62 (d, J = 8.7 Hz, 1H), 7.44 (s, 1H), 7.24 (dd, J = 8.7, 2.1 Hz, 1H), 7.21-7.06 (m, 5H), 6.64-6.56 (m, 2H), 5.48 (s, 2H), 5.34 (t, J = 3.3 Hz, 1H), 2.89 (d, J = 3.2 Hz, 2H), 2.29-2.20 (m, 8H), 0.97 (s, 6H). |
| 15-3 | 5-methyl-1-(1-(4-(2-methyl-2-azaspiro[3.5]non-6-en-7-yl)benzyl)-1H-indol-5-yl)-1H-pyrazole-3-carboxamide | 466.5 1.49 min A | (DMSO-d6) δ 7.69 (d, J = 2.0 Hz, 1H), 7.65 (d, J = 3.1 Hz, 1H), 7.57 (d, J = 8.7 Hz, 1H), 7.44 (s, 1H), 7.39-7.30 (m, 2H), 7.26-7.13 (m, 4H), 6.62-6.55 (m, 2H), 6.09-6.00 (m, 1H), 5.46 (s, 2H), 2.97 (m, 4H), 2.42-2.29 (m, 4H), 2.28-2.19 (m, 6H), 1.82 (t, J = 6.2 Hz, 2H). |

(400 MHz, DMSO-d6) δ 7.70 (d, J=1.9 Hz, 1H), 7.64 (d, J=3.1 Hz, 1H), 7.61 (d, J=8.8 Hz, 1H), 7.44 (s, 1H), 7.23 (dd, J=8.7, 2.0 Hz, 1H), 7.18 (s, 1H), 7.16-7.06 (m, 4H), 6.62-6.55 (m, 2H), 5.46 (s, 2H), 2.93-2.79 (m, 1H), 2.51-2.38 (m, 1H), 2.30-2.08 (m, 8H), 1.93-1.62 (m, 2H), 1.43-1.32 (m, 1H), 0.79 (s, 3H), 0.64 (s, 3H).

Example 16-2 and 16-3: Synthesis of Enantiomers of 5-methyl-1-(1-(4-(1,3,3-trimethylpiperidin-4-yl)benzyl)-1H-indol-5-yl)-1H-pyrazole-3-carboxamide

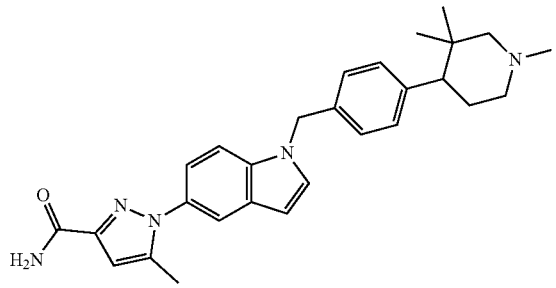 [SMILES: Cc1cc(C(N)=O)nn1-c1ccc2c(ccn2Cc2ccc(C3CCN(C)CC3(C)C)cc2)c1]

Example 16-1 was purified by Chiral SFC to afford the pure enantiomers. Conditions: The purification of the racemic material was performed using supercritical fluid chromatography on a Sepiatec Prep SFC 100. An isocratic method was developed for the preparative purification utilizing a mobile phase of 15% methanol, 1% 1M ammoniated methanol and 84% carbon dioxide at a flow rate of 80 mL/min on the Chiralcel OJ-H (21×250 mm, 5 μm). The automated back pressure regulator set point was 100 bar with UV based collection set to observe 220 nm. Two isolates were generated from the purification process with analysis performed using an isocratic method that was developed utilizing 15% methanol (with 10 mM ammonium hydroxide) and 85% carbon dioxide at a flow rate of 5 mL/min on the Chiralcel OJ-H (4.6×100 mm, 5 μm). The automated back pressure regulator set point for the analysis was set to 120 bar with both UV and MS analysis performed.

Example 16-2: Enantiomer 1

5-methyl-1-(1-(4-(1,3,3-trimethylpiperidin-4-yl)benzyl)-1H-indol-5-yl)-1H-pyrazole-3-carboxamide (1.7 mg, 8%). SFC Rt=6.2 min. LCMS Rt=1.38 min (condition A), MS (M+1)=456.2. $^1$H NMR (400 MHz, DMSO-d6) δ 7.70 (d, J=1.9 Hz, 1H), 7.64 (d, J=3.1 Hz, 1H), 7.61 (d, J=8.8 Hz, 1H), 7.44 (s, 1H), 7.23 (dd, J=8.7, 2.0 Hz, 1H), 7.18 (s, 1H), 7.16-7.06 (m, 4H), 6.62-6.55 (m, 2H), 5.46 (s, 2H), 2.93-2.79 (m, 1H), 2.51-2.38 (m, 1H), 2.30-2.08 (m, 8H), 1.93-1.62 (m, 2H), 1.43-1.32 (m, 1H), 0.79 (s, 3H), 0.64 (s, 3H).

Example 16-3: Enantiomer 2

5-methyl-1-(1-(4-(1,3,3-trimethylpiperidin-4-yl)benzyl)-1H-indol-5-yl)-1H-pyrazole-3-carboxamide (1.9 mg, 9%). SFC Rt=7.5 min. LCMS Rt=1.38 min (condition A), MS (M+1)=456.2. $^1$H NMR (400 MHz, DMSO-d6) δ 7.70 (d, J=1.9 Hz, 1H), 7.64 (d, J=3.1 Hz, 1H), 7.61 (d, J=8.8 Hz, 1H), 7.44 (s, 1H), 7.23 (dd, J=8.7, 2.0 Hz, 1H), 7.18 (s, 1H), 7.16-7.06 (m, 4H), 6.62-6.55 (m, 2H), 5.46 (s, 2H), 2.93-2.79 (m, 1H), 2.51-2.38 (m, 1H), 2.30-2.08 (m, 8H), 1.93-1.62 (m, 2H), 1.43-1.32 (m, 1H), 0.79 (s, 3H), 0.64 (s, 3H).

The following compound was prepared using a similar procedure as in Example 16-1

| Example | Compound | LCMS M + 1, Rt, conditions | 1H NMR, 400 MHz |
|---|---|---|---|
| 16-4 | 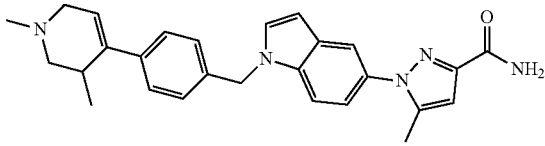 [SMILES: Cc1cc(C(N)=O)nn1-c1ccc2c(ccn2Cc2ccc(C3=CCN(C)CC3C)cc2)c1]<br>5-methyl-1-(1-(4-(2-methyl-2-azaspiro[3.5]nonan-7-yl)benzyl)-1H-indol-5-yl)-1H-pyrazole-3-carboxamide | 458.5<br>1.50 min<br>A | (DMSO-d6) δ 7.69 (d, J = 2.0 Hz, 1H), 7.64 (d, J = 3.1 Hz, 1H), 7.60 (d, J = 8.7 Hz, 1H), 7.43 (s, 1H), 7.26-7.16 (m, 2H), 7.15 (s, 4H), 6.65-6.53 (m, 2H), 5.43 (s, 2H), 2.97 (s, 2H), 2.86 (s, 2H), 2.44-2.33 (m, 1H), 2.29-2.17 (m, 6H), 1.96-1.83 (m, 2H), 1.69-1.55 (m, 2H), 1.53-1.26 (m, 4H). |

Example 17-1: Synthesis of 1-(1-(4-(1,3-dimethyl-1,2,3,6-tetrahydropyridin-4-yl)benzyl)-1H-indol-5-yl)-5-methyl-1H-pyrazole-3-carboxamide Step 1: 1,3-dimethyl-1,2,3,6-tetrahydropyridin-4-yl trifluoromethanesulfonate 1,3-dimethylpiperidin-4-one (0.5 g, 3.93 mmol) and 1,1,1-trifluoro-N-phenyl-N-((trifluoromethyl)sulfonyl)methanesulfonamide (1.5 g, 4.32 mmol) were reacted according to General Method V for triflate formation to afford crude 1,3-dimethyl-1,2,3,6-tetrahydropyridin-4-yl trifluoromethanesulfonate (1.0 g): $^1$H NMR (400 MHz, Chloroform-d) δ 5.58-5.49 (m, 1H), 3.10-2.96 (m, 1H), 2.96-2.85 (m, 1H), 2.77-2.68 (m, 1H), 2.66-2.51 (m, 1H), 2.25 (s, 3H), 2.19-2.10 (m, 1H), 0.98 (d, J=6.9 Hz, 3H).

Step 2: 1-(1-(4-(1,3-dimethyl-1,2,3,6-tetrahydropyridin-4-yl)benzyl)-1H-indol-5-yl)-5-methyl-1H-pyrazole-3-carboxamide 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) (130 mg, 0.285 mmol) and 1,3-dimethyl-1,2,3,6-tetrahydropyridin-4-yl trifluoromethanesulfonate (123 mg, 0.285) were reacted according to General Method III for the Suzuki coupling to afford 1-(1-(4-(1,3-dimethyl-1,2,3,6-tetrahydropyridin-4-yl)benzyl)-1H-indol-5-yl)-5-methyl-1H-pyrazole-3-carboxamide: (35 mg, 27%): LCMS Rt=1.43 min (condition A), MS (M+1)=440.3. $^1$H NMR (400 MHz, DMSO-d6) δ 7.70 (d, J=1.9 Hz, 1H), 7.66 (d, J=3.1 Hz, 1H), 7.61 (d, J=8.7 Hz, 1H), 7.45 (s, 1H), 7.37-7.28 (m, 2H), 7.27-7.15 (m, 4H), 6.62-6.56 (m, 2H), 5.87 (t, J=3.3 Hz, 1H), 5.48 (s, 2H), 3.16-3.02 (m, 1H), 2.91-2.71 (m, 2H), 2.48-2.37 (m, 2H), 2.30-2.21 (m, 6H), 0.95-0.87 (m, 3H).

Examples 17-2 and 17-3: Synthesis of Enantiomers of 1-(1-(4-(1,3-dimethyl-1,2,3,6-tetrahydropyridin-4-yl)benzyl)-1H-indol-5-yl)-5-methyl-1H-pyrazole-3-carboxamide

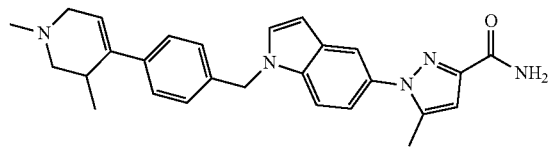 [SMILES: Cc1cc(C(N)=O)nn1-c1ccc2c(ccn2Cc2ccc(C3=CCN(C)CC3C)cc2)c1]

Example 17-1 was purified by Chiral SFC to afford the pure enantiomers. Conditions: The purification of the racemic material was performed using supercritical fluid chromatography on a Sepiatec Prep SFC 100. An isocratic method was developed for the preparative purification utilizing a mobile phase of 40% 2-propanol, 1% 1M ammoniated methanol and 59% carbon dioxide at a flow rate of 80 mL/min on the Chiralpak AD-H (21×250 mm, 5 μm). The automated back pressure regulator set point was 125 bar with UV based collection set to observe 210 nm. Two isolates were generated from the purification process with analysis performed using an gradient method that was developed utilizing 5-55% 2-propanol (with 10 mM ammonium hydroxide) in carbon dioxide over 3.5 minutes at a flow rate of 5 mL/min on the Chiralpak AD-H (4.6×100 mm, 5 μm). The automated back pressure regulator set point for the analysis was set to 120 bar with both UV and MS analysis performed. Example 17-2: Enantiomer 1: 1-(1-(4-(1,3-dimethyl-1,2,3,6-tetrahydropyridin-4-yl)benzyl)-1H-indol-5-yl)-5-methyl-1H-pyrazole-3-carboxamide (16.4 mg, 7%). SFC Rt=3.1 min. LCMS Rt=1.43 min (condition A), MS (M+1)=440.3. $^1$H NMR (400 MHz, DMSO-d6) δ 7.70 (d, J=1.9 Hz, 1H), 7.66 (d, J=3.1 Hz, 1H), 7.61 (d, J=8.7 Hz, 1H), 7.45 (s, 1H), 7.37-7.28 (m, 2H), 7.27-7.15 (m, 4H), 6.62-6.56 (m, 2H), 5.87 (t, J=3.3 Hz, 1H), 5.48 (s, 2H), 3.16-3.02 (m, 1H), 2.91-2.71 (m, 2H), 2.48-2.37 (m, 2H), 2.30-2.21 (m, 6H), 0.95-0.87 (m, 3H).

Example 17-3: Enantiomer 2

1-(1-(4-(1,3-dimethyl-1,2,3,6-tetrahydropyridin-4-yl)benzyl)-1H-indol-5-yl)-5-methyl-1H-pyrazole-3-carboxamide (29.2 mg, 12%). SFC Rt=6.0 min. LCMS Rt=1.43 min (condition A), MS (M+1)=440.3. $^1$H NMR (400 MHz, DMSO-d6) δ 7.70 (d, J=1.9 Hz, 1H), 7.66 (d, J=3.1 Hz, 1H), 7.61 (d, J=8.7 Hz, 1H), 7.45 (s, 1H), 7.37-7.28 (m, 2H), 7.27-7.15 (m, 4H), 6.62-6.56 (m, 2H), 5.87 (t, J=3.3 Hz, 1H), 5.48 (s, 2H), 3.16-3.02 (m, 1H), 2.91-2.71 (m, 2H), 2.48-2.37 (m, 2H), 2.30-2.21 (m, 6H), 0.95-0.87 (m, 3H).

Example 18: Synthesis of 1-(1-((4'-((2-hydroxyethyl)sulfonyl)-[1,1'-biphenyl]-4-yl)methyl)-1H-indol-5-yl)-5-methyl-1H-pyrazole-3-carboxamide

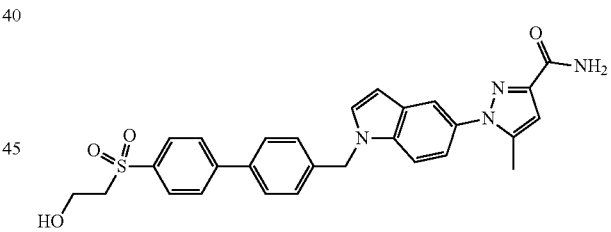

Step 1: 2-((4-bromophenyl)thio)ethanol

To a stirred solution of 4-bromobenzenethiol (2.7 g, 14.28 mmol) and 5 M NaOH (aq) (2.9 mL, 14.28 mmol) in water (1 mL) was added 2-bromoethanol (1.0 mL, 14.28 mmol) dropwise over 10 min. The resulting solution was then stirred at ambient temperature for 2 h. Then the reaction was diluted with brine and extracted with EtOAc (3×). The organic layers were combined, dried over sodium sulfate and concentrated in vacuo to afford (4.2 g) of crude 2-((4-bromophenyl)thio)ethanol: $^1$H NMR (400 MHz, Chloroform-d) δ 7.47-7.38 (m, 2H), 7.31-7.22 (m, 2H), 3.76 (t, J=6.0 Hz, 2H), 3.11 (t, J=6.0 Hz, 2H), 2.23 (s, 1H).

Step 2: 2-((4-bromophenyl)sulfonyl)ethanol

To a solution of 2-((4-bromophenyl)thio)ethanol (3 g, 12.87 mmol) in MeCN (82 mL) and Water (21 mL) was added oxone (16.2 g, 26.4 mmol). The resulting mixture was heated at 60° C. for 2 h. The reaction was diluted with water and extracted with EtOAc (3×). The combined organics were washed with brine, dried over magnesium sulfate, and concentrated in vacuo to afford (3.4 g) of crude 2-((4-bromophenyl)sulfonyl)ethanol: $^1$H NMR (400 MHz, Chloroform-d) b 7.87-7.79 (m, 2H), 7.79-7.71 (m, 2H), 4.08-3.99 (m, 2H), 3.44-3.31 (m, 2H), 2.81 (s, 1H).

Step 3: 1-(1-((4'-((2-hydroxyethyl)sulfonyl)-[1,1'-biphenyl]-4-yl)methyl)-1H-indol-5-yl)-5-methyl-1H-pyrazole-3-carboxamide 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) and 2-((4-bromophenyl)sulfonyl)ethanol were reacted according to General Method III for the Suzuki coupling to afford 1-(1-((4'-((2-hydroxyethyl)sulfonyl)-[1,1'-biphenyl]-4-yl)methyl)-1H-indol-5-yl)-5-methyl-1H-pyrazole-3-carboxamide: LCMS Rt=1.97 min (condition A), MS (M+1)=515.2. $^1$H NMR (400 MHz, DMSO-d6) δ 7.99-7.85 (m, 4H), 7.78-7.69 (m, 4H), 7.64 (d, J=8.8 Hz, 1H), 7.44 (s, 1H), 7.37 (d, J=8.3 Hz, 2H), 7.25 (dd, J=8.7, 2.1 Hz, 1H), 7.18 (s, 1H), 6.62 (d, J=3.0 Hz, 1H), 6.60-6.56 (m, 1H), 5.58 (s, 2H), 3.69 (t, J=6.3 Hz, 2H), 3.47 (t, J=6.4 Hz, 2H), 2.27 (s, 3H).

Example 19: Synthesis of 5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide

Step 1: 5-methyl-1-(1-((4'-(vinylsulfonyl)-[1,1'-biphenyl]-4-yl)methyl)-1H-indol-5-yl)-1H-pyrazole-3-carboxamide To 1-(1-((4'-((2-hydroxyethyl)sulfonyl)-[1,1'-biphenyl]-4-yl)methyl)-1H-indol-5-yl)-5-methyl-1H-pyrazole-3-carboxamide (Example 18) (226 mg, 0.439 mmol) in DCM (2.2 mL) was added TEA (0.18 mL, 1.32 mmol) followed by methanesulfonyl chloride (0.04 mL, 0.527 mmol). The reaction mixture was stirred at ambient temperature for 1 h. The mixture was then diluted with saturated aqueous ammonium chloride and extracted with DCM. The organic layer was dried over sodium sulfate and concentrated in vacuo to afford (218 mg) of crude 5-methyl-1-(1-((4'-(vinylsulfonyl)-[1,1'-biphenyl]-4-yl)methyl)-1H-indol-5-yl)-1H-pyrazole-3-carboxamide: LCMS Rt=0.98 min (condition B), MS (MS)=496.8.

Step 2: 5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide To 5-methyl-1-(1-((4'-(vinylsulfonyl)-[1,1'-biphenyl]-4-yl)methyl)-1H-indol-5-yl)-1H-pyrazole-3-carboxamide (138 mg, 0.278 mmol) in DCM (4.6 mL) was added 1-methylpiperazine (0.31 mL, 2.78 mmol). The resulting solution was stirred at ambient temperature for 0.5 h, then concentrated in vacuo. The crude was purified by preparative HPLC followed by purification by SCX-BSA according to General Method IV to afford (30.5 mg, 18%) of 5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide: LCMS Rt=1.54 min (condition A), MS (M+1)=597.0. $^1$H NMR (400 MHz, DMSO-d6) δ 7.97-7.91 (m, 2H), 7.91-7.84 (m, 2H), 7.78-7.68 (m, 4H), 7.64 (d, J=8.8 Hz, 1H), 7.43 (s, 1H), 7.37 (d, J=8.3 Hz, 2H), 7.25 (dd, J=8.7, 2.0 Hz, 1H), 7.19 (s, 1H), 6.62 (d, J=3.1 Hz, 1H), 6.59 (d, J=0.7 Hz, 1H), 5.57 (s, 2H), 3.52 (t, J=6.8 Hz, 2H), 2.59 (t, J=6.8 Hz, 2H), 2.41-1.86 (m, 14H).

The following compounds were prepared from bromoindole Intermediate IV using General Method II

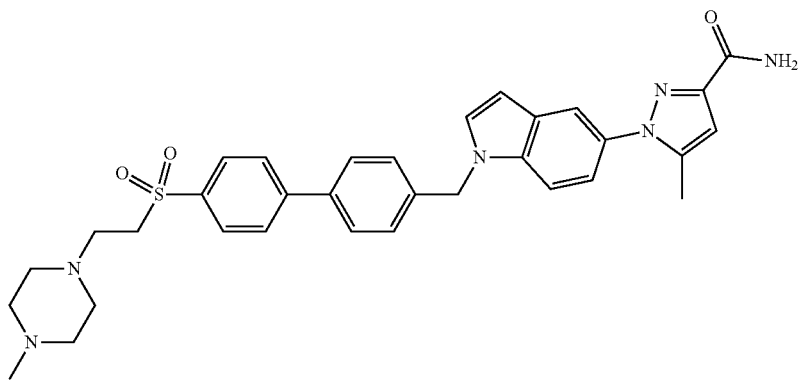 [SMILES: Cc1cc(C(N)=O)nn1-c1ccc2c(ccn2Cc2ccc(-c3ccc(S(=O)(=O)CCN4CCN(C)CC4)cc3)cc2)c1]

| Example | Compound | MS (M + 1), LC/MS Rt | ¹H NMR 400 MHz |
|---|---|---|---|
| 19-1 | 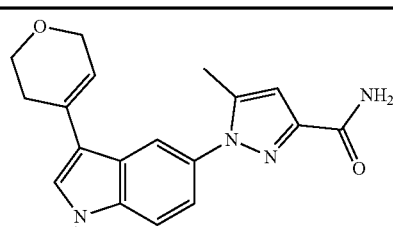<br>1-(3-(3,6-dihydro-2H-pyran-4-yl)-1-((4'-(methylsulfonyl)-[1,1'-biphenyl]-4-yl)methyl)- | 567.1<br>2.20 min | Methanol-d4 δ 8.00 (d, J = 8.6 Hz, 2H), 7.96 (d, J = 1.8 Hz, 1H), 7.86 (d, J = 8.6 Hz, 2H), 7.67 (d, J = 8.4 Hz, 2H), 7.59 (s, 1H), 7.52 (d, J = 8.7 Hz, 1H), 7.33 (d, J = 8.4 Hz, 2H), 7.25 (dd, J = 8.7, 2.0 Hz, 1H), 6.69 (d, J = 0.7 Hz, 1H), 5.53 (s, 2H), 4.35 (d, J = 2.6 Hz, 2H), 3.96 (t, J = 5.5 Hz, 2H), 3.13 (s, 3H), 2.34-2.28 (m, 3H). |
| 19-2 | 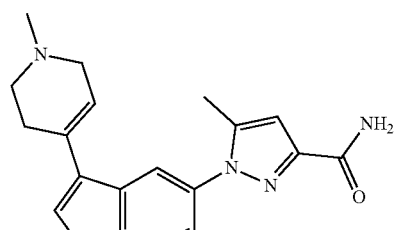<br>5-methyl-1-(3-(1-methyl-1,2,3,6-tetrahydropyridin-4-yl)-1-((4'-(methylsulfonyl)-[1,1'-biphenyl]-4-yl)methyl)-1H-indol-5-yl)-1H-pyrazole-3-carboxamide | 580.3<br>1.43 min | Methanol-d4 δ 8.35 (s, 2H), 8.03-7.96 (m, 3H), 7.88-7.82 (m, 2H), 7.72 (s, 1H), 7.70-7.65 (m, 2H), 7.58 (d, J = 8.7 Hz, 1H), 7.34 (d, J = 8.4 Hz, 2H), 7.30 (dd, J = 8.7, 2.0 Hz, 1H), 6.71-6.68 (m, 1H), 6.22 (s, 1H), 5.56 (s, 2H), 3.56-3.47 (m, 2H), 3.14 (s, 3H), 2.97 (s, 5H), 2.30 (d, J = 0.6 Hz, 3H). |

The following compound was prepared using a similar procedure as in Example 19

| Example | Compound | LCMS M + 1, Rt, conditions | 1H NMR, 400 MHz |
|---|---|---|---|
| 19-3 | 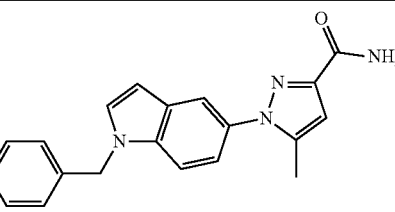<br>1-(1-((4'-((2-(dimethylamino)ethyl)sulfonyl)-[1,1'-biphenyl]-4-yl)methyl)-1H-indol-5-yl)-5-methyl-1H-pyrazole-3-carboxamide | 541.8<br>1.57 min<br>A | (DMSO-d6) δ 8.02-7.86 (m, 4H), 7.79-7.68 (m, 4H), 7.63 (d, J = 8.8 Hz, 1H), 7.43 (s, 1H), 7.37 (d, J = 8.3 Hz, 2H), 7.25 (dd, J = 8.7, 2.0 Hz, 1H), 7.18 (s, 1H), 6.62 (d, J = 2.6 Hz, 1H), 6.62-6.57 (m, 1H), 5.58 (s, 2H), 3.54-3.45 (m, 2H), 2.58-2.52 (m, 2H), 2.30-2.23 (m, 3H), 2.05 (s, 6H). |

127

Example 20: Synthesis of 5-methyl-1-(1-((4'-(methylsulfonyl)-[1,1'-biphenyl]-4-yl)methyl)-3-(tetrahydro-2H-pyran-4-yl)-1H-indol-5-yl)-1H-pyrazole-3-carboxamide

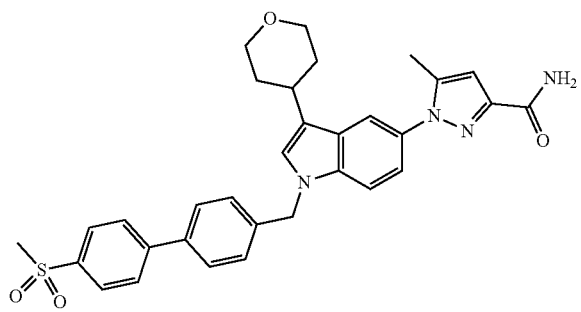 [SMILES: Cc1cc(C(N)=O)nn1-c1ccc2c(c1)c(C1CCOCC1)cn2Cc1ccc(-c2ccc(S(C)(=O)=O)cc2)cc1]

1-(3-(3,6-dihydro-2H-pyran-4-yl)-1-((4'-(methylsulfonyl)-[1,1'-biphenyl]-4-yl)methyl)-1H-indol-5-yl)-5-methyl-1H-pyrazole-3-carboxamide (Example 19-1) (14 mg, 0.025 mmol) was added to a 7 mL vial and dissolved in DMF (0.5 mL). 10% Pd/C (1.5 mg) was added, and the reaction vessel was purged with hydrogen and then stirred under a balloon of hydrogen for 2 hours. The reaction mixture was filtered over a plug of celite and washed with MeOH. The solvent was removed to afford 5-methyl-1-(1-((4'-(methylsulfonyl)-[1,1'-biphenyl]-4-yl)methyl)-3-(tetrahydro-2H-pyran-4-yl)-1H-indol-5-yl)-1H-pyrazole-3-carboxamide (5 mg, 35%): LCMS Rt=2.21 min (condition A), MS (M+1)=569.3.

Example 21: Synthesis of 5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide

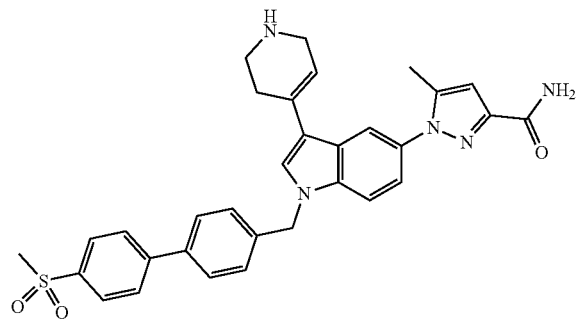 [SMILES: Cc1cc(C(N)=O)nn1-c1ccc2c(c1)c(C1=CCNCC1)cn2Cc1ccc(-c2ccc(S(C)(=O)=O)cc2)cc1]

Step 1: tert-butyl 4-(5-(3-carbamoyl-5-methyl-1H-pyrazol-1-yl)-1-((4'-(methylsulfonyl)-[1,1'-biphenyl]-4-yl)methyl)-1H-indol-3-yl)-3,6-dihydropyridine-1 (2H)-carboxylate Intermediate IV and tert-butyl 4-(4,4,5,5-tetramethyl-1,3,2-dioxaborolan-2-yl)-5,6-dihydropyridine-1 (2H)-carboxylate were reacted according to General Method II for Suzuki coupling and purified by FCC gradient (0-100% EtOAc in heptane) to afford tert-butyl 4-(5-(3-carbamoyl-5-methyl-1H-pyrazol-1-yl)-1-((4'-(methylsulfonyl)-[1,1'-biphenyl]-4-yl)methyl)-1H-indol-3-yl)-3,6-dihydropyridine-1(2H)-carboxylate: LCMS Rt=2.66 min (condition A), MS (M+45)=710.4.

128

Step 2: 5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide tert-butyl 4-(5-(3-carbamoyl-5-methyl-1H-pyrazol-1-yl)-1-((4'-(methylsulfonyl)-[1,1'-biphenyl]-4-yl)methyl)-1H-indol-3-yl)-3,6-dihydropyridine-1 (2H)-carboxylate (100 mg, 0.150 mmol) was dissolved in DCM (1 mL) and cooled to 0° C. The reaction was incubated at 0° C. for 10 minutes and then TFA (0.225 mL, 3 mmol) was added, and the reaction was stirred for 1 hour at 0° C. The reaction mixture was then diluted with 50 mL of PhMe and concentrated, and the residue was taken up in 5 mL of MeOH and 10 mL of PhMe and concentrated. This process was repeated two more times to afford 5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide (80 mg, 78%). LCMS Rt=1.46 min (condition A), MS (M+1)=566.3. $^1$H NMR (400 MHz, DMSO-d6) (8.77 (s, 2H), 8.01-7.92 (m, 4H), 7.93-7.87 (m, 2H), 7.72 (dd, J=8.5, 6.8 Hz, 3H), 7.41 (t, J=8.3 Hz, 3H), 7.33 (dd, J=8.7, 1.9 Hz, 1H), 7.21 (s, 2H), 6.62 (d, J=0.7 Hz, 1H), 6.22 (s, 1H), 5.57 (s, 2H), 3.78 (s, 2H), 3.24 (s, 3H), 2.74 (s, 2H), 2.29-2.25 (m, 3H).

Example 22: Synthesis of 1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide

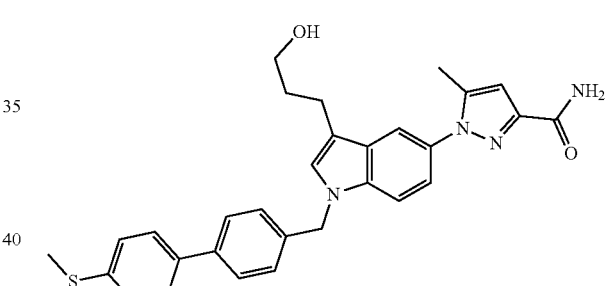

Step 1: (E)-1-(3-(3-((tert-butyldimethylsilyl)oxy)prop-1-en-1-yl)-1-((4'-(methylsulfonyl)-[1,1'-biphenyl]-4-yl)methyl)-1H-indol-5-yl)-5-methyl-1H-pyrazole-3-carboxamide The title compound was prepared from Intermediate IV and (E)-tert-butyldimethyl((3-(4,4,5,5-tetramethyl-1,3,2-dioxaborolan-2-yl)allyl)oxy)silane according to General Method II. The crude was purified by FCC (gradient 0-100% EtOAc in heptane) to afford (E)-1-(3-(3-((tert-butyldimethylsilyl)oxy)prop-1-en-1-yl)-1-((4'-(methylsulfonyl)-[1,1'-biphenyl]-4-yl)methyl)-1H-indol-5-yl)-5-methyl-1H-pyrazole-3-carboxamide: LCMS Rt=3.20 min (condition A), MS (M+1)=655.3.

Step 2: 1-(3-(3-((tert-butyldimethylsilyl)oxy)propyl)-1-((4'-(methylsulfonyl)-[1,1'-biphenyl]-4-yl)methyl)-1H-indol-5-yl)-5-methyl-1H-pyrazole-3-carboxamide (E)-1-(3-(3-((tert-butyldimethylsilyl)oxy)prop-1-en-1-yl)-1-((4'-(methylsulfonyl)-[1,1'-biphenyl]-4-yl)methyl)-

1H-indol-5-yl)-5-methyl-1H-pyrazole-3-carboxamide (260 mg, 0.397 mmol) was added to a 100 mL round bottom flask followed by 10% Pd/C (35 mg). THF (8 mL) was added, and the reaction was stirred under a balloon of hydrogen for 14 hours. The reaction mixture was then filtered over a pad of celite and concentrated to afford 1-(3-(3-((tert-butyldimethylsilyl)oxy)propyl)-1-((4'-(methylsulfonyl)-[1,1'-biphenyl]-4-yl)methyl)-1H-indol-5-yl)-5-methyl-1H-pyrazole-3-carboxamide (258 mg, 99%): LCMS Rt=3.29 min (condition A), MS (M+1)=657.3.

Step 3: 1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide 1-(3-(3-((tert-butyldimethylsilyl)oxy)propyl)-1-((4'-(methylsulfonyl)-[1,1'-biphenyl]-4-yl)methyl)-1H-indol-5-yl)-5-methyl-1H-pyrazole-3-carboxamide (255 mg, 0.388 mmol) was added to a 50 mL round bottom flask and dissolved in DMF (4 mL). Tris(dimethylamino)sulfonium difluorotrimethylsilicate (321 mg, 1.165 mmol) was added, and the reaction was stirred for 3 hours and then diluted with EtOAc (75 mL). The organic phase was washed with water (1×), saturated lithium chloride (4×) and brine (1×), dried over MgSO$_4$, and concentrated. The crude material was purified by FCC (gradient 0-5% MeOH in DCM) to afford 1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide (117 mg, 55%). LCMS Rt=1.96 min (condition A), MS (M+1)=543.3. $^1$H NMR (400 MHz, DMSO-d6) δ 7.99-7.95 (m, 2H), 7.95-7.86 (m, 2H), 7.72 (d, J=8.4 Hz, 2H), 7.66 (d, J=1.8 Hz, 1H), 7.59 (d, J=8.6 Hz, 1H), 7.47 (s, 1H), 7.44 (s, 1H), 7.36 (d, J=8.4 Hz, 2H), 7.22 (dd, J=8.7, 2.0 Hz, 1H), 7.17 (s, 1H), 6.59 (d, J=0.8 Hz, 1H), 5.50 (s, 2H), 4.44 (t, J=5.2 Hz, 1H), 3.48 (q, J=6.4 Hz, 2H), 3.24 (s, 3H), 2.76 (t, J=7.5 Hz, 2H), 2.32-2.21 (m, 3H), 1.89-1.73 (m, 2H).

Example 23: Synthesis of 1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide

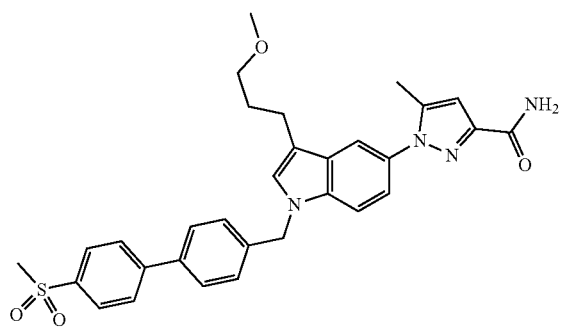 [SMILES: COCCCc1cn(Cc2ccc(-c3ccc(S(C)(=O)=O)cc3)cc2)c2ccc(-n3nc(C(N)=O)cc3C)cc12]

Step 1: (E)-1-(3-(3-methoxyprop-1-en-1-yl)-1-((4'-(methylsulfonyl)-[1,1'-biphenyl]-4-yl)methyl)-1H-indol-5-yl)-5-methyl-1H-pyrazole-3-carboxamide (E)-1-(3-(3-methoxyprop-1-en-1-yl)-1-((4'-(methylsulfonyl)-[1,1'-biphenyl]-4-yl)methyl)-1H-indol-5-yl)-5-methyl-1H-pyrazole-3-carboxamide was prepared from Intermediate IV and (E)-2-(3-methoxyprop-1-en-1-yl)-4,4,5,5-tetramethyl-1,3,2-dioxaborolane according to General Method II to afford (E)-1-(3-(3-methoxyprop-1-en-1-yl)-1-((4'-(methylsulfonyl)-[1,1'-biphenyl]-4-yl)methyl)-1H-indol-5-yl)-5-methyl-1H-pyrazole-3-carboxamide: MS (M+1)= 555.2

Step 2: 1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide (E)-1-(3-(3-methoxyprop-1-en-1-yl)-1-((4'-(methylsulfonyl)-[1,1'-biphenyl]-4-yl)methyl)-1H-indol-5-yl)-5-methyl-1H-pyrazole-3-carboxamide (60 mg, 0.108 mmol) was added to a 40 mL vial, followed by 10% Pd/C (10 mg). The reactants were dissolved in EtOH (1.5 mL) and 1,4-dioxane (0.5 mL) and stirred under an atmosphere of hydrogen for 5 hours. The reaction mixture was then filtered through a 0.45 uM PTFE membrane, diluted to 3 mL with DMSO, and purified by preparative HPLC to afford 1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide (33 mg, 52%). LCMS Rt=2.30 min (condition A), MS (M+1) =557.2. $^1$H NMR (400 MHz, DMSO-d6) δ 8.00-7.95 (m, 2H), 7.92-7.87 (m, 2H), 7.74-7.69 (m, 2H), 7.66 (d, J=1.8 Hz, 1H), 7.59 (d, J=8.7 Hz, 1H), 7.48 (s, 1H), 7.44 (s, 1H), 7.36 (d, J=8.4 Hz, 2H), 7.23 (dd, J=8.7, 2.0 Hz, 1H), 7.17 (s, 1H), 6.59 (d, J=0.7 Hz, 1H), 5.51 (s, 2H), 3.38 (t, J=6.4 Hz, 2H), 3.24 (d, J=1.1 Hz, 6H), 2.76 (t, J=7.5 Hz, 2H), 2.29-2.25 (m, 3H), 1.94-1.83 (m, 2H).

Example 24: Synthesis of racemic (cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide

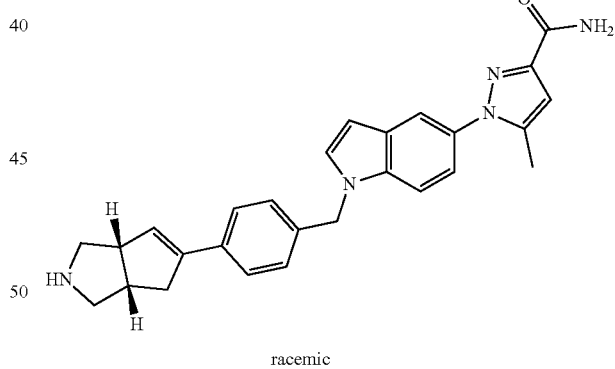

racemic

Step 1: racemic (cis)-tert-butyl 5-(((trifluoromethyl)sulfonyl)oxy)-3,3a,4,6a-tetrahydrocyclopenta[c]pyrrole-2(1H)-carboxylate Tert-butyl 5-oxohexahydrocyclopenta[c]pyrrole-2(1H)-carboxylate was reacted according to General Method V for triflate formation to afford racemic (cis)-tert-butyl 5-(((trifluoromethyl)sulfonyl)oxy)-3,3a,4,6a-tetrahydrocyclopenta [c]pyrrole-2(1H)-carboxylate: $^1$H NMR (400 MHz, Chloroform-d) δ 5.47-5.35 (m, 1H), 3.58-3.32 (m, 2H), 3.30-3.15 (m, 2H), 3.00 (s, 1H), 2.85-2.71 (m, 2H), 2.23 (d, J=15.2 Hz, 1H), 1.30 (s, 9H).

Step 2: racemic (cis)-tert-butyl 5-(4-((5-(3-carbamoyl-5-methyl-1H-pyrazol-1-yl)-1H-indol-1-yl)methyl)phenyl)-3,3a,4,6a-tetrahydrocyclopenta[c]pyrrole-2(1H)-carboxylate 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) and racemic (cis)-tert-butyl 5-(((trifluoromethyl)sulfonyl)oxy)-3,3a,4,6a-tetrahydrocyclopenta[c]pyrrole-2(1H)-carboxylate were reacted according to General Method III for the Suzuki coupling to afford crude racemic (cis)-tert-butyl 5-(4-((5-(3-carbamoyl-5-methyl-1H-pyrazol-1-yl)-1H-indol-1-yl)methyl)phenyl)-3,3a,4,6a-tetrahydrocyclopenta[c]pyrrole-2(1H)-carboxylate: LCMS Rt=1.19 min (condition B), MS (M–99)=438.3.

Step 3: racemic (cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide racemic (cis)-tert-butyl 5-(4-((5-(3-carbamoyl-5-methyl-1H-pyrazol-1-yl)-1H-indol-1-yl)methyl)phenyl)-3,3a,4,6a-tetrahydrocyclopenta[c]pyrrole-2(1H)-carboxylate was reacted according to General Method VII for Boc deprotection to afford racemic (cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide: LCMS Rt=1.45 min (condition A), MS (M+1)=438.2. $^1$H NMR (400 MHz, DMSO-d6) δ 7.69 (d, J=1.9 Hz, 1H), 7.65 (d, J=3.1 Hz, 1H), 7.58-7.52 (m, 1H), 7.49-7.33 (m, 3H), 7.27-7.11 (m, 4H), 6.59 (s, 2H), 6.03 (s, 1H), 5.46 (s, 2H), 2.89-2.71 (m, 4H), 2.60 (dd, J=11.0, 2.7 Hz, 1H), 2.56-2.51 (m, 2H), 2.45-2.34 (m, 1H), 2.26 (s, 3H).

Example 25: Synthesis of racemic (cis)-5-methyl-1-(1-(4-(2-methyl-1,2,3,3a,4,6a-hexahydrocyclopenta[c]pyrrol-5-yl)benzyl)-1H-indol-5-yl)-1H-pyrazole-3-carboxamide

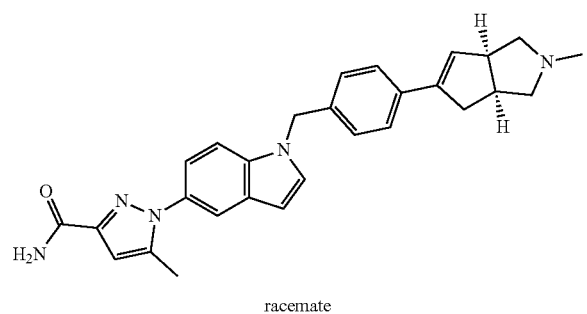 [SMILES: Cc1cc(C(N)=O)nn1-c1ccc2c(ccn2Cc2ccc(C3=C[C@H]4CN(C)C[C@H]4C3)cc2)c1]

racemate

Racemic (cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide (Example 24) was reacted according to General Method VI for the N-methylation to afford racemic (cis)-5-methyl-1-(1-(4-(2-methyl-1,2,3,3a,4,6a-hexahydrocyclopenta[c]pyrrol-5-yl)benzyl)-1H-indol-5-yl)-1H-pyrazole-3-carboxamide: LCMS Rt=1.45 min (condition A), MS (M+1)=452.2. $^1$H NMR (400 MHz, DMSO-d6) δ 7.69 (d, J=1.8 Hz, 1H), 7.65 (d, J=3.1 Hz, 1H), 7.56 (d, J=8.7 Hz, 1H), 7.44 (s, 1H), 7.41-7.35 (m, 2H), 7.26-7.13 (m, 4H), 6.62-6.55 (m, 2H), 6.10-6.05 (m, 1H), 5.47 (s, 2H), 2.92-2.81 (m, 2H), 2.49-2.30 (m, 6H), 2.29-2.23 (m, 3H), 2.16 (s, 3H).

Examples 26-1 and 26-2: Synthesis of 5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide and 5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide A round bottom flask was charged with racemic (cis)-5-methyl-1-(1-(4-(2-methyl-1,2,3,3a,4,6a-hexahydrocyclopenta[c]pyrrol-5-yl)benzyl)-1H-indol-5-yl)-1H-pyrazole-3-carboxamide (Example 25) (269 mg, 0.596 mmol), 10% Pd/C (63 mg, 0.060 mmol) and MeOH (6.0 mL). The flask was sealed and charged with hydrogen gas under atmospheric pressure, and the suspension was stirred at ambient temperature for 18 h. The suspension was filtered through celite, and the filtrate was concentrated in vacuo. The crude material was purified by preparative HPLC.

Example 26-1: 5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide

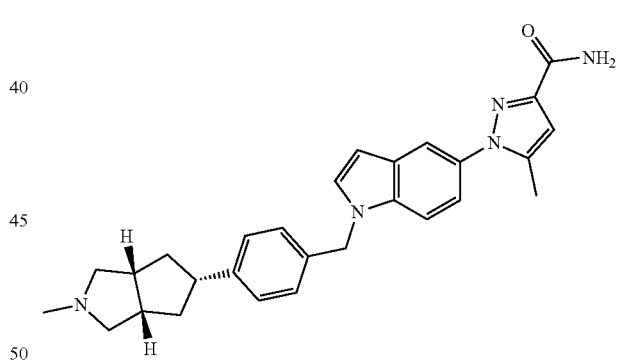

5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide was obtained as the major diastereomer (109 mg, 40%): LCMS Rt=1.41 min (condition A), MS (M+1)=454.3. $^1$H NMR (400 MHz, DMSO-d6) δ 7.69 (d, J=1.9 Hz, 1H), 7.64 (d, J=3.1 Hz, 1H), 7.59 (d, J=8.7 Hz, 1H), 7.44 (s, 1H), 7.26-7.11 (m, 6H), 6.62-6.55 (m, 2H), 5.43 (s, 2H), 2.81 (dq, J=12.2, 6.0 Hz, 1H), 2.54 (d, J=8.6 Hz, 4H), 2.26 (s, 3H), 2.22 (s, 3H), 2.18-2.02 (m, 4H), 1.41-1.28 (m, 2H). The relative stereochemistry was determined by x-ray crystallography.

Example 26-2: 5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide

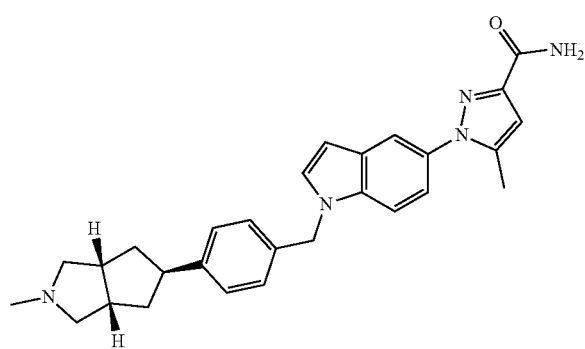 [SMILES: Cc1cc(C(N)=O)nn1-c1ccc2c(ccn2Cc2ccc([C@H]3C[C@@H]4CN(C)C[C@@H]4C3)cc2)c1]

5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide was obtained as the minor diastereomer (59 mg, 22%): LCMS Rt=1.42 min (condition A), MS (M+1)=454.1. $^1$H NMR (400 MHz, DMSO-d6) δ 7.69 (d, J=1.9 Hz, 1H), 7.64 (d, J=3.1 Hz, 1H), 7.60 (d, J=8.7 Hz, 1H), 7.43 (s, 1H), 7.31-7.08 (m, 6H), 6.64-6.54 (m, 2H), 5.43 (s, 2H), 3.25-3.11 (m, 1H), 2.80-2.61 (m, 4H), 2.31-2.09 (m, 8H), 1.79-1.59 (m, 4H). The relative stereochemistry was determined by x-ray crystallography.

Example 27: Synthesis of 5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide

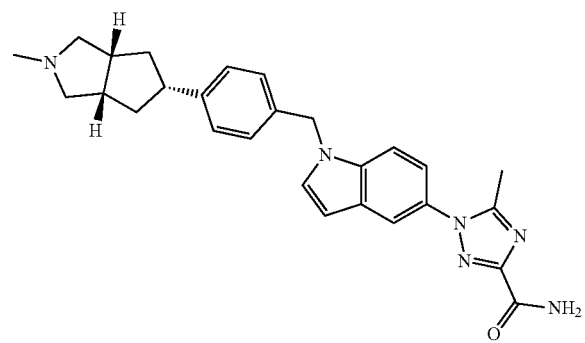 [SMILES: Cc1nc(C(N)=O)nn1-c1ccc2c(ccn2Cc2ccc([C@@H]3C[C@@H]4CN(C)C[C@@H]4C3)cc2)c1]

Step 1: 1-(1-(4-(4,4,5,5-tetramethyl-1,3,2-dioxaborolan-2-yl)benzyl)-1H-indol-5-yl)-1H-1,2,4-triazole-3-carboxamide To a stirred solution of 1-(1-(4-bromobenzyl)-1H-indol-5-yl)-5-methyl-1H-1,2,4-triazole-3-carboxamide, Intermediate V, (3.5 g, 8.55 mmol) in 1,4-dioxane (30 mL) was added bispinacolatodiborane (6.5 g, 25.67 mmol) and Potassium acetate (3.37 g, 34.23 mmol). The reaction mixture was degassed with nitrogen for 5 min. To the resulting reaction mixture was added Pd$_2$(dba)$_3$ (0.1 g, 0.428 mmol) and Xphos (0.407 g, 0.856 mmol) at RT. The mixture was again degassed with nitrogen for 5 min. Then the reaction was sealed and heated at 110° C. for 8 h. The reaction mixture was then cooled, diluted with ethyl acetate and washed with water (100 mL×3) and brine solution (100 mL×3). Then the organic layer was separated, dried over anhydrous sodium sulfate, and concentrated in vacuo. The crude material was triturated with n-heptane to afford 5-methyl-1-(1-(4-(4,4,5,5-tetramethyl-1,3,2-dioxaborolan-2-yl)benzyl)-1H-indol-5-yl)-1H-1,2,4-triazole-3-carboxamide (3.4 g, 87%).

Step 2: racemic (cis)-tert-butyl 5-(((trifluoromethyl)sulfonyl)oxy)-3,3a,4,6a-tetrahydrocyclopenta[c]pyrrole-2(1H)-carboxylate To the stirred solution of (cis)-tert-butyl 5-oxohexahydrocyclopenta[c]pyrrole-2(1H)-carboxylate (3.0 g, 13.32 mmol) in dry THF (50 mL) was added at 1N solution of LiHMDS in THF (20 mL, 19.98 mmol) under inert atmosphere and allowed to stir for 1 h at −78° C. To the resulting reaction mixture was added a solution of PhNTf$_2$ (5.2 g, 14.65 mmol) in THF (10 mL) at −78° C. and the resulting mixture was allowed to stir at RT for 16 h. The mixture was diluted with ethyl acetate and washed with water (100 mL×3) and brine solution (100 mL×3). Then the organic layer was separated, dried over anhydrous sodium sulfate, and concentrated in vacuo. The crude material was adsorbed onto celite and purified by column chromatography (gradient 3-5% EtOAc in Hexanes) to afford racemic (cis)-tert-butyl 5-(((trifluoromethyl)sulfonyl)oxy)-3,3a,4,6a-tetrahydrocyclopenta[c]pyrrole-2(1H)-carboxylate (3.0 g, 63%).

Step 3: racemic (cis)-tert-butyl 5-(4-((5-(3-carbamoyl-5-methyl-1H-1,2,4-triazol-1-yl)-1H-indol-1-yl)methyl)phenyl)-3,3a,4,6a-tetrahydrocyclopenta[c]pyrrole-2(1H)-carboxylate To the stirred solution of 1-(1-(4-(4,4,5,5-tetramethyl-1,3,2-dioxaborolan-2-yl)benzyl)-1H-indol-5-yl)-1H-1,2,4-triazole-3-carboxamide (3.5 g, 7.67 mmol) in THF:Water (5:1) was added racemic (cis)-tert-butyl 5-(((trifluoromethyl)sulfonyl)oxy)-3,3a,4,6a-tetrahydrocyclopenta[c]pyrrole-2(1H)-carboxylate (3.28 g, 9.21 mmol) and Na$_2$CO$_3$ (2.44 g, 23.03 mmol). The reaction was degassed with nitrogen for 15 min. To the resulting reaction mixture was added PdCl$_2$dppf (0.56 g, 0.767 mmol) at RT. The mixture was again degassed with nitrogen for 10 min. Then the reaction was sealed and heated at 100° C. for 16 h. The mixture was diluted with ethyl acetate and washed with water (100 mL×3) and brine solution (100 mL×3). Then the organic layer was separated, dried over anhydrous sodium sulfate, and concentrated in vacuo. The crude material was adsorbed onto celite and purified by column chromatography (80% EtOAc in Hexanes) to afford racemic (cis)-tert-butyl 5-(4-((5-(3-carbamoyl-5-methyl-1H-1,2,4-triazol-1-yl)-1H-indol-1-yl)methyl)phenyl)-3,3a,4,6a-tetrahydrocyclopenta[c]pyrrole-2(1H)-carboxylate (3.0 g, 72%).

Step 4: tert-butyl (3aR,5r,6aS)-5-(4-((5-(3-carbamoyl-5-methyl-1H-1,2,4-triazol-1-yl)-1H-indol-1-yl)methyl)phenyl)hexahydrocyclopenta[c]pyrrole-2(1H) carboxylate To the stirred solution of racemic (cis)-tert-butyl 5-(4-((5-(3-carbamoyl-5-methyl-1H-1,2,4-triazol-1-yl)-1H-indol-1-yl)methyl)phenyl)-3,3a,4,6a-tetrahydrocyclopenta[c]pyrrole-2(1H)-carboxylate (3.0 g, 5.58 mmol) in dry MeOH (100 mL) was added 10% Pd/C (0.3 g) at RT. The flask was sealed and charged with hydrogen gas under atmospheric pressure, and the suspension was stirred at ambient temperature for 18 h. The suspension was filtered through celite, and the filtrate was concentrated in vacuo. The crude was triturated with diethyl ether/pentane to obtain tert-butyl (3aR,5r,6aS)-5-(4-((5-(3-carbamoyl-5-methyl-1H-1,2,4-triazol-1-yl)-1H-indol-1-yl)methyl)phenyl)hexahydrocyclopenta[c]pyrrole-2(1H)-carboxylate (2.7 g, 89%).

Step 5: 5-methyl-1-(1-(4-((3aR,5r,6aS)-octahydrocyclopenta[c]pyrrol-5-yl)benzyl)-1H-indol-5-yl)-1H-1,2,4-triazole-3-carboxamide To the stirred solution of tert-butyl (3aR,5r,6aS)-5-(4-((5-(3-carbamoyl-5-methyl-1H-1,2,4-triazol-1-yl)-1H-indol-1-yl)methyl)phenyl)hexahydrocyclopenta[c]pyrrole-2(1H)-carboxylate (3.2 g, 5.94 mmol) in dry DCM (30 mL) was added TFA (3.38 ml, 29.68 mmol) at 00° C. The reaction was allowed to stir for 2 h at RT. The reaction mixture was concentrated in vacuo. The crude was triturated with diethyl ether to obtain the TFA salt of 5-methyl-1-(1-(4-((3aR,5r,6aS)-octahydrocyclopenta[c]pyrrol-5-yl)benzyl)-1H-indol-5-yl)-1H-1,2,4-triazole-3-carboxamide (2.6 g, 81%).

Step 6: 5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide To a stirred solution of the TFA salt of 5-methyl-1-(1-(4-((3aR,5r,6aS)-octahydrocyclopenta[c]pyrrol-5-yl)benzyl)-1H-indol-5-yl)-1H-1,2,4-triazole-3-carboxamide (2.6 g, 5.92 mmol) in MeOH (25 mL) was added 37% aqueous formaldehyde (0.36 g, 11.84 mmol) and Na(OAc)$_3$CN (2.51 g, 11.84 mmol) at RT. Then reaction was allowed to stir at RT for 4 h. Then progress of reaction was monitored by LCMS and TLC. The reaction mixture was concentrated in vacuo. The crude material was taken up in ethyl acetate and washed with water (100 mL×3) and brine solution (100 mL×3). Then the organic layer was separated, dried over anhydrous sodium sulfate, and concentrated in vacuo. The crude material was adsorbed onto celite and purified by column chromatography (gradient 4-5% MeOH in DCM) followed by preparative HPLC to afford 5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide (40 mg, 37%). LCMS Rt=1.29 min (condition A), MS (M+1)=455.1. $^1$H NMR (400 MHz, DMSO-d6) δ 7.80 (d, J=15.6 Hz, 2H), 7.71-7.62 (m, 2H), 7.56 (s, 1H), 7.28 (d, J=8.9 Hz, 1H), 7.18 (s, 4H), 6.61 (d, J=3.2 Hz, 1H), 5.45 (s, 2H), 2.82 (m, 1H), 2.54 (m, 2H), 2.44 (s, 3H), 2.30-1.92 (m, 9H), 1.35 (d, J=8.6 Hz, 2H).

Example 28: Synthesis of 5-methyl-1-(1-((4'-(pyrrolidin-1-ylmethyl)-[1,1'-biphenyl]-4-yl)methyl)-1H-indol-5-yl)-1H-1,2,4-triazole-3-carboxamide

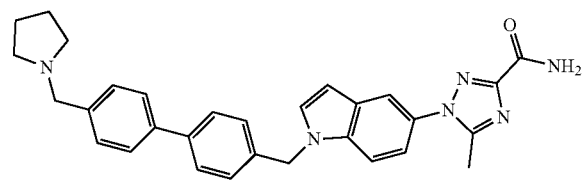 [SMILES: Cc1nc(C(N)=O)nn1-c1ccc2c(ccn2Cc2ccc(-c3ccc(CN4CCCC4)cc3)cc2)c1]

To the stirred solution of 1-(1-(4-bromobenzyl)-1H-indol-5-yl)-5-methyl-1H-1,2,4-triazole-3-carboxamide, Intermediate V (0.2 g, 0.488 mmol) in THF:Water (5:1) was added 1-(4-(4,4,5,5-tetramethyl-1,3,2-dioxaborolan-2-yl)benzyl)pyrrolidine (0.154 g, 0.537 mmol) and K$_3$PO$_4$ (0.310 g, 1.47 mmol), and then the reaction mixture was degassed with nitrogen for 10 min. PdCl$_2$(dppf).DCM (0.39 g, 0.048 mmol) was added, and again the reaction mixture was degassed with nitrogen for another 5 min. Then reaction vessel was sealed and heated at 120° C. for 1 h. The reaction mixture was then cooled, diluted with ethyl acetate (30 mL) and washed with water (10 mL×3) and brine solution (5 mL×3). Then organic layer was separated, dried over anhydrous sodium sulfate, and concentrated in vacuo. The crude material was purified by preparative HPLC to afford 5-methyl-1-(1-((4'-(pyrrolidin-1-ylmethyl)-[1,1'-biphenyl]-4-yl)methyl)-1H-indol-5-yl)-1H-1,2,4-triazole-3-carboxamide (35 mg, 14%): LCMS Rt=1.42 min (condition A), MS (M+1)=491.0. $^1$H NMR (400 MHz, DMSO) δ 7.82 (d, J=13.2 Hz, 2H), 7.79-7.65 (m, 2H), 7.56 (dt, J=56.0, 28.1 Hz, 5H), 7.28 (dt, J=106.3, 52.7 Hz, 5H), 6.64 (d, J=2.9 Hz, 1H), 5.55 (s, 2H), 3.58 (s, 2H), 2.43 (d, J=7.1 Hz, 7H), 1.69 (s, 4H).

Examples 29-1 and 29-2: Synthesis of Enantiomers of 5-methyl-1-(1-(4-(1-methylazepan-4-yl)benzyl)-1H-indol-5-yl)-1H-pyrazole-3-carboxamide

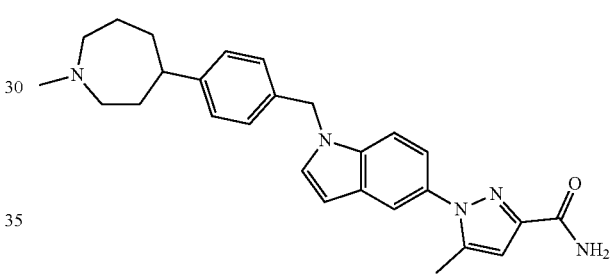

Step 1: tert-butyl 4-(4-((5-(3-carbamoyl-5-methyl-1H-pyrazol-1-yl)-1H-indol-1-yl)methyl)phenyl)-2,3,6,7-tetrahydro-1H-azepine-1-carboxylate To a stirred solution of Intermediate III (1.0 g, 2.1 mmol) in THF:Water (5:1) was added tert-butyl 4-((((trifluoromethyl)sulfonyl)oxy)-2,3,6,7-tetrahydro-1H-azepine-1-carboxylate (1.13 g, 3.2 mmol) and Na$_2$CO$_3$ (0.69 g, 6.5 mmol). The reaction mixture was degassed with nitrogen for 10 min. PdCl$_2$(dppf) (0.2 g, 0.2 mmol) was added to the reaction mixture and again the mixture was degassed with nitrogen for 10 min. Then the reaction vessel was sealed and heated at 80° C. for 4 h. Then the reaction mixture was diluted with EtOAc (50 mL), washed with water (5 mL×3) and brine solution (5 mL×3), dried over anhydrous Na$_2$SO$_4$, and concentrated in vacuo. The crude material was purified by column chromatography to afford (0.86 g, 74%) of tert-butyl 4-(4-((5-(3-carbamoyl-5-methyl-1H-pyrazol-1-yl)-1H-indol-1-yl)methyl)phenyl)-2,3,6,7-tetrahydro-1H-azepine-1-carboxylate.

Step 2: 5-methyl-1-(1-(4-(2,3,6,7-tetrahydro-1H-azepin-4-yl)benzyl)-1H-indol-5-yl)-1H-pyrazole-3-carboxamide To a stirred solution of tert-butyl 4-(4-((5-(3-carbamoyl-5-methyl-1H-pyrazol-1-yl)-1H-indol-1-yl)methyl)phenyl)-2,3,6,7-tetrahydro-1H-azepine-1-carboxylate (0.85 g, 1.6 mmol) in dry DCM (5 mL) was added TFA (5 mL) at 00° C. The resulting mixture was allowed to stir for 1 h at ambient temperature. The reaction mixture was concentrated in vacuo, and the crude material was triturated with diethyl ether to afford 5-methyl-1-(1-(4-(2,3,6,7-tetrahydro-1H-azepin-4-yl)benzyl)-1H-indol-5-yl)-1H-pyrazole-3-carboxamide (0.95 g, 100%).

Step 3: 5-methyl-1-(1-(4-(1-methyl-2,3,6,7-tetrahydro-1H-azepin-4-yl)benzyl)-1H-indol-5-yl)-1H-pyrazole-3-carboxamide To a stirred solution of 5-methyl-1-(1-(4-(2,3,6,7-tetrahydro-1H-azepin-4-yl)benzyl)-1H-indol-5-yl)-1H-pyrazole-3-carboxamide (0.95 g, 2.2 mmol) in MeOH (15 mL) was added 37% aqueous formaldehyde (0.134 g, 4.4 mmol) and Na(OAc)$_3$BH (0.947 g, 4.4 mmol) at ambient temperature. The reaction was allowed to stir at ambient temperature for 3 h. Then the reaction mixture was concentrated in vacuo to remove methanol. The resulting mixture was diluted with EtOAc (50 mL). The organic layer was separated, dried over anhydrous Na$_2$SO$_4$, and concentrated in vacuo. The crude material was then purified by preparative HPLC to afford 5-methyl-1-(1-(4-(1-methyl-2,3,6,7-tetrahydro-1H-azepin-4-yl)benzyl)-1H-indol-5-yl)-1H-pyrazole-3-carboxamide (150 mg): $^1$H NMR (400 MHz, DMSO-d6) δ 7.68 (dd, J=15.2, 2.4 Hz, 2H), 7.59 (d, J=8.7 Hz, 1H), 7.40 (d, J=39.3 Hz, 2H), 7.24 (dt, J=14.8, 8.1 Hz, 5H), 6.59 (s, 2H), 5.89 (t, J=6.0 Hz, 1H), 5.47 (s, 2H), 3.24 (s, 2H), 2.80 (s, 2H), 2.57 (s, 3H), 2.28 (d, J=14.8 Hz, 5H), 1.71 (s, 2H).

Step 4: 5-methyl-1-(1-(4-(1-methylazepan-4-yl)benzyl)-1H-indol-5-yl)-1H-pyrazole-3-carboxamide To a stirred solution of 5-methyl-1-(1-(4-(1-methyl-2,3,6,7-tetrahydro-1H-azepin-4-yl)benzyl)-1H-indol-5-yl)-1H-pyrazole-3-carboxamide (0.45 g, 1.0 mmol) in dry MeOH (20 mL) was added 10% Pd/C (0.05 g). The resulting suspension was allowed to stir for 4 h at ambient temperature in the presence of hydrogen at atmospheric pressure. The reaction mixture was then filtered through celite, washing with excess MeOH. The filtrate was concentrated in vacuo. The crude material was purified by Chiral HPLC to afford the pure enantiomers. Conditions: The purification of the racemic material was performed using normal phase HPLC with an isocratic method developed for the preparative purification utilizing a mobile phase of 24% (1:1) methanol/2-propanol (with 0.1% diethylamine) and 76% hexane (with 0.1% diethylamine) at a flow rate of 18 mL/min on the Chiralpak AD-H (21×250 mm, 5 μm).

Example 29-1

Enantiomer 1, 5-methyl-1-(1-(4-(1-methylazepan-4-yl)benzyl)-1H-indol-5-yl)-1H-pyrazole-3-carboxamide (10 mg): Chiral Rt=16.69 min. LCMS Rt=0.72 min (condition B), MS (M+1)=442.1. $^1$H NMR (400 MHz, DMSO-d6) δ 7.70-7.53 (m, 3H), 7.42 (s, 1H), 7.27-7.08 (m, 6H), 6.57 (s, 2H), 5.41 (s, 2H), 2.69 (d, J=35.7 Hz, 5H), 2.42-2.28 (m, 3H), 2.24 (s, 3H), 1.69 (dd, J=28.1, 15.3 Hz, 6H).

Example 29-2

Enantiomer 2, 5-methyl-1-(1-(4-(1-methylazepan-4-yl)benzyl)-1H-indol-5-yl)-1H-pyrazole-3-carboxamide (10 mg): Chiral Rt=17.84 min. LCMS Rt=0.73 min (condition B), MS (M+1)=442.1. $^1$H NMR (400 MHz, DMSO-d6) δ 7.70-7.53 (m, 3H), 7.42 (s, 1H), 7.27-7.08 (m, 6H), 6.57 (s, 2H), 5.41 (s, 2H), 2.69 (d, J=35.7 Hz, 5H), 2.42-2.28 (m, 3H), 2.24 (s, 3H), 1.69 (dd, J=28.1, 15.3 Hz, 6H).

Example 30-1: Synthesis of 5-methyl-1-(1-(4-(6-(methylsulfonyl)pyridin-3-yl)benzyl)-1H-indol-5-yl)-1H-pyrazole-3-carboxamide

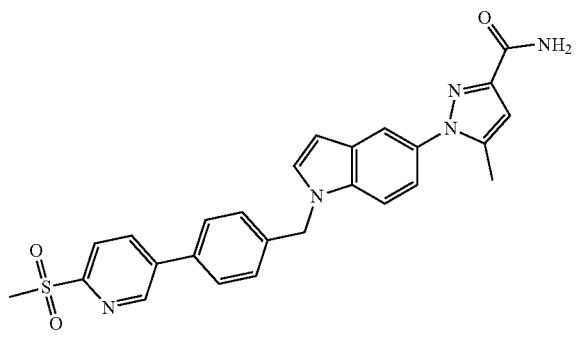 [SMILES: Cc1cc(C(N)=O)nn1-c1ccc2c(ccn2Cc2ccc(-c3ccc(S(C)(=O)=O)nc3)cc2)c1]

A reaction vial was charged with X-Phos-Pd-Cycle G2 (23 mg, 0.03 mmol), 5-methyl-1-(1-(4-(4,4,5,5-tetramethyl-1,3,2-dioxaborolan-2-yl)benzyl)-1H-indol-5-yl)-1H-pyrazole-3-carboxamide (Intermediate III) (162 mg, 0.356 mmol), 5-bromo-2-(methylsulfonyl)pyridine (70 mg, 0.3 mmol), and K$_3$PO$_4$ (189 mg, 0.89 mmol). The vial was sealed and evacuated under hi-vac/backfilled with N$_2$ (3×). Degased 1,4-dioxane (1.2 mL) and degased water (0.25 mL) were added and the mixture was heated at 100° C. overnight. The reaction was diluted with EtOAc and filtered through a pad of celite. The filtrate was concentrated and the crude material was purified by preparative HPLC and dried under lyophilization to afford 5-methyl-1-(1-(4-(6-(methylsulfonyl)pyridin-3-yl)benzyl)-1H-indol-5-yl)-1H-pyrazole-3-carboxamide. LCMS Rt=1.99 min (condition A), MS (M+1)=486.4. $^1$H NMR (400 MHz, DMSO-d6) δ 9.07 (d, J=2.2 Hz, 1H), 8.38 (dd, J=8.2, 2.3 Hz, 1H), 8.09 (d, J=8.2 Hz, 1H), 7.80 (d, J=8.3 Hz, 2H), 7.74-7.70 (m, 2H), 7.64 (d, J=8.6 Hz, 2H), 7.43 (s, 1H), 7.40 (d, J=8.2 Hz, 2H), 7.25 (dd, J=8.7, 2.0 Hz, 1H), 7.19 (s, 1H), 6.63 (d, J=3.1 Hz, 1H), 6.59 (s, 1H), 5.59 (s, 2H), 3.30 (s, 3H), 2.27 (s, 3H).

The following compounds were prepared using a similar procedure as in Example 30-1

| Example | Compound | LCMS M + 1, Rt, conditions | 1H NMR, 400 MHz |
|---|---|---|---|
| 30-2 | 1-(1-(4-(5-(2-hydroxypropan-2-yl)pyridin-2-yl)benzyl)-1H-indol-5-yl)-5-methyl-1H-pyrazole-3-carboxamide | 466.4 1365 min A | (DMSO-d6) δ 8.74 (d, J = 2.3 Hz, 1H), 8.02 (d, J = 8.3 Hz, 2H), 7.94-7.81 (m, 2H), 7.72 (t, J = 3.0 Hz, 2H), 7.63 (d, J = 8.7 Hz, 1H), 7.47 (s, 1H), 7.34 (d, J = 8.1 Hz, 2H), 7.29-7.18 (m, 2H), 6.65-6.57 (m, 2H), 5.56 (s, 2H), 5.24 (s, 1H), 2.27 (s, 3H), 1.47 (s, 6H) |
| 30-3 | 1-(1-(4-(6-(2-hydroxypropan-2-yl)pyridin-3-yl)benzyl)-1H-indol-5-yl)-5-methyl-1H-pyrazole-3-carboxamide | 466.4 1.59 min A | (DMSO-d6) δ 8.76 (d, J = 2.3 Hz, 1H), 8.02 (dd, J = 8.3, 2.4 Hz, 1H), 7.76-7.63 (m, 6H), 7.47 (s, 1H), 7.36 (d, J = 8 0 Hz, 2H), 7.27 (dd, J = 8.7, 2.1 Hz, 1H), 7.22 (s, 1H), 6.66-6.58 (m, 2H), 5.58 (s, 2H), 5.27 (s, 1H), 2.29 (s, 3H), 1.47 (s, 6H). |

Example 31: Synthesis of rac-5-methyl-1-(1-(4-((1-methylpyrrolidin-3-yl)methyl)benzyl)-1H-indol-5-yl)-1H-pyrazole-3-carboxamide

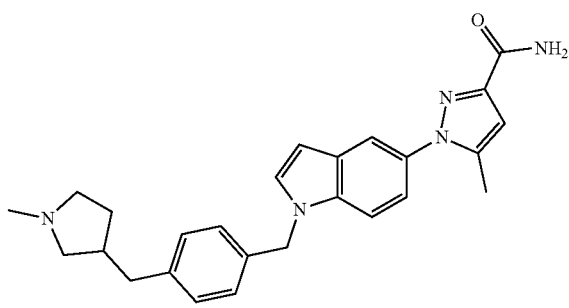 [SMILES: Cc1cc(C(N)=O)nn1-c1ccc2c(ccn2Cc2ccc(CC3CCN(C)C3)cc2)c1]

Step 1: tert-Butyl 3-methylenepyrrolidine-1-carboxylate

Methyltriphenylphosphonium bromide (4.24 g, 11.89 mmol) was suspended in dry THF (20 mL) and n-BuLi (12 mL, 32.4 mmol) was added dropwise at −78° C. under a nitrogen atmosphere. The reaction mixture was stirred for 30 min. at −78° C. tert-Butyl 3-oxopyrrolidine-1-carboxylate (2.0 g, 10.81 mmol) was added slowly and the reaction was allowed to warm to RT and stirred overnight. The reaction mixture was filtered. The filtrate was diluted with water (20 mL) and extracted with ethyl acetate (3×20 mL). The combined organic layers were washed with water (1×20 mL) and brine (1×20 mL). The organic layer was dried over sodium sulfate, filtered and the filtrate was concentrated. The crude material was purified by FCC to afford tert-butyl 3-methylenepyrrolidine-1-carboxylate (1.2 g, 61%). ¹H NMR (400 MHz, CDCl₃): δ 5.01 (m, 2H), 3.94-3.97 (t, 2H), 3.47-3.51 (t, 2H), 2.60 (d, J=7.3 Hz, 2H), 1.50 (s, 9H).

Step 2: rac-tert-Butyl 3-(4-((5-(3-carbamoyl-5-methyl-1H-pyrazol-1-yl)-1H-indol-1-yl)methyl)benzyl)pyrrolidine-1-carboxylate A solution of rac-tert-Butyl 3-methylenepyrrolidine-1-carboxylate (0.178 g, 0.97 mmol) in dry THF (1.8 mL) was degassed with N₂ for 15-20 min. followed by dropwise addition of 9-borabicyclo [3.3.1]nonane (0.5M in THF, 2.2 mL, 1.07 mmol). The resulting solution was heated at 65° C. for 2.5 h. The solution was cooled to ambient temperature and added to a mixture of 1-(1-(4-bromobenzyl)-1H-indol- 5-yl)-5-methyl-1H-pyrazole-3-carboxamide (Intermediate II) (0.4 g, 0.97 mmol) and K₂CO₃ (0.15 g, 1.07 mmol) in DMF (6 mL) and water (0.4 mL). The resulting mixture was degassed with N₂ for 15 min., then PdCl₂(dppf)-CH₂Cl₂ (79 mg, 0.09 mmol) was added and the mixture was again degassed for 5-10 min. The reaction mixture was heated at 80° C. for 18 h. The reaction was then diluted with EtOAc (30 mL) and washed with water (3×10 mL) and brine solution (13×10 mL). The organic layer was separated, dried over anhydrous Na₂SO₄, filtered and the filtrate was concentrated. The crude material was purified by preparative HPLC to afford rac-tert-Butyl 3-(4-((5-(3-carbamoyl-5-methyl-1H-pyrazol-1-yl)-1H-indol-1-yl)methyl)benzyl)pyrrolidine-1-carboxylate (250 mg, 50%).

Step 3: rac-5-methyl-1-(1-(4-(pyrrolidin-3-ylmethyl)benzyl)-1H-indol-5-yl)-1H-pyrazole-3-carboxamide rac-tert-Butyl 3-(4-((5-(3-carbamoyl-5-methyl-1H-pyrazol-1-yl)-1H-indol-1-yl)methyl)benzyl)pyrrolidine-1-carboxylate (205 mg, 0.4 mmol) was dissolved in DCM (1.3 mL). Then TFA (0.67 mL) was added and the mixture was stirred at RT for 1 h. The mixture was concentrated and purified according to General Method IV to afford rac-5-methyl-1-(1-(4-(pyrrolidin-3-ylmethyl)benzyl)-1H-indol-5-yl)-1H-pyrazole-3-carboxamide (169 mg, 98%). LCMS Rt=2.53 min (condition A), MS (M+1)=414.3.

Step 4: rac-5-methyl-1-(1-(4-((1-methylpyrrolidin-3-yl)methyl)benzyl)-1H-indol-5-yl)-1H-pyrazole-3-carboxamide rac-5-methyl-1-(1-(4-(pyrrolidin-3-ylmethyl)benzyl)-1H-indol-5-yl)-1H-pyrazole-3-carboxamide (165 mg, 0.4 mmol) was dissolved in DCE (1.7 mL) and MeOH (0.33 mL). Formaldehyde (35% wt. in water) (0.11 mL, 1.40 mmol) was added and the reaction mixture was stirred at RT for 5 min, and then cooled in an ice bath. Sodium triacetoxyborohydride (254 mg, 1.20 mmol) was added and the mixture was allowed to warm to RT and stir for 10 min. The reaction was then quenched with saturated aqueous sodium bicarbonate and extracted with DCM (3×20 mL). The organic layer was washed with brine (1×20 mL), dried over sodium sulfate and concentrated. The crude material was purified by preparative HPLC and dried under lyophilization to afford rac-5-methyl-1-(1-(4-((1-methylpyrrolidin-3-yl)methyl)benzyl)-1H-indol-5-yl)-1H-pyrazole-3-carboxamide. LCMS Rt=2.51 min (condition A), MS (M+1)=428.4. ¹H NMR (400 MHz, DMSO-d6) δ 7.69 (d, J=1.9 Hz, 1H), 7.64 (d, J=3.1 Hz, 1H), 7.60 (d, J=8.7 Hz, 1H), 7.44 (s, 1H), 7.23 (dd, J=8.7, 2.0 Hz, 1H), 7.18 (s, 1H), 7.14 (s, 4H), 6.60-6.57 (m, 2H), 5.44 (s, 2H), 2.56 (d, J=7.6 Hz, 2H), 2.47-2.35 (m, 4H), 2.26 (s, 3H), 2.17 (s, 3H), 2.05 (dd, J=8.8, 6.0 Hz, 1H), 1.86-1.73 (m, 1H), 1.42-1.30 (m, 1H).

Example 32: Synthesis of 5-methyl-1-(1-(4-((1-methylazetidin-3-yl)methyl)benzyl)-1H-indol-5-yl)-1H-pyrazole-3-carboxamide

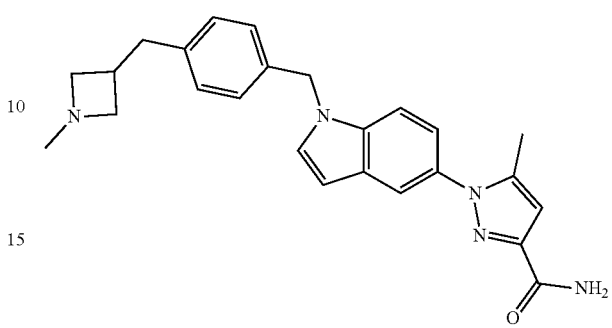

Step 1: tert-Butyl 3-(4-((5-(3-carbamoyl-5-methyl-1H-pyrazol-1-yl)-1H-indol-1-yl)methyl)benzyl)azetidine-1-carboxylate To a solution of tert-Butyl 3-methyleneazetidine-1-carboxylate (0.413 g, 2.442 mmol) in dry THF (20 mL) was added 9-BBN (6.1 mL, 6.11 mmol, 1M solution in THF) and the resulting mixture was stirred for 16 hours at 60° C. in a sealed reaction vial. A second reaction vial was charged with Intermediate II (0.5 g, 1.22 mmol) in DMF (9 mL) and H₂O (1 mL). Then K₂CO₃ (0.51 g, 3.67 mmol) was added and the mixture was degassed with nitrogen for 10 min. The above prepared BBN-complex in THF was then added at ambient temperature and again degassed with nitrogen for 10 min followed by the addition of PdCl₂(dppf)DCM (0.01 g, 0.122 mmol). The mixture was then heated at 80° C. for 16 hours in a sealed reaction vessel. The reaction was cooled and filtered. The filtrate was diluted with EtOAc and washed with water (3×30 mL) and brine solution (3×30 mL). The organic layer was separated, dried over anhydrous sodium sulfate, and concentrated. The crude material was purified by column chromatography (eluent: 50% ethyl acetate in heptane) to afford tert-Butyl 3-(4-((5-(3-carbamoyl-5-methyl-1H-pyrazol-1-yl)-1H-indol-1-yl)methyl)benzyl)azetidine-1-carboxylate (0.5 g, 81%). ¹H NMR (400 MHz, DMSO-d6) δ 7.73-7.57 (m, 3H), 7.46 (s, 1H), 7.31-7.18 (m, 4H), 6.59 (d, J=4.3 Hz, 2H), 5.45 (s, 2H), 3.51 (s, 4H), 2.80-2.67 (m, 3H), 2.27 (s, 3H), 1.35 (s, 12H).

Step 2: 1-(1-(4-(azetidin-3-ylmethyl)benzyl)-1H-indol-5-yl)-5-methyl-1H-pyrazole-3-carboxamide To a stirred solution of tert-Butyl 3-(4-((5-(3-carbamoyl-5-methyl-1H-pyrazol-1-yl)-1H-indol-1-yl)methyl)benzyl)azetidine-1-carboxylate (0.5 g, 1.0 mmol) in dry DCM (5 mL) was added TFA (0.38 mL, 5.01 mmol) at 00° C. The reaction was allowed to stir for 6 h at ambient temperature. The mixture was then concentrated and the crude material was triturated with diethyl ether and purified by preparative HPLC to afford 1-(1-(4-(azetidin-3-ylmethyl)benzyl)-1H-indol-5-yl)-5-methyl-1H-pyrazole-3-carboxamide (38 mg). ¹H NMR (400 MHz, DMSO-d6) δ 7.73-7.57 (m, 3H), 7.47 (s, 1H), 7.27-7.19 (m, 2H), 7.18-7.08 (m, 2H), 6.59 (d, J=4.8 Hz, 2H), 5.44 (s, 2H), 3.37-3.17 (m, 4H), 2.78 (s, 2H), 2.27 (s, 3H).

Step 3: 5-methyl-1-(1-(4-((1-methylazetidin-3-yl)methyl)benzyl)-1H-indol-5-yl)-1H-pyrazole-3-carboxamide To a stirred solution of 1-(1-(4-(azetidin-3-ylmethyl)benzyl)-1H-indol-5-yl)-5-methyl-1H-pyrazole-3-carboxamide (0.3 g, 0.61 mmol) in MeOH (10 mL) was added 37% aqueous formaldehyde (0.04 g, 1.21 mmol) and Na(OAc)₃BH (0.26 g, 1.21 mmol) at ambient temperature. The reaction was allowed to stir at ambient temperature for 2 h then concentrated. The crude material was purified by preparative HPLC to afford 5-methyl-1-(1-(4-(((1-methylazetidin-3-yl)methyl)benzyl)-1H-indol-5-yl)-1H-pyrazole-3-carboxamide (16 mg, 6.7%). LCMS Rt=1.26 min (condition A), MS (M+1)=414.3. ¹H NMR (400 MHz, DMSO-d6) δ 7.56-7.68 (m, 3H), 7.44 (s, 1H), 7.19-7.21 (m, 2H), 7.18-7.08 (m, 4H), 6.59 (d, J=4.8 Hz, 2H), 5.42 (s, 2H), 3.21 (m, 2H), 2.71-2.78 (m, 4H), 2.58 (m, 1H), 2.24 (s, 3H), 2.15 (s, 3H).

Example 33: Synthesis of 5-methyl-1-(1-(4-(((1R,5S)-3-methyl-3-azabicyclo[3.1.0]hexan-1-yl)benzyl)-1H-indol-5-yl)-1H-pyrazole-3-carboxamide

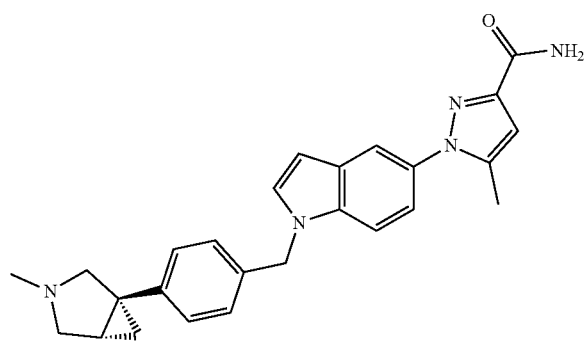 [SMILES: Cc1cc(C(N)=O)nn1-c1ccc2c(ccn2Cc2ccc([C@@]34C[C@@H]3CN(C)C4)cc2)c1]

Step 1: (1R,5S)-1-(4-bromophenyl)-3-methyl-3-azabicyclo[3.1.0]hexane (1R,5S)-1-(4-bromophenyl)-3-azabicyclo[3.1.0]hexane (400 mg, 1.680 mmol) (see WO 2010/150281) was dissolved in DCE (7 mL) and MeOH (1.4 mL). Then formaldehyde (35% wt. in water) (0.46 mL, 5.88 mmol) was added and the reaction was stirred for 5 min. at RT. The mixture was then cooled in an ice bath. Sodium triacetoxyborohydride (1.07 g, 5.04 mmol) was added and the reaction was allowed to warm to RT and stirred for 10 minutes. Saturated aqueous NaHCO₃ was added and the resulting mixture was extracted with DCM (3×20 mL). The organic layer was then washed with with brine (1×20 mL), dried over sodium sulfate and concentrated in vacuo to afford (1R,5S)-1-(4-bromophenyl)-3-methyl-3-azabicyclo[3.1.0]hexane (424 mg, quantitative yield) as a colorless oil. LCMS Rt=1.11 min (condition B), MS (M+1)=252.1.

Step 2: (4-((1R,5S)-3-methyl-3-azabicyclo[3.1.0]hexan-1-yl)phenyl)methanol (1R,5S)-1-(4-bromophenyl)-3-methyl-3-azabicyclo[3.1.0]hexane (424 mg, 1.68 mmol) was dissolved in dry THF (8.4 mL). The solution was then cooled to −78° C. and n-BuLi (2.5M in THF) (0.8 mL, 2.02 mmol) was added dropwise. The reaction was stirred at −78° C. for 1 h. Then anhydrous N,N-dimethylformamide (0.26 mL, 3.36 mmol) was added and the resulting mixture was stirred at −78° C. for 1 h. The reaction was allowed to warm to 0° C. and MeOH (5 mL) was added followed by sodium borohydride (127 mg, 3.36 mmol). The resulting mixture was allowed to warm to RT and stirred overnight. The mixture was then quenched with water (20 mL) and extracted with DCM (4×20 mL). The combined organic layers were dried over sodium sulfate, filtered and concentrated in vacuo. The crude material was purified according to General Method IV to afford (4-((1R,5S)-3-methyl-3-azabicyclo[3.1.0]hexan-1-yl)phenyl)methanol (300 mg, 88%) as a colorless oil. LCMS Rt=1.33 min (condition A), MS (M+1)=204.4.

Step 3: 4-((1R,5S)-3-methyl-3-azabicyclo[3.1.0]hexan-1-yl)benzyl 4-methylbenzenesulfonate (4-((1R,5S)-3-methyl-3-azabicyclo[3.1.0]hexan-1-yl)phenyl)methanol (300 mg, 1.48 mmol) was dissolved in DCM (4.9 mL) and DMF (1 mL). p-Toluenesulfonyl chloride (338 mg, 1.77 mmol), triethylamine (0.41 mL, 2.95 mmol) and DMAP (18 mg, 0.148 mmol) were added and the mixture was allowed to stir at RT for 5 h. The reaction was then diluted with water (10 mL). The aqueous was extracted with DCM (2×20 mL) and the combined organic layers were washed with saturated aqueous NaHCO₃ (1×20 mL) and brine (1×20 mL), dried over sodium sulfate, and concentrated in vacuo to afford 4-((1R,5S)-3-methyl-3-azabicyclo[3.1.0]hexan-1-yl)benzyl 4-methylbenzenesulfonate as a red oil. The resulting product was used without further purification in the next step.

Step 4: Synthesis of 5-methyl-1-(1-(4-((1R,5S)-3-methyl-3-azabicyclo[3.1.0]hexan-1-yl)benzyl)-1H-indol-5-yl)-1H-pyrazole-3-carboxamide 1-(1H-indol-5-yl)-5-methyl-1H-pyrazole-3-carboxamide (525 mg, 1.47 mmol) was dissolved in anhydrous DMF (3.7 mL). The solution was then cooled to 0° C. and potassium tert-butoxide (181 mg, 1.62 mmol) was added portionwise over 5 min. The reaction was allowed to warm to RT and stirred for 40 min. The reaction was then cooled to 0° C. and 4-((1R,5S)-3-methyl-3-azabicyclo[3.1.0]hexan-1-yl)benzyl 4-methylbenzenesulfonate (353 mg, 1.47 mmol) was added as a solution in DMF (3 mL). The mixture was allowed to warm to RT and stirred overnight. The mixture was quenched with water (20 mL) and extracted with EtOAc (3×20 mL). The organic layer was washed with brine (1×20 mL), dried over sodium sulfate, and concentrated in vacuo. The crude material was purified by preparative HPLC to afford 5-methyl-1-(1-(4-((1R,5S)-3-methyl-3-azabicyclo[3.1.0]hexan-1-yl)benzyl)-1H-indol-5-yl)-1H-pyrazole-3-carboxamide. LCMS Rt=1.26 min (condition A), MS (M+1)=426.5. ¹H NMR (400 MHz, DMSO-d6) δ 7.69 (d, J=1.9 Hz, 1H), 7.64 (d, J=3.1 Hz, 1H), 7.58 (d, J=8.7 Hz, 1H), 7.44 (s, 1H), 7.22 (dd, J=8.7, 2.0 Hz, 1H), 7.20-7.13 (m, 3H), 7.07 (d, J=8.3 Hz, 2H), 6.59 (d, 1H), 6.57 (d, J=3.1 Hz, 1H), 5.43 (s, 2H), 3.18 (d, J=8.5 Hz, 1H), 2.93 (d, J=8.6 Hz, 1H), 2.42 (d, J=8.5 Hz, 1H), 2.33 (dd, J=8.6, 3.4 Hz, 1H), 2.26 (m, 6H), 1.72 (dt, J=7.8, 3.9 Hz, 1H), 1.29 (t, J=4.0 Hz, 1H), 0.68 (dd, J=7.9, 3.8 Hz, 1H).

Example 34-1: Synthesis of (S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide

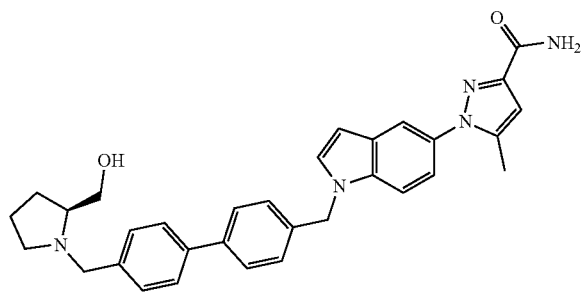 [SMILES: Cc1cc(C(N)=O)nn1-c1ccc2c(ccn2Cc2ccc(-c3ccc(CN4CCC[C@H]4CO)cc3)cc2)c1]

Step 1: 1-(1-((4'-formyl-[1,1'-biphenyl]-4-yl)methyl)-1H-indol-5-yl)-5-methyl-1H-pyrazole-3-carboxamide 1-(1-(4-bromobenzyl)-1H-indol-5-yl)-5-methyl-1H-pyrazole-3-carboxamide (Intermediate II) (350 mg, 0.85 mmol) and 4-(4,4,5,5-tetramethyl-1,3,2-dioxaborolan-2-yl)benzaldehyde (198 mg, 0.85 mmol) were suspended in THF (3.1 mL). Then water (1 mL) and K$_3$PO$_4$ (544 mg, 2.56 mmol) were added and the reaction mixture was purged with nitrogen for 15 min. Then X-Phos-Pd-Cycle G1 (63 mg, 0.085 mmol) was added and the resulting mixture was heated for 3 h at 100° C. The reaction mixture was then filtered through celite and the filtrate was diluted with water. The aqueous layer was extracted with ethyl acetate (3×20 mL) and the combined organic layers were dried over sodium sulfate, filtered, concentrated in vacuo. The crude material was purified by FCC to afford 1-(1-((4'-formyl-[1,1'-biphenyl]-4-yl)methyl)-1H-indol-5-yl)-5-methyl-1H-pyrazole-3-carboxamide (350 mg, 94%). Mass (m/z): 435.50 (M+1).

Step 2: (S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide To a stirred solution of 1-(1-((4'-formyl-[1,1'-biphenyl]-4-yl)methyl)-1H-indol-5-yl)-5-methyl-1H-pyrazole-3-carboxamide (75 mg, 0.172 mmol) in 1,2-dichloroethane (1.5 mL) was added acetic acid (catalytic, 1 drop) and (S)-pyrrolidin-2-ylmethanol (20 mg, 0.20 mmol). The reaction was allowed to stir for 30 min. at RT. Then sodium triacetoxyborohydride (0.11 g, 0.51 mmol) was added and reaction was allowed to stir for 18 h at RT. The reaction was then diluted with DCM (25 mL) and washed with water (2×25 mL) and brine (1×25 mL), dried over sodium sulfate, filtered and concentrated. The crude material was purified by preparative HPLC to afford (S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide. LCMS Rt=2.46 min (condition A), MS (M+1)=520.4. 1H NMR (400 MHz, Methanol-d4) δ 7.71 (d, J=2.0 Hz, 1H), 7.62-7.56 (m, 4H), 7.55-7.50 (m, 2H), 7.43 (d, J=7.8 Hz, 2H), 7.28 (d, J=8.1 Hz, 2H), 7.23 (d, J=6.5 Hz, 1H), 6.70 (s, 1H), 6.67 (d, J=3.3 Hz, 1H), 5.54 (s, 2H), 4.12 (m, 1H), 3.61 (m, J=4.4 Hz, 1H), 3.50 (m, 2H), 2.89 (m, 1H), 2.79-2.66 (m, 1H), 2.32 (m, 4H), 2.03 (m, 1H), 1.73 (m, 3H).

The following compounds were prepared using a similar procedure as in Example 34-1:

| Example | Compound | LCMS M + 1, Rt, conditions | 1H NMR, 400 MHz |
|---|---|---|---|
| 34-2 | (R)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide | 520.7 1.46 min A | (DMSO-d6) δ 7.75-7.68 (m, 2H), 7.66-7.41 (m, 6H), 7.40-7.14 (m, 6H), 6.64-6.56 (m, 2H), 5.54 (s, 2H), 4.41 (t, J = 5.4 Hz, 1H), 4.06 (d, J = 13.4 Hz, 1H), 3.51-3.40 (m, 1H), 3.31-3.23 (m, 1H), 2.83-2.72 (m, 1H), 2.60-2.53 (m, 1H), 2.30-2.23 (m, 3H), 2.20-2.10 (m, 1H), 1.90-1.77 (m, 1H), 1.67-1.48 (m, 3H). |

| Example | Compound | LCMS M + 1, Rt, conditions | 1H NMR, 400 MHz |
|---|---|---|---|
| 34-3 | 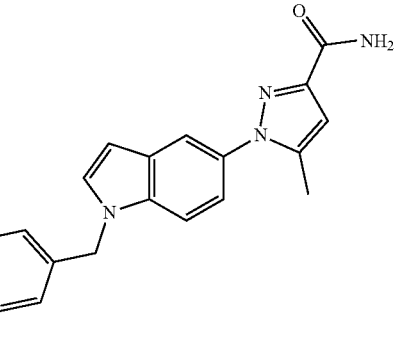<br>5-methyl-1-(1-((4'-((4-methylpiperazin-1-yl)methyl)-[1,1'-biphenyl]-4-yl)methyl)-1H-indol-5-yl)-1H-pyrazole-3-carboxamide | 519.4<br>2.42 min<br>A | (Methanol-d4) δ 7.71 (d, J = 2.0 Hz, 1H), 7.58 (dd, J = 8.2, 4.2 Hz, 4H), 7.55-7.50 (m, 2H), 7.40 (d, J = 8.3 Hz, 2H), 7.28 (d, J = 8.3 Hz, 2H), 7.23 (dd, J = 8.7, 2.1 Hz, 1H), 6.70 (s, 1H), 6.67 (d, J = 3.3 Hz, 1H), 5.54 (s, 2H), 3.58 (s, 2H), 2.74-2.26 (m, 14H). |

Example 35: Synthesis of 5-methyl-1-(1-((4'-(piperazin-1-ylmethyl)-[1,1'-biphenyl]-4-yl)methyl)-1H-indol-5-yl)-1H-pyrazole-3-carboxamide

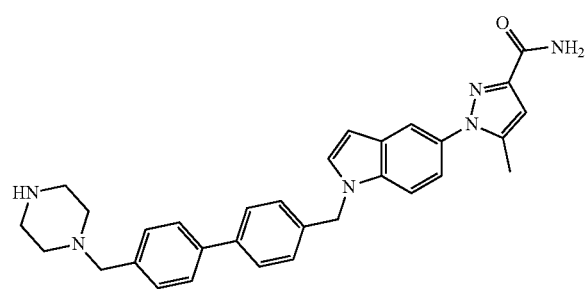 [SMILES: Cc1cc(C(N)=O)nn1-c1ccc2c(ccn2Cc2ccc(-c3ccc(CN4CCNCC4)cc3)cc2)c1]

Step 1: tert-Butyl 4-((4'-((5-(3-carbamoyl-5-methyl-1H-pyrazol-1-yl)-1H-indol-1-yl)methyl)-[1,1'-biphenyl]-4-yl)methyl)piperazine-1-carboxylate To a stirred solution of 1-(1-((4'-formyl-[1,1'-biphenyl]-4-yl)methyl)-1H-indol-5-yl)-5-methyl-1H-pyrazole-3-carboxamide (75 mg, 0.172 mmol) in 1,2-dichloroethane (1.5 mL) were added Acetic acid (catalytic, 1 drop) and tert-Butyl piperazine-1-carboxylate (35 mg, 0.19 mmol). The reaction was allowed to stir for 30 min. at RT. Then sodium triacetoxyborohydride (0.11 g, 0.51 mmol) was added and reaction was allowed to stir for 18 h at RT. The reaction was diluted with DCM (25 mL) and washed with water (2×25 mL). The organic layer was washed with brine (25 mL), dried over sodium sulfate, filtered and concentrated. The crude material was purified by preparative HPLC to afford tert-butyl tert-butyl 4-((4'-((5-(3-carbamoyl-5-methyl-1H-pyrazol-1-yl)-1H-indol-1-yl)methyl)-[1,1'-biphenyl]-4-yl)methyl)piperazine-1-carboxylate.

Step 2: 5-methyl-1-(1-((4'-(piperazin-1-ylmethyl)-[1,1'-biphenyl]-4-yl)methyl)-1H-indol-5-yl)-1H-pyrazole-3-carboxamide To the stirred solution of tert-Butyl 4-((4'-((5-(3-carbamoyl-5-methyl-1H-pyrazol-1-yl)-1H-indol-1-yl)methyl)-[1,1'-biphenyl]-4-yl)methyl)piperazine-1-carboxylate (0.115 g, 0.172 mmol) in dry DCM (2.3 mL) was added 4M HCl in 1,4-dioxane (1.2 mL) at 00° C. The resulting mixture was allowed to stir for 3 h at RT then concentrated in vacuo. The crude material was purified by preparative HPLC to afford 5-methyl-1-(1-((4'-(piperazin-1-ylmethyl)-[1,1'-biphenyl]-4-yl)methyl)-1H-indol-5-yl)-1H-pyrazole-3-carboxamide. LCMS Rt=1.40 min (condition A), MS (M+1)=505.4. $^1$H NMR (400 MHz, Methanol-d4) δ 7.71 (s, 1H), 7.59 (d, J=6.2 Hz, 4H), 7.55-7.51 (m, 2H), 7.41 (d, J=8.2 Hz, 2H), 7.28 (d, J=8.2 Hz, 2H), 7.24 (d, J=8.4 Hz, 1H), 6.70 (s, 1H), 6.67 (d, J=3.2 Hz, 1H), 5.54 (s, 2H), 3.59 (s, 2H), 3.00-2.90 (m, 4H), 2.60-2.45 (m, 4H), 2.32 (s, 3H).

Example 36: Synthesis of 5-methyl-1-(1-((4'-(4-methylpiperazine-1-carbonyl)-[1,1'-biphenyl]-4-yl)methyl)-1H-indol-5-yl)-1H-pyrazole-3-carboxamide

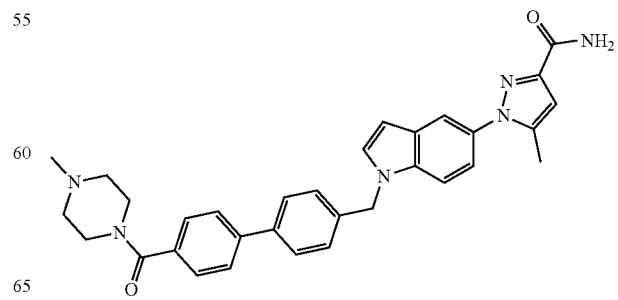

Step 1: tert-butyl 4'-((5-(3-carbamoyl-5-methyl-1H-pyrazol-1-yl)-1H-indol-1-yl)methyl)-[1,1'-biphenyl]-4-carboxylate To a stirred solution of 1-(1-(4-bromobenzyl)-1H-indol-5-yl)-5-methyl-1H-pyrazole-3-carboxamide (Intermediate II) (100 mg, 0.24 mmol) in THF (1.5 mL) and water (0.5 mL) was added tert-butyl 4-(4,4,5,5-tetramethyl-1,3,2-dioxaborolan-2-yl)benzoate (89 mg, 0.29 mmol) and potassium phosphate (0.155 g, 0.73 mmol). The reaction mixture was degassed with nitrogen for 15 min. Then X-Phos-Pd-Cycle G1 (18 mg, 0.024 mmol) was added at ambient temperature. The reaction was again degassed with nitrogen for 10 min, sealed and heated at 100° C. for 16 h. The mixture was then diluted with EtOAc (30 mL) and washed with water (25 mL) and brine solution (25 mL), dried over anhydrous sodium sulfate, and concentrated in vacuo. The crude material was purified by column chromatography to afford tert-Butyl 4'-((5-(3-carbamoyl-5-methyl-1H-pyrazol-1-yl)-1H-indol-1-yl)methyl)-[1,1'-biphenyl]-4-carboxylate (120 mg, 97%): MS (M+1)=507.8.

Step 2: 4'-((5-(3-carbamoyl-5-methyl-1H-pyrazol-1-yl)-1H-indol-1-yl)methyl)-[1,1'-biphenyl]-4-carboxylic acid To a stirred solution of tert-Butyl 4'-((5-(3-carbamoyl-5-methyl-1H-pyrazol-1-yl)-1H-indol-1-yl)methyl)-[1,1'-biphenyl]-4-carboxylate (120 mg, 0.23 mmol) in dry DCM (4 mL) was added 4M HCl in 1,4-dioxane (1 mL) at 00° C. The reaction mixture was allowed to stir for 3 h at ambient temperature and concentrated in vacuo. The crude material was triturated with diethyl ether to obtain 4'-((5-(3-carbamoyl-5-methyl-1H-pyrazol-1-yl)-1H-indol-1-yl)methyl)-[1,1'-biphenyl]-4-carboxylic acid (100 mg, 93%): MS (M+1)=451.5.

Step 3: 5-methyl-1-(1-((4'-(4-methylpiperazine-1-carbonyl)-[1,1'-biphenyl]-4-yl)methyl)-1H-indol-5-yl)-1H-pyrazole-3-carboxamide 4'-((5-(3-carbamoyl-5-methyl-1H-pyrazol-1-yl)-1H-indol-1-yl)methyl)-[1,1'-biphenyl]-4-carboxylic acid (100 mg, 0.22 mmol) was dissolved in DMF (1.5 mL). Then HATU (126 mg, 0.33 mmol) and DIPEA (0.075 mL, 0.44 mmol) were added. After stirring for 5 min. 1-methylpiperazine (26 mg, 0.26 mmol) was added and the mixture was allowed to stirred at ambient temperature 4 h. The mixture was then dilute with 1N HCl (aq) (20 mL) and ethyl acetate (20 mL). The organic layer was separated, washed with saturated sodium bicarbonate solution (20 mL) and brine solution (20 mL), dried over $Na_2SO_4$, and concentrated in vacuo. The crude material was purified by preparative HPLC to afford 5-methyl-1-(1-((4'-(4-methylpiperazine-1-carbonyl)-[1,1'-biphenyl]-4-yl)methyl)-1H-indol-5-yl)-1H-pyrazole-3-carboxamide (46 mg, 39%). LCMS Rt=1.47 min (conditions A), MS (M+1)=533.3. $^1$H NMR (400 MHz, DMSO-D6) δ 7.65-7.73 (m, 7H), 7.44-7.47 (m, 3H), 7.34-7.66 (d, J=8.0 Hz, 2H), 7.19-7.28 (m, 2H), 6.60-6.63 (m, 2H), 5.57 (s, 2H), 3.61 (br s, 2H), 2.56 (br s, 2H), 2.33 (br s, 4H), 2.28 (s, 3H), 2.20 (s, 3H).

Example 37-1 and 37-2: Synthesis of enantiomers of (5-methyl-1-(1-(4-((1-methylpyrrolidin-3-yl)amino)benzyl)-1H-indol-5-yl)-1H-pyrazole-3-carboxamide

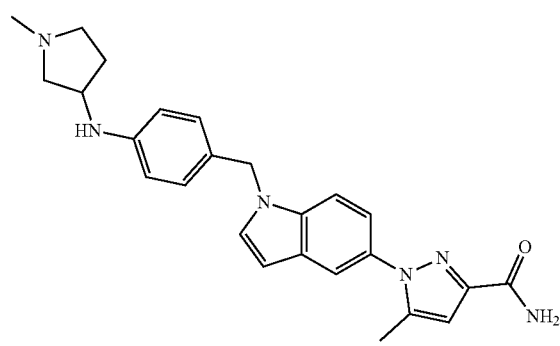 [SMILES: Cc1cc(C(N)=O)nn1-c1ccc2c(ccn2Cc2ccc(NC3CCN(C)C3)cc2)c1]

Intermediate II (0.500 g, 1.22 mmol) and 1-methylpyrrolidin-3-amine (0.293 g, 2.93 mmol) were taken up in THF (20 mL). Then $Pd(OAc)_2$ (0.109 g, 0.488 mmol) and potassium tert-butoxide (0.410 g, 3.66 mmol) were added and the mixture was purged with nitrogen for 15 min. BrettPhos Pd $G_3$ (0.221 g, 0.244 mmol) was added and the mixture was again purged with nitrogen for 5 min. and heated for 18 h at 70° C. The mixture then was cooled to ambient temperature and filtered through celite. The filtrate was dilute with water (20 mL) and extracted with ethyl acetate (3×50 mL). The combined organic layers were washed with brine solution (20 mL), dried over sodium sulphate and concentrated in vacuo. The crude material was then purified by preparative HPLC to afford racemic (5-methyl-1-(1-(4-((1-methylpyrrolidin-3-yl)amino)benzyl)-1H-indol-5-yl)-1H-pyrazole-3-carboxamide. This material was then purified by chiral HPLC to afford the pure enantiomers. The absolute stereochemistry was not determined. Conditions: The purification of the racemic material was performed using HPLC on a Shimadzu LC-20AP with UV Detector. An isocratic method was developed for the preparative purification utilizing a mobile phase of 75% of 0.1% DEA in Hexane and 25% 0.1% DEA in isopropanol at a flow rate of 8 mL/min on the CHIRAL PAK AD-H (250*21)mm, 5p. UV based collection set to observe 258 nm.

Example 37-1: Enantiomer 1

5-Methyl-1-(1-(4-((1-methylpyrrolidin-3-yl)amino)benzyl)-1H-indol-5-yl)-1H-pyrazole-3-carboxamide (28 mg): SFC Rt=13.45 LCMS Rt=1.24 min (condition A), MS (M+1)=429.3. $^1$H NMR (400 MHz, DMSO-d6): δ 7.61-7.69 (m, 3H), 7.47 (s, 1H), 7.21-7.25 (m, 2H), 7.06-7.08 (d, J=8.4 Hz, 2H), 6.60 (s, 1H), 6.49-6.56 (m, 3H), 5.75-5.76 (d, 1H), 5.28 (s, 2H), 3.82 (m, 1H), 2.70-2.75 (m, 1H), 2.57 (m, 1H), 2.40-2.44 (m, 1H), 2.30-2.34 (m, 1H), 2.20-2.28 (m, 6H), 2.17-2.19 (m, 1H), 1.54-1.55 (m, 1H).

Example 37-2: Enantiomer 2

5-methyl-1-(1-(4-((1-methylpyrrolidin-3-yl)amino)benzyl)-1H-indol-5-yl)-1H-pyrazole-3-carboxamide (27 mg): SFC Rt=15.92 LCMS Rt=1.22 min (condition A), MS (M+1)=429.3. $^1$H NMR (400 MHz, DMSO-d6): δ 7.61-7.69 (m, 3H), 7.47 (s, 1H), 7.21-7.25 (m, 2H), 7.06-7.08 (d, J=8.4 Hz, 2H), 6.60 (s, 1H), 6.49-6.56 (m, 3H), 5.75-5.76 (d, 1H), 5.28 (s, 2H), 3.83 (m, 1H), 2.69-2.75 (m, 1H), 2.57 (m, 1H), 2.40-2.44 (m, 1H), 2.30-2.34 (m, 1H), 2.20-2.28 (m, 6H), 2.17-2.19 (m, 1H), 1.54-1.55 (m, 1H).

Example 38: Synthesis of 1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide

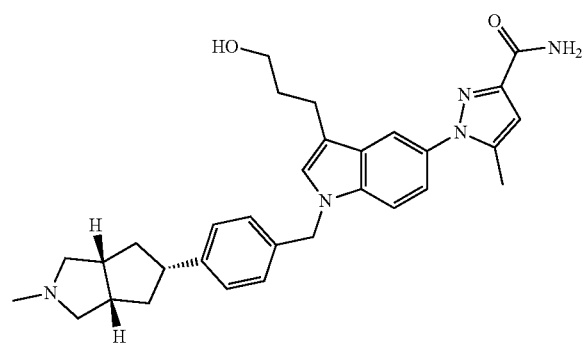 [SMILES: Cc1cc(C(N)=O)nn1-c1ccc2c(c1)c(CCCO)cn2Cc1ccc([C@@H]2C[C@@H]3CN(C)C[C@@H]3C2)cc1]

Step 1: 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide, Example 26-1, (400 mg, 0.882 mmol) was taken up in DMF (8.8 mL) followed by the addition of N-bromosuccinamide (157 mg, 0.882 mmol). The resulting reaction mixture was stirred at ambient temperature for 3 h. Then the mixture was diluted with water and extracted with ethyl acetate (3×). The combined organic extracts were washed with brine, dried over sodium sulfate and concentrated in vacuo. The crude material was taken up in MeOH and purified by SCX-BSA according to General Method IV to afford 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide (297 mg, 63%). LCMS Rt=0.81 min (condition B), MS (M+1)=532.3.

Step 2: 1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide 1-(3-((E)-3-((tert-Butyldimethylsilyl)oxy)prop-1-en-1-yl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide was prepared from 1-(3-bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide and (E)-tert-butyldimethyl((3-(4,4,5,5-tetramethyl-1,3,2-dioxaborolan-2-yl)allyl)oxy)silane according to General Method II. Then 10% Pd/C (40 mg) was added and the resulting mixture was stirred under a balloon of hydrogen for 18 hours. The reaction mixture was then filtered over a pad of celite and concentrated to afford 1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide (13 mg, 13%). LCMS Rt=1.33 min (condition A), MS (M+1)=512.2. $^1$H NMR (400 MHz, DMSO-d$_6$): δ 7.64 (d, J=2.0 Hz, 1H), 7.54 (d, J=8.7 Hz, 1H), 7.46 (s, 1H), 7.39 (s, 1H), 7.23-7.12 (m, 6H), 6.59 (d, J=0.9 Hz, 1H), 5.36 (s, 2H), 4.43 (t, J=5.2 Hz, 1H), 4.09 (q, J=5.3 Hz, 1H), 3.50-3.41 (m, 2H), 2.89-2.77 (m, 1H), 2.73 (t, J=7.6 Hz, 2H), 2.55-2.52 (m, 2H), 2.26 (d, J=0.8 Hz, 3H), 2.21 (s, 3H), 2.18-2.01 (m, 5H), 1.85-1.72 (m, 2H), 1.40-1.28 (m, 2H).

Example 39: Synthesis of 5-methyl-1-(1-(4-((3aR,5r,6aS)-octahydrocyclopenta[c]pyrrol-5-yl)benzyl)-1H-indol-5-yl)-1H-pyrazole-3-carboxamide

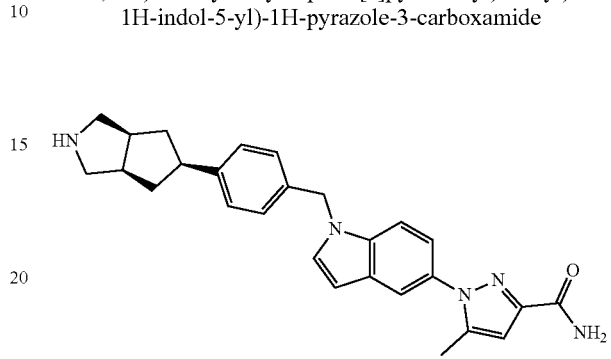

Step 1: 5-methyl-1-(1-(4-((3aR,5r,6aS)-octahydrocyclopenta[c]pyrrol-5-yl)benzyl)-1H-indol-5-yl)-1H-pyrazole-3-carboxamide To a stirred solution of 1-(1-(4-((3aS,6aR)-1,2,3,3a,4,6a-hexahydrocyclopenta[c]pyrrol-5-yl)benzyl)-1H-indol-5-yl)-5-methyl-1H-pyrazole-3-carboxamide, Example 24, (0.45 g, 1.029 mmol) in dry MeOH (10 mL) was added 10% Pd/C (0.06 g) at ambient temperature. The reaction was allowed to stir for 16 h at ambient temperature under hydrogen atmosphere. The suspension was then filtered through celite washing with MeOH. The filtrate was concentrated and the crude was purified by preparative HPLC to afford 5-methyl-1-(1-(4-((3aR,5r,6aS)-octahydrocyclopenta[c]pyrrol-5-yl)benzyl)-1H-indol-5-yl)-1H-pyrazole-3-carboxamide (0.16 g). LCMS Rt=1.40 min (condition A), MS (M+1)=440.3. $^1$H NMR (400 MHz, DMSO-d6) δ 7.59-7.698 (m, 3H), 7.47 (s, 1H), 7.14-7.24 (m, 6H), 6.57-6.59 (m, 2H), 5.43 (s, 2H), 3.19-3.35 (m, 1H), 3.03 (s, 1H), 2.78-2.81 (m, 1H), 2.60-2.62 (m, 2H), 2.27 (s, 3H), 2.08-2.65 (m, 4H), 1.24-1.35 (m, 2H).

Example 40: Synthesis of 1-(1-(4-((3aR,5r,6aS)-2-(cyclopropylmethyl)octahydrocyclopenta[c]pyrrol-5-yl)benzyl)-1H-indol-5-yl)-5-methyl-1H-pyrazole-3-carboxamide

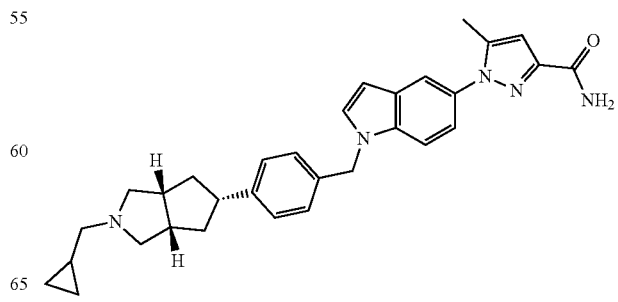

To a stirred solution of 5-methyl-1-(1-(4-((3aR,5r,6aS)-octahydrocyclopenta[c]pyrrol-5-yl)benzyl)-1H-indol-5-yl)-1H-pyrazole-3-carboxamide, (Example 39), (0.1 g, 0.186 mmol) in DMF (3 mL) was added K$_2$CO$_3$ (0.05 g, 0.373 mmol) followed by cyclopropyl methyl bromide (0.028 g, 0.205 mmol) at 00° C. under N$_2$ atmosphere. The resulting mixture allowed to stir for 4 h at 80° C. The mixture was then cooled, diluted with ethyl acetate and washed with cold water (3×30 mL) and brine solution (3×30 mL). The organic layer was separated, dried over anhydrous sodium sulfate, concentrated in vacuo. The crude material was purified by preparative HPLC to afford 1-(1-(4-((3aR,5r,6aS)-2-(cyclopropylmethyl)octahydrocyclopenta[c]pyrrol-5-yl)benzyl)-1H-indol-5-yl)-5-methyl-1H-pyrazole-3-carboxamide (0.011 g, 11.9%). LCMS Rt=1.58 min (condition A), MS (M+2)=495.2. $^1$H NMR (400 MHz, DMSO-d6) δ 7.65-7.70 (m, 3H), 7.45 (s, 1H), 7.18-7.24 (m, 6H), 6.59 (s, 2H), 5.44 (s, 2H), 2.90-2.84 (m, 2H), 2.60-2.68 (m, 3H), 2.4 (m, 1H), 2.33 (s, 3H), 2.14-2.26 (m, 5H), 1.31-1.41 (m, 2H), 0.82-0.70 (m, 1H), 0.42 (d, J=8.0 Hz, 2H), 0.06 (d, J=8.0 Hz, 2H).

Example 41: Synthesis of 5-methyl-1-(1-(4-((3aR,5r,6aS)-2-(methylsulfonyl)octahydrocyclopenta[c]pyrrol-5-yl)benzyl)-1H-indol-5-yl)-1H-pyrazole-3-carboxamide

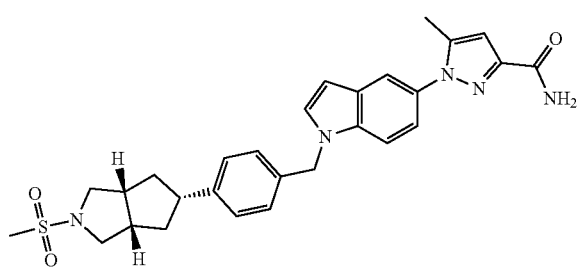 [SMILES: Cc1cc(C(N)=O)nn1-c1ccc2c(ccn2Cc2ccc([C@@H]3C[C@@H]4CN(S(C)(=O)=O)C[C@@H]4C3)cc2)c1]

To a stirred solution of 5-methyl-1-(1-(4-((3aR,5r,6aS)-octahydrocyclopenta[c]pyrrol-5-yl)benzyl)-1H-indol-5-yl)-1H-pyrazole-3-carboxamide, (Example 39), (0.040 g, 0.091 mmol) in DCM (5 mL) was added TEA (27 mg, 0.27 mmol) and methanesulfonyl chloride (12 mg, 0.11 mmol) at −20° C. The reaction was allowed to stir for 10 min. The mixture was then quenched with water and diluted with DCM (22 mL). The organic layer was separated and washed with water (3×15 mL) and brine solution (3×5 mL), dried over anhydrous Na$_2$SO$_4$, and concentrated. The crude material was then purified by preparative HPLC to afford 5-methyl-1-(1-(4-((3aR,5r,6aS)-2-(methylsulfonyl)octahydrocyclopenta[c]pyrrol-5-yl)benzyl)-1H-indol-5-yl)-1H-pyrazole-3-carboxamide (16 mg, 34%). LCMS Rt=2.28 min (condition A), MS (M+2)=518.2. $^1$H NMR (400 MHz, DMSO) δ 7.55-7.64 (m, 3H), 7.4 (s, 1H), 7.17-7.20 (m, 6H), 6.57 (s, 2H), 5.43 (s, 2H), 3.19 (m, 2H), 3.06 (m, 2H), 2.88 (s, 3H), 2.65-2.7 (m, 3H), 2.31 (s, 3H), 2.24 (m, 2H), 1.38-1.36 (m, 2H).

Example 42: Synthesis of 5-Methyl-1-(1-(4-((3aR,5r,6aS)-2-(2-(methylsulfonyl)ethyl)octahydrocyclopenta[c]pyrrol-5-yl)benzyl)-1H-indol-5-yl)-1H-pyrazole-3-carboxamide

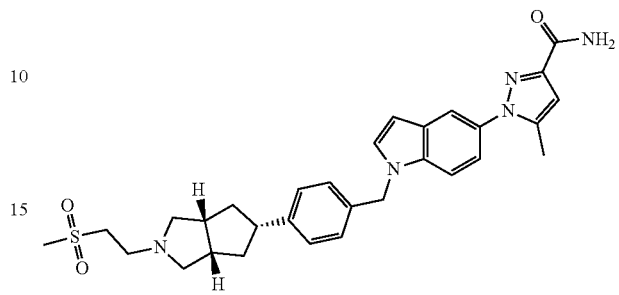

5-Methyl-1-(1-(4-((3aR,5r,6aS)-octahydrocyclopenta[c]pyrrol-5-yl)benzyl)-1H-indol-5-yl)-1H-pyrazole-3-carboxamide (Example 42) (100 mg, 0.23 mmol) was dissolved in DCM (1.1 mL). Then triethylamine (63 µL, 0.46 mmol) was added followed by (methylsulfonyl)ethene (36.2 mg, 0.341 mmol) and the mixture was stirred at RT for 2 h. The reaction mixture was then concentrated and purified by preparative HPLC to afford 5-Methyl-1-(1-(4-((3aR,5r,6aS)-2-(2-(methylsulfonyl)ethyl)octahydrocyclopenta[c]pyrrol-5-yl)benzyl)-1H-indol-5-yl)-1H-pyrazole-3-carboxamide: LCMS Rt=2.37 min (condition A), MS (M+1)=546.0. $^1$H NMR (400 MHz, DMSO-d6) δ 7.69 (d, J=2.0 Hz, 1H), 7.64 (d, J=3.2 Hz, 1H), 7.59 (d, J=8.8 Hz, 1H), 7.43 (s, 1H), 7.22 (dd, J=8.7, 2.0 Hz, 1H), 7.18 (s, 1H), 7.16-7.12 (m, 4H), 6.58 (d, J=5.5 Hz, 2H), 5.43 (s, 2H), 3.31-3.23 (m, 3H), 3.05 (s, 3H), 2.76 (t, J=6.6 Hz, 2H), 2.70 (d, J=9.0 Hz, 2H), 2.26 (s, 3H), 2.13 (s, 4H), 1.38-1.21 (m, 2H). 2H are obscured by DMSO-d6.

Example 43: Synthesis of 5-Methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide

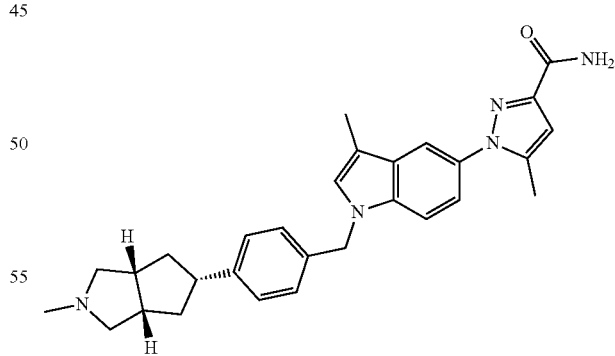

Step 1: 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide, Example 26-1, (400 mg, 0.882 mmol) was taken up in DMF (8.8 mL) followed by the addition of N-bromosuccinamide (157 mg, 0.882 mmol). The resulting reaction mixture was stirred at ambient temperature for 3 h. Then the mixture was diluted with water and extracted with ethyl acetate (3×). The combined organic extracts were washed with brine, dried over sodium sulfate and concentrated. The crude material was taken up in MeOH and purified by SCX-BSA according to General Method IV to afford 1-(3-bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide (297 mg, 63%). LCMS Rt=0.81 min (condition B), MS (M+1)=532.3.

Step 2: 5-Methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide 1-(3-Bromo-1-(4-((3aR,5r,6aS)-2-methyloctahydrocyclopenta[c]pyrrol-5-yl)benzyl)-1H-indol-5-yl)-5-methyl-1H-pyrazole-3-carboxamide (156 mg, 0.293 mmol), potassium methyltrifluoroborate (71.4 mg, 0.586 mmol) and $Cs_2CO_3$ (573 mg, 1.758 mmol) were dissolved in 1,4-dioxane (2.6 mL) and water (0.37 mL). The reaction mixture was purged with nitrogen and PdCl2(dppf).$CH_2Cl_2$ adduct (23.9 mg, 0.029 mmol) was added. The resulting mixture was allowed to stir at 95° C. for 48 hours. Then potassium methyltrifluoroborate (71.4 mg, 0.586 mmol) was added and the reaction was stirred at 95° C. for 18 hours. The reaction was then diluted with water and extracted with ethyl acetate. The organic layer was dried over sodium sulfate and concentrated. The crude was purified by preparative HPLC to afford 5-Methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide (1.7 mg, 1.2%). LCMS Rt=1.56 min (condition A), MS (M+1)=468.2. $^1$H NMR (400 MHz, DMSO-d6) δ 7.62 (d, J=2.1 Hz, 1H), 7.54 (d, J=8.7 Hz, 1H), 7.44 (s, 1H), 7.38 (s, 1H), 7.23-7.14 (m, 6H), 6.59 (s, 1H), 5.35 (s, 2H), 2.93-2.59 (m, 6H), 2.48-2.36 (m, 2H), 2.29-2.22 (m, 6H), 2.19-2.09 (m, 2H), 1.46-1.35 (m, 2H), 1.27-1.18 (m, 2H).

Activity of Compounds

Assay Example 1: FoxO3a Inhibition and AKT Activation Assay

Phosphorylation of AKT on S473 and FoxO3a nuclear to cytoplasmic translocation were used as readouts of PI3K/Akt/mTOR pathway activation downstream of growth factor signaling.

Reporter cell line. U2OS GFP-FoxO3a H212R reporter cell line was established by transducing U2OS cells with the retroviral plasmid pLEGFP-C1 containing FoxO3a H212R transgene and selecting for G418 resistant clones.

Reporter assay. U2OS GFP-FoxO3a H212R cells were plated in 384-well plates at 4000 cells per well in 30 microliters of McCoy's 5 A medium containing 10% FBS. On day 1 the cells were washed with serum free medium and serum starved overnight. On day 2 the cells were treated with different doses of the compounds for 30 minutes, fixed with 4% Paraformaldehyde for 1 hour and stained with Phospho-AKT (Ser473) antibody (Cell Signaling Technology, catalog #4060) overnight at 4 degrees Celcius. After nuclei staining with Hoechst 33342 (Life Technologies, catalog # H3570) the plates were imaged with InCell 2000 (GE Healthcare Bio-Sciences). FoxO3a inhibition activity is calculated as the ratio of nuclear to cytosolic GFP intensity in percent. AKT activation is measured as the total cellular intensity of Phospho-AKT antibody staining in percent. DMSO control is set as 0% activity.

Results. The measured FoxO3a inhibition activity and AKT activation activity are reported in the following table:

| Example # | FoxO $AC_{50}$ (μM) | Akt $AC_{50}$ (μM) |
|---|---|---|
| 1-1 | 0.053 | 0.138 |
| 1-2 | 0.102 | N/A |
| 1-3 | 0.201 | >10 |
| 1-4 | 0.121 | 0.252 |
| 1-5 | 0.285 | >10 |
| 1-6 | 0.101 | 0.250 |
| 1-7 | 0.194 | 0.680 |
| 1-8 | 0.517 | >10 |
| 1-9 | 0.109 | 0.318 |
| 1-10 | 0.072 | 0.234 |
| 1-11 | 0.069 | 0.388 |
| 1-12 | 0.124 | 0.346 |
| 1-13 | 0.084 | 0.230 |
| 1-14 | 0.284 | 1.050 |
| 1-15 | 0.056 | 0.172 |
| 1-16 | 0.147 | 0.451 |
| 1-17 | 0.088 | 0.199 |
| 1-18 | 0.095 | 0.352 |
| 1-19 | 0.140 | 0.500 |
| 1-20 | 0.126 | >10 |
| 1-21 | 0.420 | 2.970 |
| 1-22 | 0.167 | 0.507 |
| 1-23 | 0.093 | 0.293 |
| 1-24 | 0.123 | 0.349 |
| 1-25 | 0.056 | 0.197 |
| 1-26 | 0.129 | >10 |
| 1-27 | 0.229 | >10 |
| 1-28 | 0.223 | 1.170 |
| 1-29 | 0.340 | 0.774 |
| 1-30 | 0.216 | 0.952 |
| 1-31 | 0.055 | 0.138 |
| 1-32 | 0.205 | 0.578 |
| 1-33 | 0.082 | 0.351 |
| 1-34 | 0.248 | 0.743 |
| 1-35 | 0.060 | 0.217 |
| 1-36 | 0.477 | 1.050 |
| 1-37 | 0.075 | 0.206 |
| 1-38 | 0.078 | 0.240 |
| 2-1 | 0.733 | 2.510 |
| 2-2 | 0.536 | 2.110 |
| 2-3 | 0.630 | 2.370 |
| 2-4 | 0.429 | 1.630 |
| 2-5 | 0.281 | 0.760 |
| 3 | 0.476 | 1.170 |
| 4 | 0.109 | 0.306 |
| 8 | 0.466 | N/A |
| 9 | 0.301 | N/A |
| 10 | 0.189 | 0.512 |
| 11-1 | 4.085 | >10 |
| 11-2 | 0.341 | 1.060 |
| 11-3 | 1.158 | 2.970 |
| 12 | 0.402 | 1.190 |
| 13 | 0.437 | 1.530 |
| 14 | 0.652 | 2.100 |
| 15-1 | 0.242 | 0.391 |
| 15-2 | 0.197 | 0.389 |
| 15-3 | 0.096 | 0.398 |
| 16-1 | 0.171 | 0.966 |
| 16-2 | 0.161 | 1.220 |
| 16-3 | 1.039 | 3.190 |
| 16-4 | 0.186 | 0.756 |
| 17-1 | 0.102 | 0.460 |
| 17-2 | 0.047 | 0.123 |
| 17-3 | 0.251 | 0.840 |
| 18 | 0.057 | 0.110 |
| 19 | 0.061 | 0.142 |
| 19-1 | 0.052 | 0.081 |
| 19-2 | 0.346 | 1.020 |
| 19-3 | 0.099 | 0.128 |
| 20 | 0.068 | 0.186 |
| 21 | 0.598 | 1.650 |
| 22 | 0.032 | 0.081 |

-continued

| Example # | FoxO AC$_{50}$ (μM) | Akt AC$_{50}$ (μM) |
|---|---|---|
| 23 | 0.056 | 0.173 |
| 24 | 0.381 | 1.200 |
| 25 | 0.215 | 1.120 |
| 26-1 | 0.095 | 0.314 |
| 26-2 | 0.080 | 0.362 |
| 27 | 0.224 | 0.947 |
| 28 | 0.087 | 0.251 |
| 29-1 | 0.483 | 1.690 |
| 29-2 | 0.818 | 2.100 |
| 30-1 | 0.124 | 0.633 |
| 30-2 | 0.223 | 0.320 |
| 30-3 | 0.126 | 0.572 |
| 31 | 0.350 | 0.747 |
| 32 | 1.045 | 4.355 |
| 33 | 0.383 | 2.808 |
| 34-1 | 0.119 | 0.184 |
| 34-2 | 0.042 | 0.003 |
| 34-3 | 0.131 | 0.266 |
| 35 | 0.181 | 0.603 |
| 36 | 0.049 | 0.039 |
| 37-1 | 0.724 | 4.793 |
| 37-2 | 0.928 | 4.075 |
| 38 | 0.081 | N/A |
| 39 | 0.175 | 0.907 |
| 40 | 0.161 | 1.218 |
| 41 | 0.113 | 0.304 |
| 42 | 0.069 | 0.230 |
| 43 | 0.215 | 0.740 |

The compounds, compositions, or methods described herein can be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

What is claimed is:

1. A compound of formula (I) or a pharmaceutically acceptable salt thereof:

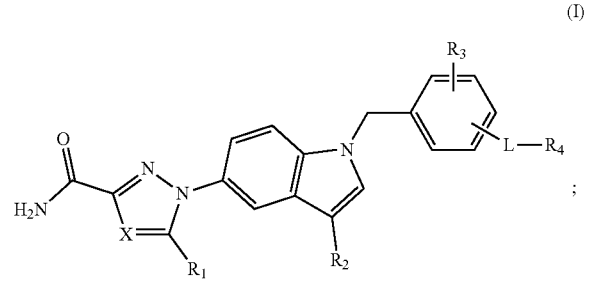

(I)

wherein:

L is absent, O, S, NHCO or CONH;

X is CH or N;

$R_1$ is H, $C_{1-4}$alkyl, $C_{1-4}$haloalkyl, or 3-6 membered cycloalkyl;

$R_2$ is H, —OH, halo, —CN, nitro, $C_{1-4}$alkoxy, $C_{1-4}$alkyl, $C_{1-4}$alkoxy-$C_{1-4}$alkyl, $C_{1-4}$haloalkyl, $C_{1-4}$hydroxyalkyl, a 5-10 membered heterocyclyl optionally substituted with 1-3 $C_{1-4}$alkyl groups, —(CH$_2$)$_n$-(6 or 10 membered aryl optionally substituted with 1-3 $C_{1-4}$alkyl groups), or —(CH$_2$)$_n$-(5-10 membered heteroaryl optionally substituted with 1-3 $C_{1-4}$alkyl groups);

$R_3$ is H, halo, —OH, $C_{1-4}$alkyl, $C_{1-4}$alkoxy, $C_{1-4}$haloalkyl or $C_{1-4}$ haloalkoxy;

$R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (=O), —CN, nitro, $C_{1-4}$alkyl, —$C_{1-4}$alkyl-(3-6 membered cycloalkyl), $C_{1-4}$alkoxy, —SO$_2$—$C_{1-4}$alkyl, —SO$_2$—$C_{1-4}$hydroxyalkyl, —SO$_2$—$C_{1-4}$alkyl-NR$_5$R$_6$, —NHSO$_2$—$C_{1-4}$alkyl, $C_{1-4}$hydroxyalkyl, —SO$_2$NR$_5$R$_6$, —CO—$C_{1-4}$hydroxyalkyl, —CONR$_5$R$_6$, —CO—$C_{1-4}$alkyl-NR$_5$R$_6$, —CO—NH—$C_{1-4}$alkyl-NR$_5$R$_6$, —NR$_5$R$_6$, —$C_{1-4}$alkyl-NR$_5$R$_6$ and —CO—$C_{1-4}$alkyl;

$R_5$ and $R_6$ are each, independently, selected from H, $C_{1-4}$alkyl, $C_{1-4}$hydroxyalkyl, —CO—$C_{1-4}$alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl groups; and n is 0 or 1.

2. The compound according to claim 1 or a pharmaceutically acceptable salt thereof, wherein:

L is absent, O, S, NHCO or CONH;

$R_4$ is a substituted $C_{2-4}$alkynyl, a substituted or unsubstituted 5-10 membered heterocyclyl, a substituted or unsubstituted 5-10 membered heteroaryl, a substituted or unsubstituted 5-10 membered fused heterocyclyl-aryl, a substituted or unsubstituted 5-10 membered fused heterocyclyl-heteroaryl, or a substituted or unsubstituted 6 or 10 membered aryl, wherein when $R_4$ is substituted, $R_4$ is substituted with 1-3 substituents independently selected from halo, —OH, oxo (=O), —CN, nitro, $C_{1-4}$alkyl, —$C_{1-4}$alkyl-(3-6 membered cycloalkyl), $C_{1-4}$alkoxy, —SO$_2$—$C_{1-4}$alkyl, —SO$_2$—$C_{1-4}$hydroxyalkyl, —SO$_2$—$C_{1-4}$alkyl-NR$_5$R$_6$, —NHSO$_2$—$C_{1-4}$alkyl, $C_{1-4}$hydroxyalkyl, —SO$_2$NR$_5$R$_6$, —CO—$C_{1-4}$hydroxyalkyl, —CONR$_5$R$_6$, —CO—$C_{1-4}$alkyl-NR$_5$R$_6$, —CO—NH—$C_{1-4}$alkyl-NR$_5$R$_6$, —NR$_5$R$_6$, —$C_{1-4}$alkyl-NR$_5$R$_6$ and —CO—$C_{1-4}$alkyl; and $R_5$ and $R_6$ are each, independently, selected from H, $C_{1-4}$alkyl, $C_{1-4}$hydroxyalkyl, —CO—$C_{1-4}$alkyl and -(4-10 membered heterocyclyl)-$C_{1-4}$alkyl; or $R_5$ and $R_6$, together with the nitrogen atom to which they are attached, form a 5-7 membered heterocyclyl optionally substituted with 1-3 $C_{1-4}$alkyl groups.

3. The compound according to claim 1, or a pharmaceutically acceptable salt thereof, wherein L is absent.

4. The compound according to claim 1, wherein the compound is of formula (I-B):

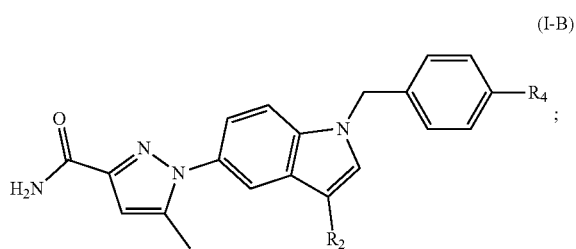

or a pharmaceutically acceptable salt thereof.

5. The compound according to claim 1 or a pharmaceutically acceptable salt thereof, wherein R$_4$ is selected from a group consisting of:

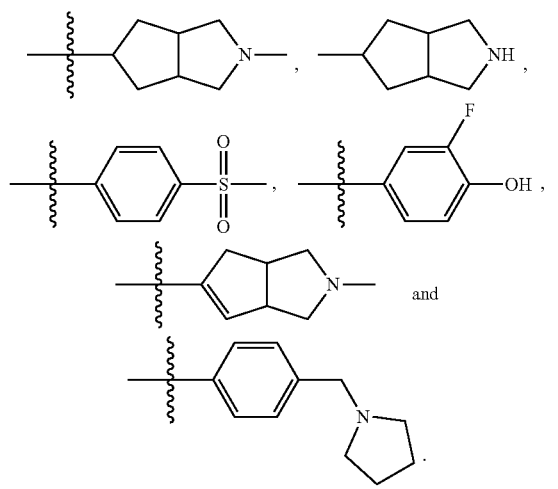

6. The compound according to claim 1 or a pharmaceutically acceptable salt thereof, wherein R$_4$ is or

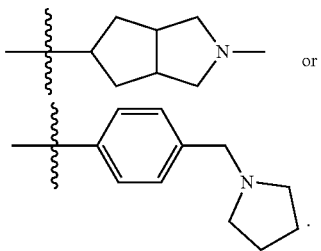

7. The compound according to claim 1 or a pharmaceutically acceptable salt thereof, wherein R$_2$ is H.

8. A compound according to claim 2 or a pharmaceutically acceptable salt thereof, wherein the compound is selected from a group consisting of:

5-methyl-1-(1-(4-(1-methyl-1,2,3,6-tetrahydropyridin-4-yl)benzyl)-1H-indol-5-yl)-1H-pyrazole-3-carboxamide;
5-methyl-1-(1-(4-(pyridin-4-yl)benzyl)-1H-indol-5-yl)-1H-pyrazole-3-carboxamide;
1-(1-(4-(3,6-dihydro-2H-pyran-4-yl)benzyl)-1H-indol-5-yl)-5-methyl-1H-pyrazole-3-carboxamide;
1-(1-(4-(1-acetyl-1,2,3,6-tetrahydropyridin-4-yl)benzyl)-1H-indol-5-yl)-5-methyl-1H-pyrazole-3-carboxamide;
1-(1-((4'-cyano-[1,1'-biphenyl]-4-yl)methyl)-1H-indol-5-yl)-5-methyl-1H-pyrazole-3-carboxamide;
5-methyl-1-(1-((4'-(methylsulfonyl)-[1,1'-biphenyl]-4-yl)methyl)-1H-indol-5-yl)-1H-pyrazole-3-carboxamide;
1-(1-(4-(imidazo[1,2-a]pyridin-6-yl)benzyl)-1H-indol-5-yl)-5-methyl-1H-pyrazole-3-carboxamide;
5-methyl-1-(1-(4-(1-methyl-1,2,5,6-tetrahydropyridin-3-yl)benzyl)-1H-indol-5-yl)-1H-pyrazole-3-carboxamide;
5-methyl-1-(1-(4-(4-methyl-3,4-dihydro-2H-pyrido[3,2-b][1,4]oxazin-7-yl)benzyl)-1H-indol-5-yl)-1H-pyrazole-3-carboxamide;
5-methyl-1-(1-(4-(2-methyl-2H-indazol-6-yl)benzyl)-1H-indol-5-yl)-1H-pyrazole-3-carboxamide;
5-methyl-1-(1-((4'-((4-methylpiperazin-1-yl)sulfonyl)-[1,1'-biphenyl]-4-yl)methyl)-1H-indol-5-yl)-1H-pyrazole-3-carboxamide;
5-methyl-1-(1-((3'-(4-methylpiperazine-1-carbonyl)-[1,1'-biphenyl]-4-yl)methyl)-1H-indol-5-yl)-1H-pyrazole-3-carboxamide;
1-(1-((4'-(N,N-dimethylsulfamoyl)-[1,1'-biphenyl]-4-yl)methyl)-1H-indol-5-yl)-5-methyl-1H-pyrazole-3-carboxamide;
1-(1-(4-(1H-indazol-6-yl)benzyl)-1H-indol-5-yl)-5-methyl-1H-pyrazole-3-carboxamide;
1-(1-((3'-fluoro-4'-hydroxy-[1,1'-biphenyl]-4-yl)methyl)-1H-indol-5-yl)-5-methyl-1H-pyrazole-3-carboxamide;
1-(1-(4-(1H-pyrrolo[2,3-b]pyridin-5-yl)benzyl)-1H-indol-5-yl)-5-methyl-1H-pyrazole-3-carboxamide;
1-(1-(4-(1H-indazol-5-yl)benzyl)-1H-indol-5-yl)-5-methyl-1H-pyrazole-3-carboxamide;
1-(1-(4-(isoquinolin-6-yl)benzyl)-1H-indol-5-yl)-5-methyl-1H-pyrazole-3-carboxamide;
5-methyl-1-(1-(4-(1-methyl-1H-pyrazol-4-yl)benzyl)-1H-indol-5-yl)-1H-pyrazole-3-carboxamide;
5-methyl-1-(1-((3'-sulfamoyl-[1,1'-biphenyl]-4-yl)methyl)-1H-indol-5-yl)-1H-pyrazole-3-carboxamide;
1-(1-(4-(1H-indol-6-yl)benzyl)-1H-indol-5-yl)-5-methyl-1H-pyrazole-3-carboxamide;
5-methyl-1-(1-(4-(1-methyl-1H-indazol-6-yl)benzyl)-1H-indol-5-yl)-1H-pyrazole-3-carboxamide;
1-(1-(4-(6-(dimethylamino)pyridin-3-yl)benzyl)-1H-indol-5-yl)-5-methyl-1H-pyrazole-3-carboxamide;
1-(1-(4-(2-methoxypyridin-4-yl)benzyl)-1H-indol-5-yl)-5-methyl-1H-pyrazole-3-carboxamide;
5-methyl-1-(1-(4-(1-oxo-1,2,3,4-tetrahydroisoquinolin-6-yl)benzyl)-1H-indol-5-yl)-1H-pyrazole-3-carboxamide;
1-(1-((4'-amino-[1,1'-biphenyl]-4-yl)methyl)-1H-indol-5-yl)-5-methyl-1H-pyrazole-3-carboxamide;
1-(1-((4'-fluoro-[1,1'-biphenyl]-4-yl)methyl)-1H-indol-5-yl)-5-methyl-H-pyrazole-3-carboxamide;
1-(1-(4-(2-methoxypyrimidin-5-yl)benzyl)-1H-indol-5-yl)-5-methyl-1H-pyrazole-3-carboxamide;
1-(1-(4-(2-aminopyrimidin-5-yl)benzyl)-1H-indol-5-yl)-5-methyl-1H-pyrazole-3-carboxamide;
1-(1-((4'-methoxy-[1,1'-biphenyl]-4-yl)methyl)-1H-indol-5-yl)-5-methyl-H-pyrazole-3-carboxamide;
5-methyl-1-(1-(4-(2-oxoindolin-5-yl)benzyl)-1H-indol-5-yl)-1H-pyrazole-3-carboxamide;
1-(1-((4'-(hydroxymethyl)-[1,1'-biphenyl]-4-yl)methyl)-1H-indol-5-yl)-5-methyl-1H-pyrazole-3-carboxamide;
5-methyl-1-(1-((4'-(methylsulfonamido)-[1,1'-biphenyl]-4-yl)methyl)-1H-indol-5-yl)-1H-pyrazole-3-carboxamide;
1-(1-((4'-(aminomethyl)-[1,1'-biphenyl]-4-yl)methyl)-1H-indol-5-yl)-5-methyl-1H-pyrazole-3-carboxamide;

1-(1-((4'-(dimethylcarbamoyl)-[1,1'-biphenyl]-4-yl)methyl)-1H-indol-5-yl)-5-methyl-1H-pyrazole-3-carboxamide;
1-(1-(4-(2-(dimethylamino)pyrimidin-5-yl)benzyl)-1H-indol-5-yl)-5-methyl-1H-pyrazole-3-carboxamide;
5-methyl-1-(1-((4'-(morpholinomethyl)-[1,1'-biphenyl]-4-yl)methyl)-1H-indol-5-yl)-1H-pyrazole-3-carboxamide;
5-methyl-1-(1-((4'-((2-morpholinoethyl)carbamoyl)-[1,1'-biphenyl]-4-yl)methyl)-1H-indol-5-yl)-1H-pyrazole-3-carboxamide;
5-methyl-1-(1-(4-(1-methylpyrrolidin-3-yl)benzyl)-1H-indol-5-yl)-1H-pyrazole-3-carboxamide;
(S)-5-methyl-1-(1-(4-(1-methylpyrrolidin-3-yl)benzyl)-1H-indol-5-yl)-1H-pyrazole-3-carboxamide;
(R)-5-methyl-1-(1-(4-(1-methylpyrrolidin-3-yl)benzyl)-1H-indol-5-yl)-1H-pyrazole-3-carboxamide;
5-methyl-1-(1-(4-(piperidin-3-yl)benzyl)-1H-indol-5-yl)-1H-pyrazole-3-carboxamide;
5-methyl-1-(1-(4-(1-methylpiperidin-4-yl)benzyl)-1H-indol-5-yl)-1H-pyrazole-3-carboxamide;
5-methyl-1-(1-(4-(1,2,3,6-tetrahydropyridin-4-yl)benzyl)-1H-indol-5-yl)-1H-pyrazole-3-carboxamide;
5-methyl-1-(1-(4-(1-(methylsulfonyl)-1,2,3,6-tetrahydropyridin-4-yl)benzyl)-1H-indol-5-yl)-1H-pyrazole-3-carboxamide;
1-(1-(4-(1-(2-hydroxyacetyl)-1,2,3,6-tetrahydropyridin-4-yl)benzyl)-1H-indol-5-yl)-5-methyl-1H-pyrazole-3-carboxamide;
1-(1-(4-(1-(cyclopropylmethyl)-1,2,3,6-tetrahydropyridin-4-yl)benzyl)-1H-indol-5-yl)-5-methyl-1H-pyrazole-3-carboxamide;
1-(1-(4-(1-(dimethylglycyl)-1,2,3,6-tetrahydropyridin-4-yl)benzyl)-1H-indol-5-yl)-5-methyl-1H-pyrazole-3-carboxamide;
1-(1-(4-(1-(3-aminopropyl)piperidin-4-yl)benzyl)-1H-indol-5-yl)-5-methyl-1H-pyrazole-3-carboxamide;
1-(1-(4-(1-(3-acetamidopropyl)piperidin-4-yl)benzyl)-1H-indol-5-yl)-5-methyl-1H-pyrazole-3-carboxamide;
1-(1-(4-(1-(dimethylglycyl)-1,2,3,6-tetrahydropyridin-4-yl)benzyl)-1H-indol-5-yl)-5-methyl-1H-pyrazole-3-carboxamide;
5-methyl-1-(1-(4-(piperazin-1-yl)benzyl)-1H-indol-5-yl)-1H-pyrazole-3-carboxamide;
5-methyl-1-(1-(4-(4-methylpiperazin-1-yl)benzyl)-1H-indol-5-yl)-1H-pyrazole-3-carboxamide;
5-methyl-1-(1-(4-(5-methylhexahydropyrrolo[3,4-c]pyrrol-2(1H)-yl)benzyl)-1H-indol-5-yl)-1H-pyrazole-3-carboxamide;
1-(1-(4-(3-(dimethylamino)prop-1-yn-1-yl)benzyl)-1H-indol-5-yl)-5-methyl-1H-pyrazole-3-carboxamide;
1-(1-(4-(1-azabicyclo[3.3.1]non-3-en-4-yl)benzyl)-1H-indol-5-yl)-5-methyl-1H-pyrazole-3-carboxamide;
1-(1-(4-((5S)-1-azabicyclo[3.3.1]non-3-en-4-yl)benzyl)-1H-indol-5-yl)-5-methyl-1H-pyrazole-3-carboxamide;
1-(1-(4-((5R)-1-azabicyclo[3.3.1]non-3-en-4-yl)benzyl)-1H-indol-5-yl)-5-methyl-1H-pyrazole-3-carboxamide;
5-methyl-1-(1-(4-(1,2,2-trimethyl-1,2,3,6-tetrahydropyridin-4-yl)benzyl)-1H-indol-5-yl)-1H-pyrazole-3-carboxamide;
5-methyl-1-(1-(4-(1,3,3-trimethyl-1,2,3,6-tetrahydropyridin-4-yl)benzyl)-1H-indol-5-yl)-1H-pyrazole-3-carboxamide;
5-methyl-1-(1-(4-(1,3,3-trimethylpiperidin-4-yl)benzyl)-1H-indol-5-yl)-1H-pyrazole-3-carboxamide;
(S)-5-methyl-1-(1-(4-(1,3,3-trimethylpiperidin-4-yl)benzyl)-1H-indol-5-yl)-1H-pyrazole-3-carboxamide;
(R)-5-methyl-1-(1-(4-(1,3,3-trimethylpiperidin-4-yl)benzyl)-1H-indol-5-yl)-1H-pyrazole-3-carboxamide;
1-(1-(4-(1,3-dimethyl-1,2,3,6-tetrahydropyridin-4-yl)benzyl)-1H-indol-5-yl)-5-methyl-1H-pyrazole-3-carboxamide;
(S)-1-(1-(4-(1,3-dimethyl-1,2,3,6-tetrahydropyridin-4-yl)benzyl)-1H-indol-5-yl)-5-methyl-1H-pyrazole-3-carboxamide;
(R)-1-(1-(4-(1,3-dimethyl-1,2,3,6-tetrahydropyridin-4-yl)benzyl)-1H-indol-5-yl)-5-methyl-1H-pyrazole-3-carboxamide;
1-(1-((4'-((2-hydroxyethyl)sulfonyl)-[1,1'-biphenyl]-4-yl)methyl)-1H-indol-5-yl)-5-methyl-1H-pyrazole-3-carboxamide;
5-methyl-1-(1-((4'-((2-(4-methylpiperazin-1-yl)ethyl)sulfonyl)-[1,1'-biphenyl]-4-yl)methyl)-1H-indol-5-yl)-1H-pyrazole-3-carboxamide;
1-(3-(3,6-dihydro-2H-pyran-4-yl)-1-((4'-(methylsulfonyl)-[1,1'-biphenyl]-4-yl)methyl)-1H-indol-5-yl)-5-methyl-1H-pyrazole-3-carboxamide;
5-methyl-1-(3-(1-methyl-1,2,3,6-tetrahydropyridin-4-yl)-1-((4'-(methylsulfonyl)-[1,1'-biphenyl]-4-yl)methyl)-1H-indol-5-yl)-1H-pyrazole-3-carboxamide;
5-methyl-1-(1-((4'-(methylsulfonyl)-[1,1'-biphenyl]-4-yl)methyl)-3-(tetrahydro-2H-pyran-4-yl)-1H-indol-5-yl)-1H-pyrazole-3-carboxamide;
5-methyl-1-(1-((4'-(methylsulfonyl)-[1,1'-biphenyl]-4-yl)methyl)-3-(1,2,3,6-tetrahydropyridin-4-yl)-1H-indol-5-yl)-1H-pyrazole-3-carboxamide;
1-(3-(3-hydroxypropyl)-1-((4'-(methylsulfonyl)-[1,1'-biphenyl]-4-yl)methyl)-1H-indol-5-yl)-5-methyl-1H-pyrazole-3-carboxamide;
1-(3-(3-methoxypropyl)-1-((4'-(methylsulfonyl)-[1,1'-biphenyl]-4-yl)methyl)-1H-indol-5-yl)-5-methyl-1H-pyrazole-3-carboxamide;
(cis)-1-(1-(4-(1,2,3,3a,4,6a-hexahydrocyclopenta[c]pyrrol-5-yl)benzyl)-1H-indol-5-yl)-5-methyl-1H-pyrazole-3-carboxamide;
(cis)-5-methyl-1-(1-(4-((2-methyl-1,2,3,3a,4,6a-hexahydrocyclopenta[c]pyrrol-5-yl)benzyl)-1H-indol-5-yl)-1H-pyrazole-3-carboxamide;
5-methyl-1-(1-(4-((3aR,6aS)-2-methyloctahydrocyclopenta[c]pyrrol-5-yl)benzyl)-1H-indol-5-yl)-1H-pyrazole-3-carboxamide;
5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide;
5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide;
5-methyl-1-(1-(4-((3aR,6aS)-2-methyloctahydrocyclopenta[c]pyrrol-5-yl)benzyl)-1H-indol-5-yl)-1H-1,2,4-triazole-3-carboxamide;
5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide;
5-methyl-1-(1-((4'-(pyrrolidin-1-ylmethyl)-[1,1'-biphenyl]-4-yl)methyl)-1H-indol-5-yl)-1H-1,2,4-triazole-3-carboxamide;
5-methyl-1-(1-(4-(1-methylazepan-4-yl)benzyl)-1H-indol-5-yl)-1H-pyrazole-3-carboxamide;
(S)-5-methyl-1-(1-(4-(1-methylazepan-4-yl)benzyl)-1H-indol-5-yl)-1H-pyrazole-3-carboxamide; and
(R)-5-methyl-1-(1-(4-(1-methylazepan-4-yl)benzyl)-1H-indol-5-yl)-1H-pyrazole-3-carboxamide.

9. The compound according to claim 1 or a pharmaceutically acceptable salt thereof, wherein the compound is selected from a group consisting of:

5-methyl-1-(1-(4-(2-methyl-2-azaspiro[3.5]non-6-en-7-yl)benzyl)-1H-indol-5-yl)-1H-pyrazole-3-carboxamide;

5-methyl-1-(1-(4-(2-methyl-2-azaspiro[3.5]nonan-7-yl)benzyl)-1H-indol-5-yl)-1H-pyrazole-3-carboxamide;

1-(1-((4'-((2-(dimethylamino)ethyl)sulfonyl)-[1,1'-biphenyl]-4-yl)methyl)-1H-indol-5-yl)-5-methyl-1H-pyrazole-3-carboxamide;

5-methyl-1-(1-(4-(6-(methylsulfonyl)pyridin-3-yl)benzyl)-1H-indol-5-yl)-1H-pyrazole-3-carboxamide;

1-(1-(4-(5-(2-hydroxypropan-2-yl)pyridin-2-yl)benzyl)-1H-indol-5-yl)-5-methyl-1H-pyrazole-3-carboxamide;

1-(1-(4-(6-(2-hydroxypropan-2-yl)pyridin-3-yl)benzyl)-1H-indol-5-yl)-5-methyl-1H-pyrazole-3-carboxamide;

5-methyl-1-(1-(4-((1-methylpyrrolidin-3-yl)methyl)benzyl)-1H-indol-5-yl)-1H-pyrazole-3-carboxamide;

5-methyl-1-(1-(4-((1-methylazetidin-3-yl)methyl)benzyl)-1H-indol-5-yl)-1H-pyrazole-3-carboxamide;

5-methyl-1-(1-(4-((1R,5S)-3-methyl-3-azabicyclo[3.1.0]hexan-1-yl)benzyl)-1H-indol-5-yl)-1H-pyrazole-3-carboxamide;

1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;

(S)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;

(R)-1-(1-((4'-((2-(hydroxymethyl)pyrrolidin-1-yl)methyl)-[1,1'-biphenyl]-4-yl)methyl)-1H-indol-5-yl)-5-methyl-1H-pyrazole-3-carboxamide;

5-methyl-1-(1-((4'-((4-methylpiperazin-1-yl)methyl)-[1,1'-biphenyl]-4-yl)methyl)-1H-indol-5-yl)-1H-pyrazole-3-carboxamide;

5-methyl-1-(1-((4'-(piperazin-1-ylmethyl)-[1,1'-biphenyl]-4-yl)methyl)-1H-indol-5-yl)-1H-pyrazole-3-carboxamide;

5-methyl-1-(1-((4'-(4-methylpiperazine-1-carbonyl)-[1,1'-biphenyl]-4-yl)methyl)-1H-indol-5-yl)-1H-pyrazole-3-carboxamide;

5-methyl-1-(1-(4-((1-methylpyrrolidin-3-yl)amino)benzyl)-1H-indol-5-yl)-1H-pyrazole-3-carboxamide;

(S)-5-methyl-1-(1-(4-((1-methylpyrrolidin-3-yl)amino)benzyl)-1H-indol-5-yl)-1H-pyrazole-3-carboxamide;

(R)-5-methyl-1-(1-(4-((1-methylpyrrolidin-3-yl)amino)benzyl)-1H-indol-5-yl)-1H-pyrazole-3-carboxamide;

1-(3-(3-hydroxypropyl)-1-(4-((3aR,5r,6aS)-2-methyloctahydrocyclopenta[c]pyrrol-5-yl)benzyl)-1H-indol-5-yl)-5-methyl-1H-pyrazole-3-carboxamide;

5-methyl-1-(1-(4-((3aR,5r,6aS)-octahydrocyclopenta[c]pyrrol-5-yl)benzyl)-1H-indol-5-yl)-1H-pyrazole-3-carboxamide;

1-(1-(4-((3aR,5r,6aS)-2-(cyclopropylmethyl)octahydrocyclopenta[c]pyrrol-5-yl)benzyl)-1H-indol-5-yl)-5-methyl-1H-pyrazole-3-carboxamide;

5-methyl-1-(1-(4-((3aR,5r,6aS)-2-(methylsulfonyl)octahydrocyclopenta[c]pyrrol-5-yl)benzyl)-1H-indol-5-yl)-1H-pyrazole-3-carboxamide;

5-methyl-1-(1-(4-((3aR,5r,6aS)-2-(2-(methylsulfonyl)ethyl)octahydrocyclopenta[c]pyrrol-5-yl)benzyl)-1H-indol-5-yl)-1H-pyrazole-3-carboxamide; and 5-methyl-1-(3-methyl-1-(4-((3aR,5r,6aS)-2-methyloctahydrocyclopenta[c]pyrrol-5-yl)benzyl)-1H-indol-5-yl)-1H-pyrazole-3-carboxamide.

10. The compound according to claim 2 or a pharmaceutically acceptable salt thereof, wherein the compound is 5-methyl-1-(1-(4-(1-methyl-1,2,3,6-tetrahydropyridin-4-yl)benzyl)-1H-indol-5-yl)-1H-pyrazole-3-carboxamide.

11. The compound according to claim 2 or a pharmaceutically acceptable salt thereof, wherein the compound is 5-methyl-1-(1-(4-((3aR,5r,6aS)-2-methyloctahydrocyclopenta[c]pyrrol-5-yl)benzyl)-1H-indol-5-yl)-1H-pyrazole-3-carboxamide.

12. The compound according to claim 2 or a pharmaceutically acceptable salt thereof, wherein the compound is 5-methyl-1-(1-(4-((3aR,5s,6aS)-2-methyloctahydrocyclopenta[c]pyrrol-5-yl)benzyl)-1H-indol-5-yl)-1H-pyrazole-3-carboxamide.

13. The compound according to claim 2 or a pharmaceutically acceptable salt thereof, wherein the compound is 5-methyl-1-(1-(4-((3aR,5r,6aS)-2-methyloctahydrocyclopenta[c]pyrrol-5-yl)benzyl)-1H-indol-5-yl)-1H-1,2,4-triazole-3-carboxamide.

14. The compound according to claim 2 or a pharmaceutically acceptable salt thereof, wherein the compound is 5-methyl-1-(1-((4'-(pyrrolidin-1-ylmethyl)-[1,1'-biphenyl]-4-yl)methyl)-1H-indol-5-yl)-1H-1,2,4-triazole-3-carboxamide.

15. A pharmaceutical composition comprising a compound according to claim 1 or a pharmaceutically acceptable salt thereof, and one or more pharmaceutically acceptable carriers.

16. A pharmaceutical combination comprising a compound according to claim 1 or a pharmaceutically acceptable salt thereof, and one or more other therapeutically active agents.

17. A method of activating the PI3K/Akt/mTOR pathway in a subject in need thereof, the method comprising administering to the subject a therapeutically effective amount of the compound according to claim 1 or a pharmaceutically acceptable salt thereof.

* * * * *